United States Patent
Dhar et al.

(10) Patent No.: US 9,663,469 B2
(45) Date of Patent: May 30, 2017

(54) RORγ MODULATORS

(71) Applicant: BRISTOL-MYERS SQUIBB COMPANY, Princeton, NJ (US)

(72) Inventors: T. G. Murali Dhar, Newtown, PA (US); Jingwu Duan, Yardley, PA (US); Hua Gong, Newtown, PA (US); Bin Jiang, Bryn Mawr, PA (US); Zhonghui Lu, King of Prussia, PA (US); David S. Weinstein, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/917,420

(22) PCT Filed: Sep. 8, 2014

(86) PCT No.: PCT/US2014/054489
§ 371 (c)(1),
(2) Date: Mar. 8, 2016

(87) PCT Pub. No.: WO2015/035278
PCT Pub. Date: Mar. 12, 2015

(65) Prior Publication Data
US 2016/0318870 A1    Nov. 3, 2016

Related U.S. Application Data

(60) Provisional application No. 61/875,220, filed on Sep. 9, 2013.

(51) Int. Cl.
| | | |
|---|---|---|
| *C07D 279/16* | (2006.01) |
| *C07D 401/06* | (2006.01) |
| *C07D 417/06* | (2006.01) |
| *C07D 215/58* | (2006.01) |
| *C07D 401/14* | (2006.01) |
| *C07D 401/12* | (2006.01) |
| *C07D 405/12* | (2006.01) |
| *C07D 413/12* | (2006.01) |
| *C07D 417/12* | (2006.01) |
| *C07D 491/04* | (2006.01) |
| *C07D 491/10* | (2006.01) |
| *C07D 405/14* | (2006.01) |
| *C07D 409/12* | (2006.01) |
| *C07D 471/10* | (2006.01) |
| *C07D 487/10* | (2006.01) |
| *C07D 491/044* | (2006.01) |

(52) U.S. Cl.
CPC ......... *C07D 215/58* (2013.01); *C07D 279/16* (2013.01); *C07D 401/06* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 417/12* (2013.01); *C07D 471/10* (2013.01); *C07D 487/10* (2013.01); *C07D 491/04* (2013.01); *C07D 491/044* (2013.01); *C07D 491/10* (2013.01); *C07D 417/06* (2013.01)

(58) Field of Classification Search
CPC .. C07D 215/58; C07D 417/06; C07D 401/06; C07D 471/00; C07D 487/00; C07D 279/16
See application file for complete search history.

(56) References Cited

U.S. PATENT DOCUMENTS

2015/0191483 A1    7/2015  Duan et al.

FOREIGN PATENT DOCUMENTS

| WO | WO 03/031436 | 4/2003 | |
|---|---|---|---|
| WO | WO 2007050425 A2 * | 5/2007 | ........... C07D 279/16 |
| WO | WO 2012/064744 | 5/2012 | |
| WO | WO 2014/062658 | 4/2014 | |
| WO | WO 2014/062938 | 4/2014 | |
| WO | WO 2015/035278 | 3/2015 | |
| WO | WO 2015/042212 | 3/2015 | |
| WO | WO 2015/103507 | 7/2015 | |
| WO | WO 2015/103508 | 7/2015 | |
| WO | WO 2015/103509 | 7/2015 | |
| WO | WO 2015/103510 | 7/2015 | |

OTHER PUBLICATIONS

Hibi, et al., Journal of Med Chem, vol. 41, No. 17, pp. 3245-3252 (1998).
Huang et al., Expert Opinion on Therapeutic Targets, vol. 11, No. 6, pp. 737-743 (2007).

* cited by examiner

*Primary Examiner* — Samira Jean-Louis
(74) *Attorney, Agent, or Firm* — Elliott Korsen

(57) ABSTRACT

Described are RORγ modulators of the formula (I), or pharmaceutically acceptable salts thereof, wherein all substituents are defined herein. The invention includes stereoisomeric forms of the compounds of formula I, including stereoisomerically-pure, scalemic and racemic form, as well as tautomers thereof. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

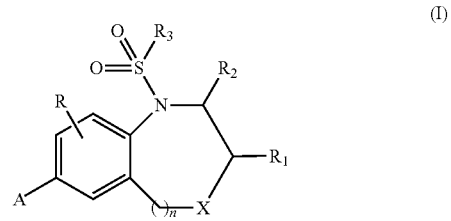

6 Claims, No Drawings

RORγ MODULATORS

CROSS-REFERENCE TO RELATED APPLICATIONS

This application claims the benefit of U.S. Provisional Application No. 61/875,220 filed Sep. 9, 2013, the disclosure of which is incorporated herein by reference in its entirety.

BACKGROUND OF THE INVENTION

Field of the Invention

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include psoriasis, arthritis, asthma, inflammatory bowel disease and multiple sclerosis.

Summary of the Related Art

The retinoid-related orphan receptors RORα, RORβ and RORγ play an important role in numerous biological processes including organ development, immunity, metabolism, and circadian rhythms. See, for example, Dussault et al. in *Mech. Dev.* (1998) vol. 70, 147-153; Andre et al. in *EMBO J.* (1998) vol. 17, 3867-3877; Sun et al. in *Science* (2000) vol. 288, 2369-2373; and Jetten in *Nucl. Recept. Signal.* (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in *Biochem. Biophys. Res. Commun.* (1994) vol. 205, 1976-1983; Oritz et al. in *Mol. Endocrinol.* (1995) vol. 9, 1679-1691; and He et al. in *Immunity* (1998) vol. 9, 797-806. Expression of RORγt is restricted to lymphoid cell types including CD4$^+$CD8$^+$ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in *Science* (2000) vol. 288, 2369-2373; Ivanov et al. in *Cell* (2006) vol. 126, 1121-1133; Eberl et al. in *Nat. Immunol.* (2004) vol. 5, 64-73; Ivanov et al. in *Semin. Immunol.* (2007) vol. 19, 409-417; and Cua and Tato in *Nat. Rev. Immunol.* (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracelluar pathogens. See, for example, Ivanov et al. in *Semin. Immunol.* (2007) vol. 19: 409-417; and Marks and Craft in *Semin. Immunol.* (2009) vol. 21, 164-171. RORγ directly regulates IL-17 transcription and disruption of RORγ in mice attenuates IL-17 production. See, for example, Ivanov et al. in *Cell* (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in *Nat. Med.* (2002) vol. 8, 500-508; Tzartos et al. in *Am. J. Pathol.* (2008) vol. 172, 146-155; Kotake et al. in *J. Clin. Invest.* (1999) vol. 103, 1345-1352; Kirkham et al. in *Arthritis Rheum.* (2006) vol. 54, 1122-1131; Lowes et al. in *J. Invest. Dermatol.* (2008) vol. 128, 1207-1211; Leonardi et al. in *N. Engl. J. Med.* (2012) vol. 366, 1190-1199; Fujino et al. in *Gut* (2003) vol. 52, 65-70; Seiderer et al. in *Inflamm. Bowel Dis.* (2008) vol. 14, 437-445; Wong et al. in *Clin. Exp. Immunol.* (2001) vol. 125, 177-183; and Agache et al. in *Respir. Med.* (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in *Ann. N.Y. Acad. Sci.* (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in *Cell* (2006) vol. 126, 1121-1133; Yang et al. in *Immunity* (2008) vol. 28, 29-39; Pantelyushin et al. in *J. Clin. Invest.* (2012) vol. 122, 2252-2256; Leppkes et al. in *Gastroenterology* (2009) vol. 136, 257-267; and Tilley et al. in *J. Immunol.* (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

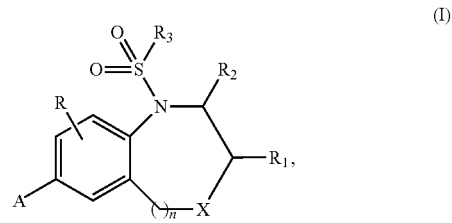

or pharmaceutically acceptable salts thereof, wherein all substituents are defined herein. The invention includes stereoisomeric forms of the compounds of formula I, including stereoisomerically-pure, scalemic and racemic form, as well as tautomers thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

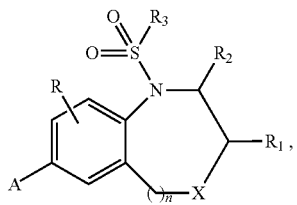

(I)

wherein
X is O, S,

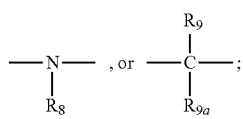

n is 0 or 1, provided that n is 1 when X is other than S;
A is

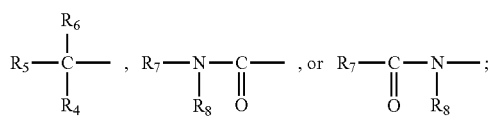

R is H, halo, OH, optionally substituted $C_1$-$C_4$ alkoxy, CN, or optionally substituted $C_1$-$C_4$ alkyl;
$R_1$ is H,

or optionally substituted $C_1$-$C_4$ alkyl, or OH (where X is

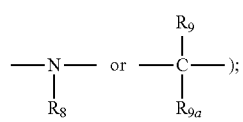

);

$R_2$ is

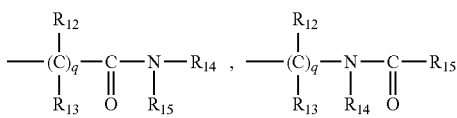

or

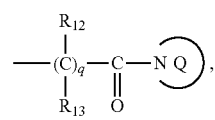

where q is 0, 1, 2, or 3;
$R_3$ is optionally substituted 6- to 10-membered monocyclic or bicyclic aryl or optionally substituted 5- to 10-membered monocyclic or bicyclic heteroaryl;
$R_4$ and $R_5$ are independently H, OH, optionally substituted $C_1$-$C_6$ alkyl, optionally substituted monocyclic or bicyclic $C_3$-$C_{10}$ cycloalkyl, optionally substituted $C_6$-$C_{10}$ monocyclic or bicyclic arylsulfonyl, optionally substituted dideutero-$C_1$-$C_4$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted 4- to 7-membered monocyclic heteroaryl, optionally substituted 8- to 10-membered bicyclo heteroaryl, optionally substituted $C_2$-$C_6$ alkenyl, or optionally substituted monocyclic or bicyclic $C_4$-$C_{10}$ cycloalkenyl;
$R_6$ is selected from OH, optionally substituted $C_1$-$C_4$ alkyl, or optionally substituted halo-$C_1$-$C_4$-alkyl;
each $R_4$, $R_5$ and $R_6$ group being optionally substituted with 1 to 3 groups;
provided that only one of $R_4$, $R_5$ and $R_6$ can be hydroxy;
$R_7$ and $R_8$ are independently selected from H, optionally substituted $C_1$-$C_4$ alkyl, optionally substituted monocyclic or bicyclic $C_3$-$C_{10}$ cycloalkyl, or cyano;
$R_9$ and $R_{9a}$ are independently selected from H, halo, optionally substituted $C_1$-$C_4$ alkyl, optionally substituted monocyclic or bicyclic $C_3$-$C_{10}$ cycloalkyl, or cyano;
$R_{10}$ and $R_{11}$ are independently selected from H, optionally substituted $C_1$-$C_4$ alkyl, or optionally substituted monocyclic or bicyclic $C_3$-$C_{10}$ cycloalkyl, or $R_{10}$ and $R_{11}$ can be taken together to form a ring;
$R_{12}$ and $R_{13}$ are independently selected from H, optionally substituted $C_1$-$C_4$ alkyl, or optionally substituted monocyclic or bicyclic $C_3$-$C_{10}$ cycloalkyl; and
$R_{14}$ is selected from H or optionally substituted $C_1$-$C_4$ alkyl; and
$R_{15}$ is selected from optionally substituted $C_1$-$C_4$ alkyl, optionally substituted $C_1$-$C_4$ alkoxy, optionally substituted 4- to 10-membered monocyclic or bicyclic heterocyclo, optionally substituted amino, optionally substituted monocyclic or bicyclic $C_3$-$C_{10}$ cycloalkyl, optionally substituted $C_2$-$C_6$ alkynyl, optionally substituted 4- to 10-membered monocyclic or bicyclic heteroaryl, optionally $C_6$-$C_{10}$ monocyclic or bicyclic aryl, or optionally substituted monocyclic or bicyclic $C_6$-$C_{10}$ aryloxy;
provided that both of $R_{14}$ and $R_{15}$ cannot be H, alkyl or haloalkyl; and

is an optionally substituted 4- to 16-membered nitrogen containing monocyclic, bicyclic or tricyclic ring which contains 0, 1 or 2 additional heteroatoms selected from N, S and O;

and/or a pharmaceutically acceptable salt thereof, and/or stereoisomers thereof, and/or tautomers thereof.

In another aspect, there is provided the compound of Formula (II):

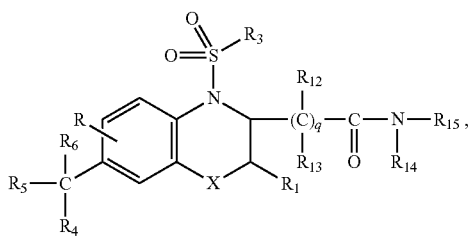

(II)

wherein
X is $CH_2$ or S;
R is H;
$R_1$ is H;
$R_3$ is optionally substituted $C_6$-$C_{10}$ monocyclic or bicyclic aryl or optionally substituted 5- to 10-membered monocyclic or bicyclic heteroaryl;
$R_4$ and $R_5$ are independently H, OH, optionally substituted $C_1$-$C_4$ alkyl, optionally substituted $C_3$-$C_{10}$ monocyclic or bicyclic cycloalkyl, optionally substituted monocyclic or bicyclic arylsulfonyl, optionally substituted dideutero-$C_1$-$C_4$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted 4- to 7-membered monocyclic heteroaryl, optionally substituted 8- to 10-membered bicyclo heteroaryl, optionally substituted $C_2$-$C_6$ alkenyl, or optionally substituted $C_4$-$C_8$ cycloalkenyl;
$R_6$ is selected from hydroxy or optionally substituted $C_1$-$C_4$ alkyl;
each $R_4$, $R_5$ and $R_6$ group, where possible, being optionally substituted with 1 to 3 groups;
provided that only one of $R_4$, $R_5$ and $R_6$ can be hydroxy;
q is 1;
$R_{14}$ is H or optionally substituted $C_1$-$C_4$ alkyl;
$R_{15}$ is optionally substituted $C_1$-$C_4$ alkyl, optionally substituted monocyclic or bicyclic 4- to 10-membered heterocyclo, optionally substituted amino, optionally substituted monocyclic or bicyclic $C_3$-$C_{10}$ cycloalkyl, optionally substituted $C_2$-$C_6$ alkynyl, optionally substituted monocyclic or bicyclic 4- to 10-membered heteroaryl, or optionally substituted monocyclic or bicyclic $C_6$-$C_{10}$ aryl;
$R_{12}$ is H; and
$R_{13}$ is H;
and/or a pharmaceutically acceptable salt thereof, and/or stereoisomers thereof, and/or tautomers thereof.

In another aspect, there is provided a compound of the formula

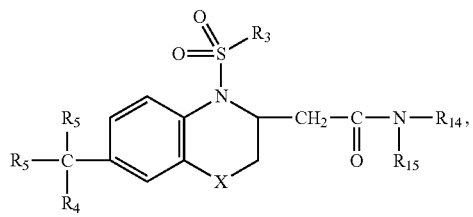

wherein
X is $CH_2$ or S;
$R_3$ is optionally substituted monocyclic or bicyclic $C_6$-$C_{10}$ aryl or optionally substituted monocyclic or bicyclic 5- to 10-membered heteroaryl;
$R_4$ and $R_5$ are each trihalo-$C_1$-$C_3$-alkyl;
$R_6$ is hydroxy;
$R_{14}$ is H or optionally substituted $C_1$-$C_4$ alkyl; and
$R_{15}$ is optionally substituted $C_1$-$C_4$ alkyl, optionally substituted 5- to 10-membered monocyclic or bicyclic heterocyclo, optionally substituted amino, optionally substituted monocyclic or bicyclic $C_3$-$C_{10}$ cycloalkyl, optionally substituted $C_2$-$C_6$ alkynyl, optionally substituted 5- to 10-membered monocyclic or bicyclic heteroaryl, or optionally substituted monocyclic or bicyclic $C_6$-$C_{10}$ aryl;
and/or a pharmaceutically acceptable salt thereof, and/or a stereoisomer thereof, and/or a tautomer thereof.

In another aspect within the prior aspects, there is provided a compound of the formula

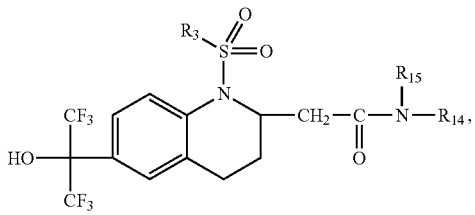

wherein:
$R_3$ is optionally substituted halophenyl, optionally substituted dihalophenyl, optionally substituted $C_1$-$C_6$ alkoxyphenyl, optionally substituted cyanophenyl, or optionally substituted halo 5- to 10-membered monocyclic or bicyclic heteroaryl or

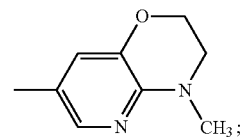

$R_{14}$ is H or optionally substituted $C_1$-$C_4$ alkyl; and
$R_{15}$ is optionally substituted $C_1$-$C_4$ alkyl, optionally substituted monocyclic or bicyclic 5- to 10-membered heterocyclo-$C_1$-$C_3$-alkyl, optionally substituted amino-$C_1$-$C_3$-alkyl, optionally substituted aminocarbonyl-$C_1$-$C_3$-alkyl, optionally substituted mono- or di-hydroxy-$C_1$-$C_3$-alkyl, optionally substituted $C_1$-$C_3$-alkoxy-$C_1$-$C_3$-alkyl, optionally substituted monocyclic or bicyclic 5- to 10-membered heterocyclo-monocyclic or bicyclic 5- to 8-membered heterocyclo-$C_1$-$C_3$-alkyl, optionally substituted $C_1$-$C_3$-alkylcarbonylamino-$C_1$-$C_3$-alkyl, optionally substituted-monocyclic or bicyclic 5- to 10-membered heterocyclocarbonyl-$C_1$-$C_3$-alkyl, optionally substituted phenyl-$C_1$-$C_3$-alkyloxycarbonyl-$C_1$-$C_3$-alkyl, optionally substituted carboxy-$C_1$-$C_3$-alkyl, optionally substituted monocyclic or bicyclic 5- to 10-membered heteroaryl-$C_1$-$C_3$-alkyl, optionally substituted monocyclic or bicyclic $C_3$-$C_{10}$-cycloalkylaminocarbonyl-$C_1$-$C_3$-alkyl, optionally substituted monocyclic or bicyclic 5- to 10-membered heterocycloaminocarbonyl-$C_1$-$C_3$-alkyl, optionally substituted cyano-$C_1$-$C_3$-alkyl, optionally substituted aminocarbonyl-$C_1$-$C_3$-alkyl, optionally substituted aminosulfonylphenyl-$C_1$-$C_3$-alkyl, optionally substituted $C_1$-$C_3$-alkoxycarbonyl-$C_1$-$C_3$-alkyl, or optionally substituted phenyl-$C_1$-$C_3$-alkyl, or $R_{15}$ is optionally substituted monocyclic or bicyclic 4- to 10-membered heterocyclo, which is optionally substituted $C_1$-$C_4$ alkoxycarbonylamino monocyclic or bicyclic 4- to 10-membered heterocyclo, optionally substituted phenyl-$C_1$-$C_3$-alkoxycarbonyl($C_1$-$C_3$-alkyl)-(hydroxy) monocyclic or bicyclic 4- to 10-membered heterocyclo, optionally substituted (mono- or di-hydroxy)(mono- or di-$C_1$-$C_3$-alkyl) monocyclic or bicyclic 4- to 10-membered heterocyclo, optionally substituted $C_1$-$C_3$ alkylcarbonyl($C_1$-$C_3$ alkyl)-(hydroxy) monocyclic or bicyclic 4- to 10-membered heterocyclo, optionally substituted phenyl-$C_1$-$C_3$-alkoxycarbonyl(halo-$C_1$-$C_3$-alkyl) monocyclic or bicyclic 4- to 10-membered heterocyclo, optionally substituted $C_1$-$C_3$ alkylamino monocyclic or bicyclic 4- to 10-membered heterocyclo, optionally substituted amino monocyclic or bicyclic 4- to 10-membered heterocyclo, optionally substituted imidazolidinone, optionally substituted dioxoimidazolidinone, optionally substituted oxatetrahydrofuranyl, optionally substituted oxapyrrolidinyl, optionally substituted tetrahydrofuranyl, optionally substituted oxapiperidinyl, optionally substituted

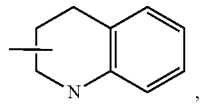, optionally substituted

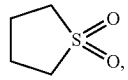, optionally substituted thienyl

, optionally substituted

,

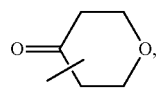, optionally substituted

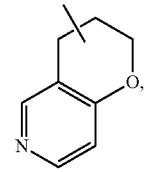

optionally substituted

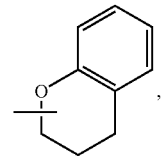, or optionally substituted oxabicycloheptanyl

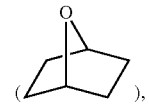, or $R_{15}$ is optionally substituted amino, which is optionally substituted 5- to 10-membered heterocyclocarbonylamino, optionally substituted hydroxy-$C_1$-$C_3$-alkylcarbonylamino, or optionally substituted amino-$C_1$-$C_3$-alkylcarbonylamino, or $R_{15}$ is optionally substituted monocyclic or bicyclic 4- to 10-membered heteroaryl, which is optionally substituted hydroxy-$C_1$-$C_3$-alkylpyridyl, or optionally substituted thiadiazole, or $R_{15}$ is optionally substituted $C_6$-$C_{10}$ aryl, which is optionally substituted hydroxy-$C_1$-$C_3$-alkylphenyl, optionally substituted phenyl, optionally substituted

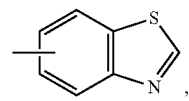, or optionally substituted oxazolylphenyl, or $R_{15}$ is optionally substituted $C_2$-$C_6$ alkynyl, which is optionally substituted CH≡C—$C_1$-$C_3$ alkyl, or $R_{15}$ is optionally substituted monocyclic or bicyclic $C_3$-$C_{10}$ cycloalkyl, which is optionally substituted cyclopentyl, optionally substituted cyclohexyl, optionally substituted bicycloheptanyl

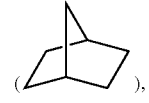, optionally substituted cyclopentenyl

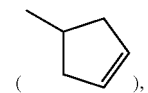, optionally substituted cyclobutyl, optionally substituted cyclopropyl, or optionally substituted

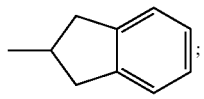

and/or a pharmaceutically acceptable salt thereof, and/or a stereoisomer thereof, and/or a tautomer thereof.

In another aspect within the prior aspects, there is provided a compound of the formula

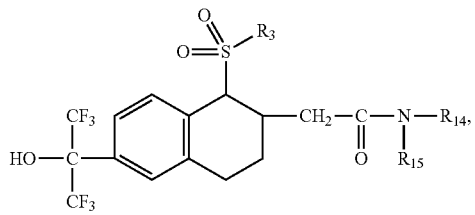

wherein
$R_3$ is

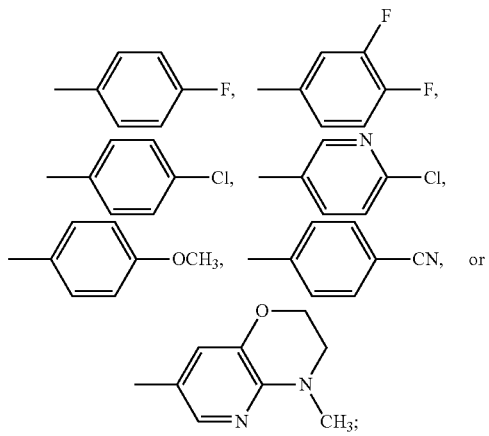

$R_{14}$ is H or optionally substituted $C_1$-$C_4$ alkyl; and $R_{15}$ is optionally substituted $C_1$-$C_4$ alkyl, optionally substituted 5- to 10-membered monocyclic or bicyclic heterocyclo, optionally substituted amino, optionally substituted monocyclic or bicyclic $C_3$-$C_{10}$ cycloalkyl, optionally substituted $C_2$-$C_6$ alkynyl, optionally substituted 5- to 10-membered monocyclic or bicyclic heteroaryl, or optionally substituted monocyclic or bicyclic $C_6$-$C_{10}$ aryl;

and/or a pharmaceutically acceptable salt thereof, and/or a stereoisomer thereof, and/or a tautomer thereof.

In another aspect within the prior aspects, there is provided a compound of the formula

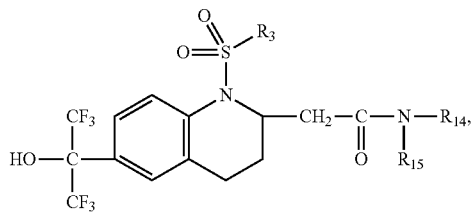

wherein
$R_3$ is H or optionally substituted monocyclic or bicyclic $C_6$-$C_{10}$ aryl or optionally substituted monocyclic or bicyclic 5- to 10-membered heteroaryl;

$R_{14}$ is H or $CH_3$; and $R_{15}$ is optionally substituted amino wherein the optional substituents comprise 1, 2 or 3 groups independently selected from amino(di-$C_1$-$C_4$-alkyl)$C_1$-$C_4$ alkylcarbonyl or monocyclic or bicyclic 4- to 8-membered heteroarylcarbonyl, or $R_{15}$ is optionally substituted monocyclic or bicyclic 4- to 8-membered heterocyclo-$C_1$-$C_4$-alkyl which is:

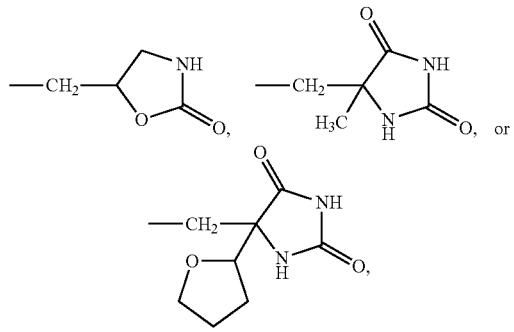

or $R_{15}$ is optionally substituted $C_1$-$C_4$ alkyl wherein the substituent is 1, 2 or 3 groups independently selected from $NH_2$, OH, $NH_2CO$—, CN, $C_1$-$C_4$ alkylcarbonylamino, monocyclic or bicyclic 4- to 10-membered heterocyclo (which itself is optionally substituted, where possible, with 1, 2 or 3 substituents independently selected from $C_1$-$C_4$ alkyl, halo-$C_1$-$C_4$-alkyl, hydroxy-$C_1$-$C_4$-alkyl, hydroxy, or monocyclic or bicyclic 4- to 10-membered heterocyclo), hydroxy-$C_1$-$C_4$-alkyl, oxo, monocyclic or bicyclic 4- to 10-membered heteroaryl (which itself is optionally substituted, where possible, with 1, 2 or 3 groups independently selected from OH, hydroxy, $C_1$-$C_4$ alkyl, $C_1$-$C_4$ alkylthio, or $C_1$-$C_4$ alkyl), benzyloxycarbonyl, carboxy, hydroxy monocyclic or bicyclic $C_3$-$C_{10}$-cycloalkylaminocarbonyl, aminosulfonylphenyl, $C_1$-$C_4$ alkoxycarbonyl, $C_2$-$C_4$ alkynyl, monocyclic or bicyclic $C_6$-$C_{10}$ aryl (which itself is optionally substituted with 1 or 2 groups independently selected from $C_1$-$C_4$ alkoxy, monocyclic or bicyclic 4- to 10-membered heterocyclo, halo, or OH), aminosulfonyl, monocyclic or bicyclic 4- to 10-membered heterocyclo-$C_1$-$C_4$ alkyl, di-$C_1$-$C_4$-alkylaminocarbonyl, $C_1$-$C_4$ alkylaminocarbonyl, monocyclic or bicyclic 4- to 10-membered heterocyclocarbonyl, $C_1$-$C_4$ alkyl monocyclic or bicyclic 4- to 10-membered heterocyclo($C_1$-$C_4$-alkyl)aminocarbonyl, $C_1$-$C_4$ alkoxycarbonyl, $C_1$-$C_4$ alkyl(hydroxycarbonyl)-di-$C_1$-$C_4$-alkylamino, or $C_1$-$C_4$ alkynyl, or $R_{15}$ is optionally substituted 5- to 10-membered heteroaryl, wherein the heteroaryl is

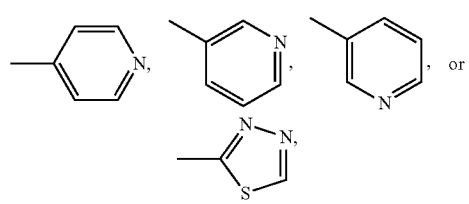

and the optional substituents are 1, 2 or 3 groups independently selected from COOH or hydroxy-$C_1$-$C_4$-alkyl, or $R_{15}$ is $C_6$-$C_{10}$ aryl, wherein the aryl is phenyl or

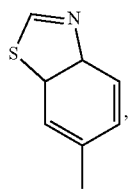

and the optional substituents are 1, 2 or 3 groups independently selected from monocyclic or bicyclic 4- to 8-membered heteroaryl, or $R_{15}$ is optionally substituted 5- to 10-membered heterocyclo, wherein the heterocyclo is

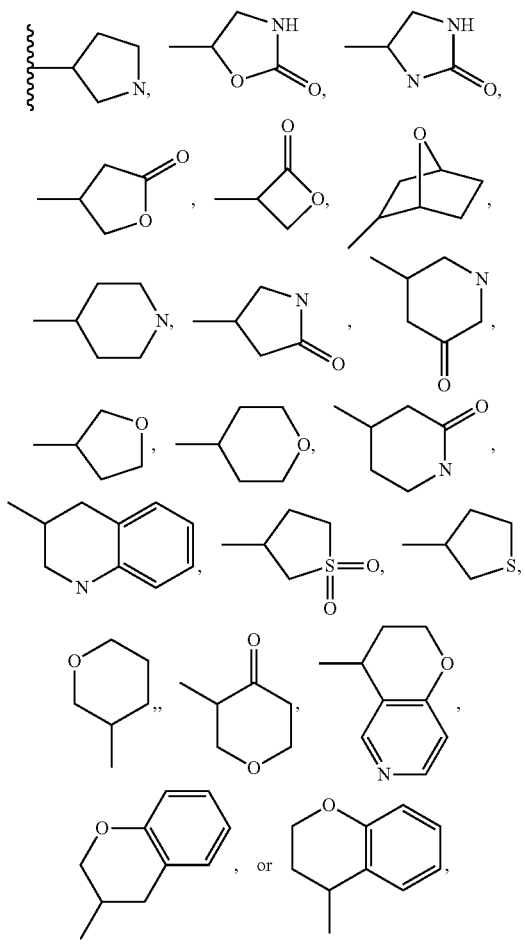

and the optional substituents are 1, 2 or 3 groups independently selected from OH, CN, $C_1$-$C_4$ alkyl, phenyl-$C_1$-$C_4$-alkoxycarbonyl, $C_1$-$C_4$ alkylcarbonyl, oxo, halo-$C_1$-$C_4$-alkyl, $C_1$-$C_4$ alkoxycarbonyl, or phenyl-$C_1$-$C_4$-alkyl, or $R_{15}$ is optionally substituted $C_3$-$C_{10}$ cycloalkyl, wherein the cycloalkyl is

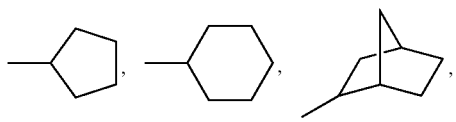

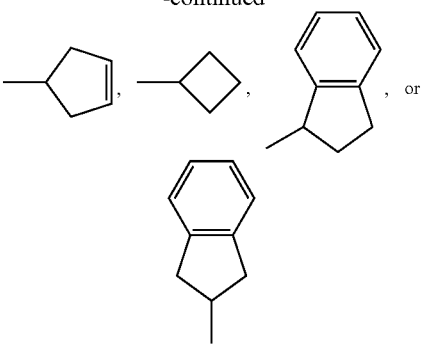

and the optional substituents are 1, 2, 3 or 4 groups independently selected from $C_1$-$C_4$ alkyl, $NH_2$, OH, $NO_2$, $C_1$-$C_4$ alkoxycarbonylamino, $C_1$-$C_4$ alkylcarbonylamino, phenyl, hydroxy-$C_1$-$C_4$-alkyl, monocyclic or bicyclic 4- to 10-membered heteroaryl, $C_1$-$C_4$ alkoxy monocyclic or bicyclic 4- to 10-membered heteroaryl, halophenyl, halo monocyclic or bicyclic 4- to 10-membered heteroaryl, monocyclic or bicyclic 4- to 10-membered heteroarylaminocarbonyl, dihalophenyloxy, or halo;

and/or a pharmaceutically acceptable salt thereof, and/or a stereoisomer thereof, and/or a tautomer thereof.

In another aspect within the prior aspects, there is provided a compound of the formula

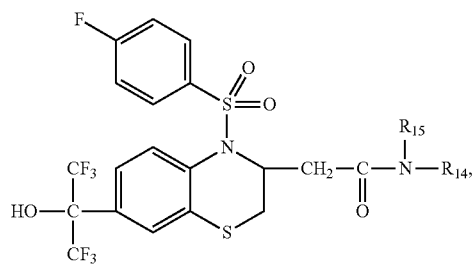

wherein $R_{14}$ is H or $C_1$-$C_4$ alkyl; and $R_{15}$ is optionally substituted hydroxy-$C_1$-$C_4$-alkyl, optionally substituted amino-$C_1$-$C_4$-alkyl, optionally substituted $C_3$-$C_8$ cycloalkyl, or optionally substituted hydroxy (hydroxy-$C_1$-$C_4$-alkyl)$C_1$-$C_4$-alkyl;

and/or a pharmaceutically acceptable salt thereof, and/or a stereoisomer thereof, and/or a tautomer thereof.

In another aspect within the first aspect, there is provided a compound of the formula

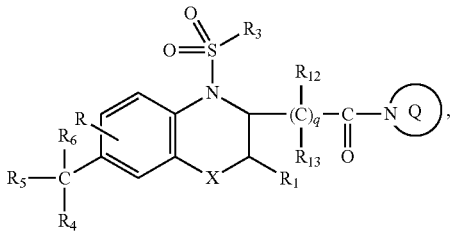

wherein

X is $CH_2$ or S;

R is H;

$R_1$ is H;

$R_3$ is optionally substituted aryl or optionally substituted monocyclic or bicyclic 5- to 10-membered heteroaryl;

R₄ and R₅ are independently H, OH, optionally substituted $C_1$-$C_4$ alkyl, optionally substituted monocyclic or bicyclic $C_3$-$C_{10}$ cycloalkyl, optionally substituted monocyclic or bicyclic arylsulfonyl, optionally substituted dideutero-$C_1$-$C_4$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted 5- to 7-membered monocyclic heteroaryl, optionally substituted 8- to 10-membered bicyclo heteroaryl, optionally substituted $C_2$-$C_6$ alkenyl, or optionally substituted monocyclic or bicyclic $C_4$-$C_{10}$ cycloalkenyl; and R₆ is selected from OH, optionally substituted $C_1$-$C_4$ alkyl, or optionally substituted halo-$C_1$-$C_4$-alkyl;

each R₄, R₅ and R₆ group being optionally substituted with 1 to 3 groups;

provided that only one of R₄, R₅ and R₆ can be hydroxy;

R₁₂ and R₁₃ are independently selected from H, optionally substituted $C_1$-$C_4$ alkyl, or optionally substituted monocyclic or bicyclic $C_3$-$C_{10}$ cycloalkyl;

is an optionally substituted 4- to 16-membered nitrogen containing monocyclic, bicyclic or tricyclic heterocyclo ring which contains 0, 1 or 2 additional heteroatoms selected from N, S and O; and q is 1 or 2;

and/or a pharmaceutically acceptable salt thereof, and/or stereoisomers thereof, and/or tautomers thereof.

In another aspect within the prior aspects, there is provided a compound of the formula

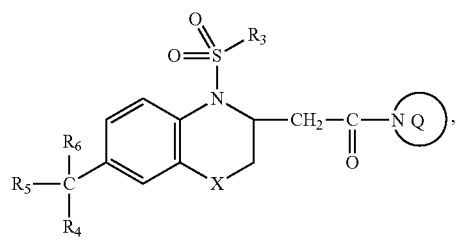

wherein

X is CH₂ or S;

R₆ is OH;

R₄ and R₅ are each trihalo-$C_1$-$C_4$-alkyl;

is a 4- to 16-membered monocyclic, bicyclic or tricyclic heterocyclo ring which is optionally substituted with 0, 1 or 2 substituents; and R₃ is optionally substituted halophenyl, optionally substituted dihalophenyl, optionally substituted $C_1$-$C_6$ alkoxyphenyl, optionally substituted cyanophenyl, optionally substituted halo monocyclic or bicyclic 5- to 10-membered heteroaryl, or

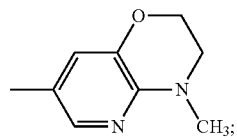

and/or a pharmaceutically acceptable salt thereof, and/or a stereoisomer thereof, and/or a tautomer thereof.

In another aspect within the prior aspect, there is provided a compound wherein

is an optionally substituted monocyclic, bicyclic or tricyclic 4- to 16-membered heterocyclo ring which is optionally substituted pyrazolidinyl

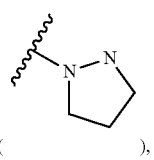

( ), optionally substituted pyrrolidinyl

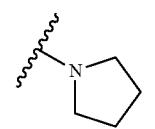

( ), optionally substituted triazaspirodecanedione

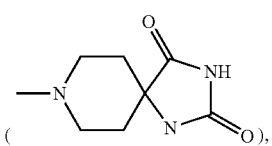

( ), optionally substituted triazaspirononanedione

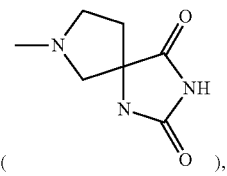

( ), optionally substituted

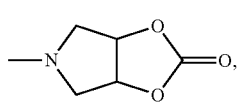

optionally substituted azetidinyl

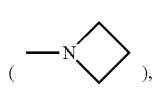
( ), optionally substituted morpholinyl

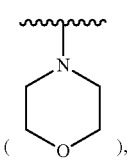
( ), optionally substituted piperazinyl

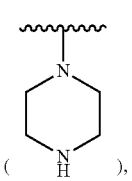
( ), optionally substituted piperidinyl

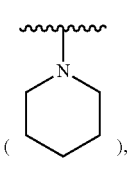
( ), optionally substituted

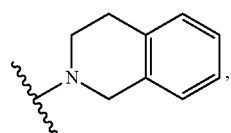 [SMILES: *N1CCc2ccccc2C1]
, optionally substituted

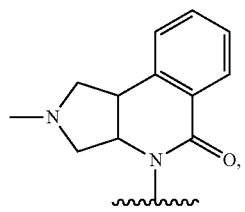 [SMILES: *N1C(=O)c2ccccc2C2CN(C)CC21]
, optionally substituted

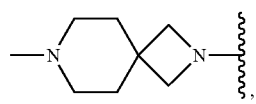
, optionally substituted

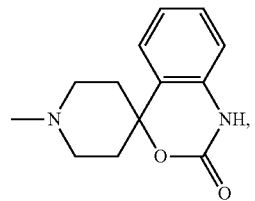
, optionally substituted

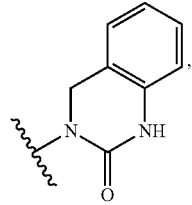 [SMILES: *N1Cc2ccccc2NC1=O]
, optionally substituted

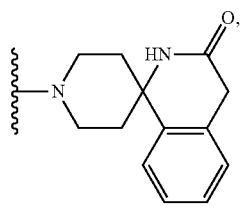 [SMILES: *N1CCC2(CC1)NC(=O)Cc1ccccc12]
, optionally substituted

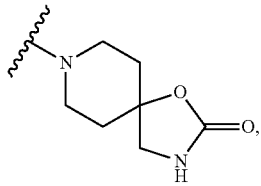 [SMILES: *N1CCC2(CC1)CNC(=O)O2]
, optionally substituted pyrazolidinone

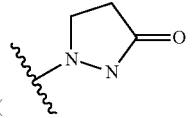
( ), optionally substituted

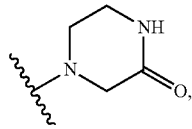
, optionally substituted

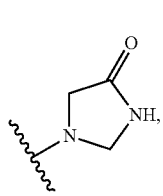 [SMILES: *N1CNC(=O)C1]
, or optionally substituted

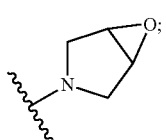 [SMILES: *N1CC2OC2C1]

and/or a pharmaceutically acceptable salt thereof, and/or a stereoisomer thereof, and/or a tautomer thereof.

In another aspect, there is provided a compound wherein

where possible, is substituted with 1, 2, 3 or 4 groups independently selected from OH, $C_{1-6}$ alkoxycarbonylamino, oxo, amino, halo-$C_{1-4}$-alkyl, halo, $C_{1-6}$ alkyl, hydroxy-$C_{1-6}$-alkyl, amino-$C_{1-4}$-alkyl, phenylcarbonylamino, $C_{1-4}$-alkylaminocarbonylamino-$C_{1-4}$-alkyl, $C_{1-4}$-alkoxycarbonylamino-$C_{1-4}$-alkyl, aminocarbonyl, di-$C_{1-4}$-alkylamino, $C_{1-4}$ alkoxy, $C_{6-10}$ aryl, $C_{1-4}$ alkylcarbonyl, $C_{1-4}$ alkylaminocarbonylamino, optionally substituted 4- to 10-membered monocyclic or bicyclic heteroaryl, $C_{1-4}$ alkylcarbonyloxy, $C_{1-4}$-alkoxyphenyl-$C_{1-4}$-alkyl, ($C_{6-10}$ aryl) 4- to 10-membered (dioxo)cycloalkenylamino aryl-$C_{1-4}$-alkyl, halophenyl, optionally substituted 4- to 10-membered monocyclic or bicyclic heterocyclo, optionally substituted 4- to 10-membered monocyclic heteroarylcarbonyl, optionally substituted 4- to 10-membered monocyclic or bicyclic heterocyclo-$C_{1-4}$-alkyl, or 4- to 10-membered monocyclic heteroarylphenyl-$C_{1-4}$-alkylaminocarbonyl, and/or a pharmaceutically acceptable salt thereof, and/or a stereoisomer thereof, and/or a tautomer thereof.

In another aspect, there is provided a compound of the invention wherein $R_3$ is

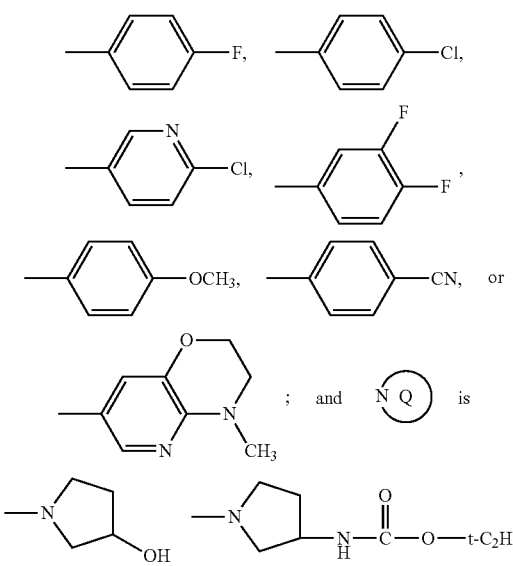

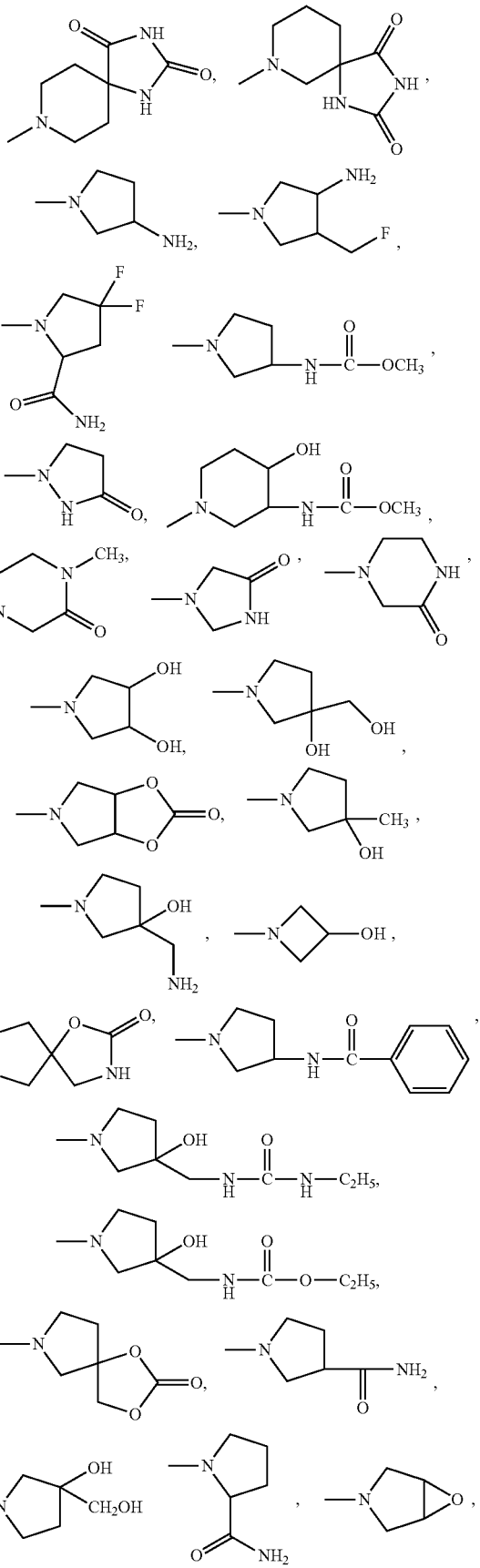

-continued
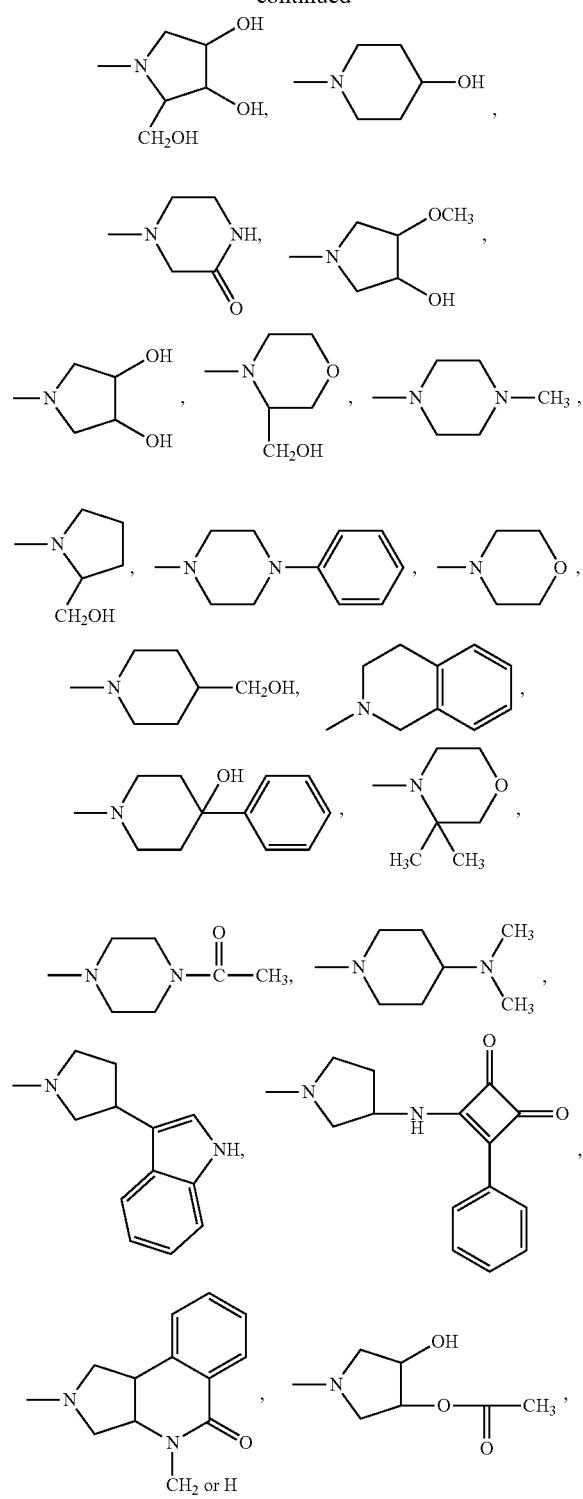
-continued
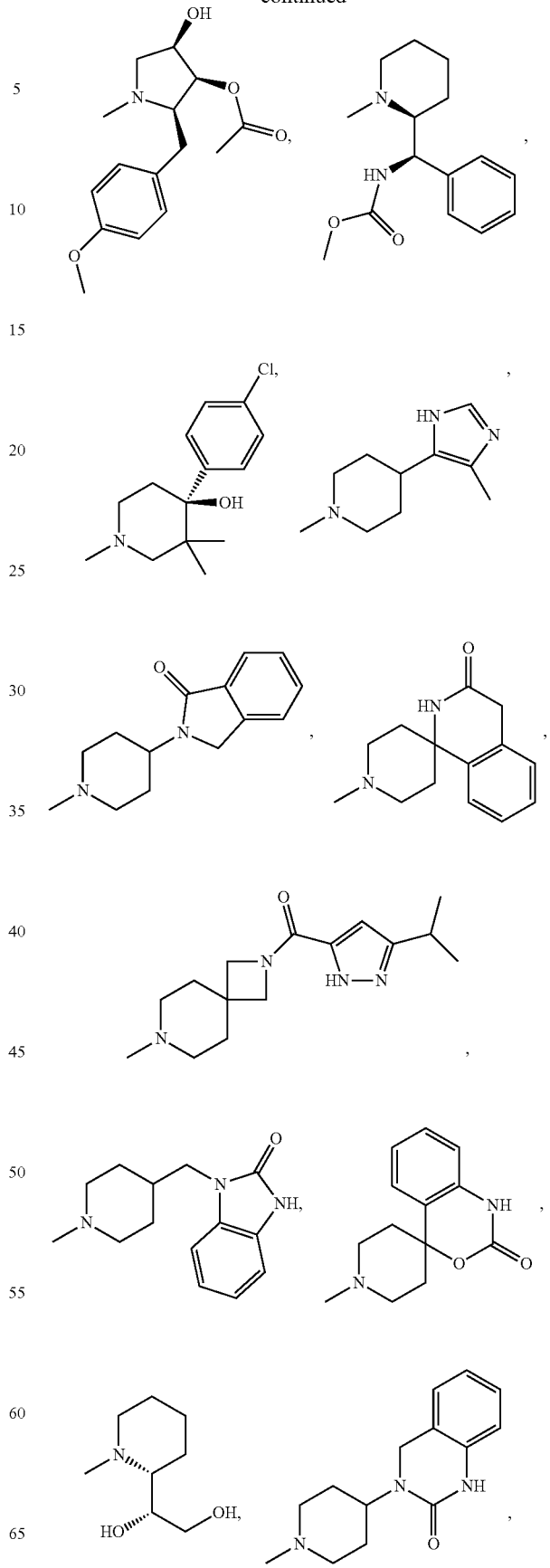

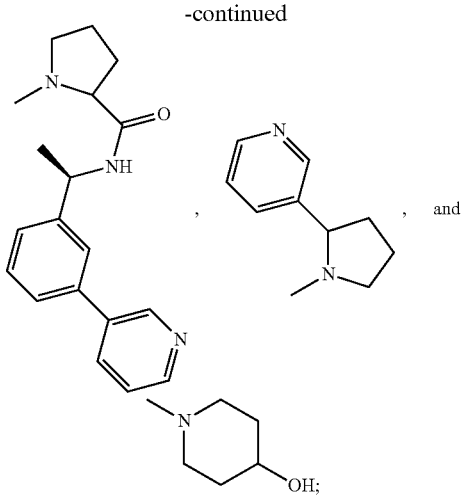

, and and/or a pharmaceutically acceptable salt thereof, and/or a stereoisomer thereof, and/or a tautomer thereof.

As noted above, each alkyl moiety (i.e., defined as "alkyl") is optionally substituted with one or more substituents (e.g., in various embodiments, from 1-5, from 1-3, from 1-2 or one) selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF$_3$, and each R$^{21}$ is independently selected from the group consisting of —H, —CH$_3$ and —CH$_2$CH$_3$. In certain embodiments of the invention as described herein, each alkyl is optionally substituted with one or more substituents selected from the group consisting of -D, -halogen, —O—R$^{20}$ and —N(R$^{21}$)$_2$ and —S(R$^{20}$), in which each R$^{20}$ is independently selected from the group consisting of —H, and —CH$_3$, and each R$^{21}$ is independently selected from the group consisting of —H and —CH$_3$. In other embodiments, each alkyl is optionally substituted with one or more substituents selected from the group consisting of -D, -halogen, —OH, —NH$_2$ and —SH. In other embodiments, each alkyl is unsubstituted.

As used herein, the "alkyl" groups are defined as having a given number of carbons. Accordingly, "(C$_1$-C$_4$)alkyl" is an alkyl group having from one to four carbons. An alkyl group can be branched or unbranched. Thus, "(C$_1$-C$_4$)alkyl" encompasses methyl, ethyl, n-propyl, isopropyl, n-butyl, sec-butyl and t-butyl, in unsubstituted and substituted forms as described above.

The term "fluoroalkyl" as used herein, means an alkyl group substituted with one or more fluorines and no other substituents. In certain embodiments, one or more carbons of the fluoroalkyl group is persubstituted with fluorine. Examples of fluoroalkyl moieties include, without limitation, fluoromethyl, difluromethyl, trifluoromethyl, pentafluoroethyl, 2,2,2-trifluoroethyl, and 1,1,1,3,3,3-hexafluoroisopropyl. "Fluoroalkyl" is encompassed within optionally-substituted alkyl as described above.

In general, any hydrogen atom of the compounds described herein (whether described explicitly as "—H" or as part of another moiety such as an alkyl or a phenyl) can be provided as a protium, or a deuterium. Thus, while deuterium is often described herein as a "substituent," the person of skill in the art will understand that deuterium can be used as the hydrogen atom species at any position in the compound. However, in certain embodiments of the compounds described herein, every hydrogen atom, unless otherwise explicitly specified, is a protium.

The term "deuteroalkyl" as used herein means an alkyl group substituted with one or more deuteria and no other substituents. Examples of "deuteroalkyl" include deuteromethyl and dideuteromethyl.

Individual compounds of certain embodiments of the present invention are provided One of skill in the art can adapt the reaction sequences of Schemes 1-50 to fit the desired target molecule. For example, use of a 2-ethylpyrimidine will result in compounds in which R$^1$ is ethyl, instead of methyl as in many of the example compounds. Similarly, while the schemes generally depict the -("B" ring system)-(R$^b$)$_y$ moiety as ortho-disubstituted phenyl, the person of skill will appreciate that use of different starting materials will provide different rings and/or different patterns of substitution. Of course, in certain situations one of skill in the art will use different reagents to affect one or more of the individual steps or to use protected versions of certain of the substituents. Additionally, one skilled in the art would recognize that compounds of structural formula (I) can be synthesized using different routes altogether.

The compounds of the present invention can be provided in a number of stereoisomeric forms. Accordingly, another aspect of the invention is a stereoisomeric form of a compound as described herein. For example, a compound of the present invention can be provided in racemic form. In other embodiments, a compound of the present invention is provided in scalemic form, or in a stereoisomerically pure form (e.g., substantially as a single enantiomer).

Another aspect of the invention is an N-oxide of a compound or stereoisomeric form as described herein.

Another aspect of the invention is a pharmaceutically acceptable salt of a compound, stereoisomeric form, or N-oxide as described herein. As used herein, the phrase "pharmaceutically acceptable salt" refers to both pharmaceutically acceptable acid and base addition salts. Such pharmaceutically acceptable salts include salts of acids such as hydrochloric, phosphoric, hydrobromic, sulfuric, sulfinic, formic, trifluoroacetic, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Another aspect of the invention is a solvate or hydrate of a compound, stereoisomeric form, N-oxide or pharmaceutically acceptable salt as described herein. The person of skill in the art can determine whether a particular compound will form a solvate or a hydrate.

Another aspect of the invention is a pharmaceutical composition including a compound, stereoisomeric form, N-oxide, pharmaceutical salt, solvate or hydrate as described herein The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets*, 2012 April; 11(2):159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology*, 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 June 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease or disorder in an individual who is experiencing or displaying the pathology or symptomatology of the disease, condition or disorder.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

Those experiments specifying that they were performed in a microwave oven were conducted in a SmithSynthesizer™ oven manufactured by Personal Chemistry or a Discover™ microwave oven manufactured by CEM corporation. The microwave ovens generate a temperature which can be selected to be between 60-250° C. The microwave ovens automatically monitor the pressure which is between 0-300 PSI. Reaction hold times and temperature set points are reported.

Abbreviations for HPLC Conditions:

Condition A: Chromolith SpeedROD 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$ Condition B: Column: Waters Xbridge C18, 19×150 mm, 5-µM particles; Guard Column: Mobile phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min Condition C: Column: PursuitXRs C18 250×30 mm; 30 to 100% solvent B in solvent A, 20 min.; Solvent A=10% MeOH, 90% $H_2O$, 0.1% TFA; Solvent B=90% MeOH, 10% $H_2O$, 0.1% TFA.

Condition D: Column: Sunfire C18 3.5 um, 3.0×150 mm; (12 min); Solvent A=0.05% TFA in $H_2O$:MeCN (95:5); Solvent B=0.05% TFA in $H_2O$:MeCN (5:95)

Condition E: Column: YMC Combiscreen ODS-A 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$ Condition F: Column: Sunfire C18 3.5 um, 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$.

Condition G: Column: BEH C18 2.1×50 mm (4 min.); Solvent A=5% acetonitrile 95% $H_2O$, 10 mM $NH_4OAc$; Solvent A=95% acetonitrile 5% $H_2O$, 10 mM $NH_4Oac$ Condition H: Column: Low pH Col-1: Sunfire C18 3.5 um, 4.6×150 mm; Start % B=10; 12 Min. 100%; 15 Min. 100%; Flow Rate=1 mL/min; Wavelength1=220; Wavelength2=254; Solvent Pair=TFA—MeCN/$H_2O$; Solvent A=0.05% TFA in $H_2O$:MeCN (95:5); Solvent B=0.05% TFA in $H_2O$:MeCN (5:95); Column 1=LOW pH—Parallel HPLC; At 220 nm Condition I: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min.

Intermediate 1

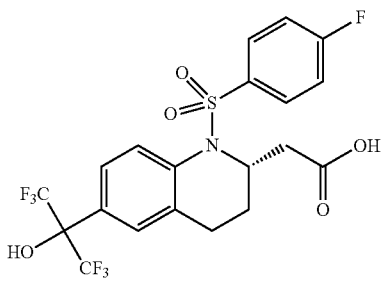

Intermediate 2

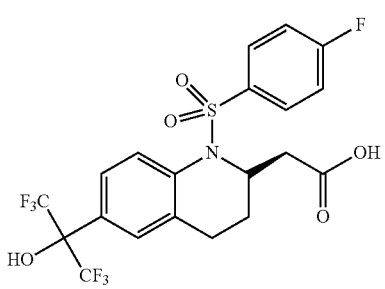

Step A: Tert-butyl 2-oxo-3,4-dihydroquinoline-1(2H)-carboxylate

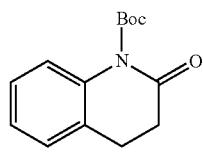 [SMILES: CC(C)(C)OC(=O)N1C(=O)CCc2ccccc21]

A mixture of 3,4-dihydroquinolin-2(1H)-one (8.46 g, 57.4 mmol), (BOC)$_2$O (13.3 mL, 57.4 mmol) and DMAP (0.702 g, 5.74 mmol) in acetonitrile (60 mL) was stirred at rt for 40 hrs and concentrated under vacuum. The residue was diluted with ethyl acetate (400 ml) and washed with 1N HCl (2×20 ml), water (20 ml), brine(20 ml), dried over anhydrous magnesium sulfate and concentrated under reduced pressure to afford tert-butyl 2-oxo-3,4-dihydroquinoline-1(2H)-carboxylate (13.5 g, 54.6 mmol, 95% yield). LC/MS M-t-Bu+1=192.1; $^1$H NMR (400 MHz, CDCl$_3$) δ ppm 7.39-7.14 (m, 2H), 7.14-7.04 (m, 1H), 6.96 (m, 1H), 3.11-2.87 (m, 2H), 2.80-2.62 (m, 2H), 1.62 (s, 9H).

Step B: Tert-butyl 2-hydroxy-3,4-dihydroquinoline-1(2H)-carboxylate

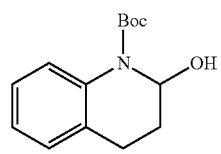 [SMILES: CC(C)(C)OC(=O)N1c2ccccc2CCC1O]

1.0 M THF solution of lithium triethylborohydride (65.5 mL, 65.5 mmol) was added dropwise to the solution of tert-butyl 2-oxo-3,4-dihydroquinoline-1(2H)-carboxylate (13.5 g, 54.6 mmol) in THF (200 mL) at −78° C. and stirred for 60 min. Saturated Na$_2$CO$_3$ (50 ml) was added and the contents warmed to −15° C. 30% H$_2$O$_2$ (50 ml) was then added dropwise. The resultant mixture was warmed to rt over a period of 1 hr and filtered. The filtrate was extracted with ethyl acetate (2×200 ml), washed with water, brine, dried over anhydrous magnesium sulfate and concentrated under reduced pressure to afford tert-butyl 2-hydroxy-3,4-dihydroquinoline-1(2H)-carboxylate (13.8 g) which was used as such for the next step without further purification. LC/MS M+Na=272.1; $^1$H-NMR (400 MHz, CD$_3$OD) δ ppm 7.49 (m, 1H), 7.17-7.07 (m, 1H), 7.05-6.88 (m, 1H), 5.96 (t, J=5.9 Hz, 1H), 2.83-2.68 (m, 1H), 2.62-2.49 (m, 1H), 2.26 (m, 1H), 1.89-1.65 (m, 2H), 1.57-1.48 (m, 9H).

Step C: Tert-butyl 2-(2-(benzyloxy)-2-oxoethyl)-3,4-dihydroquinoline-1(2H)-carboxylate

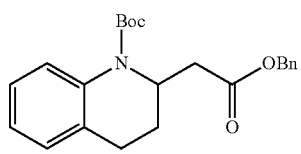 [SMILES: CC(C)(C)OC(=O)N1c2ccccc2CCC1CC(=O)OCc1ccccc1]

60% sodium hydride in mineral oil (3.88 g, 97 mmol) was added portion wise to a solution of benzyl 2-(dimethoxyphosphoryl)acetate (25.1 g, 97 mmol) in THF (200 mL) at 0° C. The resultant mixture was stirred at 0° C. for 1 hr. To this was added a solution of tert-butyl 2-hydroxy-3,4-dihydroquinoline-1(2H)-carboxylate (12.1 g, 48.5 mmol) in THF (100 ml) at 0° C. The resultant mixture was warmed to rt over 1 h, quenched with saturated aqueous NH$_4$Cl (100 ml) and extracted with ethyl acetate (2×200 ml). The combined organic layers were washed with water, brine, dried over anhydrous magnesium sulfate. Concentration under reduced pressure followed by purification by flash silica gel chromatography using a 10% mixture of ethyl acetate in hexane afforded tert-butyl 2-(2-(benzyloxy)-2-oxoethyl)-3,4-dihydroquinoline-1(2H)-carboxylate (13.8 g, 36.2 mmol, 75% yield). LC/MS(M+1): 382.3; $^1$H-NMR (400 MHz, CDCl$_3$) δ ppm 7.45 (d, J=8.1 Hz, 1H), 7.38-7.28 (m, 5H), 7.19-6.90 (m, 3H), 5.12-4.98 (m, 2H), 4.90 (m, 1H), 2.76-2.58 (m, 3H), 2.43 (m, 1H), 2.28 (m, 1H), 1.68-1.60 (m, 1H), 1.48 (s, 9H).

Step D: Benzyl 2-(1,2,3,4-tetrahydroquinolin-2-yl)acetate

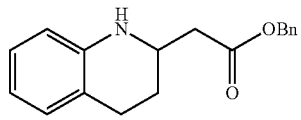 [SMILES: O=C(CC1CCc2ccccc2N1)OCc1ccccc1]

TFA (27.3 mL, 354 mmol) was added to a solution of tert-butyl 2-(2-(benzyloxy)-2-oxoethyl)-3,4-dihydroquinoline-1(2H)-carboxylate (13.5 g, 35.4 mmol) in DCM (50 mL) at rt, stirred for 2 hrs. and concentrated under vacuum. The residue was extracted with ethyl acetate (200 ml) washed with saturated aq. NaHCO$_3$, water, brine, dried over anhydrous magnesium sulfate and concentrated under reduced pressure to afford benzyl 2-(1,2,3,4-tetrahydroquinolin-2-yl)acetate (10.0 g, 35.5 mmol, 100% yield). LC/MS (M+1): 282.1; ¹H-NMR (400 MHz, CDCl₃) δ ppm 7.37-7.31 (m, 1H), 7.27-7.18 (m, 2H), 7.19-7.07 (m, 3H), 7.06-6.78 (m, 2H), 6.61 (td, J=7.4, 0.9 Hz, 1H), 6.45 (d, J=7.9 Hz, 1H), 5.15 (s, 2H), 4.54-4.23 (m, 1H), 3.88-3.57 (m, 1H), 2.89-2.69 (m, 2H), 2.54 (m, 2H), 2.00-1.84 (m, 1H), 1.79-1.53 (m, 1H).

Step E: Benzyl 2-(6-(1,1,1,3,3,3-hexafluoro-2-hydroxypropan-2-yl)-1,2,3,4-tetrahydroquinolin-2-yl)acetate

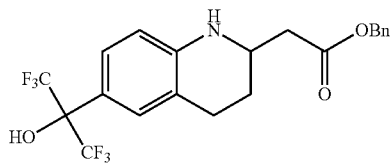 [SMILES: O=C(CC1CCc2cc(C(O)(C(F)(F)F)C(F)(F)F)ccc2N1)OCc1ccccc1]

A mixture of benzyl 2-(1,2,3,4-tetrahydroquinolin-2-yl)acetate (10.0 g, 35.5 mmol), 1,1,1,3,3,3-hexafluoropropan-2-one, 1.5H₂O (4.47 mL, 39.1 mmol) and 4 Å molecular sieve (4 g) in Toluene (40 mL) was heated in a sealed tube at 120° C. for 7 hrs. The mixture was cooled to rt, filtered through a celite pad and washed with ethyl acetate. The filtrate was concentrated under vacuum. The residue was purified by flash silica gel chromatography using a 20% mixture of ethyl acetate in hexane to afford benzyl 2-(6-(1,1,1,3,3,3-hexafluoro-2-hydroxypropan-2-yl)-1,2,3,4-tetrahydroquinolin-2-yl)acetate (10.5 g, 23.5 mmol, 66% yield). LC/MS(M+1): 448.3; ¹H-NMR (400 MHz, CDCl₃) δ ppm 7.55-7.31 (m, 5H), 7.27-7.09 (m, 2H), 6.69-6.02 (m, 2H), 5.28-5.03 (m, 2H), 4.71 (br. s., 1H), 3.93-3.56 (m, 1H), 3.01-2.67 (m, 2H), 2.66-2.41 (m, 2H), 1.98 (m, 1H), 1.80-1.67 (m, 1H).

Step F: Benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate

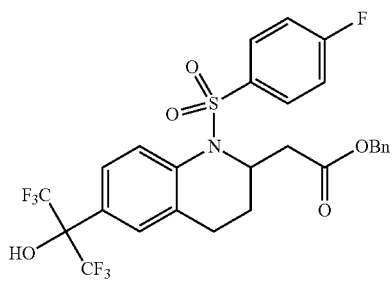 [SMILES: O=C(CC1CCc2cc(C(O)(C(F)(F)F)C(F)(F)F)ccc2N1S(=O)(=O)c1ccc(F)cc1)OCc1ccccc1]

A mixture of benzyl 2-(6-(1,1,1,3,3,3-hexafluoro-2-hydroxypropan-2-yl)-1,2,3,4-tetrahydroquinolin-2-yl)acetate (10.1 g, 22.6 mmol), 4-fluorobenzene-1-sulfonyl chloride (4.83 g, 24.8 mmol) and pyridine (7.30 mL, 90 mmol) in DCM (100 mL) was stirred at rt for 60 hrs. and concentrated under vacuum. The residue was diluted with ethyl acetate (300 ml), washed with 1N HCl (2×30 ml), water (30 ml), brine (30 ml), dried over anhydrous magnesium sulfate, concentrated under reduced pressure and purified by flash silica gel chromatography using a 10% mixture of ethyl acetate in hexane to afford benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (10.2 g, 16.8 mmol, 75% yield). LC/MS(M+1): 606.3; ¹H-NMR (400 MHz, CDCl₃) δ ppm 7.78 (d, J=8.8 Hz, 1H), 7.56 (d, J=8.6 Hz, 1H), 7.54-7.44 (m, 2H), 7.44-7.33 (m, 5H), 7.26 (s, 1H), 7.11-6.93 (m, 2H), 5.32-4.98 (m, 2H), 4.76-4.59 (m, 1H), 3.62 (br. s., 1H), 2.89 (dd, J=15.4, 5.5 Hz, 1H), 2.67-2.36 (m, 2H), 1.99-1.71 (m, 2H), 1.53-1.40 (m, 1H).

Step G: (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate & (S)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate

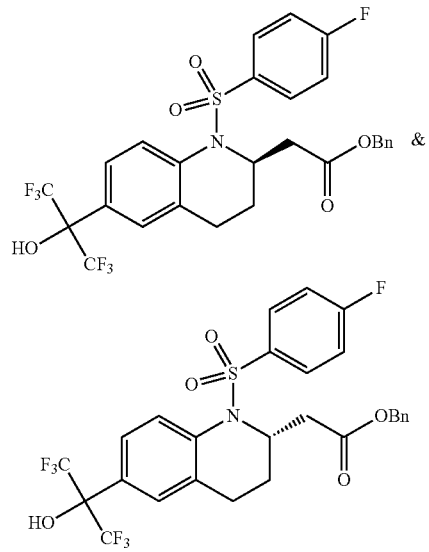

Racemic benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (10.2 g, 16.8 mmol) obtained above was separated into its homochiral components using a chiral Whelk-O1 (RR) column (46×25 cm, 5um), 25% MeOH in CO₂, 3 ml/min, 35° C., 100 bars to afford: (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (3.90 g) as the first eluent off the column. The product had an HPLC ret. time=3.53 min. on the chiral column; >98.5% ee. (S)-benzyl 2-(1-((4-fluorophenyl)sulfonyl)-6-(1,1,3,3,3-hexafluoro-2-hydroxypropan-2-yl)-1,2,3,4-tetrahydroquinolin-2-yl)acetate (3.90 g) as the second eluent off the column. The product had an HPLC ret. time=4.07 min. on the chiral column; 98.2% ee. The absolute stereochemistry of the second eluting enantiomer was determined to be (S) based on a single crystal X-ray of the corresponding acid (step H-2), from the anomalous dispersion signal using the Flack method.

Step H-1: (R)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (Intermediate 2)

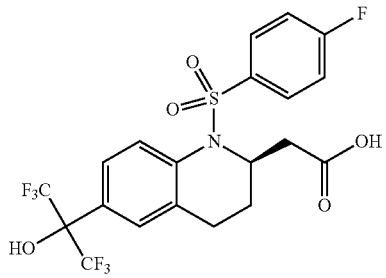 [SMILES: O=C(O)C[C@H]1CCc2cc(C(O)(C(F)(F)F)C(F)(F)F)ccc2N1S(=O)(=O)c1ccc(F)cc1]

A mixture of (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (0.088 g, 0.144 mmol) and 5% palladium on carbon (0.020 g, 0.009 mmol) in MeOH (5 mL) was stirred under a $H_2$ atmosphere at rt for 2 hrs and filtered. The filtrate was concentrated under vacuum to afford (R)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (0.074 g, 0.144 mmol, 100% yield). LC/MS(M+1): 516.2; $^1$H-NMR (400 MHz, CDCl$_3$) δ ppm 7.98-7.69 (m, 1H), 7.69-7.52 (m, 3H), 7.43 (s, 1H), 7.30-7.12 (m, 2H), 4.73-4.58 (m, 1H), 2.86-2.64 (m, 1H), 2.63-2.43 (m, 2H), 2.07-1.86 (m, 2H), 1.65-1.54 (m, 1H).

Step H-2 Preparation of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (Intermediate 1)

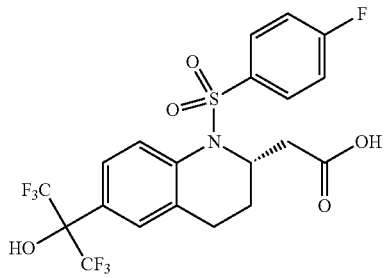 [SMILES: O=C(O)C[C@@H]1CCc2cc(C(O)(C(F)(F)F)C(F)(F)F)ccc2N1S(=O)(=O)c1ccc(F)cc1]

A mixture of (S)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (2.20 g, 3.63 mmol) and 5% palladium on carbon (0.387 g, 0.182 mmol) in MeOH (40 mL) was stirred under a $H_2$ atmosphere at rt for 4 hrs and filtered. The filtrate was concentrated under vacuum to afford (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (1.87 g, 3.63 mmol, 100% yield). LC/MS(M+1): 516.2; $^1$H-NMR (400 MHz, CDCl$_3$) δ ppm 7.98-7.69 (m, 1H), 7.69-7.52 (m, 3H), 7.43 (s, 1H), 7.30-7.12 (m, 2H), 4.73-4.58 (m, 1H), 2.86-2.64 (m, 1H), 2.63-2.43 (m, 2H), 2.07-1.86 (m, 2H), 1.65-1.54 (m, 1H).

Intermediate 3

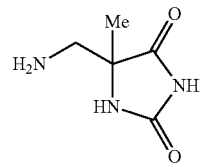

Step A: 1-(Dibenzylamino)propan-2-one

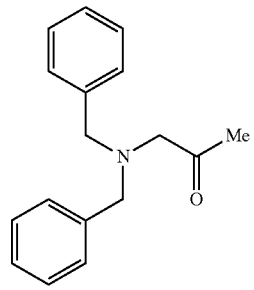 [SMILES: CC(=O)CN(Cc1ccccc1)Cc1ccccc1]

A mixture of dibenzylamine (650 mg, 3.29 mmol), 1-chloropropan-2-one (610 mg, 6.59 mmol) and TEA (0.551 mL, 3.95 mmol) in THF (5 mL) was stirred at rt for 15 hrs and filtered. The filtrate was diluted with ethyl acetate (80 ml), washed with saturated aq. NaHCO$_3$, water, brine, dried over anhydrous magnesium sulfate and concentrated under reduced pressure to afford 1-(dibenzylamino)propan-2-one (710 mg, 2.80 mmol, 85% yield). LC/MS(M+1): 254.1; $^1$H NMR (400 MHz, CD$_3$OD) δ ppm 8.94-8.42 (m, 10H), 5.00 (s, 4H), 4.57 (s, 2H), 3.50-3.34 (m, 3H).

Step B: 5-((Dibenzylamino)methyl)-5-methylimidazolidine-2,4-dione

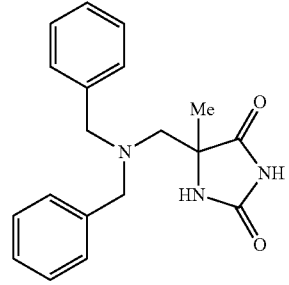 [SMILES: CC1(CN(Cc2ccccc2)Cc2ccccc2)NC(=O)NC1=O]

A mixture of 1-(dibenzylamino)propan-2-one (300 mg, 1.18 mmol), potassium cyanide (154 mg, 2.37 mmol) and ammonium carbonate (455 mg, 4.74 mmol) in ethanol (8 mL) and water (2 ml) was heated to 65° C. for 4 hrs. The mixture was cooled to rt and partitioned between ethyl acetate (80 ml) and water (10 mL). The ethyl acetate layer was washed with brine, dried over anhydrous magnesium sulfate, concentrated under reduced pressure and purified by flash silica gel chromatography using a 5% mixture of methanol in dichloromethane to afford 5-((dibenzylamino)

methyl)-5-methylimidazolidine-2,4-dione (150 mg, 0.46 mmol, 39% yield). LC/MS(M+1): 324.1; $^1$H NMR (400 MHz, CD$_3$OD) δ ppm 7.70-6.95 (m, 10H), 3.66 (s, 4H), 3.05 (m, 1H), 2.75 (m, 1H), 1.25 (s, 3H).

Step C:
5-(Aminomethyl)-5-methylimidazolidine-2,4-dione

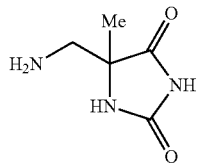

A mixture of 5-((dibenzylamino)methyl)-5-methylimidazolidine-2,4-dione (100 mg, 0.309 mmol) and 5% PALLADIUM ON CARBON (65.8 mg, 0.031 mmol) in EtOH (5 mL) was heated to 60° C. under a H$_2$ atmosphere at 55 Psi for 6 hrs and filtered. The filtrate was concentrated under reduced pressure to afford 5-(aminomethyl)-5-methylimidazolidine-2,4-dione (44 mg, 0.31 mmol, 99% yield). LC/MS (M+1): 143.9; $^1$H NMR (400 MHz, CD$_3$OD) δ ppm 2.90 (d, J=13.4 Hz, 1H), 2.72 (d, J=13.6 Hz, 1H), 1.34 (s, 3H).

Intermediate 4

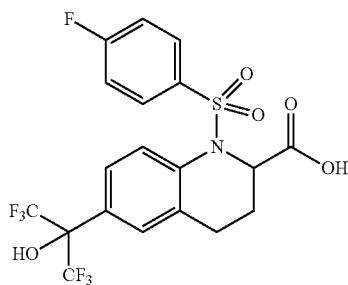 [SMILES: O=C(O)C1CCc2cc(C(O)(C(F)(F)F)C(F)(F)F)ccc2N1S(=O)(=O)c1ccc(F)cc1]

Step A: Methyl 6-(1,1,1,3,3,3-hexafluoro-2-hydroxypropan-2-yl)-1,2,3,4-tetrahydroquinoline-2-carboxylate

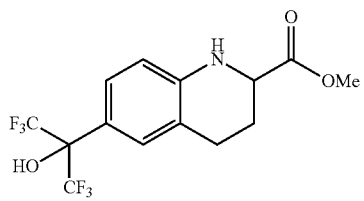 [SMILES: COC(=O)C1CCc2cc(C(O)(C(F)(F)F)C(F)(F)F)ccc2N1]

Methyl 1,2,3,4-tetrahydroquinoline-2-carboxylate (1 g, 5.23 mmol) and 1,1,1,3,3,3-hexafluoropropan-2-one, 1.5H$_2$O (1.211 g, 6.28 mmol) in Toluene (3 mL) were transferred to a pressure tube, and then molecular sieves (500 mg) was added. The pressure tube was sealed and heated at 120° C. for 12 h. The reaction mixture was filtered through a pad of Celite, washed with EtOAc (100 mL), dried (Na$_2$SO$_4$) and concentrated. The crude product was purified by silica gel chromatography, eluting with 10 to 30% ethyl acetate in hexane, to give the desired product as a light yellow solid (585 mg, 29% yield). The product had an HPLC ret. time=3.25 min. Column: (condition A); LC/MS M+1=358.1. $^1$H NMR (400 MHz, CHLOROFORM-d) δ 7.44 (d, J=8.1 Hz, 1H), 7.17 (dd, J=7.5, 1.3 Hz, 1H), 7.09-6.97 (m, 1H), 4.00 (dd, J=9.6, 4.5 Hz, 1H), 3.84 (s, 3H), 3.01-2.86 (m, 2H), 2.34 (dd, J=13.2, 5.3 Hz, 1H), 2.03-1.86 (m, 1H).

Step B: Methyl 1-((4-fluorophenyl)sulfonyl)-6-(1,1,1,3,3,3-hexafluoro-2-hydroxypropan-2-yl)-1,2,3,4-tetrahydroquinoline-2-carboxylate

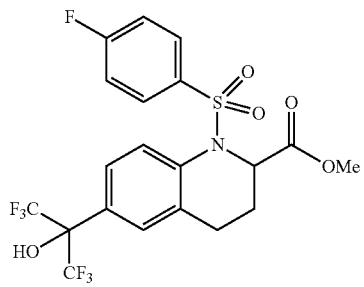 [SMILES: COC(=O)C1CCc2cc(C(O)(C(F)(F)F)C(F)(F)F)ccc2N1S(=O)(=O)c1ccc(F)cc1]

To a solution of methyl 6-(1,1,1,3,3,3-hexafluoro-2-hydroxypropan-2-yl)-1,2,3,4-tetrahydroquinoline-2-carboxylate (100 mg, 0.280 mmol) in CH$_2$Cl$_2$ (1 mL) was added pyridine (0.113 mL, 1.400 mmol) and 4-fluorobenzene-1-sulfonyl fluoride (100 mg, 0.560 mmol). The resulting mixture was stirred at rt for 12 h. EtOAc (10 mL) and Water (2 mL) were added, the reaction mixture was partitioned, the aqueous was extracted with EtOAc (10 mL). The combined organic phases were washed with water (5 mL), dried (Na$_2$SO$_4$) and concentrated. The crude product was purified by prep-HPLC to give the desired product as white powder (100 mg, 64.5% yield). The product had an HPLC ret. time=3.29 min.—Column: (condition A); LC/MS M+1=516.1. $^1$H NMR (400 MHz, CHLOROFORM-d) δ 7.82 (d, J=8.8 Hz, 1H), 7.73-7.64 (m, 2H), 7.54 (d, J=10.3 Hz, 1H), 7.36 (s, 1H), 7.11 (t, J=8.5 Hz, 2H), 5.01 (t, J=6.7 Hz, 1H), 3.76 (s, 3H), 2.69-2.55 (m, 1H), 2.26-2.13 (m, 2H), 2.13-1.98 (m, 1H).

Step C: 1-((4-fluorophenyl)sulfonyl-6-(1,1,1,3,3,3-hexafluoro-2-hydroxypropan-2-yl)-1,2,3,4-tetrahydroquinoline-2-carboxylic acid

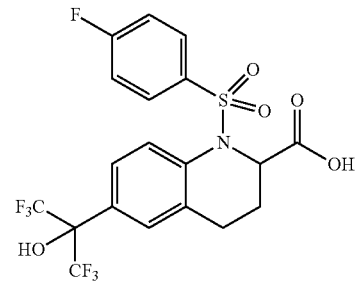 [SMILES: O=C(O)C1CCc2cc(C(O)(C(F)(F)F)C(F)(F)F)ccc2N1S(=O)(=O)c1ccc(F)cc1]

To a solution of methyl 1-((4-fluorophenyl)sulfonyl)-6-(1,1,1,3,3,3-hexafluoro-2-hydroxypropan-2-yl)-1,2,3,4-tetrahydroquinoline-2-carboxylate (50 mg, 0.097 mmol) in MeOH (1 mL) and Water (0.500 mL) was added lithium hydroxide (11.62 mg, 0.485 mmol). The resulting mixture was stirred at room temperature for 2 h. EtOAc (10 mL) was added, the reaction mixture was partitioned, the aqueous layer was extracted with EtOAc (10 mL). The combined organic phases were washed with water (5 mL), dried ($Na_2SO_4$) and concentrated. The crude product was purified by prep-HPLC to give the desired product as white solid (100 mg, 64.5% yield). The product had an HPLC ret. time=3.07 min.—Column: (condition A); LC/MS M+1=502.1. $^1$H NMR (400 MHz, METHANOL-$d_4$) δ 7.84 (d, J=8.8 Hz, 1H), 7.79-7.71 (m, 2H), 7.57 (d, J=9.0 Hz, 1H), 7.44 (s, 1H), 7.31-7.18 (m, 2H), 5.07 (t, J=6.8 Hz, 1H), 2.75-2.57 (m, 1H), 2.31-2.14 (m, 2H), 2.08-1.95 (m, 1H).

Intermediates 5 and 6

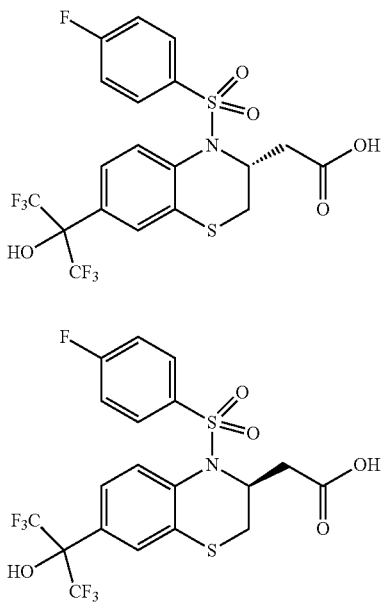

Step A: tert-butyl 3-oxo-2H-benzo[b][1,4]thiazine-4(3H)-carboxylate

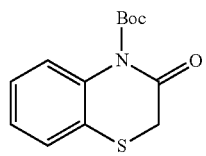 [SMILES: CC(C)(C)OC(=O)N1C(=O)CSc2ccccc21]

A mixture of 2H-benzo[b][1,4]thiazin-3(4H)-one (5 g, 30.3 mmol), $BOC_2O$ (7.03 mL, 30.3 mmol) and DMAP (0.370 g, 3.03 mmol) in acetonitrile (30 mL) was stirred at rt for 15 hrs. and concentrated under vacuum. The residue was extracted with ethyl acetate (200 mL), washed with 1 N HCl (2×10 mL), water (10 mL), brine (10 mL), dried with anhydrous $Na_2SO_4$ and concentrated to yield 8.0 g of the title compound as a light yellow solid. The product had an HPLC ret. time=2.90 min.—Column: (condition A); LC/MS M+1=266.2.

Step B: tert-butyl 3-(2-ethoxy-2-oxoethyl)-2H-benzo[b][1,4]thiazine-4(3H)-carboxylate

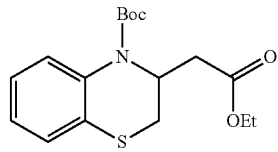 [SMILES: CCOC(=O)CC1CSc2ccccc2N1C(=O)OC(C)(C)C]

Under nitrogen, 1M lithium triethylborohydride (9.05 mL, 9.05 mmol) in THF was added dropwise to a solution of tert-butyl 3-oxo-2H-benzo[b][1,4]thiazine-4(3H)-carboxylate (2 g, 7.54 mmol) in anhydrous THF (30 mL) at −78° C. and stirred for 30 min. Then saturated $Na_2CO_3$ (15 ml) was added and the contents were warmed up to −15° C. 30% $H_2O_2$ (15 ml) was then added dropwise. The resulting mixture was warmed to rt over a period of 1 hr. The reaction mixture was filtered and the filtrate was extracted with ethyl acetate (2×70 ml). The combined organic layers were washed with water, brine, dried ($MgSO_4$) and concentrated. The crude tert-butyl 3-hydroxy-2H-benzo[b][1,4]thiazine-4(3H)-carboxylate (2 g, 7.48 mmol) was redissolved in THF (30 ml) and added to a mixture of sodium hydride (0.598 g, 14.96 mmol) and triethyl phosphonoacetate (2.99 ml, 14.96 mmol) in THF (30 ml) at 0° C. dropwise. The resultant mixture was warmed to rt over 1 hour and quenched with saturated $NH_4Cl$ (30 ml). It was extracted with ethyl acetate (2×80 ml). The combined organic layers were washed with water, brine, dried ($MgSO_4$) and concentrated and the residue was purified by silica gel chromatography, eluting with 10 to 50% ethyl acetate in hexane, to give the desired product as colorless oil (1.3 g, 65% yield). The product had an HPLC ret. time=3.43 min.—Column: (condition A); LC/MS M+1=338.1. $^1$H NMR (400 MHz, CHLOROFORM-d) δ 7.36 (dd, J=7.9, 1.3 Hz, 1H), 7.17-7.13 (m, 1H), 7.10-7.00 (m, 2H), 5.39-5.32 (m, 1H), 4.14 (q, J=7.0 Hz, 2H), 3.44 (dd, J=12.5, 4.6 Hz, 1H), 3.02 (dd, J=12.7, 3.6 Hz, 1H), 2.63-2.46 (m, 2H), 1.51 (s, 9H), 1.25 (t, J=7.2 Hz, 3H).

Step C Ethyl 2-(3,4-dihydro-2H-benzo[b][1,4]thiazin-3-yl)acetate

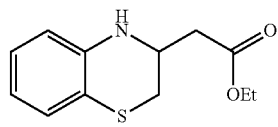 [SMILES: CCOC(=O)CC1CSc2ccccc2N1]

To a solution of tert-butyl 3-(2-ethoxy-2-oxoethyl)-2H-benzo[b][1,4]thiazine-4(3H)-carboxylate (900 mg, 2.67 mmol) in DCM (1 mL) was added TFA (1.027 mL, 13.34 mmol) at room temperature. The reaction mixture was stirred for 1 hour and concentrated. To the residue was added ethyl acetate (40 ml) and saturated aq. $NaHCO_3$ (10 ml) and the contents stirred for 5 min. The EtOAc layer was washed with saturated aq. $NaHCO_3$ (10 ml), water (10 ml), brine (10 ml), dried ($Na_2SO_4$) and concentrated to give the desired product which was used as such for the subsequent step without further purification. The product had an HPLC ret. time=2.08 min.—Column: (condition A); LC/MS M+1=238.1. ¹H NMR (400 MHz, CHLOROFORM-d) δ 7.01 (dd, J=7.7, 1.5 Hz, 1H), 6.95-6.88 (m, 1H), 6.63 (td, J=7.5, 1.1 Hz, 1H), 6.50 (dd, J=7.9, 1.1 Hz, 1H), 4.23-4.06 (m, 3H), 3.04 (dd, J=12.8, 3.1 Hz, 1H), 2.84 (dd, J=12.7, 5.8 Hz, 1H), 2.79-2.70 (m, 1H), 2.64-2.57 (m, 1H), 1.32-1.26 (m, 3H).

Step D Ethyl 2-(7-(1,1,1,3,3,3-hexafluoro-2-hydroxypropan-2-yl)-3,4-dihydro-2H-benzo[b][1,4]thiazin-3-yl)acetate

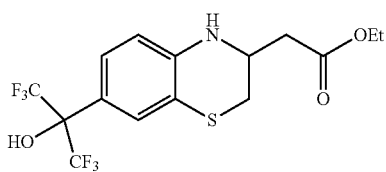 [SMILES: CCOC(=O)CC1CSc2cc(C(O)(C(F)(F)F)C(F)(F)F)ccc2N1]

The mixture of ethyl 2-(3,4-dihydro-2H-benzo[b][1,4]thiazin-3-yl)acetate (2.5 g, 10.53 mmol), 1,1,1,3,3,3-hexafluoropropan-2-one, 1.5H₂O (1.444 ml, 12.64 mmol) and pTsOH (0.401 g, 2.107 mmol) in a pressure tube was heated to 135° C. for 2 h. The reaction mixture was cooled to rt, extracted with EtOAc (100 mL), washed with water (3×30 mL), dried (Na₂SO₄) and concentrated. The crude product was purified by silica gel chromatography, eluting with 10 to 30% ethyl acetate in hexane, to give the desired product as brownish oil (1.99 g, 47% yield). The product had an HPLC ret. time=3.21 min.—Column: (condition A); LC/MS M+1=404.0. ¹H NMR (400 MHz, CHLOROFORM-d) δ 7.36 (d, J=1.8 Hz, 1H), 7.22 (d, J=8.8 Hz, 1H), 6.54 (d, J=8.6 Hz, 1H), 4.17-4.13 (m, 2H), 2.90-2.71 (m, 3H), 2.66-2.60 (m, 1H), 1.32-1.30 (m, J=2.4 Hz, 3H).

Step E Ethyl 2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetate

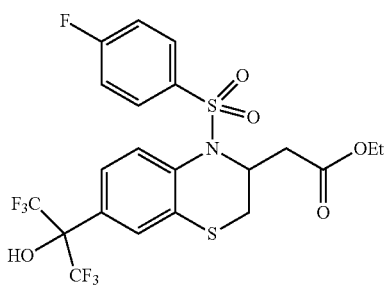 [SMILES: CCOC(=O)CC1CSc2cc(C(O)(C(F)(F)F)C(F)(F)F)ccc2N1S(=O)(=O)c1ccc(F)cc1]

To a solution of ethyl 2-(7-(1,1,1,3,3,3-hexafluoro-2-hydroxypropan-2-yl)-3,4-dihydro-2H-benzo[b][1,4]thiazin-3-yl)acetate (1.99 g, 4.93 mmol) in CH₂Cl₂ (10 mL) was added pyridine (1.197 mL, 14.80 mmol) and 4-fluorobenzene-1-sulfonyl chloride (1.440 g, 7.40 mmol). The resulting mixture was stirred at rt for 12 h. and partitioned between EtOAc (30 mL) and water (10 mL). The EtOAc layer was washed with water (10 mL), dried (Na₂SO₄) and concentrated. The crude product was purified by silica gel chromatography, eluting with 10 to 50% ethyl acetate in hexane, to give the desired product as brownish oil (1.20 g, 43% yield). The product had an HPLC ret. time=3.49 min.—Column: (condition A); LC/MS M+1=562.2. ¹H NMR (400 MHz, CHLOROFORM-d) δ 7.84-7.69 (m, 1H), 7.61-7.43 (m, 4H), 7.17-7.02 (m, 2H), 5.21-5.04 (m, 1H), 4.16 (qd, J=7.1, 1.1 Hz, 2H), 3.03 (dd, J=13.1, 5.0 Hz, 1H), 2.82 (dd, J=13.2, 4.6 Hz, 1H), 2.66-2.54 (m, 2H), 1.39-1.19 (m, 3H).

Step F: Preparation of 2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetic acid

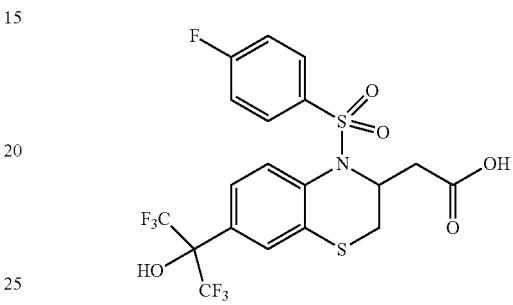

To a solution of ethyl 2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetate (1.2 g, 2.137 mmol) in MeOH (5 mL) and Water (5.00 mL) was added lithium hydroxide (0.256 g, 10.69 mmol). The resulting mixture was stirred at rt for 2 h. 1N HCl (10 mL) was added and the mixture extracted with EtOAc (3×10 mL). The combined organic layers were washed with brine, water, dried (Na₂SO₄) and concentrated. The crude product was purified by silica gel chromatography, eluting with 10 to 30% ethyl acetate in hexane, to give the desired product as a white solid (1.10 g, 93% yield). The product had an HPLC ret. time=3.21 min.—Column: (condition A); LC/MS M+1=534.0. ¹H NMR (400 MHz, CHLOROFORM-d) δ 7.78 (d, J=9.0 Hz, 1H), 7.60-7.53 (m, 2H), 7.53-7.46 (m, 2H), 7.11 (t, J=8.6 Hz, 2H), 5.18-5.06 (m, 1H), 3.09 (dd, J=13.3, 4.7 Hz, 1H), 2.84 (dd, J=13.1, 4.5 Hz, 1H), 2.76-2.65 (m, 2H).

Step G: Preparation of (S)-2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetic acid and (R)-2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetic acid Intermediate 5

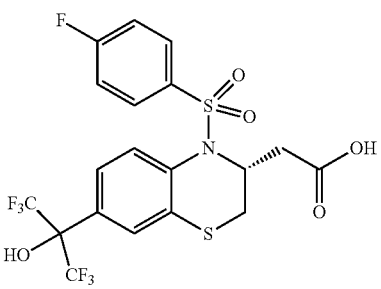

Intermediate 6

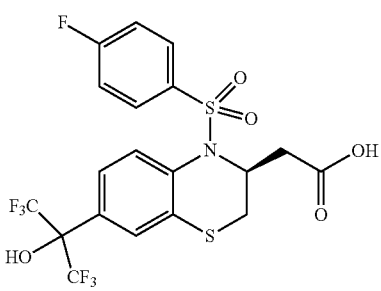

The racemic acid (498 mg) was resolved into its corresponding enantiomers using chiral supercritical fluid chromatography (SFC) with the following conditions: Column, (R, R)-Whelk-O1 (5×50 cm, 10 μm); Mobile phase, $CO_2$/IPA w 0.1% TFA (83/17), 100 Bar; temperature 28° C.; flow rate, 300 mL/min; detection UV (230 nm). Retention time: first enantiomer (220 mgs), 3.82 min (>98% ee); second eluting enantiomer (220 mgs), 4.60 min (>99% ee). A sample of the first eluting enantiomer was co-crystallized with (R)-(+)-α-methylbenzylamine. A single crystal X-ray structure determination of the crystalline material established the (R) absolute stereochemistry for the $1^{st}$ eluted isomer (intermediate 6).

Example 1

Step A: 5-(Aminomethyl)oxazolidin-2-one

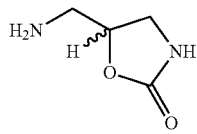

A solution of 5-(chloromethyl)oxazolidin-2-one (310 mg, 2.29 mmol) and sodium azide (297 mg, 4.57 mmol) in DMF (2 mL) was heated at 80° C. for 15 hrs. The reaction mixture was cooled to rt and DMF was removed under reduced pressure. To the residue was added MeOH (5 ml) and the contents stirred at rt for 1 hr and filtered. The filtrate was charged with 5% palladium on carbon (97 mg, 0.046 mmol) and stirred under an atmosphere of $H_2$ at 30 psi for 1 hr and filtered. Concentration of the filtrate provided 5-(Aminomethyl)oxazolidin-2-one (0.270 g) which was used as such for the next step without purification. $^1$H-NMR (400 MHz, $CD_3OD$) δ ppm 4.72-4.62 (m, 1H), 3.75-3.63 (m, 1H), 3.44-3.34 (m, 1H), 2.99-2.87 (m, 2H).

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((2-oxooxazolidin-5-yl)methyl)acetamide

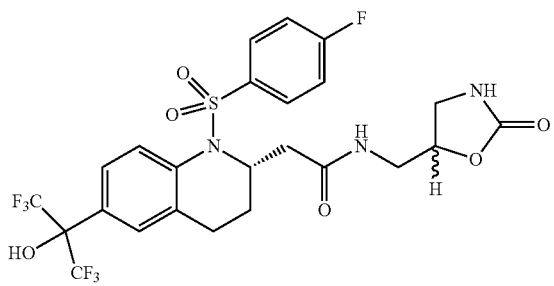 [SMILES: O=C(C[C@@H]1CCc2cc(C(O)(C(F)(F)F)C(F)(F)F)ccc2N1S(=O)(=O)c1ccc(F)cc1)NCC1CNC(=O)O1]

To a solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (intermediate 1, 18 mg, 0.035 mmol) in DMF (0.6 mL) was added DIEA (0.018 mL, 0.105 mmol), BOP (23.17 mg, 0.052 mmol) and 5-(aminomethyl)oxazolidin-2-one (6.09 mg, 0.052 mmol). The reaction mixture was stirred at rt for 1 h and purified by preparative HPLC (condition C) to yield the title compound (9.0 mgs, 42% yield) as a diastereomeric mixture.
LC/MS(M+1): 614.0; $^1$H-NMR (400 MHz, $CD_3OD$) δ ppm 7.81 (m, 1H), 7.68-7.55 (m, 3H), 7.44 (s, 1H), 7.30-7.05 (m, 2H), 4.80-4.66 (m, 1H), 3.66 (m, 1H), 3.55-3.37 (m, 4H), 2.69-2.50 (m, 2H), 2.39 (m, 1H), 2.11-2.01 (m, 1H), 1.82 (m, 1H), 1.61-1.44 (m, 1H).

Example 2

(S)—N-(2-amino-2-methylpropyl)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetamide

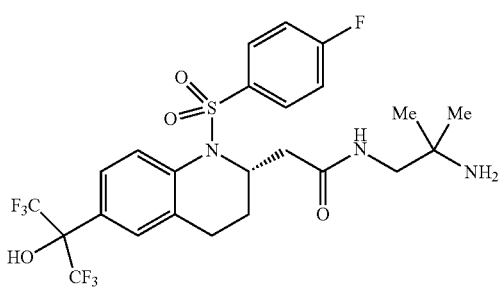 [SMILES: CC(C)(N)CNC(=O)C[C@@H]1CCc2cc(C(O)(C(F)(F)F)C(F)(F)F)ccc2N1S(=O)(=O)c1ccc(F)cc1]

Following similar procedure as in step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (18 mg, 0.035 mmol) was treated with 2-methylpropane-1,2-diamine (6.16 mg, 0.070 mmol) to provided the title compound (11.4 mg, 0.019 mmol, 56% yield). LC/MS(M+1): 586.2; $^1$H-NMR (400 MHz, 1 to 1 mixture of $CDCl_3$ and $CD_3OD$) δ ppm 7.82 (d, J=8.9 Hz, 2H), 7.70-7.60 (m, 1H), 7.61-7.50 (m, 2H), 7.45 (s, 1H), 7.14 (t, J=8.4 Hz, 2H), 4.92-4.77 (m, 1H), 3.43 (d, J=14.4 Hz, 1H), 3.15 (d, J=14.4 Hz, 1H), 2.66-2.48 (m, 2H), 2.40 (m, 1H), 2.07-1.99 (m, 1H), 1.80 (m, 1H), 1.56 (m, 1H), 1.43-1.24 (m, 6H).

Example 3

(S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-(2-hydroxy-2-methylpropyl)-N-methylacetamide

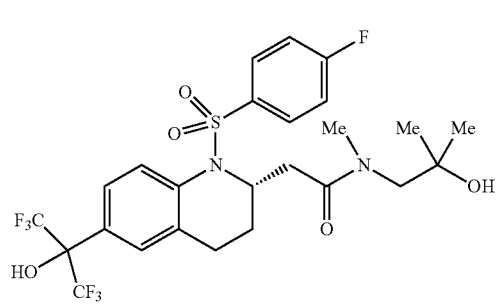 [SMILES: CN(CC(C)(C)O)C(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with 2-methyl-1-(methylamino)propan-2-ol (6.00 mg, 0.058 mmol) to provide the title compound (8.4 mg, 0.014 mmol, 48% yield). LC/MS(M+1): 601.2; $^1$H-NMR (400 MHz, 1 to 1 mixture of CDCl$_3$ and CD$_3$OD) δ ppm 7.79 (d, J=8.4 Hz, 1H), 7.65-7.58 (m, 1H), 7.57-7.49 (m, 2H), 7.42 (m, 1H), 7.21-7.01 (m, 2H), 3.55-3.42 (m, 1H), 3.39 (m, 1H), 3.13 (s, 3H), 3.05-2.93 (m, 2H), 2.62 (m, 1H), 2.57-2.40 (m, 1H), 2.11-2.01 (m, 1H), 1.90-1.75 (m, 1H), 1.63-1.49 (m, 1H), 1.24-1.16 (m, 6H).

Example 4

Tert-butyl ((R)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)carbamate

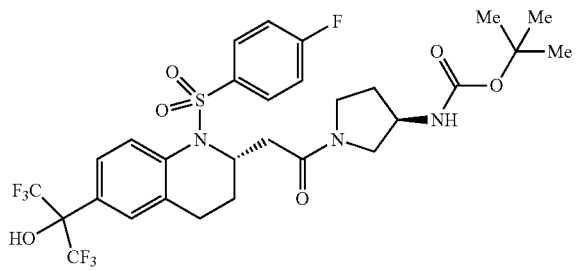 [SMILES: CC(C)(C)OC(=O)N[C@@H]1CCN(C(=O)C[C@@H]2CCc3cc(C(O)(C(F)(F)F)C(F)(F)F)ccc3N2S(=O)(=O)c2ccc(F)cc2)C1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (R)-tert-butyl pyrrolidin-3-ylcarbamate (8.67 mg, 0.047 mmol) to provide the title compound (15 mg, 0.022 mmol, 94% yield). LC/MS(M+1): 628.0; $^1$H-NMR (500 MHz, 1 to 1 mixture of CDCl$_3$ and CD$_3$OD) δ ppm 7.78 (dd, J=12.6, 8.7 Hz, 1H), 7.69-7.61 (m, 2H), 7.52 (dd, J=8.4, 5.0 Hz, 2H), 7.13 (td, J=8.5, 1.7 Hz, 2H), 4.73-4.56 (m, 1H), 4.24-4.02 (m, 1H), 3.72-3.59 (m, 1H), 3.59-3.46 (m, 2H), 3.30 (m, 1H), 2.86-2.72 (m, 1H), 2.57-2.42 (m, 2H), 2.25-2.05 (m, 2H), 1.95-1.78 (m, 2H), 1.63-1.52 (m, 1H), 1.44 (s, 9H).

Example 5

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-((R)-3-hydroxypyrrolidin-1-yl)ethanone

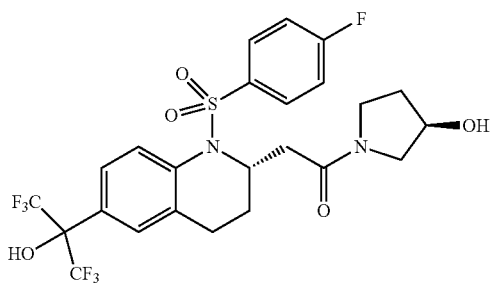 [SMILES: O=C(C[C@@H]1CCc2cc(C(O)(C(F)(F)F)C(F)(F)F)ccc2N1S(=O)(=O)c1ccc(F)cc1)N1CC[C@@H](O)C1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (R)-pyrrolidin-3-ol (4.06 mg, 0.047 mmol). to provide the title compound (8.4 mg, 0.014 mmol, 61% yield). LC/MS (M+1): 585.0; $^1$H-NMR (500 MHz, 1 to 1 mixture of CDCl$_3$ and CD$_3$OD) δ ppm 7.86-7.72 (m, 1H), 7.67-7.58 (m, 1H), 7.52 (dd, J=8.2, 5.2 Hz, 2H), 7.51-7.32 (m, 1H), 7.13 (t, J=8.7 Hz, 2H), 4.73-4.60 (m, 1H), 4.56-4.22 (m, 1H), 3.69-3.38 (m, 4H), 2.85-2.80 (m, 1H), 2.66-2.40 (m, 2H), 2.11-1.89 (m, 3H), 1.88-1.76 (m, 1H), 1.67-1.49 (m, 1H).

Example 6

Tert-butyl ((S)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)carbamate

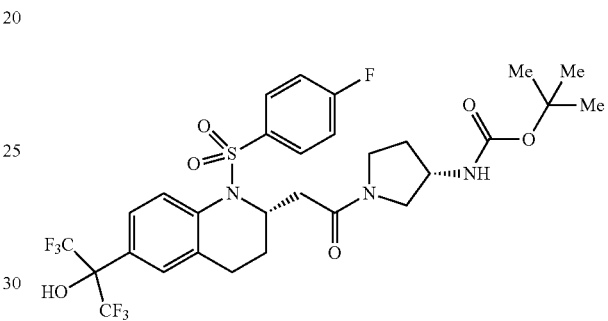

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (R)-tert-butyl 2-(pyrrolidin-3-yl)acetate (4.31 mg, 0.023 mmol) to provide the title compound (15 mg, 0.022 mmol, 94% yield). LC/MS(M+1): 628.0; $^1$H-NMR (500 MHz, 1 to 1 mixture of CDCl$_3$ and CD$_3$OD) δ ppm 7.76 (dd, J=8.9, 5.4 Hz, 1H), 7.68-7.58 (m, 1H), 7.55-7.47 (m, 2H), 7.42-7.33 (m, 1H), 7.13 (t, J=8.7 Hz, 2H), 4.72-4.57 (m, 1H), 4.20-3.99 (m, 1H), 3.79-3.43 (m, 4H), 2.84-2.71 (m, 1H), 2.56-2.36 (m, 2H), 2.25-2.04 (m, 2H), 1.99-1.73 (m, 2H), 1.64-1.53 (m, 1H), 1.53-1.35 (m, 9H).

Example 7

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-((S)-3-hydroxypyrrolidin-1-yl)ethanone

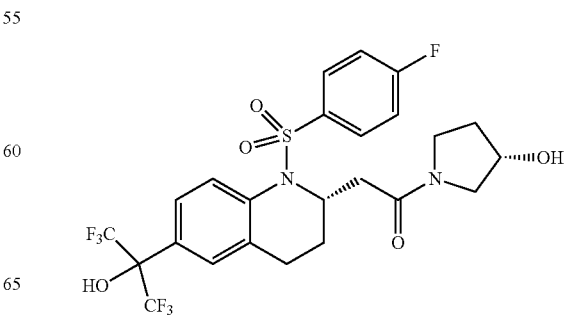

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (S)-pyrrolidin-3-ol (2.028 mg, 0.023 mmol) to provide the title compound (6.4 mg, 0.011 mmol, 47% yield). LC/MS (M+1): 585.0; $^1$H-NMR (500 MHz, 1 to 1 mixture of CDCl$_3$ and CD$_3$OD) δ ppm 7.76 (dd, J=8.7, 1.2 Hz, 1H), 7.70-7.60 (m, 1H), 7.52 (dd, J=8.7, 5.2 Hz, 2H), 7.42 (d, J=8.4 Hz, 1H), 7.13 (t, J=8.7 Hz, 2H), 4.74-4.60 (m, 1H), 4.54-4.20 (m, 1H), 3.69-3.43 (m, 4H), 2.88-2.75 (m, 1H), 2.66-2.26 (m, 3H), 2.17-1.95 (m, 2H), 1.91-1.69 (m, 1H), 1.65-1.41 (m, 1H).

Example 8

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((4-methyl-2,5-dioxoimidazolidin-4-yl)methyl)acetamide

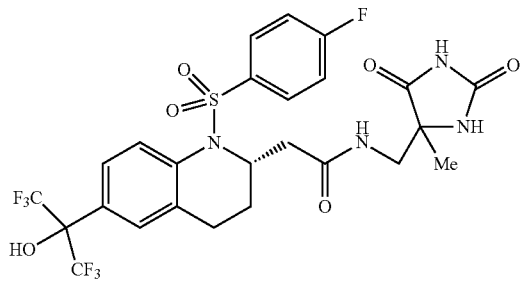 [SMILES: CC1(CNC(=O)C[C@@H]2CCc3cc(C(O)(C(F)(F)F)C(F)(F)F)ccc3N2S(=O)(=O)c2ccc(F)cc2)NC(=O)NC1=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (14 mg, 0.027 mmol) was treated with 5-(aminomethyl)-5-methylimidazolidine-2,4-dione (intermediate 3, 7.78 mg, 0.054 mmol) to provide the title compound (11.8 mg, 0.018 mmol, 68% yield) as a mixture of diastereomers. LC/MS(M+1): 641.0; $^1$H-NMR (500 MHz, DMSO-d$_6$) δ ppm 7.74 (d, J=5.0 Hz, 1H), 7.63 (m, 2H), 7.52 (d, J=8.9 Hz, 1H), 7.46-7.24 (m, 3H), 4.67 (m, 1H), 3.57-3.44 (m, 1H), 3.13-3.04 (m, 1H), 2.76-2.62 (m, 1H), 2.45-2.29 (m, 2H), 2.17 (m, 1H), 1.62-1.42 (m, 2H), 1.26-1.16 (m, 3H).

Example 9

(S)-8-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-1,3,8-triazaspiro[4.5]decane-2,4-dione

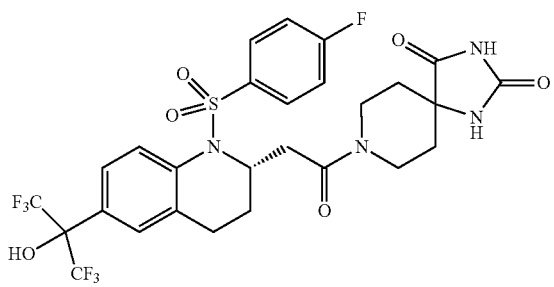 [SMILES: O=C1NC(=O)C2(CCN(C(=O)C[C@@H]3CCc4cc(C(O)(C(F)(F)F)C(F)(F)F)ccc4N3S(=O)(=O)c3ccc(F)cc3)CC2)N1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (14 mg, 0.027 mmol) was treated with 1,3,8-triazaspiro[4.5]decane-2,4-dione (15.39 mg, 0.054 mmol) to provide the title compound (8.1 mg, 0.012 mmol, 45% yield). LC/MS(M+1): 667.0; $^1$H-NMR (500 MHz, 1 to 1 mixture of CDCl$_3$ and CD$_3$OD) δ ppm 7.79 (dd, J=8.9, 6.4 Hz, 1H), 7.66-7.61 (m, 1H), 7.50 (dt, J=8.3, 4.5 Hz, 2H), 7.43 (s, 1H), 7.13 (t, J=8.4 Hz, 2H), 4.65-4.55 (m, 1H), 4.27-4.14 (m, 1H), 4.01-3.87 (m, 1H), 3.57-3.42 (m, 2H), 2.96 (m, 2H), 2.64-2.41 (m, 2H), 2.18-1.90 (m, 3H), 1.86-1.67 (m, 2H), 1.66-1.42 (m, 1H).

Example 10

7-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-1,3,7-triazaspiro[4.4]nonane-2,4-dione

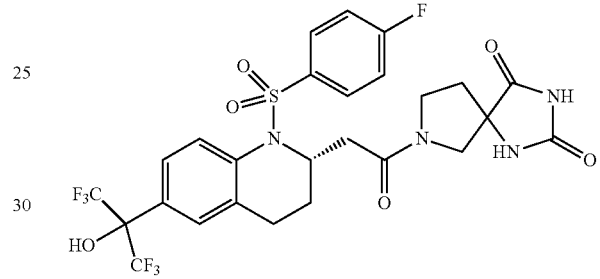

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (11 mg, 0.021 mmol) was treated with 1,3,7-triazaspiro[4.4]nonane-2,4-dione (6.62 mg, 0.043 mmol) to provide the title compound (6.6 mg, 0.098 mmol, 46% yield). LC/MS(M+1): 653.0; $^1$H-NMR (500 MHz, 1 to 1 mixture of CDCl$_3$ and CD$_3$OD) δ ppm 7.87-7.70 (m, 1H), 7.65-7.60 (m, 1H), 7.59-7.49 (m, 2H), 7.42 (br. s., 1H), 7.19-6.93 (m, 2H), 4.71-4.57 (m, 1H), 3.94-3.54 (m, 4H), 2.92-2.82 (m, 1H), 2.60-2.32 (m, 3H), 2.24-2.01 (m, 2H), 1.90-1.74 (m, 1H), 1.63-1.41 (m, 1H).

Example 11

1-((R)-3-aminopyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

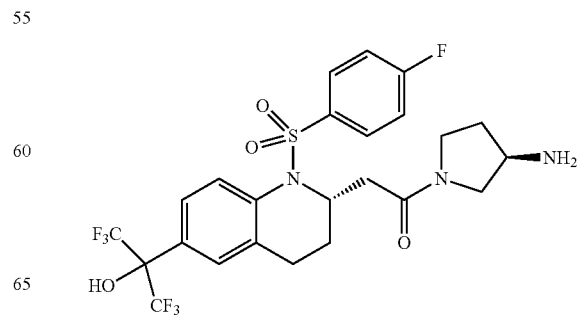

To a solution of tert-butyl ((R)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)carbamate (Example 4, 10 mg, 0.015 mmol) in DCM (0.6 mL) was added TFA (0.2 ml, 2.60 mmol). The resulting mixture was stirred at rt for 1 h, concentrated and purified by preparative HPLC (condition C) to provide the title compound (4.6 mg, 0.079 mmol, 54% yield). LC/MS(M+1): 584.0; ¹H-NMR (500 MHz, 1 to 1 mixture of CDCl₃ and CD₃OD) δ ppm 7.78 (dd, J=8.7, 3.7 Hz, 1H), 7.68-7.61 (m, 1H), 7.61-7.47 (m, 2H), 7.42 (s, 1H), 7.12 (t, J=8.7 Hz, 2H), 4.70-4.45 (m, 1H), 3.75-3.45 (m, 4H), 3.30-3.21 (m, 1H), 2.88-2.76 (m, 1H), 2.66-2.34 (m, 2H), 2.32-2.16 (m, 1H), 2.16-2.05 (m, 1H), 1.99-1.87 (m, 1H), 1.87-1.70 (m, 1H), 1.61-1.48 (m, 1H).

Example 12

1-((S)-3-aminopyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

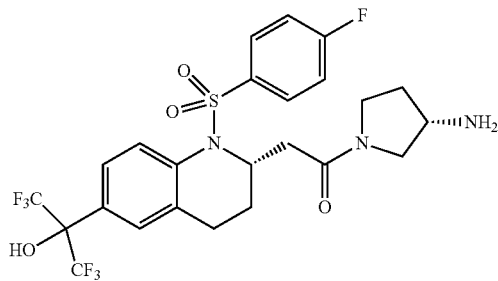 [SMILES: N[C@H]1CCN(C(=O)C[C@@H]2CCc3cc(C(O)(C(F)(F)F)C(F)(F)F)ccc3N2S(=O)(=O)c2ccc(F)cc2)C1]

To a solution of tert-butyl ((S)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)carbamate (Example 6, 10 mg, 0.015 mmol) in DCM (0.6 mL) was added TFA (0.2 ml, 2.60 mmol). The resulting mixture was stirred at rt for 1 h, concentrated and purified by preparative HPLC (condition C) to provide the title compound (4.6 mg, 0.079 mmol, 54% yield). LC/MS(M+1): 584.0; ¹H-NMR (500 MHz, 1 to 1 mixture of CDCl₃ and CD₃OD) δ ppm 7.88-7.74 (m, 1H), 7.72-7.63 (m, 1H), 7.60-7.46 (m, 2H), 7.42 (d, J=6.4 Hz, 1H), 7.20-7.00 (m, 2H), 4.69-4.50 (m, 1H), 3.73-3.58 (m, 3H), 3.56-3.41 (m, 1H), 3.32-3.26 (m, 1H), 2.84 (m, 1H), 2.61-2.42 (m, 2H), 2.32-2.04 (m, 2H), 1.95-1.69 (m, 2H), 1.60-1.45 (m, 1H).

Example 13

N-((2,5-dioxo-4-(tetrahydrofuran-2-yl)imidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

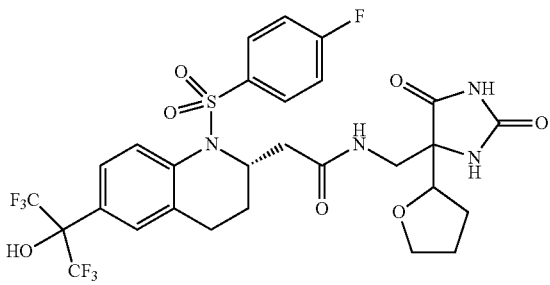 [SMILES: O=C(C[C@@H]1CCc2cc(C(O)(C(F)(F)F)C(F)(F)F)ccc2N1S(=O)(=O)c1ccc(F)cc1)NCC1(C2CCCO2)NC(=O)NC1=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with 5-(aminomethyl)-5-(tetrahydrofuran-2-yl)imidazolidine-2,4-dione (11.60 mg, 0.058 mmol) to provide the title compound (7.6 mg, 0.011 mmol, 38% yield) as a mixture of diastereomers. LC/MS(M+1): 697.1; ¹H-NMR (500 MHz, DMSO-d₆) δ ppm 8.93-8.69 (m, 1H), 8.06 (s, 1H), 7.96 (s, 1H), 7.91-7.77 (m, 1H), 7.79-7.48 (m, 3H), 7.49-7.33 (m, 2H), 4.86-4.57 (m, 1H), 4.00-3.82 (m, 1H), 3.78-3.45 (m, 3H), 3.23-2.96 (m, 2H), 2.75-2.57 (m, 2H), 2.47-2.10 (m, 2H), 2.00-1.70 (m, 3H), 1.66-1.43 (m, 2H).

Example 14

N—((S)-2-fluoro-3-hydroxy-3-methylbutyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

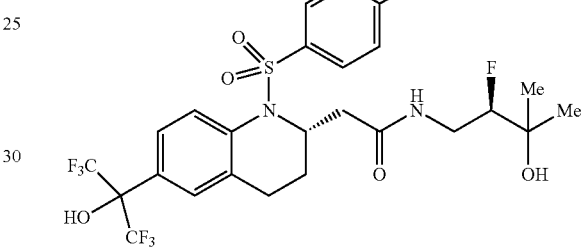

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (S)-4-amino-3-fluoro-2-methylbutan-2-ol (5.64 mg, 0.047 mmol) to provided the title compound (8.4 mg, 0.014 mmol, 58% yield). LC/MS(M+1): 619.0; ¹H-NMR (500 MHz, 1 to 1 mixture of CDCl₃ and CD₃OD) δ ppm 7.77 (d, J=8.9 Hz, 1H), 7.60-7.51 (m, 3H), 7.43 (s, 1H), 7.13 (t, J=8.4 Hz, 2H), 4.41-4.25 (m, 1H), 4.26-4.12 (m, 1H), 3.84-3.66 (m, 1H), 3.27-3.13 (m, 1H), 2.68 (m, 1H), 2.63-2.51 (m, 1H), 2.40 (m, 1H), 2.03-1.76 (m, 2H), 1.66-1.54 (m, 1H), 1.30-1.15 (m, 6H).

Example 15

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((4-methyl-2-oxooxazolidin-4-yl)methyl)acetamide

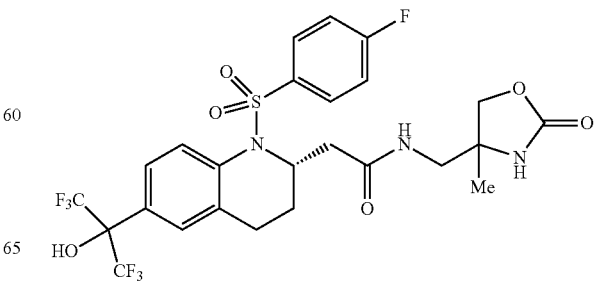

Step A: 4-(Hydroxymethyl)-4-methyloxazolidin-2-one

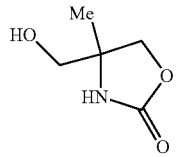

A solution of 2-amino-2-methylpropane-1,3-diol (3.32 g, 31.6 mmol) and diethyl carbonate (9.80 g, 83 mmol) was heated to 140° C. with a dean-stark trap for 6 hrs. The mixture was cooled down to rt and left at rt overnight. A white solid precipitated out. It was filtered and washed with small amount of cold methanol. The white solid was dried under vacuum to provide 4-(Hydroxymethyl)-4-methyloxazolidin-2-one (2.60 g, 19.8 mmol, 63% yield). LC/MS(M+1): 132.0; $^1$H NMR (400 MHz, CD$_3$OD) δ ppm 4.34 (d, J=8.6 Hz, 1H), 4.02 (d, J=8.6 Hz, 1H), 3.52-3.37 (m, 2H), 1.28 (s, 3H).

Step B: 4-(aminomethyl)-4-methyloxazolidin-2-one

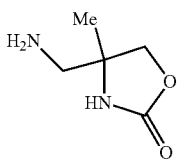

Ms-Cl (0.193 mL, 2.471 mmol) was added dropwise to the mixture of 4-(hydroxymethyl)-4-methyloxazolidin-2-one (270 mg, 2.059 mmol) and TEA (0.574 mL, 4.12 mmol) in THF (4 mL) at rt and stirred for 1 hr. It was quenched with saturated aq. NaHCO$_3$ (2 ml) and diluted with ethyl acetate (100 ml). The EtOAc layer was washed with water, brine, dried (MgSO$_4$) and concentrated. The residue was dissolved in DMF (2 ml) and sodium azide (402 mg, 6.18 mmol) was added at rt. The resultant mixture was heated to 80° C. for 15 hrs. It was cooled to rt, extracted with ethyl acetate (60 ml), washed with water, brine, dried (MgSO$_4$) and concentrated. The residue was dissolved in MeOH (5 ml) and 5% PALLADIUM ON CARBON (21.91 mg, 0.206 mmol) was added. The resultant mixture was stirred under H$_2$ at 24 psi for 1 hr and filtered. The filtrate was concentrated under vacuum to afford 4-(aminomethyl)-4-methyloxazolidin-2-one as crude material (201 mg) which was used as such for the subsequent step without further purification. LC/MS(M+1): 131.9; $^1$H NMR (400 MHz, CD$_3$OD) δ ppm 4.32 (d, J=8.8 Hz, 1H), 4.04 (d, J=8.8 Hz, 1H), 2.74-2.55 (m, 2H), 1.29 (s, 3H).

Step C: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((4-methyl-2-oxooxazolidin-4-yl)methyl)acetamide

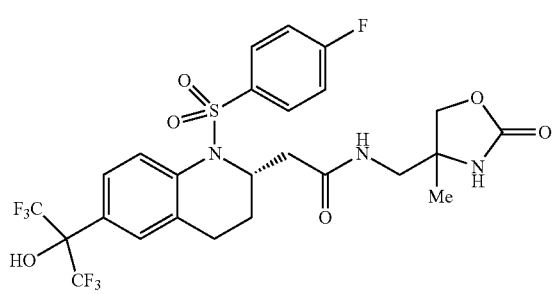 [SMILES: CC1(CNC(=O)C[C@@H]2CCc3cc(C(O)(C(F)(F)F)C(F)(F)F)ccc3N2S(=O)(=O)c2ccc(F)cc2)COC(=O)N1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 4-(aminomethyl)-4-methyloxazolidin-2-one (6.06 mg, 0.047 mmol) to provide the title compound (7.6 mg, 0.012 mmol, 52% yield). LC/MS(M+1): 628.0; $^1$H-NMR (500 MHz, 1 to 1 mixture of CDCl$_3$ and CD$_3$OD) δ ppm 7.91-7.75 (m, 1H), 7.67-7.61 (m, 1H), 7.58-7.48 (m, 2H), 7.43 (s, 1H), 7.13 (t, J=8.7 Hz, 2H), 4.84-4.74 (m, 1H), 4.41-4.22 (m, 1H), 4.03 (m, 1H), 3.54-3.39 (m, 1H), 3.23 (m, 1H), 2.76-2.61 (m, 1H), 2.61-2.51 (m, 1H), 2.43-2.35 (m, 1H), 2.10-1.94 (m, 1H), 1.92-1.75 (m, 1H), 1.62-1.53 (m, 1H), 1.35 (d, J=6.9 Hz, 3H).

Example 16

(S)—N-(2-acetamido-2-methylpropyl)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetamide

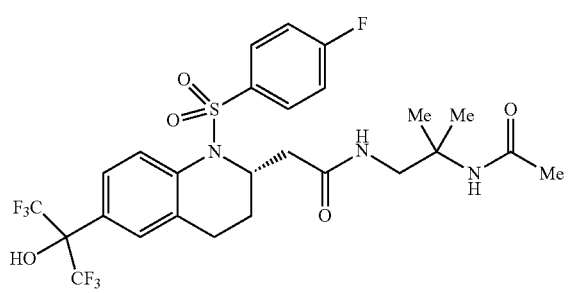 [SMILES: CC(=O)NC(C)(C)CNC(=O)C[C@@H]1CCc2cc(C(O)(C(F)(F)F)C(F)(F)F)ccc2N1S(=O)(=O)c1ccc(F)cc1]

To a solution of (S)—N-(2-amino-2-methylpropyl)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetamide (Example 2, 8 mg, 0.014 mmol) in DCM (1 mL) was added TEA (5.71 µl, 0.041 mmol) and acetic anhydride (2.58 µl, 0.027 mmol). The resulting mixture was stirred at rt for 1 h and concentrated. The residue was purified by preparative HPLC (condition C) to provide the title compound (8.0 mg, 0.013 mmol, 93% yield).

LC/MS(M+1): 628.0; $^1$H-NMR (500 MHz, 1 to DMSO-d$_6$) δ ppm 8.79 (br. s., 1H), 7.92 (t, J=6.2 Hz, 1H), 7.69 (d, J=8.9 Hz, 1H), 7.67-7.59 (m, 2H), 7.53 (d, J=8.9 Hz, 1H), 7.46-7.34 (m, 3H), 4.89-4.64 (m, 1H), 3.29-3.08 (m, 2H), 2.73-2.63 (m, 1H), 2.42-2.29 (m, 2H), 2.19 (m, 1H), 1.74 (s, 3H), 1.70-1.60 (m, 1H), 1.60-1.50 (m, 1H), 1.25-1.07 (m, 6H).

Example 17

(3R,4R)-benzyl 4-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)-3-hydroxy-3-methylpyrrolidine-1-carboxylate

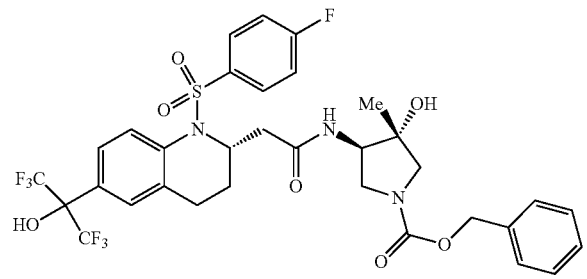 [SMILES: C[C@@]1(O)CN(C(=O)OCc2ccccc2)C[C@H]1NC(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (50 mg, 0.097 mmol) was treated with (3R,4R)-benzyl 4-amino-3-hydroxy-3-methylpyrrolidine-1-carboxylate (29.1 mg, 0.116 mmol) to provide the title compound (60 mg, 0.072 mmol, 74% yield). LC/MS(M+1): 748.1; $^1$H-NMR (400 MHz, CD$_3$OD) δ ppm 7.75 (m, 1H), 7.67-7.48 (m, 3H), 7.48-7.27 (m, 6H), 7.20 (m, 2H), 5.24-5.04 (m, 2H), 4.25 (m, 1H), 3.86 (m, 1H), 3.45-3.34 (m, 2H), 2.96-2.90 (m, 1H), 2.71-2.50 (m, 2H), 2.41-2.36 (m, 1H), 2.08 (m, 1H), 1.86 (m, 2H), 1.66-1.51 (m, 1H), 1.25 (d, J=7.5 Hz, 3H).

Example 18

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((3R,4R)-4-hydroxy-4-methylpyrrolidin-3-yl)acetamide

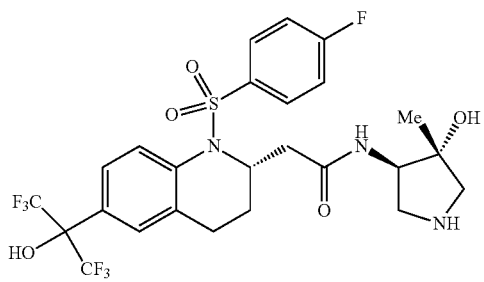 [SMILES: C[C@@]1(O)CNC[C@H]1NC(=O)C[C@@H]1CCc2cc(C(O)(C(F)(F)F)C(F)(F)F)ccc2N1S(=O)(=O)c1ccc(F)cc1]

A solution of (3R,4R)-benzyl 4-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)-3-hydroxy-3-methylpyrrolidine-1-carboxylate (Example 17, 58 mg, 0.078 mmol) in MeOH (5 mL) was added 20% palladium hydroxide on carbon (10.89 mg, 0.016 mmol) under a nitrogen atmosphere and the contents were hydrogenated at atmospheric pressure at rt for 2 hrs. The reaction mixture was filtered and the filtrate concentrated under reduced pressure to provide the title compound (43 mg, 0.070 mmol, 90% yield). LC/MS(M+1): 614.0; $^1$H-NMR (500 MHz, 1 to 1 mixture of CDCl$_3$ and CD$_3$OD) δ ppm 7.79 (d, J=8.4 Hz, 1H), 7.66-7.61 (m, 1H), 7.58-7.49 (m, 2H), 7.43 (s, 1H), 7.12 (t, J=8.4 Hz, 2H), 4.78 (t, J=6.7 Hz, 1H), 4.27 (d, J=5.4 Hz, 1H), 3.72 (m, 1H), 3.17-2.97 (m, 4H), 2.65 (m, 1H), 2.59-2.35 (m, 1H), 1.97-1.82 (m, 2H), 1.55 (m, 1H), 1.31 (s, 3H).

Example 19

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((3R,4R)-4-hydroxy-1,4-dimethylpyrrolidin-3-yl)acetamide

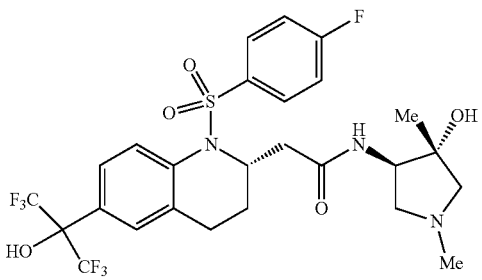 [SMILES: CN1C[C@@H](NC(=O)C[C@@H]2CCc3cc(C(O)(C(F)(F)F)C(F)(F)F)ccc3N2S(=O)(=O)c2ccc(F)cc2)[C@](C)(O)C1]

Sodium triacetoxyborohydride (10.36 mg, 0.049 mmol) was added to the mixture of 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((3R,4R)-4-hydroxy-4-methylpyrrolidin-3-yl)acetamide (Example 18, 10 mg, 0.016 mmol) and 30% aqueous formaldehyde (4.49 µl, 0.049 mmol) in DCE (1 mL) at rt and stirred for 1 hr. The mixture was quenched with saturated NH$_4$Cl (1 ml), extracted with ethyl acetate (60 ml), washed with water, brine, dried (MgSO$_4$) and concentrated by vacuum. The residue was purified by preparative HPLC (condition C) to provide the title compound (6.2 mg, 0.010 mmol, 61% yield). LC/MS (M+1): 628.1; $^1$H-NMR (500 MHz, 1 to 1 mixture of CDCl$_3$ and CD$_3$OD) δ ppm 7.79 (d, J=8.9 Hz, 1H), 7.68-7.61 (m, 1H), 7.57-7.48 (m, 2H), 7.43 (s, 1H), 7.12 (t, J=8.4 Hz, 2H), 4.92-4.74 (m, 1H), 4.38-4.20 (m, 1H), 3.76 (s, 3H), 3.54-3.37 (m, 1H), 3.02-2.84 (m, 3H), 2.74-2.51 (m, 2H), 2.48-2.29 (m, 1H), 2.08-1.78 (m, 2H), 1.64-1.51 (m, 1H), 1.29 (s, 3H).

Example 20

N-((3R,4R)-1-acetyl-4-hydroxy-4-methylpyrrolidin-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

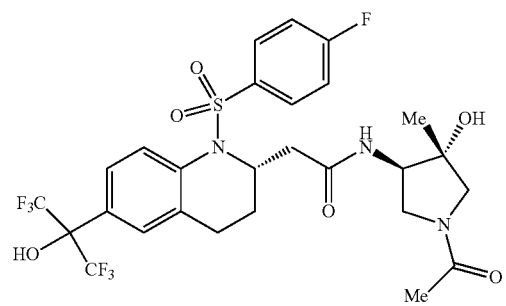 [SMILES: CC(=O)N1C[C@@H](NC(=O)C[C@@H]2CCc3cc(C(O)(C(F)(F)F)C(F)(F)F)ccc3N2S(=O)(=O)c2ccc(F)cc2)[C@](C)(O)C1]

Acetic anhydride (2.307 μl, 0.024 mmol) was added to the mixture of 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((3R,4R)-4-hydroxy-4-methylpyrrolidin-3-yl)acetamide (Example 18, 10 mg, 0.016 mmol) and TEA (6.82 μl, 0.049 mmol) in DCM (1 mL) at rt and stirred for 1 hr. It was quenched with MeOH (1 ml) and concentrated under vacuum. The residue was purified by preparative HPLC (condition C) to provide the title compound (6.6 mg, 0.0094 mmol, 57% yield). LC/MS(M+1): 656.0; $^1$H-NMR (500 MHz, 1 to 1 mixture of CDCl$_3$ and CD$_3$OD) δ ppm 7.78 (m, 1H), 7.66-7.61 (m, 1H), 7.59-7.48 (m, 2H), 7.44 (s, 1H), 7.23-7.00 (m, 2H), 4.86-4.76 (m, 1H), 4.40-4.22 (m, 1H), 4.03 (m, 1H), 3.86 (m, 1H), 3.57-3.38 (m, 2H), 2.66 (m, 1H), 2.59-2.48 (m, 1H), 2.39 (m, 1H), 2.14-1.96 (m, 4H), 1.85 (m, 1H), 1.56 (m, 1H), 1.27 (s, 3H).

Example 21

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((5-methyl-2-oxooxazolidin-5-yl)methyl)acetamide

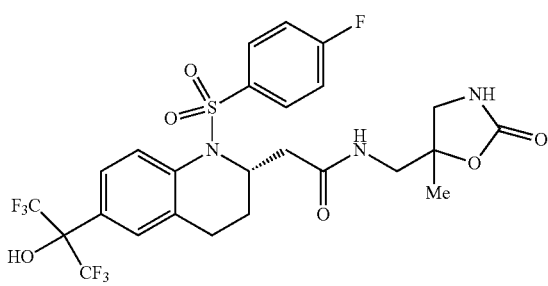 [SMILES: CC1(CNC(=O)C[C@@H]2CCc3cc(C(O)(C(F)(F)F)C(F)(F)F)ccc3N2S(=O)(=O)c2ccc(F)cc2)CNC(=O)O1]

Step A: 5-(aminomethyl)-5-methyloxazolidin-2-one

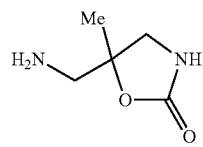

A solution of 2-(chloromethyl)-2-methyloxirane (150 mg, 1.41 mmol) and potassium cyanate (343 mg, 4.22 mmol) in water (3 ml) was heated to 100° C. for 15 hrs. The mixture was cooled to rt, and partitioned between DCM (40 ml) and brine (10 ml). The DCM layer is separated, dried (MgSO$_4$) and concentrated under reduced pressure. The residue was dissolved in DMF (2 mL) and sodium azide (275 mg, 4.22 mmol) was added and the resulting mixture was heated at 90° C. for 15 hrs, cooled to rt extracted with ethyl acetate (60 ml), washed with water, brine, dried (MgSO$_4$) and concentrated under vacuum. The residue was dissolved in MeOH (5 ml) and 5% palladium on carbon (59.9 mg, 0.028 mmol) was added and the contents hydrogenated at 24 psi for 1 hr and filtered. The filtrate was concentrated under vacuum to provide 5-(aminomethyl)-5-methyloxazolidin-2-one which was used as such for the next step without purification.

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((5-methyl-2-oxooxazolidin-5-yl)methyl)acetamide

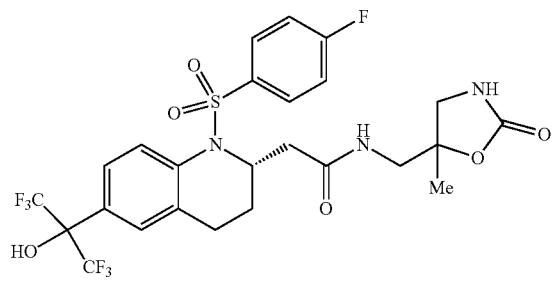 [SMILES: CC1(CNC(=O)C[C@@H]2CCc3cc(C(O)(C(F)(F)F)C(F)(F)F)ccc3N2S(=O)(=O)c2ccc(F)cc2)CNC(=O)O1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 5-(aminomethyl)-5-methyloxazolidin-2-one (6.06 mg, 0.047 mmol) to provide the title compound (7.0 mg, 0.011 mmol, 48% yield) as a mixture of diastereomers.

LC/MS(M+1): 628.0; $^1$H-NMR (500 MHz, 1 to 1 mixture of CDCl$_3$ and CD$_3$OD) δ ppm 7.82 (m, 1H), 7.68-7.62 (m, 1H), 7.57-7.49 (m, 2H), 7.44 (s, 1H), 7.12 (t, J=8.2 Hz, 2H), 4.91-4.76 (m, 1H), 3.67-3.57 (m, 1H), 3.56-3.38 (m, 2H), 3.31-3.24 (m, 2H), 2.72-2.51 (m, 1H), 2.45-2.27 (m, 1H), 2.14-2.03 (m, 1H), 1.84-1.73 (m, 1H), 1.64-1.49 (m, 1H), 1.52-1.42 (m, 3H).

Example 22

N-((3R,4R)-4-(fluoromethyl)pyrrolidin-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

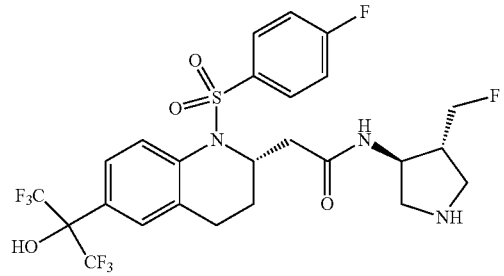 [SMILES: O=C(C[C@@H]1CCc2cc(C(O)(C(F)(F)F)C(F)(F)F)ccc2N1S(=O)(=O)c1ccc(F)cc1)N[C@@H]1CNC[C@H]1CF]

Step A: (3R,4R)-benzyl 3-(fluoromethyl)-4-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)pyrrolidine-1-carboxylate

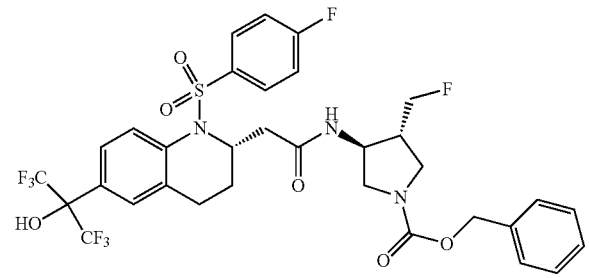 [SMILES: O=C(C[C@@H]1CCc2cc(C(O)(C(F)(F)F)C(F)(F)F)ccc2N1S(=O)(=O)c1ccc(F)cc1)N[C@@H]1CN(C(=O)OCc2ccccc2)C[C@H]1CF]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (20 mg, 0.039 mmol) was treated with (3R,4R)-benzyl 3-amino-4-(fluoromethyl)pyrrolidine-1-carboxylate (28.4 mg, 0.078 mmol) to provide (3R,4R)-benzyl 3-(fluoromethyl)-4-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)pyrrolidine-1-carboxylate (20 mg, 0.027 mmol, 69% yield). LC/MS(M+1): 750.1; $^1$H-NMR (400 MHz, CD$_3$OD) δ ppm 7.90-7.72 (m, 2H), 7.71-7.52 (m, 3H), 7.48-7.25 (m, 5H), 7.17 (t, J=8.7 Hz, 2H), 5.12 (s, 2H), 4.73-4.35 (m, 3H), 3.79-3.57 (m, 2H), 3.49-3.37 (m, 3H), 3.02-2.81 (m, 2H), 2.58-2.49 (m, 1H), 2.37 (m, 1H), 2.12-1.95 (m, 1H), 1.76 (m, 1H), 1.62-1.45 (m, 1H).

Step B: N-((3R,4R)-4-(fluoromethyl)pyrrolidin-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

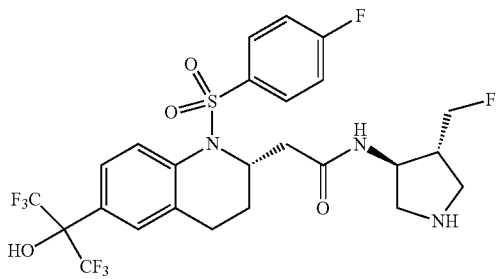 [SMILES: O=C(C[C@@H]1CCc2cc(C(O)(C(F)(F)F)C(F)(F)F)ccc2N1S(=O)(=O)c1ccc(F)cc1)N[C@@H]1CNC[C@H]1CF]

Following similar procedure as in Example 18, (3R,4R)-benzyl 3-(fluoromethyl)-4-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)pyrrolidine-1-carboxylate (20 mg, 0.027 mmol) was converted to the title compound (7.0 mg, 0.011 mmol, 43% yield).

LC/MS(M+1): 616.1; $^1$H-NMR (500 MHz, 1 to 1 mixture of CDCl$_3$ and CD$_3$OD) δ ppm 7.82 (d, J=8.9 Hz, 1H), 7.69-7.61 (m, 1H), 7.62-7.50 (m, 2H), 7.44 (s, 1H), 7.12 (t, J=8.4 Hz, 2H), 4.98-4.79 (m, 1H), 4.63-4.47 (m, 3H), 3.31-3.23 (m, 3H), 3.13-2.92 (m, 1H), 2.79-2.65 (m, 1H), 2.65-2.50 (m, 2H), 2.37 (m, 1H), 2.07 (m, 1H), 1.77 (m, 1H), 1.62-1.29 (m, 1H).

Example 23

N-((1S,3R)-3-amino-2,2,3-trimethylcyclopentyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

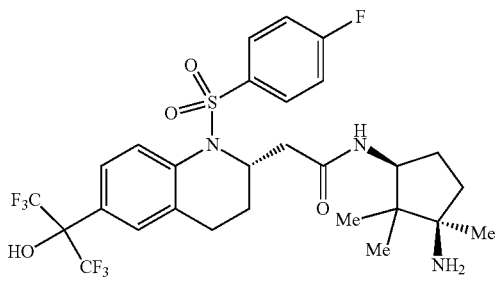 [SMILES: CC1(C)[C@@H](NC(=O)C[C@@H]2CCc3cc(C(O)(C(F)(F)F)C(F)(F)F)ccc3N2S(=O)(=O)c2ccc(F)cc2)CC[C@@]1(C)N]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (1R,3S)-1,2,2-trimethylcyclopentane-1,3-diamine (6.62 mg, 0.047 mmol) to provide the title compound (7.9 mg, 0.012 mmol, 52% yield). LC/MS(M+1): 640.1; $^1$H-NMR (500 MHz, 1 to 1 mixture of CDCl$_3$ and CD$_3$OD) δ ppm 7.82 (d, J=8.9 Hz, 1H), 7.72-7.62 (m, 1H), 7.56-7.48 (m, 2H), 7.49-7.36 (m, 1H), 7.12 (t, J=8.7 Hz, 2H), 4.81 (m, 1H), 4.22-4.08 (m, 1H), 2.73-2.48 (m, 2H), 2.37 (m, 1H), 2.23-2.00 (m, 2H), 1.94-1.50 (m, 5H), 1.28 (s, 3H), 1.02 (s, 3H), 0.89 (s, 3H).

Example 24

1-((3R,4R)-3-amino-4-(fluoromethyl)pyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

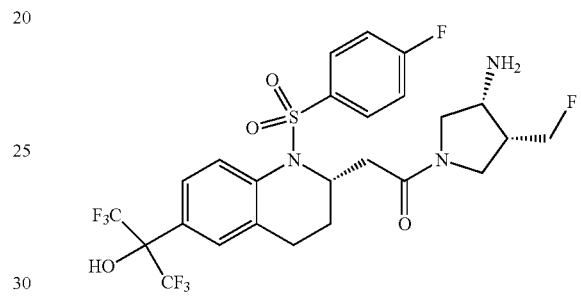

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with tert-butyl ((3R,4R)-4-(fluoromethyl)pyrrolidin-3-yl)carbamate (10.2 mg, 0.047 mmol) to provide the coupled product (16 mg) which was dissolved in DCM (1 mL) and treated with TFA (0.3 ml, 3.89 mmol). The resultant mixture was stirred at rt for 1 h, concentrated under reduced pressure and purified by preparative HPLC (condition C) to provide the title compound (10.4 mg, 0.016 mmol, 71% yield). LC/MS(M+1): 616.0; $^1$H-NMR (500 MHz, 1 to 1 mixture of CDCl$_3$ and CD$_3$OD) δ ppm 7.92-7.71 (m, 1H), 7.65-7.62 (m, 1H), 7.55-7.45 (m, 2H), 7.42 (s, 1H), 7.12 (t, J=8.4 Hz, 2H), 4.64-4.53 (m, 1H), 3.87-3.40 (m, 5H), 2.94-2.82 (m, 2H), 2.79-2.59 (m, 1H), 2.60-2.31 (m, 2H), 2.20-2.05 (m, 2H), 1.87-1.73 (m, 1H), 1.63-1.33 (m, 1H).

Example 25

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((1S,3S)-3-hydroxy-2,2,3-trimethylcyclopentyl)acetamide

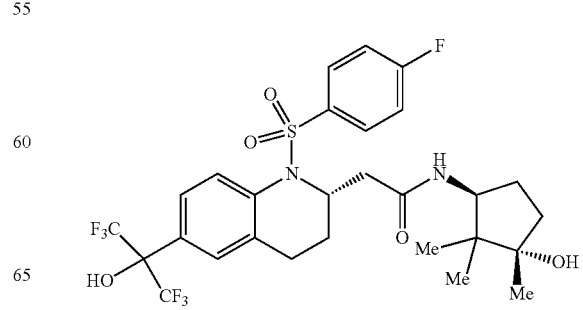

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (1S,3S)-3-amino-1,2,2-trimethylcyclopentanol (6.67 mg, 0.047 mmol) to provide the title compound (10.1 mg, 0.016 mmol, 67% yield). LC/MS(M+1): 641.1; $^1$H-NMR (500 MHz, 1 to 1 mixture of CDCl$_3$ and CD$_3$OD) δ ppm 7.80 (d, J=8.9 Hz, 1H), 7.66-7.59 (m, 1H), 7.61-7.50 (m, 2H), 7.44 (s, 1H), 7.12 (t, J=8.4 Hz, 2H), 4.78 (t, J=6.4 Hz, 1H), 4.49 (t, J=9.4 Hz, 1H), 2.68-2.49 (m, 2H), 2.38 (m, 1H), 2.07-1.96 (m, 2H), 1.86-1.76 (m, 2H), 1.67 (m, 1H), 1.60-1.54 (m, 1H), 1.43-1.34 (m, 1H), 1.17 (s, 3H), 0.96 (s, 3H), 0.75 (s, 3H).

Example 26

(S)-4,4-difluoro-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidine-2-carboxamide

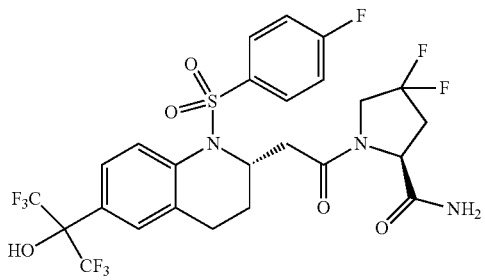 [SMILES: NC(=O)[C@@H]1CC(F)(F)CN1C(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (14 mg, 0.027 mmol) was treated with (S)-4,4-difluoropyrrolidine-2-carboxamide, HCl (7.60 mg, 0.041 mmol) to provide the title compound (14.7 mg, 0.022 mmol, 80% yield). LC/MS(M+1): 648.4; $^1$H-NMR (500 MHz, 1 to 1 mixture of CDCl$_3$ and CD$_3$OD) δ ppm 7.84-7.72 (m, 1H), 7.67-7.61 (m, 1H), 7.54-7.44 (m, 2H), 7.41 (s, 1H), 7.12 (t, J=8.7 Hz, 2H), 4.67-4.57 (m, 1H), 4.11-3.81 (m, 2H), 2.96-2.64 (m, 2H), 2.62-2.23 (m, 3H), 2.15-2.02 (m, 1H), 1.84-1.67 (m, 1H), 1.63-1.38 (m, 2H).

Example 27

N-(1,4-dimethyl-2,5-dioxoimidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

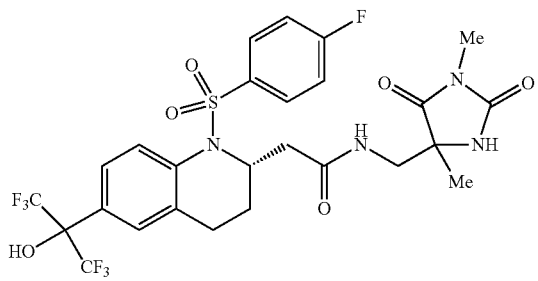 [SMILES: CN1C(=O)NC(C)(CNC(=O)C[C@@H]2CCc3cc(C(O)(C(F)(F)F)C(F)(F)F)ccc3N2S(=O)(=O)c2ccc(F)cc2)C1=O]

Step A: 5-((dibenzylamino)methyl)-3,5-dimethyl-imidazolidine-2,4-dione

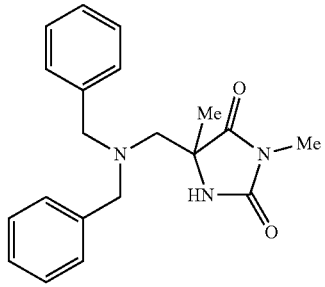 [SMILES: CN1C(=O)NC(C)(CN(Cc2ccccc2)Cc2ccccc2)C1=O]

To a solution of 5-((dibenzylamino)methyl)-5-methylimidazolidine-2,4-dione (intermediate 3, step B, 100 mg, 0.309 mmol) in DMF (0.6 mL) was added potassium carbonate (128 mg, 0.928 mmol) and MeI (0.039 mL, 0.618 mmol). The resultant mixture was stirred at rt for 8 hrs and filtered. The filtrate was purified by preparative HPLC (condition C) to afford 5-((dibenzylamino)methyl)-3,5-dimethylimidazolidine-2,4-dione as TFA salt (60 mg, 0.133 mmol, 43% yield). LC/MS(M+1): 338.1; $^1$H NMR (400 MHz, CD$_3$OD) δ ppm 7.64-7.20 (m, 10H), 3.89 (br. s., 4H), 3.27-3.21 (m, 1H), 3.05-2.89 (m, 4H), 1.26 (s, 3H).

Step B: 5-(aminomethyl)-3,5-dimethylimidazolidine-2,4-dione

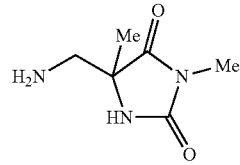 [SMILES: CN1C(=O)NC(C)(CN)C1=O]

The mixture of 5-((dibenzylamino)methyl)-3,5-dimethyl-imidazolidine-2,4-dione, TFA (60 mg, 0.133 mmol) and 5% palladium on carbon (28.3 mg, 0.013 mmol) in MeOH (5 mL) and AcOH (0.5 mL) was stirred under H$_2$ atmosphere at 55 Psi and rt for 20 hrs. The mixture was filtered and the filtrate was concentrated under reduced pressure. To the residue was added TFA (0.5 ml) and the contents concentrated under reduced pressure to afford 5-(aminomethyl)-3,5-dimethylimidazolidine-2,4-dione as TFA salt (35 mg, 0.129 mmol, 97% yield). LC/MS(M+1): 157.9; $^1$H NMR (400 MHz, CD$_3$OD) δ ppm 3.42-3.35 (m, 1H), 3.20-3.08 (m, 1H), 3.00 (s, 3H), 1.48 (s, 3H).

Step C: N-((1,4-dimethyl-2,5-dioxoimidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

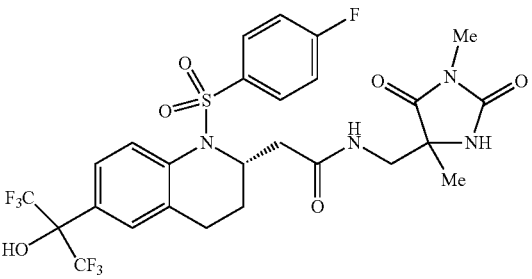 [SMILES: CN1C(=O)NC(C)(CNC(=O)C[C@@H]2CCc3cc(C(O)(C(F)(F)F)C(F)(F)F)ccc3N2S(=O)(=O)c2ccc(F)cc2)C1=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (14 mg, 0.027 mmol) was treated with 5-(aminomethyl)-3,5-dimethylimidazolidine-2,4-dione, TFA (11.05 mg, 0.041 mmol) to provide the title compound (12.6 mg, 0.019 mmol, 70% yield) as a mixture of diastereomers. LC/MS(M+1): 655.0; $^1$H-NMR (500 MHz, 1 to 1 mixture of CDCl$_3$ and CD$_3$OD) δ ppm 7.78 (d, J=8.9 Hz, 1H), 7.67-7.61 (m, 1H), 7.63-7.52 (m, 2H), 7.42 (br. s., 1H), 7.13 (m, 2H), 4.64-4.52 (m, 1H), 3.76 (s, 3H), 3.64-3.39 (m, 2H), 2.66 (m, 1H), 2.63-2.47 (m, 1H), 2.39-2.28 (m, 1H), 2.02-1.92 (m, 1H), 1.82 (m, 1H), 1.61-1.46 (m, 1H), 1.45-1.30 (m, 3H).

Example 28

1-ethyl-3-((S)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)urea

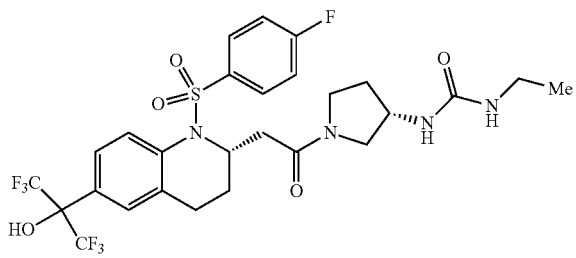 [SMILES: CCNC(=O)N[C@H]1CCN(C(=O)C[C@@H]2CCc3cc(C(O)(C(F)(F)F)C(F)(F)F)ccc3N2S(=O)(=O)c2ccc(F)cc2)C1]

Ethyl isocyanate (2.29 mg, 0.032 mmol) was added to the solution of 1-((S)-3-aminopyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone, (Example 12, 15 mg, 0.022 mmol) TFA and DIEA (8.34 mg, 0.066 mmol) in DCM (1 mL) at rt and stirred for 30 min. To the reaction mixture was added MeOH (1 ml), the contents concentrated under reduced pressure and purified by preparative HPLC (condition C) to afford the title compound (10 mg, 0.015 mmol, 68% yield). LC/MS(M+1): 655.4; $^1$H-NMR (400 MHz, CD$_3$OD) δ ppm 7.77 (m, 1H), 7.67-7.50 (m, 3H), 7.43 (br. s., 1H), 7.20 (m, 2H), 4.76-4.67 (m, 1H), 4.25 (m, 1H), 3.79-3.40 (m, 4H), 3.20-3.07 (m, 2H), 2.86-2.70 (m, 1H), 2.62-2.39 (m, 2H), 2.23-2.07 (m, 1H), 2.07-1.97 (m, 1H), 1.96-1.76 (m, 2H), 1.67-1.50 (m, 1H), 1.10 (m, 3H).

Example 29

Methyl ((S)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)carbamate

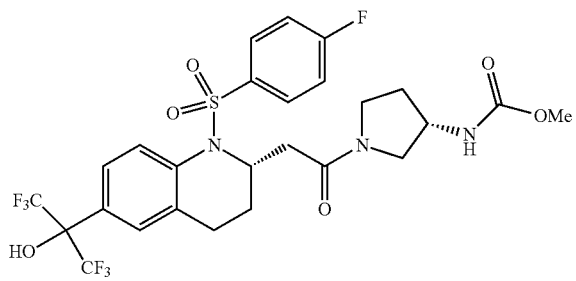 [SMILES: COC(=O)N[C@H]1CCN(C(=O)C[C@@H]2CCc3cc(C(O)(C(F)(F)F)C(F)(F)F)ccc3N2S(=O)(=O)c2ccc(F)cc2)C1]

Methyl chloroformate (3.05 mg, 0.032 mmol) was added to the solution of 1-((S)-3-aminopyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone, (Example 12, 15 mg, 0.022 mmol) TFA and DIEA (8.34 mg, 0.066 mmol) in DCM (1 mL) at rt and stirred for 30 min. The reaction mixture was concentrated under reduced pressure and purified by preparative HPLC (condition C) to afford the title compound (11 mg, 0.016 mmol, 76% yield). LC/MS(M+1): 642.3; $^1$H-NMR (400 MHz, CD$_3$OD) δ ppm 7.77 (dd, J=8.7, 5.0 Hz, 1H), 7.67-7.53 (m, 3H), 7.43 (br. s., 1H), 7.20 (t, J=8.6 Hz, 2H), 4.78-4.55 (m, 1H), 4.25-4.11 (m, 1H), 3.80-3.42 (m, 6H), 2.87-2.67 (m, 1H), 2.64-2.41 (m, 2H), 2.25-2.02 (m, 2H), 2.01-1.73 (m, 3H), 1.70-1.48 (m, 1H).

Example 30

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((4-methyl-2-oxoimidazolidin-4-yl)methyl)acetamide

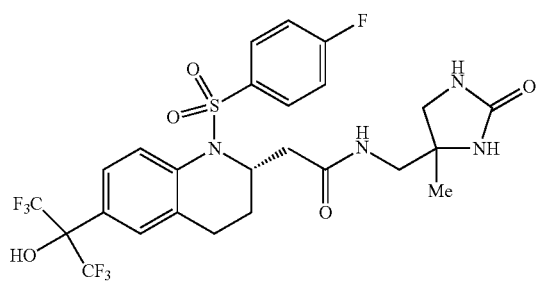 [SMILES: CC1(CNC(=O)C[C@@H]2CCc3cc(C(O)(C(F)(F)F)C(F)(F)F)ccc3N2S(=O)(=O)c2ccc(F)cc2)CNC(=O)N1]

Step A:
4-(aminomethyl)-4-methylimidazolidin-2-one

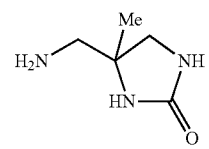

A 1.0 M THF solution of LAH (0.928 mL, 0.928 mmol) was added to a solution of 5-((dibenzylamino)methyl)-5-methylimidazolidine-2,4-dione (intermediate 3, step B, 100 mg, 0.309 mmol) in THF (2 mL) at rt. The resultant mixture was heated to reflux for 1 hr. It was cooled to rt and quenched with saturated NH$_4$Cl (2 ml). The mixture was extracted with ethyl acetate (60 ml), washed with water, brine, dried (MgSO$_4$) and concentrated under reduced pressure. The residue was dissolved in MeOH (5 mL), 5% palladium on carbon (16.5 mg, 0.155 mmol) and acetic acid (0.2 mL, 3.49 mmol) were added under a nitrogen atmosphere and the resultant mixture was stirred under H$_2$ atmosphere at 55 psi for 6 hrs. and filtered. The filtrate was concentrated under reduced pressure to provide 4-(aminomethyl)-4-methylimidazolidin-2-one as crude material (60 mg) which was used as such for the subsequent step without further purification.

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((4-methyl-2-oxoimidazolidin-4-yl)methyl)acetamide

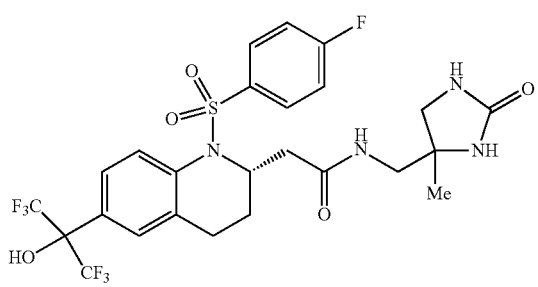 [SMILES: CC1(CNC(=O)C[C@@H]2CCc3cc(C(O)(C(F)(F)F)C(F)(F)F)ccc3N2S(=O)(=O)c2ccc(F)cc2)CNC(=O)N1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (30 mg, 0.058 mmol) was treated with 4-(aminomethyl)-4-methylimidazolidin-2-one (15.1 mg, 0.116 mmol) to provide the title compound (4.3 mg, 0.0007 mmol, 12% yield) as a mixture of diatereomers.

LC/MS(M+1): 605.3; $^1$H-NMR (500 MHz, DMSO-d$_6$) δ ppm 8.87 (br. s., 1H), 8.16-7.87 (m, 1H), 7.75-7.58 (m, 3H), 7.53 (m, 1H), 7.48-7.29 (m, 2H), 6.34-5.94 (m, 2H), 4.86-4.42 (m, 1H), 3.21-3.08 (m, 2H), 3.08-2.93 (m, 1H), 2.75-2.65 (m, 1H), 2.46-2.30 (m, 1H), 2.19 (m, 1H), 1.69-1.56 (m, 1H), 1.56-1.46 (m, 1H), 1.14-0.82 (m, 3H).

Example 31

(S)-1-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrazolidin-3-one

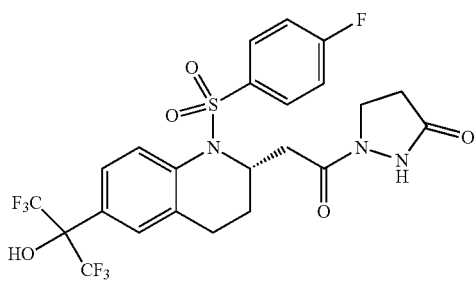 [SMILES: O=C1CCN(C(=O)C[C@@H]2CCc3cc(C(O)(C(F)(F)F)C(F)(F)F)ccc3N2S(=O)(=O)c2ccc(F)cc2)N1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with pyrazolidin-3-one (4.01 mg, 0.047 mmol) to provide the title compound (7.9 mg, 0.013 mmol, 56% yield). LC/MS(M+1): 584.2; $^1$H-NMR (500 MHz, DMSO-d$_6$) δ ppm 8.78 (br. s., 1H), 7.77-7.57 (m, 3H), 7.57-7.49 (m, 1H), 7.49-7.22 (m, 3H), 4.94-4.58 (m, 1H), 4.05-3.69 (m, 2H), 2.72-2.53 (m, 4H), 2.17 (m, 1H), 2.08-1.85 (m, 1H), 1.76 (m, 1H), 1.61 (m, 2H).

Example 32

Methyl (trans-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-4-hydroxypiperidin-3-yl)carbamate

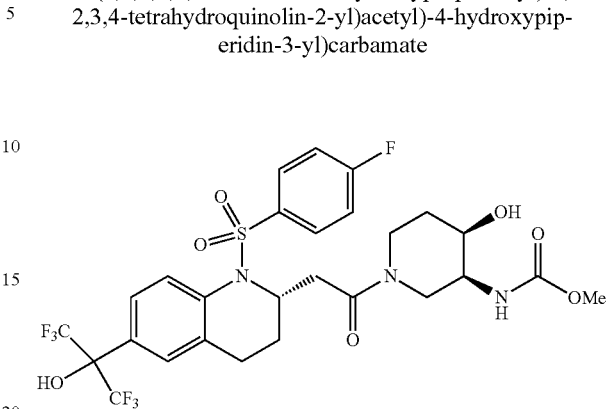

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with methyl (trans-4-hydroxypiperidin-3-yl)carbamate (6.08 mg, 0.035 mmol) to provide the title compound as a mixture of diastereomers (12.9 mg, 0.019 mmol, 82% yield). LC/MS (M+1): 672.4; $^1$H-NMR (500 MHz, DMSO-d$_6$) δ ppm 8.78 (br. s., 1H), 7.86-7.63 (m, 1H), 7.63-7.48 (m, 2H), 7.48-7.31 (m, 2H), 7.18 (d, J=7.4 Hz, 1H), 7.05 (t, J=8.9 Hz, 1H), 5.15-4.81 (m, 1H), 4.77-4.52 (m, 1H), 4.22-4.00 (m, 1H), 3.92 (s, 3H), 3.87-3.75 (m, 1H), 3.66-3.42 (m, 3H), 3.28-3.11 (m, 1H), 3.08-2.93 (m, 1H), 2.72-2.53 (m, 2H), 2.08-1.75 (m, 2H), 1.59-1.41 (m, 1H), 1.37-1.14 (m, 1H).

Example 33

(S)-4-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-1-methylpiperazin-2-one

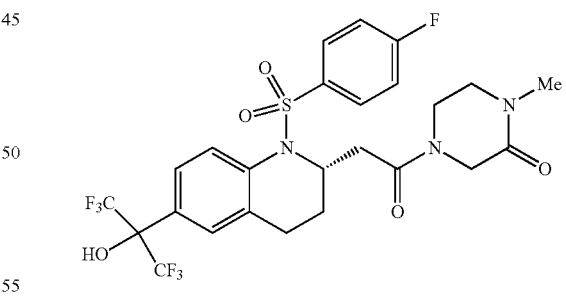

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 1-methylpiperazin-2-one (3.99 mg, 0.035 mmol) to provide the title compound (8.5 mg, 0.014 mmol, 60% yield). LC/MS(M+1): 612.3; $^1$H-NMR (500 MHz, DMSO-d$_6$) δ ppm 8.76 (br. s., 1H), 7.68 (d, J=8.9 Hz, 1H), 7.64-7.49 (m, 3H), 7.49-7.26 (m, 3H), 4.77-4.47 (m, 1H), 4.17-3.85 (m, 3H), 3.75-3.53 (m, 2H), 3.30-3.17 (m, 2H), 2.99-2.79 (m, 3H), 2.76-2.56 (m, 2H), 2.04-1.70 (m, 2H), 1.55 (m, 1H).

Example 34

(S)-1-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)imidazolidin-4-one

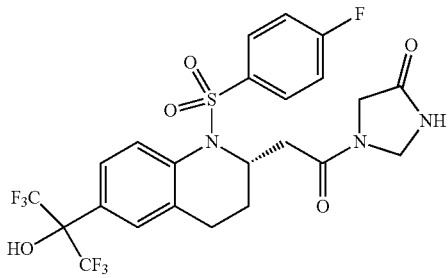 [SMILES: O=C1CN(C(=O)C[C@@H]2CCc3cc(C(O)(C(F)(F)F)C(F)(F)F)ccc3N2S(=O)(=O)c2ccc(F)cc2)CN1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with imidazolidin-4-one (3.01 mg, 0.035 mmol) to provide the title compound (2.0 mg, 0.003 mmol, 14% yield). LC/MS (M+1): 584.3; $^1$H-NMR (500 MHz, DMSO-$d_6$) δ ppm 8.75 (br. s., 1H), 8.68-8.50 (m, 1H), 7.78-7.63 (m, 1H), 7.63-7.49 (m, 3H), 7.51-7.27 (m, 3H), 4.93-4.57 (m, 3H), 4.07-3.94 (m, 1H), 3.77-3.63 (m, 1H), 2.73-2.54 (m, 3H), 2.00-1.77 (m, 2H), 1.57 (m, 1H).

Example 35

(S)-4-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)piperazin-2-one

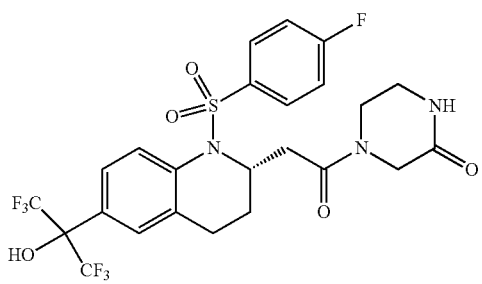 [SMILES: O=C1CN(C(=O)C[C@@H]2CCc3cc(C(O)(C(F)(F)F)C(F)(F)F)ccc3N2S(=O)(=O)c2ccc(F)cc2)CCN1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with piperazin-2-one (3.50 mg, 0.035 mmol) to provide the title compound (10.3 mg, 0.017 mmol, 73% yield). LC/MS(M+1): 598.3; $^1$H-NMR (500 MHz, DMSO-$d_6$) δ ppm 8.77 (br. s., 1H), 8.21-8.03 (m, 1H), 7.68 (m, 1H), 7.63-7.49 (m, 2H), 7.44-7.30 (m, 3H), 4.67 (m, 1H), 4.09-3.94 (m, 1H), 3.66-3.49 (m, 2H), 3.29-3.08 (m, 3H), 2.78-2.58 (m, 3H), 2.00-1.83 (m, 2H), 1.55 (m, 1H).

Example 36

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(5-oxopyrrolidin-3-yl)acetamide

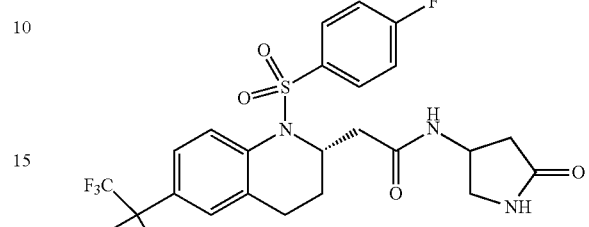

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 4-aminopyrrolidin-2-one, HCl (4.77 mg, 0.035 mmol) to provide the title compound (13.4 mg, 0.022 mmol, 95% yield) as a mixture of diastereomers. LC/MS(M+1): 598.2; $^1$H-NMR (500 MHz, DMSO-$d_6$) δ ppm 8.75 (br. s., 1H), 8.40 (t, J=6.7 Hz, 1H), 7.78-7.58 (m, 4H), 7.53 (d, J=8.4 Hz, 1H), 7.46-7.35 (m, 3H), 4.88-4.65 (m, 1H), 4.42-4.25 (m, 1H), 3.57-3.44 (m, 1H), 2.95 (m, 1H), 2.73-2.62 (m, 1H), 2.45-2.10 (m, 4H), 2.03-1.87 (m, 1H), 1.74-1.66 (m, 1H), 1.63-1.47 (m, 1H).

Example 37

Diastereomers A & B

N-(2,2-dimethyl-5-oxotetrahydrofuran-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

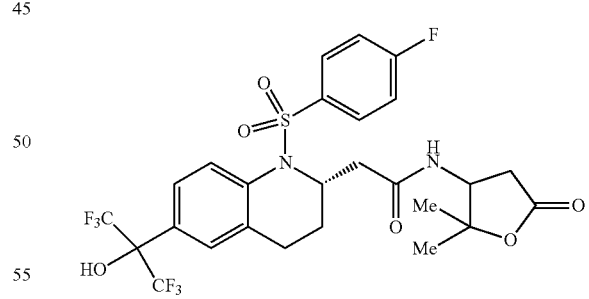

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 4-amino-5,5-dimethyldihydrofuran-2(3H)-one, HCl (5.78 mg, 0.035 mmol) to provide the title compound (10 mg, 0.016 mmol, 68% yield) as a mixture of diastereomers. LC/MS(M+1): 627.2; This compound was separated by chiral OZ column to provide diastereomer 37A as first eluent off the column. LC/MS(M+1): 627.3. $^1$H-NMR (400 MHz, CD₃OD) δ ppm 7.83 (d, J=8.8 Hz, 1H), 7.67-7.53 (m, 3H), 7.45 (s, 1H), 7.34-7.07 (m, 2H), 5.02-4.90 (m, 1H), 4.54 (m, 1H), 3.01 (m, 1H), 2.69-2.45 (m, 3H), 2.37 (m, 1H), 2.15 (m, 1H), 1.76-1.66 (m, 1H), 1.64-1.55 (m, 1H), 1.51 (s, 3H), 1.36 (s, 3H). Diastereomer 37B as second eluent off the column. LC/MS(M+1): 627.3. ¹H-NMR (400 MHz, CD₃OD) δ ppm 7.79 (d, J=8.8 Hz, 1H), 7.68-7.56 (m, 3H), 7.44 (s, 1H), 7.36-7.15 (m, 2H), 4.80-4.75 (m, 1H), 4.55-4.40 (m, 1H), 3.12-2.90 (m, 1H), 2.71-2.35 (m, 4H), 2.04 (m, 1H), 1.95-1.85 (m, 1H), 1.70-1.52 (m, 1H), 1.47 (s, 3H), 1.30 (s, 3H).

Example 38

Step A: (S)-1-(2,5-dihydro-1H-pyrrol-1-yl)-2-(1-((4-fluorophenyl)sulfonyl)-6-(1,1,1,3,3,3-hexafluoro-2-hydroxypropan-2-yl)-1,2,3,4-tetrahydroquinolin-2-yl)ethanone

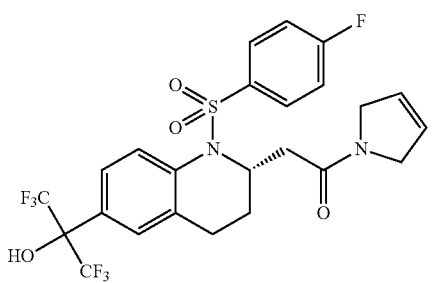 [SMILES: O=C(C[C@@H]1CCc2cc(C(O)(C(F)(F)F)C(F)(F)F)ccc2N1S(=O)(=O)c1ccc(F)cc1)N1CC=CC1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with 2,5-dihydro-1H-pyrrole (4.02 mg, 0.058 mmol) to provide (S)-1-(2,5-dihydro-1H-pyrrol-1-yl)-2-(1-((4-fluorophenyl)sulfonyl)-6-(1,1,1,3,3,3-hexafluoro-2-hydroxypropan-2-yl)-1,2,3,4-tetrahydroquinolin-2-yl)ethanone (18 mg) which was used as such for the subsequent step without further purification. LC/MS(M+1): 567.2.

Step B: 3,4-dihydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

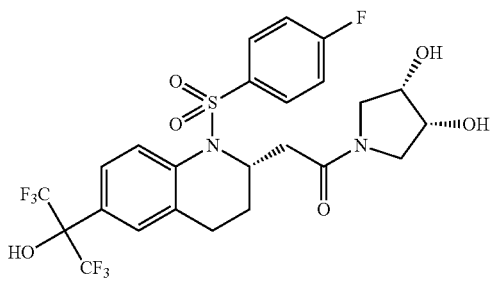 [SMILES: O=C(C[C@@H]1CCc2cc(C(O)(C(F)(F)F)C(F)(F)F)ccc2N1S(=O)(=O)c1ccc(F)cc1)N1C[C@@H](O)[C@@H](O)C1]

Following similar procedure as Step B of Example 51, crude (S)-1-(2,5-dihydro-1H-pyrrol-1-yl)-2-(1-((4-fluorophenyl)sulfonyl)-6-(1,1,1,3,3,3-hexafluoro-2-hydroxypropan-2-yl)-1,2,3,4-tetrahydroquinolin-2-yl)ethanone (18 mg) was converted to the title compound as a mixture of two diastereomers (9.9 mg, 0.015 mmol, 52% yield for two steps). LC/MS(M+1): 601.2. ¹H-NMR (500 MHz, DMSO-d₆) δ ppm 8.76 (br. s., 1H), 7.76-7.48 (m, 4H), 7.47-7.22 (m, 3H), 5.26-4.79 (m, 2H), 4.75-4.49 (m, 1H), 3.98 (d, J=18.3 Hz, 2H), 3.53 (dd, J=9.9, 5.9 Hz, 1H), 3.24-3.03 (m, 4H), 2.67-2.59 (m, 2H), 2.05-1.86 (m, 2H), 1.68-1.36 (m, 1H).

Example 39

Diasteromers A & B

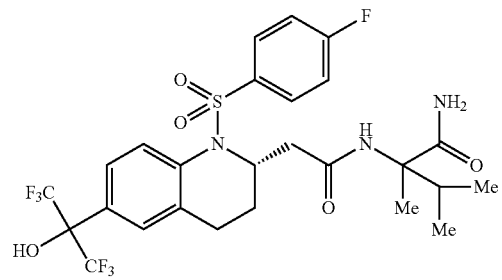 [SMILES: CC(C)C(C)(NC(=O)C[C@@H]1CCc2cc(C(O)(C(F)(F)F)C(F)(F)F)ccc2N1S(=O)(=O)c1ccc(F)cc1)C(N)=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 2-amino-2,3-dimethylbutanamide (3.03 mg, 0.023 mmol) to provide the title compound as two separable diastereomers.

Diastereomer 39A (6.2 mg, 0.010 mmol, 42% yield). LC/MS(M+1): 628.3; ¹H-NMR (500 MHz, DMSO-d₆) δ ppm 15.05-14.94 (m, 2H), 8.75 (d, J=2.5 Hz, 1H), 8.20 (dd, J=8.9, 2.5 Hz, 1H), 7.78-7.53 (m, 4H), 7.44 (s, 1H), 7.42-7.24 (m, 2H), 7.07 (d, J=8.4 Hz, 1H), 4.98-4.76 (m, 2H), 4.07-3.91 (m, 3H), 3.27-3.20 (m, 1H), 3.10 (dd, J=15.1, 8.2 Hz, 1H), 2.80-2.61 (m, 1H), 2.29-1.98 (m, 1H), 1.98-1.91 (m, 1H), 1.81-1.46 (m, 1H).

Diastereomer 39B (5.6 mg, 0.009 mmol, 38% yield). LC/MS(M+1): 628.3; ¹H-NMR (500 MHz, DMSO-d₆) δ ppm, 8.78 (br. s., 1H), 7.69 (d, J=8.4 Hz, 1H), 7.66-7.48 (m, 4H), 7.48-7.31 (m, 3H), 7.11-6.78 (m, 2H), 4.68 (m, 1H), 2.75-2.65 (m, 1H), 2.49-2.31 (m, 1H), 2.15 (m, 1H), 1.95 (m, 1H), 1.70-1.59 (m, 2H), 1.52-1.43 (m, 1H), 1.26 (s, 3H), 0.93-0.73 (m, 6H).

Example 40

N-((1-(fluoromethyl)-4-methyl-2,5-dioxoimidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

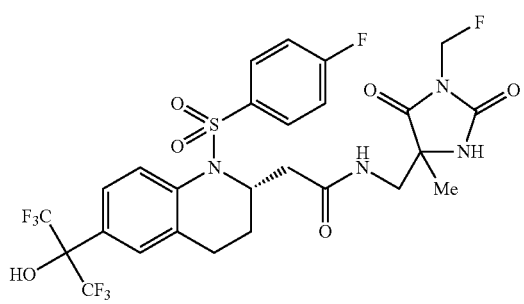 [SMILES: CC1(CNC(=O)C[C@@H]2CCc3cc(C(O)(C(F)(F)F)C(F)(F)F)ccc3N2S(=O)(=O)c2ccc(F)cc2)NC(=O)N(CF)C1=O]

Step A: 5-((dibenzylamino)methyl)-3-(fluoromethyl)-5-methylimidazolidine-2,4-dione

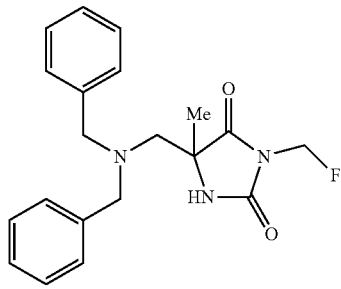 [SMILES: CC1(CN(Cc2ccccc2)Cc2ccccc2)NC(=O)N(CF)C1=O]

Following similar procedure as in Step A of Example 38, 5-((dibenzylamino)methyl)-5-methylimidazolidine-2,4-dione (intermediate 3, step AB 100 mg, 0.309 mmol) was treated with chlorofluoromethane (63.5 mg, 0.928 mmol) to provide 5-((dibenzylamino)methyl)-3-(fluoromethyl)-5-methylimidazolidine-2,4-dione as TFA salt (40 mg, 0.085 mmol, 28% yield). LC/MS(M+1): 356.2; $^1$H-NMR (400 MHz, CD$_3$OD) δ ppm 7.96-6.96 (m, 10H), 5.94-5.35 (m, 2H), 4.09-3.59 (m, 4H), 3.22-3.12 (m, 1H), 2.88 (m, 1H), 1.29 (s, 3H).

Step B: N-((1-(fluoromethyl)-4-methyl-2,5-dioxoimidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

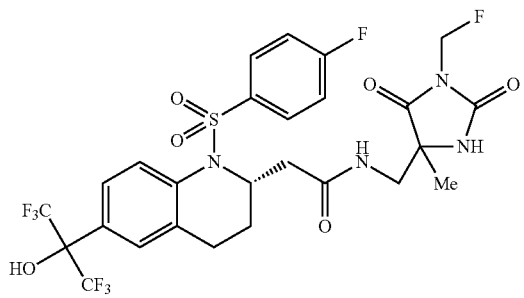

Following similar procedure as Steps A, B & C of Example 27, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was converted to the title compound (10.4 mg, 0.015 mmol, 65% yield). LC/MS(M+1): 673.2; $^1$H-NMR (500 MHz, DMSO-d$_6$) δ ppm 8.74 (br. s., 1H), 8.49 (d, J=5.0 Hz, 1H), 8.30-8.07 (m, 1H), 7.81-7.57 (m, 3H), 7.51 (d, J=8.4 Hz, 1H), 7.44-7.25 (m, 3H), 5.72-5.11 (m, 2H), 4.78-4.58 (m, 1H), 3.27-3.09 (m, 1H), 2.66-2.59 (m, 1H), 2.46-2.28 (m, 1H), 2.26-2.03 (m, 1H), 1.67-1.41 (m, 2H), 1.29 (d, J=2.5 Hz, 3H).

Example 41

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxy-3-(hydroxymethyl)pyrrolidin-1-yl)ethanone

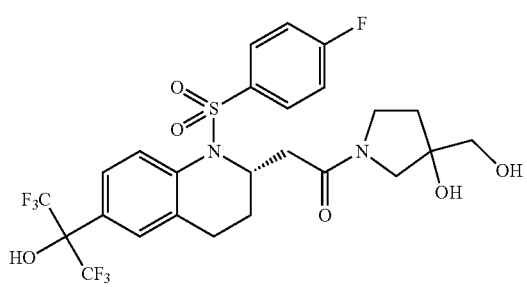 [SMILES: O=C(C[C@@H]1CCc2cc(C(O)(C(F)(F)F)C(F)(F)F)ccc2N1S(=O)(=O)c1ccc(F)cc1)N1CCC(O)(CO)C1]

Step A: tert-butyl 3-methylenepyrrolidine-1-carboxylate

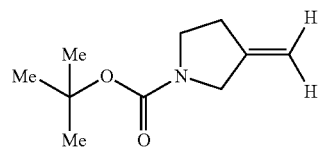 [SMILES: C=C1CCN(C(=O)OC(C)(C)C)C1]

1.0 M THF solution of potassium tert-butoxide (2.97 mL, 2.97 mmol) was added to the suspension of methyltriphenylphosphonium bromide (1.11 g, 2.97 mmol) in THF (20 mL) at 0° C. and warmed up to rt for 1 hr. The reaction mixture was cooled back to 0° C. and a solution of tert-butyl 3-oxopyrrolidine-1-carboxylate (220 mg, 1.19 mmol) in THF (2 ml) was added. The resulting reaction mixture was warmed to rt over a period of 3 hrs., quenched with saturated NH$_4$Cl (10 ml) and concentrated under reduced pressure. The reaction mixture is extracted with ethyl acetate (100 ml), washed with water, brine, dried (MgSO$_4$), concentrated and the residue was purified by flash silica gel chromatography using a mixture of 15% ethyl acetate in hexane to provide tert-butyl 3-methylenepyrrolidine-1-carboxylate (110 mg, 0.600 mmol, 51% yield). $^1$H-NMR (400 MHz, CD$_3$OD) δ ppm 5.00 (m, 2H), 3.91 (br. s., 2H), 3.44 (t, J=7.4 Hz, 2H), 2.58 (t, J=6.7 Hz, 2H), 1.46 (s, 9H).

Step B: tert-butyl 3-hydroxy-3-(hydroxymethyl)pyrrolidine-1-carboxylate

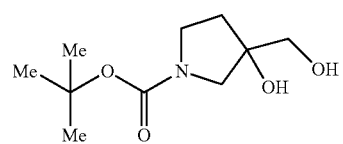 [SMILES: CC(C)(C)OC(=O)N1CCC(O)(CO)C1]

Following similar procedure as in Step B of Example 38, tert-butyl 3-methylenepyrrolidine-1-carboxylate (110 mg, 0.600 mmol) was converted to tert-butyl 3-hydroxy-3-(hydroxymethyl)pyrrolidine-1-carboxylate (101 mg, 0.465 mmol, 77% yield). LC/MS(M+1): 218.2. ¹H-NMR (400 MHz, CDCl₃) δ ppm 4.24 (br. s., 1H), 4.09 (br. s., 1H), 3.64-3.25 (m, 6H), 1.99-1.74 (m, 2H), 1.42 (s, 9H).

Step C: 3-(hydroxymethyl)pyrrolidin-3-ol

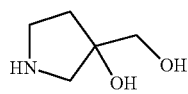

TFA (0.2 ml, 2.60 mmol) was added to the solution of tert-butyl 3-hydroxy-3-(hydroxymethyl)pyrrolidine-1-carboxylate (101 mg, 0.465 mmol) in DCM (0.8 ml) at rt. The resulting mixture was stirred for 1 hr and concentrated under reduced pressure to provide 3-(hydroxymethyl)pyrrolidin-3-ol as TFA salt (106 mg, 0.459 mmol, 99% yield). ¹H-NMR (400 MHz, CD₃OD) δ ppm 3.69-3.60 (m, 2H), 3.57-3.39 (m, 2H), 3.27 (m, 1H), 3.21-3.08 (m, 1H), 2.29-2.07 (m, 1H), 2.03-1.81 (m, 1H).

Step D: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxy-3-(hydroxymethyl)pyrrolidin-1-yl)ethanone

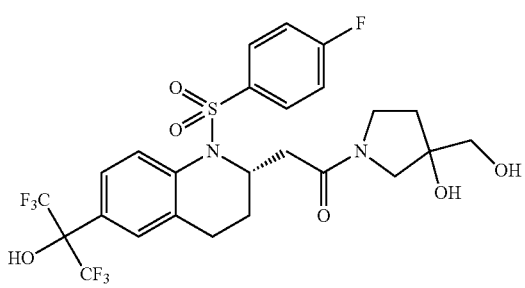 [SMILES: O=C(C[C@@H]1CCc2cc(C(O)(C(F)(F)F)C(F)(F)F)ccc2N1S(=O)(=O)c1ccc(F)cc1)N1CCC(O)(CO)C1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with 3-(hydroxymethyl)pyrrolidin-3-ol, TFA (10.1 mg, 0.044 mmol) to provide the title compound (4.5 mg, 0.0075 mmol, 26% yield). LC/MS(M+1): 615.2; ¹H-NMR (400 MHz, CD₃OD) δ ppm 7.92-7.72 (m, 1H), 7.70-7.52 (m, 3H), 7.43 (br. s., 1H), 7.20 (t, J=8.7 Hz, 2H), 4.82-4.56 (m, 1H), 3.75-3.40 (m, 6H), 2.90-2.69 (m, 1H), 2.68-2.45 (m, 2H), 2.16-1.97 (m, 2H), 1.98-1.75 (m, 2H), 1.69-1.44 (m, 1H).

Example 42

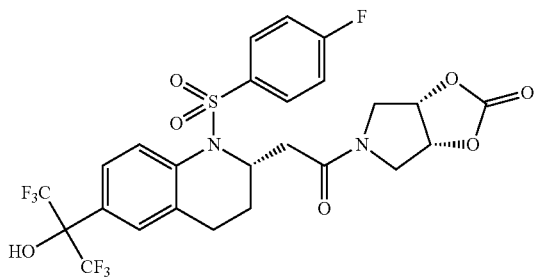 [SMILES: O=C1O[C@H]2CN(C(=O)C[C@@H]3CCc4cc(C(O)(C(F)(F)F)C(F)(F)F)ccc4N3S(=O)(=O)c3ccc(F)cc3)C[C@H]2O1]

DIEA (0.015 mL, 0.085 mmol) and di(1H-imidazol-1-yl)methanone (13.8 mg, 0.085 mmol) were added to the solution of 1-((3R,4S)-3,4-dihydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (Example 38, 17 mg, 0.028 mmol) in THF (1 mL) at rt and stirred for 4 hrs. The mixture was concentrated under reduced pressure and the residue was purified by flash silica gel chromatography using a mixture of 60% ethyl acetate in hexane to provide the title compound (8.0 mg, 0.011 mmol, 41% yield). LC/MS(M+1): 627.2; ¹H-NMR (400 MHz, CD₃OD) δ ppm 0.91-7.70 (m, 1H), 7.70-7.49 (m, 3H), 7.43 (s, 1H), 7.20 (td, J=8.7, 4.6 Hz, 2H), 5.48-5.25 (m, 2H), 4.73-4.59 (m, 1H), 4.27-4.01 (m, 3H), 3.69 (m, 1H), 3.52-3.38 (m, 1H), 2.91-2.62 (m, 1H), 2.59-2.41 (m, 1H), 2.10-1.96 (m, 1H), 1.88-1.76 (m, 1H), 1.65-1.50 (m, 1H).

Example 43

Step A: 5-((dibenzylamino)methyl)-3-(2-hydroxy-2-methylpropyl)-5-methylimidazolidine-2,4-dione

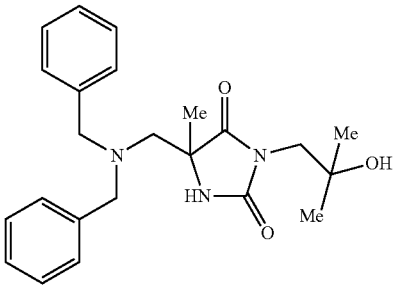 [SMILES: CC(C)(O)CN1C(=O)NC(C)(CN(Cc2ccccc2)Cc2ccccc2)C1=O]

To a solution of 5-((dibenzylamino)methyl)-5-methylimidazolidine-2,4-dione (intermediate 3, step B, 100 mg, 0.309 mmol) in EtOH (0.8 mL) was added 2,2-dimethyloxirane (111 mg, 1.55 mmol) and DIEA (0.054 mL, 0.309 mmol) at rt. The resultant mixture was heated to 170° C. in a microwave oven for 90 min., cooled to rt and purified by preparative HPLC (condition C) to provide 5-((dibenzylamino)methyl)-3-(2-hydroxy-2-methylpropyl)-5-methylimidazolidine-2,4-dione as TFA salt (25 mg, 0.049 mmol, 16% yield). LC/MS(M+1): 396.3; ¹H-NMR (400 MHz, CD₃OD) δ ppm 8.15-6.86 (m, 10H), 4.34-3.88 (m, 4H), 3.61-3.41 (m, 3H), 3.05 (m, 1H), 1.47 (s, 3H), 1.26-0.95 (m, 6H).

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-((1-(2-hydroxy-2-methylpropyl)-4-methyl-2,5-dioxoimidazolidin-4-yl)methyl)acetamide

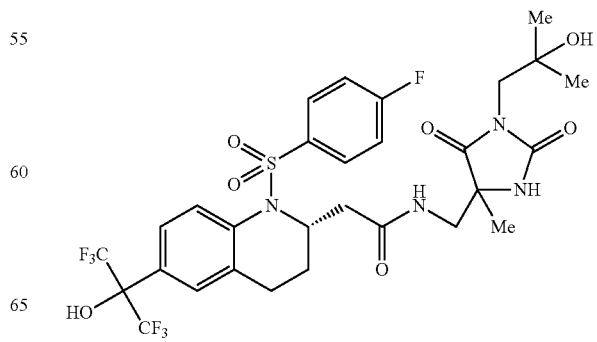

Following similar procedure as in Steps B & C of Example 27, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was converted to the title compound (8.5 mg, 0.012 mmol, 50% yield). LC/MS(M+1): 713.4; $^1$H-NMR (500 MHz, 1 to 1 mixture of CDCl$_3$ and CD$_3$OD) δ ppm 7.88-7.74 (m, 1H), 7.63-7.59 (m, 1H), 7.62-7.51 (m, 2H), 7.50-7.29 (m, 1H), 7.26-7.03 (m, 2H), 4.83-4.72 (m, 1H), 3.76 (s, 2H), 3.65-3.43 (m, 2H), 2.77-2.63 (m, 1H), 2.59-2.48 (m, 1H), 2.44-2.26 (m, 1H), 2.06-1.79 (m, 2H), 1.70-1.48 (m, 1H), 1.43 (s, 3H), 1.27-1.03 (m, 6H).

Example 44

(S)-benzyl 2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetate

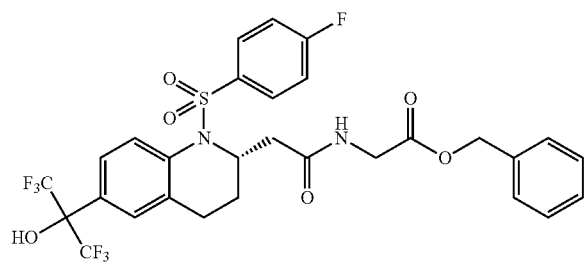 [SMILES: O=C(C[C@@H]1CCc2cc(C(O)(C(F)(F)F)C(F)(F)F)ccc2N1S(=O)(=O)c1ccc(F)cc1)NCC(=O)OCc1ccccc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (60 mg, 0.116 mmol) was treated with benzyl 2-aminoacetate, HCl (28.2 mg, 0.140 mmol) to provide the title compound (61 mg, 0.087 mmol, 75% yield). LC/MS(M+1): 663.3; $^1$H-NMR (400 MHz, CD$_3$OD) δ ppm 7.76 (d, J=8.8 Hz, 1H), 7.64-7.52 (m, 3H), 7.50-7.27 (m, 6H), 7.27-6.97 (m, 2H), 5.27-5.07 (m, 2H), 4.74 (m, 1H), 4.15-3.83 (m, 2H), 2.70 (m, 1H), 2.60-2.30 (m, 2H), 1.93 (m, 1H), 1.87-1.71 (m, 1H), 1.62-1.46 (m, 1H).

Example 45

(S)-2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetic acid

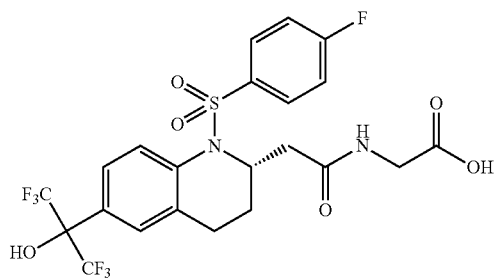 [SMILES: O=C(O)CNC(=O)C[C@@H]1CCc2cc(C(O)(C(F)(F)F)C(F)(F)F)ccc2N1S(=O)(=O)c1ccc(F)cc1]

To (S)-benzyl 2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetate (Ex. 44, 57 mg, 0.086 mmol) in MeOH (5 mL) was added 5% palladium on carbon (18.3 mg, 8.60 μmol) under a nitrogen atmosphere and the contents were stirred under a hydrogen atmosphere for 2 hrs and filtered. The filtrate was concentrated under reduced pressure to provide the title compound (49 mg, 0.081 mmol, 95% yield). LC/MS(M+1): 573.2; $^1$H-NMR (400 MHz, CD$_3$OD) δ ppm 7.78 (d, J=8.6 Hz, 1H), 7.72-7.55 (m, 3H), 7.44 (s, 1H), 7.20 (t, J=8.7 Hz, 2H), 4.78 (m, 1H), 3.93-3.73 (m, 2H), 2.77-2.52 (m, 2H), 2.44 (m, 1H), 2.09-2.01 (m, 1H), 1.93-1.84 (m, 1H), 1.62 (m, 1H).

Example 46

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N—((S)-5-oxotetrahydro furan-3-yl)acetamide

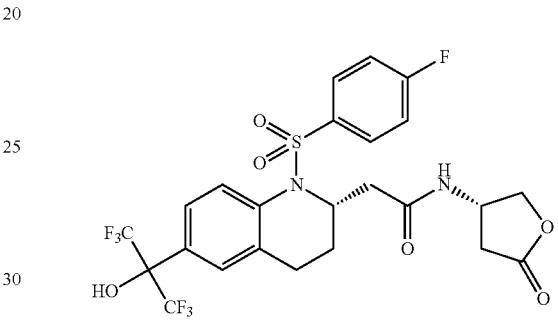

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with (S)-4-aminodihydrofuran-2(3H)-one (4.41 mg, 0.044 mmol) to provide the title compound (4.7 mg, 0.007 mmol, 27% yield). LC/MS(M+1): 599.3; $^1$H-NMR (500 MHz, DMSO-d$_6$) δ ppm 8.76 (s, 1H), 8.55 (d, J=5.9 Hz, 1H), 7.96 (s, 1H), 7.77-7.60 (m, 3H), 7.52 (d, J=8.9 Hz, 1H), 7.40-7.22 (m, 2H), 4.88-4.57 (m, 1H), 4.51-4.34 (m, 2H), 2.87-2.82 (m, 1H), 2.70-2.59 (m, 1H), 2.40-2.21 (m, 4H), 2.17 (m, 1H), 1.82-1.63 (m, 1H), 1.62-1.46 (m, 1H).

Example 47

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxy-3-methylpyrrolidin-1-yl)ethanone

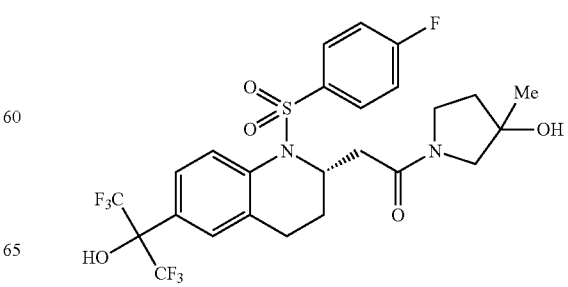

Step A: tert-butyl 3-hydroxy-3-methylpyrrolidine-1-carboxylate

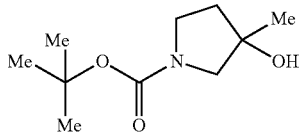 [SMILES: CC1(O)CCN(C(=O)OC(C)(C)C)C1]

3.0 M ether solution of methylmagnesium bromide (540 μl, 1.62 mmol) was added to a solution of tert-butyl 3-oxopyrrolidine-1-carboxylate (100 mg, 0.540 mmol) in THF (2 ml) at 0° C. and warmed up to rt for 1 hr., quenched with saturated NH₄Cl (2 ml), extracted with ethyl acetate (60 ml), washed with water, brine, dried (MgSO₄) and concentrated under reduced pressure to provide tert-butyl 3-hydroxy-3-methylpyrrolidine-1-carboxylate (105 mg) which was used as such for the next step without purification. ¹H NMR (400 MHz, CDCl₃) δ ppm 3.60-3.18 (m, 4H), 1.97-1.80 (m, 2H), 1.56-1.38 (m, 12H).

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxy-3-methylpyrrolidin-1-yl)ethanone

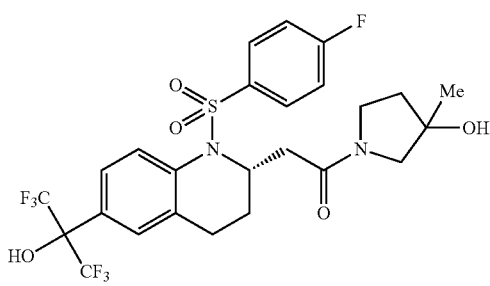 [SMILES: CC1(O)CCN(C(=O)C[C@@H]2CCc3cc(C(O)(C(F)(F)F)C(F)(F)F)ccc3N2S(=O)(=O)c2ccc(F)cc2)C1]

TFA (0.018 ml, 0.233 mmol) was added to a solution of tert-butyl 3-hydroxy-3-methylpyrrolidine-1-carboxylate (7.03 mg, 0.035 mmol) in DCM (1 mL) at rt and stirred for 1 hr. The mixture was concentrated, the residue was redissolved in DMF (1 ml) which was followed by the addition of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) BOP (15.45 mg, 0.035 mmol) and DIEA (0.016 ml, 0.093 mmol) at rt. The reaction mixture was stirred at rt for 1 hr. and purified by preparative HPLC (condition C) to provide the title compound (5.7 mg, 0.009 mmol, 40% yield). LC/MS(M+1): 599.2; ¹H-NMR (500 MHz, DMSO-d₆) δ ppm 8.75 (br. s., 1H), 7.96 (s, 1H), 7.85-7.49 (m, 4H), 7.50-7.34 (m, 2H), 4.95-4.72 (m, 1H), 4.72-4.59 (m, 1H), 3.32-3.11 (m, 2H), 3.13-2.99 (m, 1H), 2.71-2.56 (m, 2H), 2.46-2.31 (m, 1H), 2.09-1.84 (m, 2H), 1.82-1.44 (m, 3H), 1.26 (s, 3H).

Example 48

(S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-(2-(3-hydroxyazetidin-1-yl)-2-oxoethyl)acetamide

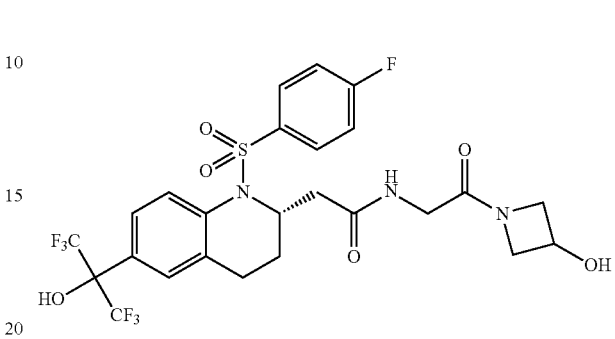

Following similar procedure as in Step B of Example 1, (S)-2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetic acid (12 mg, 0.021 mmol) was treated with azetidin-3-ol, HCl (3.44 mg, 0.031 mmol) to provide the title compound (9.0 mg, 0.014 mmol, 65% yield). LC/MS(M+1): 628.3; ¹H-NMR (400 MHz, CD₃OD) δ ppm 7.78 (d, J=8.8 Hz, 1H), 7.68-7.55 (m, 3H), 7.44 (s, 1H), 7.31-7.11 (m, 2H), 4.83-4.71 (m, 1H), 4.67-4.55 (m, 1H), 4.52-4.37 (m, 1H), 4.22 (m, 1H), 4.07-3.97 (m, 1H), 3.89-3.66 (m, 3H), 2.76-2.55 (m, 2H), 2.43 (m, 1H), 2.10-2.02 (m, 1H), 1.97-1.82 (m, 1H), 1.68-1.53 (m, 1H).

Example 49

1-(3-(aminomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

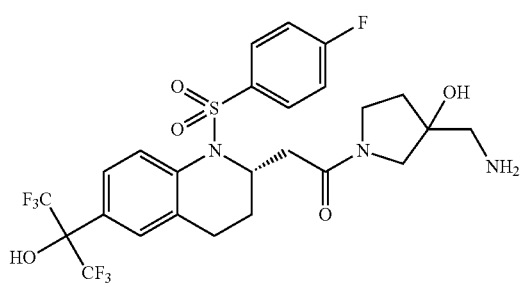 [SMILES: NCC1(O)CCN(C(=O)C[C@@H]2CCc3cc(C(O)(C(F)(F)F)C(F)(F)F)ccc3N2S(=O)(=O)c2ccc(F)cc2)C1]

Step A: tert-butyl 1-oxa-5-azaspiro[2.4]heptane-5-carboxylate

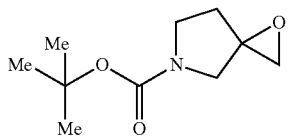 [SMILES: CC(C)(C)OC(=O)N1CCC2(CO2)C1]

mCPBA (275 mg, 1.60 mmol) was added to the solution of tert-butyl 3-methylenepyrrolidine-1-carboxylate (Ex. 41, step A, 195 mg, 1.06 mmol) in DCM (5 mL) at rt and stirred for 4 hrs. The mixture was quenched with saturated NaHCO₃ (2 ml), extracted with ethyl acetate (60 ml), washed with water, brine, dried (MgSO₄) and concentrated under reduced pressure. The residue was purified by flash silica gel chromatography with a mixture of 25% ethyl acetate in hexane to provide tert-butyl 1-oxa-5-azaspiro[2.4]heptane-5-carboxylate (150 mg, 0.753 mmol, 71% yield). ¹H NMR (400 MHz, CDCl₃) δ ppm 3.91-3.42 (m, 3H), 3.48-3.16 (m, 1H), 2.93 (s, 2H), 2.35-2.17 (m, 1H), 1.93-1.79 (m, 1H), 1.47 (s, 9H).

Step B: 3-(azidomethyl)pyrrolidin-3-ol

Sodium azide (48.9 mg, 0.753 mmol) was added to a solution of tert-butyl 1-oxa-5-azaspiro[2.4]heptane-5-carboxylate (50 mg, 0.251 mmol) in DMF (1 mL) at rt and heated to 80° C. for 15 hrs. The mixture was quenched with saturated NaHCO₃ (2 ml), extracted with ethyl acetate (60 ml), washed with water, brine, dried (MgSO₄) and concentrated under vacuum. The residue was dissolved in DCM (1 mL) and TFA (0.2 mL, 2.60 mmol) was added. The resultant mixture was stirred at rt for 1 hr and concentrated under vacuum to provide tert-butyl 3-(azidomethyl)-3-hydroxypyrrolidine-1-carboxylate as TFA salt (63 mg). The crude material was directly converted to the next step without purification. ¹H NMR (400 MHz, CD₃OD) δ ppm 4.01-3.84 (m, 1H), 3.68-3.57 (m, 1H), 3.56-3.41 (m, 3H), 3.16-3.16 (m, 1H), 2.24-1.96 (m, 2H).

Step C: 1-(3-(azidomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

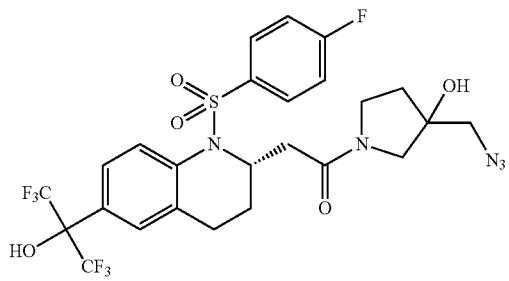 [SMILES: [N-]=[N+]=NCC1(O)CCN(C(=O)C[C@@H]2CCc3cc(C(O)(C(F)(F)F)C(F)(F)F)ccc3N2S(=O)(=O)c2ccc(F)cc2)C1]

Following a similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (70 mg, 0.136 mmol) was treated with 3-(azidomethyl)pyrrolidin-3-ol, TFA (52.2 mg, 0.204 mmol) to provide 1-(3-(azidomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (35 mg, 0.055 mmol, 40% yield). LC/MS(M+1): 640.2; ¹H-NMR (400 MHz, CD₃OD) δ ppm 7.90-7.71 (m, 1H), 7.69-7.51 (m, 3H), 7.44 (br. s., 1H), 7.20 (t, J=8.7 Hz, 2H), 4.78-4.68 (m, 1H), 3.80-3.35 (m, 6H), 2.83-2.72 (m, 1H), 2.63-2.43 (m, 2H), 2.13-1.81 (m, 4H), 1.72-1.50 (m, 1H).

Step D: 1-(3-(aminomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

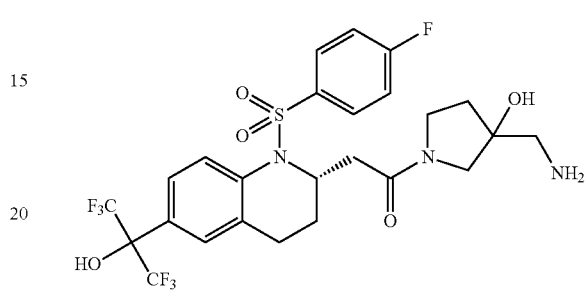

A mixture of 1-(3-(azidomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (25 mg, 0.039 mmol) and 5% palladium on carbon (16.6 mg, 7.82 μmol) in MeOH (5 ml) was stirred under a hydrogen atmosphere for 2 hrs. and filtered. The filtrate was concentrated under reduced pressure to provide the title compound (23 mg, 0.034 mmol, 86% yield) as a mixture of diastereomers.

LC/MS(M+1): 614.3; ¹H-NMR (400 MHz, CD₃OD) δ ppm 7.90-7.74 (m, 1H), 7.70-7.54 (m, 3H), 7.44 (br. s., 1H), 7.20 (t, J=8.7 Hz, 2H), 4.79-4.60 (m, 1H), 3.84-3.39 (m, 5H), 2.90-2.76 (m, 2H), 2.65-2.42 (m, 2H), 2.17-1.81 (m, 4H), 1.69-1.51 (m, 1H).

Example 50

(S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxyazetidin-1-yl)ethanone

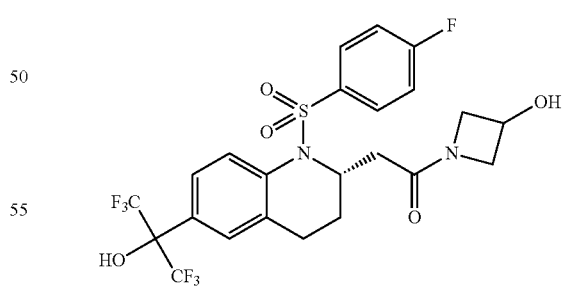

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with azetidin-3-ol, HCl (3.83 mg, 0.035 mmol) to provide the title compound (9.1 mg, 0.016 mmol, 69% yield). LC/MS(M+1): 571.2; ¹H NMR (400 MHz, CD₃OD) δ ppm 7.78 (d, J=8.8 Hz, 1H), 7.68-7.55 (m, 3H), 7.44 (s, 1H), 7.31-7.11 (m, 2H), 5.65-5.55 (m, 2H), 4.83-4.71 (m, 1H), 4.67-4.55 (m, 1H), 4.52-4.37 (m, 1H), 4.22 (m, 1H), 4.07-3.97 (m, 1H), 3.89-3.66 (m, 3H), 2.76-2.55 (m, 2H), 2.43 (m, 1H), 2.10-2.02 (m, 1H), 1.97-1.82 (m, 1H), 1.68-1.53 (m, 1H).

Example 51

7-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-1-oxa-3,7-diazaspiro[4.4]nonan-2-one

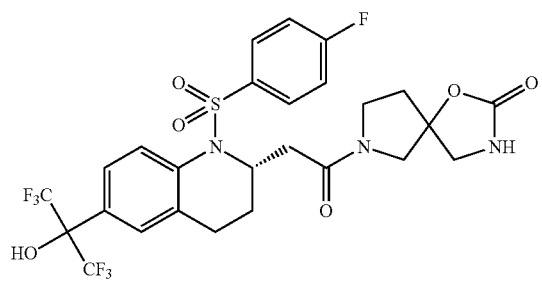

DIEA (5.98 µl, 0.034 mmol) and di(1H-imidazol-1-yl)methanone (5.55 mg, 0.034 mmol) were added to the solution of 1-(3-(aminomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (Ex. 49, 7 mg, 0.011 mmol) in THF (1 mL) at rt and stirred for 4 hrs. The mixture was concentrated under reduced pressure and purified by preparative HPLC (condition C) to provide the title compound (1.5 mg, 0.002 mmol, 20% yield). LC/MS(M+1): 640.3; $^1$H-NMR (500 MHz, DMSO-$d_6$) δ ppm 7.81-7.48 (m, 5H), 7.46-7.28 (m, 2H), 4.80-4.50 (m, 1H), 3.79-3.49 (m, 2H), 2.69-2.55 (m, 2H), 2.21-1.86 (m, 3H), 1.64-1.52 (m, 1H).

Example 52

(S)—N-((1H-tetrazol-5-yl)methyl)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetamide

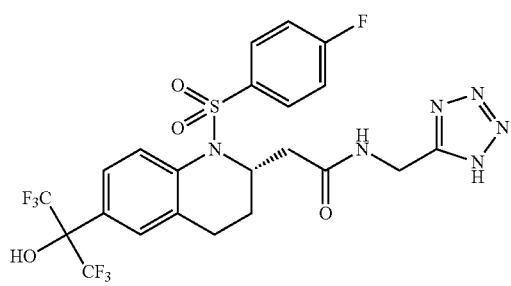 [SMILES: O=C(C[C@@H]1CCc2cc(C(O)(C(F)(F)F)C(F)(F)F)ccc2N1S(=O)(=O)c1ccc(F)cc1)NCc1nnn[nH]1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (1H-tetrazol-5-yl)methanamine (3.46 mg, 0.035 mmol) to provide the title compound (11.8 mg, 0.018 mmol, 82% yield). LC/MS(M+1): 597.2; $^1$H-NMR (500 MHz, DMSO-$d_6$) δ ppm 8.75 (br. s., 1H), 8.46 (d, J=4.5 Hz, 1H), 7.80-7.60 (m, 3H), 7.51 (d, J=8.4 Hz, 1H), 7.45-7.32 (m, 3H), 4.86-4.62 (m, 1H), 4.48-4.30 (m, 2H), 2.68 (m, 1H), 2.47-2.32 (m, 2H), 2.23-2.10 (m, 1H), 1.72-1.63 (m, 1H), 1.63-1.50 (m, 1H).

Example 53

N-(1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidin-3-yl)benzamide

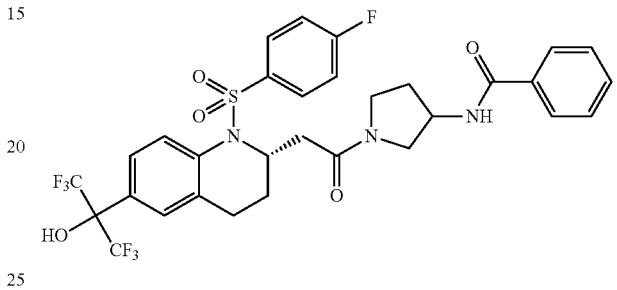

BOP (18.1 mg, 0.041 mmol) was added to the solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (14 mg, 0.027 mmol), DIEA (0.014 ml, 0.081 mmol) and tert-butyl pyrrolidin-3-ylcarbamate (7.59 mg, 0.041 mmol) in DMF (1 ml) at rt and stirred for 1 hr. The reaction mixture was extracted with ethyl acetate (60 ml), washed with water, brine, dried (MgSO$_4$) and concentrated by vacuum. The residue was dissolved in DCM (1 mL), TFA (0.2 ml, 2.60 mmol) was added and the contents stirred at rt for 1 hr and concentrated under reduced pressure. To the residue was added DMF (1 ml), followed by benzoic acid (4.98 mg, 0.041 mmol), BOP (18.1 mg, 0.041 mmol) and DIEA (0.014 ml, 0.081 mmol) at rt. The resulting mixture was stirred at rt for 1 hr. and purified by preparative HPLC (condition C) to provide the title compound (16.8 mg, 0.023 mmol, 85% yield) as a mixture of diastereomers. LC/MS(M+1): 688.4; $^1$H-NMR (500 MHz, DMSO-$d_6$) δ ppm 8.76 (br. s., 1H), 8.62-8.40 (m, 1H), 7.91-7.77 (m, 2H), 7.77-7.26 (m, 10H), 4.69 (m, 1H), 4.56-4.22 (m, 1H), 3.76-3.54 (m, 2H), 3.27-3.14 (m, 1H), 2.69-2.54 (m, 4H), 2.19-1.77 (m, 4H), 1.65-1.38 (m, 1H).

Example 54

1-ethyl-3-((1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-hydroxypyrrolidin-3-yl)methyl)urea

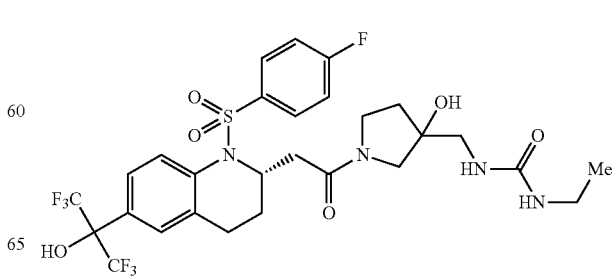

A solution of 1-(3-(aminomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (Ex. 49, 8 mg, 0.013 mmol), DIEA (6.83 μl, 0.039 mmol) and ethyl isocyante (1.854 mg, 0.026 mmol) in DCM (1 ml) was stirred at rt for 1 hr, concentrated under reduced pressure and purified by preparative HPLC (condition C) to provide the title compound (2.8 mg, 0.004 mmol, 31% yield). LC/MS(M+1): 685.3; $^1$H-NMR (500 MHz, DMSO-$d_6$) δ ppm 9.05-8.62 (m, 1H), 7.73-7.64 (m, 1H), 7.64-7.57 (m, 2H), 7.55-7.48 (m, 1H), 7.46-7.30 (m, 3H), 5.97 (m, 2H), 5.34-5.01 (m, 1H), 4.65 (br. s., 1H), 3.24-2.91 (m, 5H), 2.70-2.56 (m, 3H), 2.06-1.87 (m, 2H), 1.83-1.51 (m, 3H), 1.09-0.85 (m, 3H).

Example 55

Ethyl ((1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-hydroxypyrrolidin-3-yl)methyl)carbamate

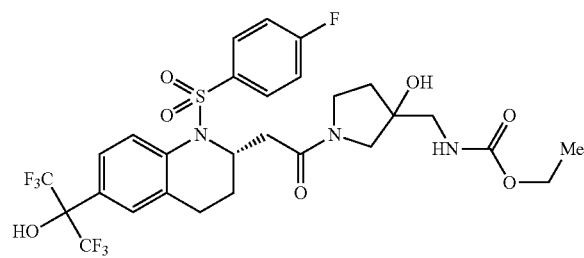 [SMILES: CCOC(=O)NCC1(O)CCN(C(=O)C[C@@H]2CCc3cc(C(O)(C(F)(F)F)C(F)(F)F)ccc3N2S(=O)(=O)c2ccc(F)cc2)C1]

A solution of 1-(3-(aminomethyl)-3-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (Ex. 49, 8 mg, 0.013 mmol), DIEA (6.83 μl, 0.039 mmol) and ethyl chloroformate (2.83 mg, 0.026 mmol) in DCM (1 ml) was stirred at rt for 1 hr, concentrated under reduced pressure and purified by preparative HPLC to provide the title compound (2.6 mg, 0.004 mmol, 28% yield). LC/MS(M+1): 686.3; $^1$H-NMR (500 MHz, DMSO-$d_6$) δ ppm 8.77 (br. s., 1H), 7.80-7.51 (m, 4H), 7.51-7.27 (m, 3H), 5.14-4.83 (m, 1H), 4.80-4.54 (m, 1H), 4.22-3.85 (m, 2H), 3.29-2.96 (m, 5H), 2.64-2.42 (m, 3H), 2.07-1.44 (m, 5H), 1.27-0.88 (m, 3H).

Example 56

7-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)-1,3-dioxa-7-azaspiro[4.4]nonan-2-one

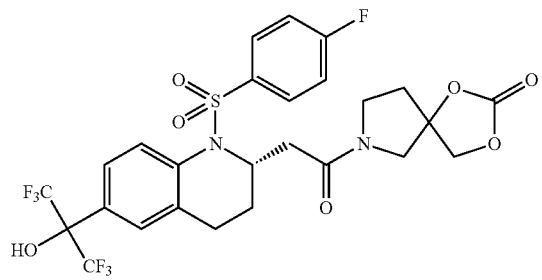 [SMILES: O=C1OCC2(CCN(C(=O)C[C@@H]3CCc4cc(C(O)(C(F)(F)F)C(F)(F)F)ccc4N3S(=O)(=O)c3ccc(F)cc3)C2)O1]

DIEA (0.012 mL, 0.068 mmol) and di(1H-imidazol-1-yl)methanone (11.08 mg, 0.068 mmol) were added to the solution of 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(3-hydroxy-3-(hydroxymethyl)pyrrolidin-1-yl)ethanone (Ex. 41.14 mg, 0.023 mmol) in THF (1 mL) at rt and stirred for 4 hrs. The reaction mixture was concentrated under vacuum and the residue was purified by preparative HPLC (condition C) to provide the title compound (5.2 mg, 0.008 mmol, 36% yield). LC/MS(M+1): 641.3; $^1$H-NMR (500 MHz, 1 to 1 mixture of $CDCl_3$ and $CD_3OD$) δ ppm 7.98 (s, 1H), 7.86-7.71 (m, 1H), 7.67-7.62 (m, 1H), 7.48 (s, 2H), 7.48-7.38 (m, 1H), 7.13 (d, J=8.4 Hz, 2H), 4.62-4.47 (m, 2H), 4.09-3.52 (m, 4H), 2.88-2.77 (m, 1H), 2.66-2.02 (m, 6H), 1.91-1.72 (m, 1H), 1.69-1.53 (m, 1H).

Example 57

N-((1-ethyl-4-methyl-2,5-dioxoimidazolidin-4-yl)methyl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamide

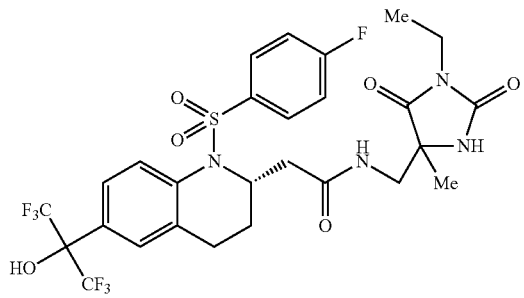 [SMILES: CCN1C(=O)NC(C)(CNC(=O)C[C@@H]2CCc3cc(C(O)(C(F)(F)F)C(F)(F)F)ccc3N2S(=O)(=O)c2ccc(F)cc2)C1=O]

Following similar procedures as in Example 27, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was converted to the title compound (9.3 mg, 0.014 mmol, 59% yield). LC/MS(M+1): 669.3; $^1$H-NMR (500 MHz, 1 to 1 mixture of $CDCl_3$ and $CD_3OD$) δ ppm 7.78 (d, J=8.4 Hz, 1H), 7.61 (s, 1H), 7.60-7.51 (m, 2H), 7.42 (s, 1H), 7.22-6.67 (m, 2H), 4.79-4.72 (m, 1H), 3.62-3.44 (m, 4H), 2.74-2.63 (m, 1H), 2.58-2.43 (m, 1H), 2.32 (m, 1H), 2.08-1.74 (m, 2H), 1.59-1.48 (m, 1H), 1.44-1.36 (m, 3H), 1.25-0.99 (m, 3H).

Example 58

Cis-2-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)cyclopentanecarboxamide

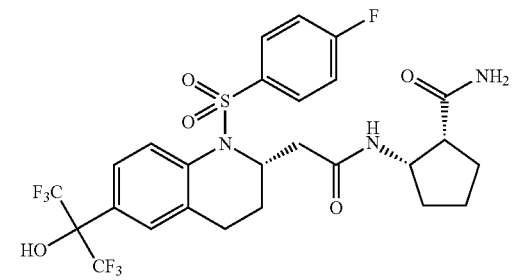 [SMILES: NC(=O)[C@@H]1CCC[C@@H]1NC(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (±) cis-2-aminocyclopentanecarboxamide (4.5 mg, 0.035 mmol) to provide the title compound (11.9 mg, 0.019 mmol, 82% yield). LC/MS(M+1): 626.3; $^1$H-NMR (500 MHz, DMSO-$d_6$) δ ppm 8.74 (br. s., 1H), 7.88-7.61 (m, 4H), 7.52 (d, J=8.9 Hz, 1H), 7.46-7.31 (m, 3H), 7.13 (br. s., 1H), 6.69 (m, 1H), 4.67 (dquin, J=10.0, 5.2 Hz, 1H), 4.34-4.14 (m, 1H), 2.73-2.62 (m, 2H), 2.44-2.05 (m, 3H), 1.91-1.29 (m, 8H).

Example 59

1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidine-3-carboxamide

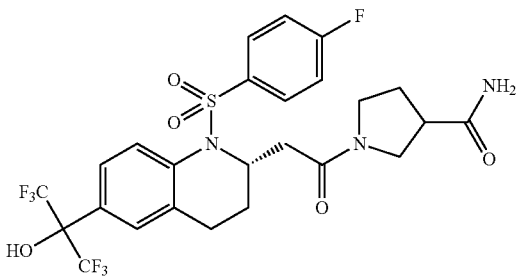 [SMILES: NC(=O)C1CCN(C(=O)C[C@@H]2CCc3cc(C(O)(C(F)(F)F)C(F)(F)F)ccc3N2S(=O)(=O)c2ccc(F)cc2)C1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with pyrrolidine-3-carboxamide, TFA (7.97 mg, 0.035 mmol) to provide the title compound (12.8 mg, 0.021 mmol, 90% yield) as a mixture of diastereomers. LC/MS(M+1): 612.3; $^1$H-NMR (500 MHz, DMSO-$d_6$) δ ppm 8.75 (m, 1H), 7.76-7.50 (m, 4H), 7.50-7.32 (m, 4H), 7.08-6.75 (m, 1H), 4.67 (m, 1H), 3.61-3.45 (m, 2H), 3.26-3.14 (m, 2H), 2.99-2.82 (m, 2H), 2.73-2.57 (m, 2H), 2.13-1.77 (m, 4H), 1.58 (m, 1H).

Example 60

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(2-oxooxetan-3-yl)acetamide

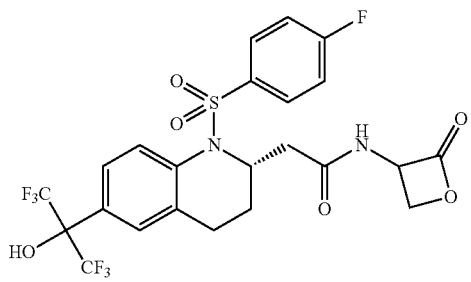 [SMILES: O=C(C[C@@H]1CCc2cc(C(O)(C(F)(F)F)C(F)(F)F)ccc2N1S(=O)(=O)c1ccc(F)cc1)NC1COC1=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with 3-aminooxetan-2-one (3.0 mg, 0.035 mmol) to provide the title compound (4.4 mg, 0.007 mmol, 31% yield) as a mixture of diastereomers. LC/MS(M+1): 585.2; $^1$H-NMR (500 MHz, DMSO-$d_6$) δ ppm 8.75 (br. s., 1H), 7.76-7.50 (m, 4H), 7.50-7.32 (m, 4H), 7.08-6.75 (m, 1H), 4.67 (m, 1H), 3.61-3.45 (m, 1H), 3.26-3.14 (m, 1H), 2.99-2.82 (m, 1H), 2.73-2.57 (m, 1H), 2.13-1.77 (m, 2H), 1.58 (m, 1H).

Example 61

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(2-(3-hydroxy-3-(hydroxymethyl)pyrrolidin-1-yl)-2-oxoethyl)acetamide

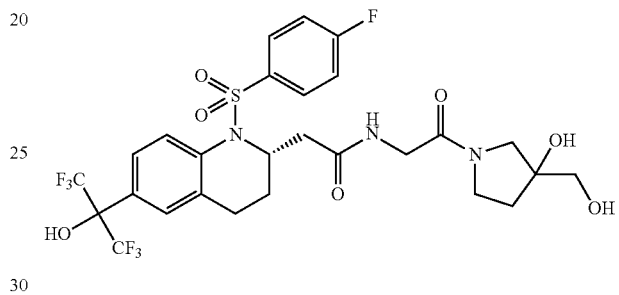

Following similar procedure as in Step B of Example 1, (S)-2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetic acid (Ex. 45, 11 mg, 0.019 mmol) was treated with 3-(hydroxymethyl)pyrrolidin-3-ol, TFA (6.66 mg, 0.029 mmol) to provide the title compound (9.6 mg, 0.014 mmol, 73% yield). LC/MS(M+1): 672.4; $^1$H-NMR (500 MHz, DMSO-$d_6$) δ ppm 8.77 (br. s., 1H), 8.14 (dt, J=10.9, 5.4 Hz, 1H), 7.80-7.63 (m, 3H), 7.52 (d, J=8.9 Hz, 1H), 7.49-7.30 (m, 3H), 5.11-4.56 (m, 3H), 3.90-3.62 (m, 2H), 3.56-3.43 (m, 2H), 3.25-3.08 (m, 1H), 2.81-2.68 (m, 1H), 2.48-2.37 (m, 2H), 2.21 (m, 1H), 2.10-1.94 (m, 1H), 1.89-1.80 (m, 1H), 1.77-1.56 (m, 4H).

Example 62

(S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-(2-(hydroxymethyl)phenyl)acetamide

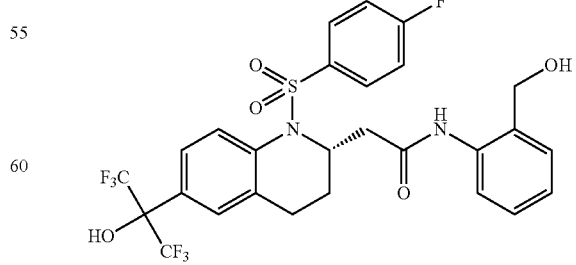

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (12 mg, 0.023 mmol) was treated with (2-aminophenyl)methanol (4.30 mg, 0.035 mmol) to provide the title compound (1.2 mg, 0.002 mmol, 8% yield). LC/MS (M+1): 621.3; $^1$H-NMR (500 MHz, DMSO-$d_6$) δ ppm 9.38 (s, 1H), 7.72 (d, J=8.4 Hz, 1H), 7.69-7.63 (m, 2H), 7.55 (d, J=8.9 Hz, 1H), 7.53-7.31 (m, 5H), 7.25-7.08 (m, 2H), 4.81 (t, J=5.4 Hz, 1H), 4.45 (s, 2H), 2.80-2.67 (m, 1H), 2.60 (d, J=6.9 Hz, 2H), 2.22 (m, 1H), 1.83-1.74 (m, 1H), 1.72-1.58 (m, 1H).

Example 63

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(2-((trans-4-hydroxycyclohexyl)amino)-2-oxoethyl)acetamide

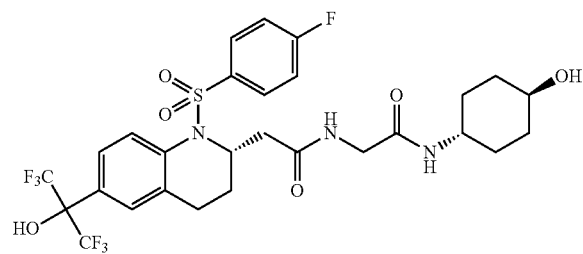 [SMILES: O=C(C[C@@H]1CCc2cc(C(O)(C(F)(F)F)C(F)(F)F)ccc2N1S(=O)(=O)c1ccc(F)cc1)NCC(=O)N[C@H]1CC[C@H](O)CC1]

Following similar procedure as in Step B of Example 1, (S)-2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetic acid (Ex. 45, 11 mg, 0.019 mmol) was treated with (±) trans-4-aminocyclohexanol, TFA (6.61 mg, 0.029 mmol) to provide the title compound (7.7 mg, 0.011 mmol, 60% yield) as a mixture of diastereomers LC/MS(M+1): 670.3; $^1$H-NMR (500 MHz, DMSO-$d_6$) δ ppm 8.76 (br. s., 1H), 8.16 (d, J=4.0 Hz, 1H), 7.76-7.58 (m, 4H), 7.52 (d, J=8.4 Hz, 1H), 7.47-7.28 (m, 3H), 4.83-4.62 (m, 1H), 4.62-4.48 (m, 1H), 4.12-3.84 (m, 1H), 3.72-3.53 (m, 2H), 3.44 (br. s., 1H), 2.74-2.67 (m, 1H), 2.45-2.31 (m, 2H), 2.25-2.09 (m, 1H), 1.88-1.53 (m, 6H), 1.33-0.98 (m, 4H).

Example 64

(R)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidine-2-carboxamide

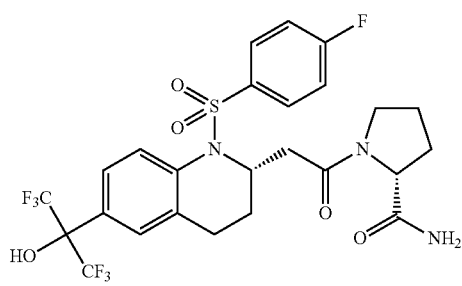 [SMILES: NC(=O)[C@H]1CCCN1C(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (11 mg, 0.021 mmol) was treated with (R)-pyrrolidine-2-carboxamide (3.65 mg, 0.032 mmol) to provide the title compound (10 mg, 0.016 mmol, 77% yield). LC/MS(M+1): 612.3; $^1$H-NMR (500 MHz, 1 to 1 mixture of CDCl$_3$ and CD$_3$OD) δ ppm 7.77 (d, J=8.4 Hz, 1H), 7.63 (s, 1H), 7.58-7.38 (m, 3H), 7.26-7.03 (m, 2H), 4.70-4.61 (m, 1H), 4.55-4.42 (m, 1H), 3.65-3.44 (m, 2H), 2.89 (m, 1H), 2.60-2.45 (m, 2H), 2.25-2.15 (m, 1H), 2.10-1.94 (m, 4H), 1.86-1.77 (m, 1H), 1.59-1.50 (m, 1H).

Example 65

(S)-1-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetyl)pyrrolidine-2-carboxamide

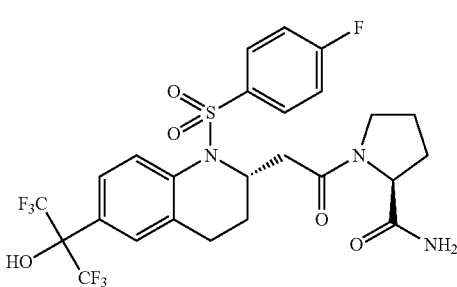 [SMILES: NC(=O)[C@@H]1CCCN1C(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (11 mg, 0.021 mmol) was treated with (S)-pyrrolidine-2-carboxamide (3.65 mg, 0.032 mmol) to provide the title compound (11.3 mg, 0.018 mmol, 87% yield). LC/MS(M+1): 612.3; $^1$H-NMR (500 MHz, 1 to 1 mixture of CDCl$_3$ and CD$_3$OD) δ ppm 7.85-7.74 (m, 1H), 7.60 (s, 1H), 7.54-7.45 (m, 2H), 7.41 (s, 1H), 7.11 (t, J=8.7 Hz, 2H), 4.67-4.57 (m, 1H), 4.42 (m, 1H), 3.68-3.50 (m, 2H), 3.08-2.83 (m, 1H), 2.62-2.42 (m, 2H), 2.34 (m, 1H), 2.21-1.88 (m, 4H), 1.87-1.74 (m, 1H), 1.64-1.51 (m, 1H).

Example 66 trans-3-(dimethylamino)-4-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

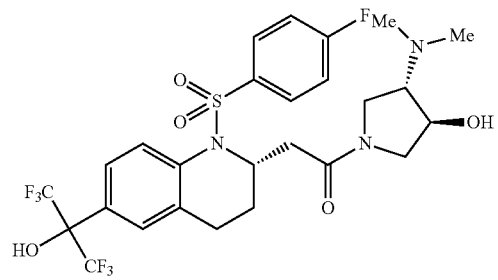 [SMILES: CN(C)[C@H]1CN(C(=O)C[C@@H]2CCc3cc(C(O)(C(F)(F)F)C(F)(F)F)ccc3N2S(=O)(=O)c2ccc(F)cc2)C[C@@H]1O]

Step A: 1-(6-oxa-3-azabicyclo[3.1.0]hexan-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

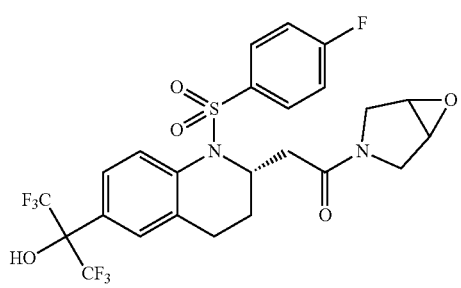 [SMILES: O=C(C[C@@H]1CCc2cc(C(O)(C(F)(F)F)C(F)(F)F)ccc2N1S(=O)(=O)c1ccc(F)cc1)N1CC2OC2C1]

mCPBA (54.8 mg, 0.318 mmol) was added to the solution of (S)-1-(2,5-dihydro-1H-pyrrol-1-yl)-2-(1-((4-fluorophenyl)sulfonyl)-6-(1,1,1,3,3,3-hexafluoro-2-hydroxypropan-2-yl)-1,2,3,4-tetrahydroquinolin-2-yl)ethanone (Ex. 38, step A, 60 mg, 0.106 mmol) in DCM (3 ml) at rt and stirred for 15 hrs. The reaction mixture was diluted with DCM (60 ml), washed with saturated aq. NaHCO$_3$, water, brine, dried (MgSO$_4$) and concentrated under vacuum. The residue was purified by flash silica gel chromatography using a mixture of 70% ethyl acetate in hexane to provide 1-(6-oxa-3-azabicyclo[3.1.0]hexan-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (54 mg, 0.093 mmol, 88% yield). LC/MS(M+1): 583.2. $^1$H-NMR (400 MHz, CD$_3$OD) δ ppm 7.92-7.70 (m, 1H), 7.67-7.51 (m, 3H), 7.44 (br. s., 1H), 7.31-7.07 (m, 2H), 4.79-4.65 (m, 1H), 3.94-3.71 (m, 3H), 3.72-3.38 (m, 3H), 2.85-2.69 (m, 1H), 2.64-2.35 (m, 2H), 2.06-1.75 (m, 2H), 1.67-1.44 (m, 1H).

Step B: trans-3-(dimethylamino)-4-hydroxypyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

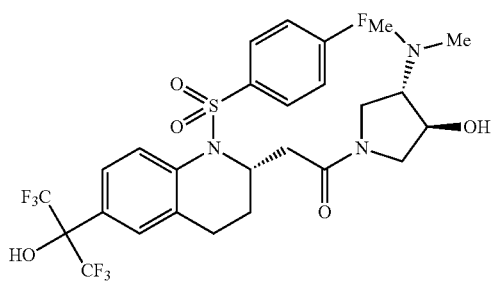

A 2.0 M THF solution of dimethylamine (0.103 ml, 0.206 mmol) was added to the mixture of 1-(6-oxa-3-azabicyclo[3.1.0]hexan-3-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone (12 mg, 0.021 mmol) in MeOH (1 ml) at rt. It was heated to 140° C. in a microwave oven for 30 min, cooled to rt and purified by preparative HPLC to provide the title compound (7.7 mg, 0.012 mmol, 57% yield as a mixture of diastereomers.

LC/MS(M+1): 628.3; $^1$H-NMR (500 MHz, 1 to 1 mixture of CDCl$_3$ and CD$_3$OD) δ ppm 7.89-7.74 (m, 1H), 7.71-7.61 (m, 1H), 7.58-7.47 (m, 2H), 7.47-7.35 (m, 1H), 7.18-7.00 (m, 2H), 4.42-4.18 (m, 3H), 3.84-3.72 (m, 2H), 3.50-3.40 (m, 1H), 3.30-3.22 (m, 1H), 2.93-2.73 (m, 2H), 2.46 (m, 1H), 2.42-2.28 (m, 6H), 2.05 (m, 1H), 1.74 (m, 1H), 1.62-1.47 (m, 1H).

Example 67

1-(cis-3,4-dihydroxy-2-(hydroxymethyl)pyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

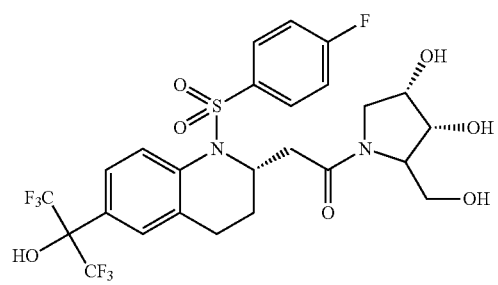 [SMILES: O=C(C[C@@H]1CCc2cc(C(O)(C(F)(F)F)C(F)(F)F)ccc2N1S(=O)(=O)c1ccc(F)cc1)N1C[C@H](O)[C@H](O)C1CO]

Step A: (2,5-dihydro-1H-pyrrol-2-yl)methanol

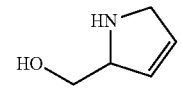

A 1.0 M THF solution of LAH (1.06 ml, 1.06 mmol) was added to a solution of 2,5-dihydro-1H-pyrrole-2-carboxylic acid (60 mg, 0.530 mmol) in THF (2 ml) at rt and stirred for 30 min. Then it was carefully quenched with saturated aq. NH$_4$Cl (5 ml) and extracted with ethyl acetate (60 ml), washed with water, brine, dried (MgSO$_4$) and concentrated under vacuum to provide (2,5-dihydro-1H-pyrrol-2-yl)methanol (20 mg) which was used as such for the subsequent step without further purification.

Step B: 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(2-(hydroxymethyl)-2,5-dihydro-1H-pyrrol-1-yl)ethanone

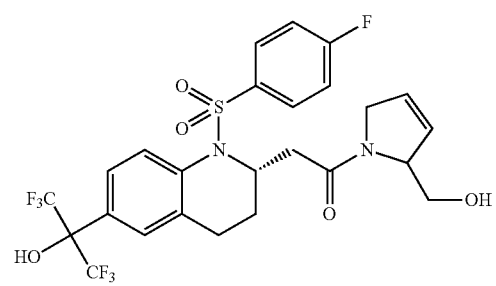 [SMILES: O=C(C[C@@H]1CCc2cc(C(O)(C(F)(F)F)C(F)(F)F)ccc2N1S(=O)(=O)c1ccc(F)cc1)N1CC=CC1CO]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (16 mg, 0.031 mmol) was treated with (2,5-dihydro-1H-pyrrol-2-yl)methanol (6.2 mg, 0.062 mmol) to provide 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(2-(hydroxymethyl)-2,5-dihydro-1H-pyrrol-1-yl)ethanone (8.0 mg, 0.013 mmol, 41% yield). LC/MS(M+1): 597.2; $^1$H-NMR (400 MHz, CDCl$_3$) δ ppm 8.07-7.75 (m, 1H), 7.60 (br. s., 1H), 7.55-7.43 (m, 2H), 7.43-7.35 (m, 1H), 7.15-6.79 (m, 2H), 5.99-5.65 (m, 1H), 4.85-4.57 (m, 1H), 4.35-4.23 (m, 2H), 3.84-3.59 (m, 1H), 3.07-2.85 (m, 2H), 2.65-2.38 (m, 3H), 2.29-1.66 (m, 3H), 1.65-1.49 (m, 1H).

Step C: 1-(cis-3,4-dihydroxy-2-(hydroxymethyl) pyrrolidin-1-yl)-2-((S)-1-((4-fluorophenyl)sulfonyl)-6-(1,1,1,3,3,3-hexafluoro-2-hydroxypropan-2-yl)-1,2,3,4-tetrahydroquinolin-2-yl)ethanone

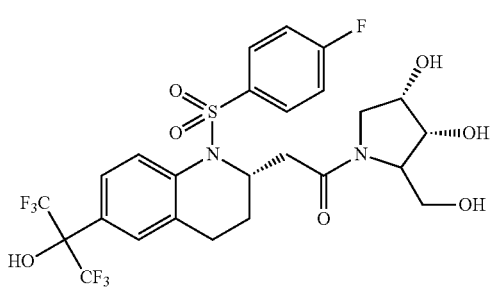 [SMILES: O=C(C[C@@H]1CCc2cc(C(O)(C(F)(F)F)C(F)(F)F)ccc2N1S(=O)(=O)c1ccc(F)cc1)N1C[C@H](O)[C@H](O)C1CO]

Following a similar procedure as in Step B of Example 38, 2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-1-(2-(hydroxymethyl)-2,5-dihydro-1H-pyrrol-1-yl)ethanone (8 mg, 0.013 mmol) was converted to the title compound as a mixture of two diastereomers (4.0 mg, 0.006 mmol, 46% yield). LC/MS(M+1): 631.3. $^1$H-NMR (500 MHz, DMSO-d$_6$) δ ppm 8.75 (m, 1H), 7.72-7.47 (m, 4H), 7.46-7.34 (m, 3H), 5.10-4.57 (m, 4H), 4.14 (m, 1H), 3.98-3.82 (m, 2H), 3.65-3.50 (m, 1H), 3.24-3.09 (m, 1H), 2.72-2.54 (m, 2H), 2.06-1.78 (m, 2H), 1.56 (m, 1H).

Example 68

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(2-oxotetrahydrofuran-3-yl)acetamide

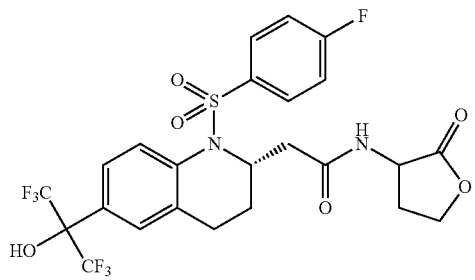 [SMILES: O=C(C[C@@H]1CCc2cc(C(O)(C(F)(F)F)C(F)(F)F)ccc2N1S(=O)(=O)c1ccc(F)cc1)NC1CCOC1=O]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (11 mg, 0.021 mmol) was treated with 3-aminodihydrofuran-2(3H)-one, hydrobromide (5.83 mg, 0.032 mmol) to provide the title compound (8.8 mg, 0.014 mmol, 68% yield). LC/MS(M+1): 599.2; $^1$H-NMR (500 MHz, DMSO-d$_6$) δ ppm 8.78 (br. s., 1H), 8.54 (dd, J=19.8, 7.4 Hz, 1H), 7.77-7.58 (m, 3H), 7.52 (d, J=8.4 Hz, 1H), 7.45-7.29 (m, 3H), 4.70 (m, 1H), 4.62-4.42 (m, 1H), 4.34 (m, 1H), 4.27-4.08 (m, 1H), 2.69-2.60 (m, 1H), 2.43-2.29 (m, 3H), 2.24-2.01 (m, 2H), 1.83-1.42 (m, 2H).

Example 69

2-((S)-1-((4-fluorophenyl)sulfonyl)-6-(1,1,1,3,3,3-hexafluoro-2-hydroxypropan-2-yl)-1,2,3,4-tetrahydroquinolin-2-yl)-N-(2-oxo-2-(((S)-5-oxotetrahydrofuran-3-yl)amino)ethyl)acetamide

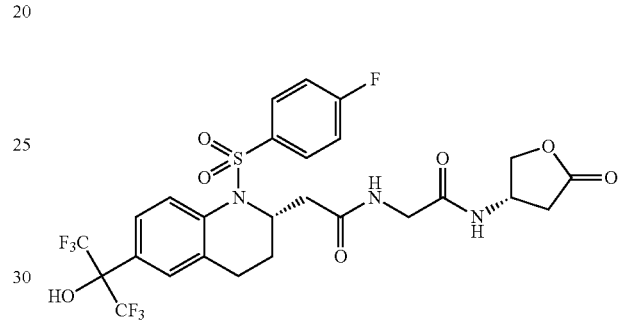

Following similar procedure as in Step B of Example 1, (S)-2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetamido)acetic acid (11 mg, 0.019 mmol) was treated with (S)-4-aminodihydrofuran-2(3H)-one (2.9 mg, 0.029 mmol) to provide the title compound (4.3 mg, 0.006 mmol, 33% yield). LC/MS(M+1): 656.3; $^1$H-NMR (500 MHz, DMSO-d$_6$) δ ppm 8.45 (d, J=5.9 Hz, 1H), 8.25 (t, J=5.7 Hz, 1H), 7.76-7.57 (m, 3H), 7.52 (m, 1H), 7.49-7.32 (m, 3H), 4.84-4.63 (m, 1H), 4.54-4.33 (m, 2H), 4.14-3.98 (m, 1H), 3.76-3.53 (m, 3H), 2.89-2.80 (m, 1H), 2.73-2.66 (m, 1H), 2.46-2.34 (m, 2H), 2.18 (m, 1H), 1.72-1.52 (m, 2H).

Example 70

Exo-3-(2-((S)-1-((4-fluorophenyl)sulfonyl)-6-(1,1,1,3,3,3-hexafluoro-2-hydroxypropan-2-yl)-1,2,3,4-tetrahydroquinolin-2-yl)acetamido)-7-oxabicyclo[2.2.1]heptane-2-carboxamide

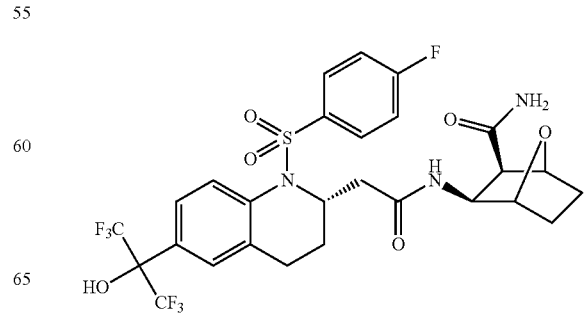

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (11 mg, 0.021 mmol) was treated with exo-3-amino-7-oxabicyclo[2.2.1]heptane-2-carboxamide (5.00 mg, 0.032 mmol) to provide the title compound as a mixture of two diatereomers (13.2 mg, 0.020 mmol, 95% yield).

LC/MS(M+1): 654.3; $^1$H-NMR (500 MHz, DMSO-$d_6$) δ 8.75 (br. s., 1H), 8.08-7.89 (m, 1H), 7.77-7.59 (m, 3H), 7.51 (d, J=8.4 Hz, 1H), 7.43-7.29 (m, 1H), 7.02-6.67 (m, 2H), 4.84-4.62 (m, 1H), 4.56 (t, J=4.5 Hz, 1H), 4.29 (m, 1H), 4.12 (m, 1H), 2.84-2.63 (m, 2H), 2.42-2.00 (m, 3H), 1.72-1.32 (m, 6H).

Example 71

(±) 2-(1-((4-fluorophenyl)sulfonyl)-6-(1,1,1,3,3,3-hexafluoro-2-hydroxypropan-2-yl)-1,2,3,4-tetrahydroquinolin-2-yl)-N-(2-hydroxy-2-methylpropyl)acetamide

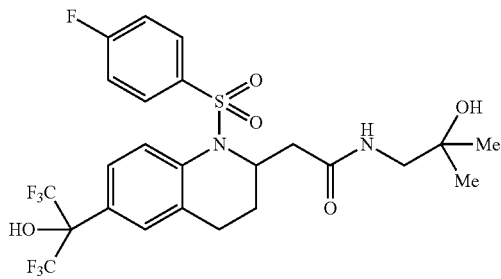 [SMILES: CC(C)(O)CNC(=O)CC1CCc2cc(C(O)(C(F)(F)F)C(F)(F)F)ccc2N1S(=O)(=O)c1ccc(F)cc1]

To a solution of 2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (20 mg, 0.039 mmol) in DMF (0.6 mL) was added DIEA (0.020 mL, 0.116 mmol), BOP (25.7 mg, 0.058 mmol) and 1-amino-2-methylpropan-2-ol (6.92 mg, 0.078 mmol). The resulted mixture was stirred at room temperature for 1 h. and purified via preparative LC/MS (condition B) to yield the title compound (15.3 mg, 67.2% yield) LC/MS M+1=587.1. $^1$H NMR (500 MHz, METHANOL-$d_4$) δ 7.77 (d, J=8.4 Hz, 1H), 7.60 (s, 1H), 7.55-7.50 (m, 2H), 7.42 (s, 1H), 7.11 (t, J=8.7 Hz, 2H), 4.80-4.69 (m, 1H), 3.19 (s, 2H), 2.70 (dd, J=14.4, 6.4 Hz, 1H), 2.55 (ddd, J=16.3, 7.9, 5.9 Hz, 1H), 2.40 (dd, J=14.4, 7.9 Hz, 1H), 1.97 (dt, J=16.3, 6.4 Hz, 1H), 1.90-1.79 (m, 1H), 1.63-1.50 (m, 1H), 1.18 (d, J=2.0 Hz, 6H).

The racemic amide (30 mg) was resolved into its corresponding enantiomers using chiral supercritical fluid chromatography (SFC) using the following conditions: Column, Lux Cell-4 25×5 cm, 5 μm; Mobile phase, $CO_2$/MeOH=85/15, 100 Bar; temperature 35° C.; flow rate, 180 mL/min; detection UV (220 nm). Retention time: first enantiomer, 3.56 min (>99% ee), yield: 5.5 mgs; second eluting enantiomer, 4.13 min (>99% ee), yield: 6 mgs. The absolute stereochemistry of the second eluting enantiomer was determined to be (S) by single crystal X-ray analysis from the anomalous dispersion signal using the Flack method.

The Examples in TABLE 1 below were prepared in the same manner as outlined in examples above, substituting the appropriate amine

TABLE 1

| Ex. No. | Structure | MW | HPLC ret. time (min.) | HPLC method | MS ($M^{+1}$) |
|---|---|---|---|---|---|
| 72 | (racemic) | 598.1 | 2.23 | B | 599.1 |
| 73 | (racemic) | 597.5 | 2.13 | B | 598.0 |

TABLE 1-continued
| Ex. No. | Structure | MW | HPLC ret. time (min.) | HPLC method | MS (M+1) |
|---|---|---|---|---|---|
| 74 | 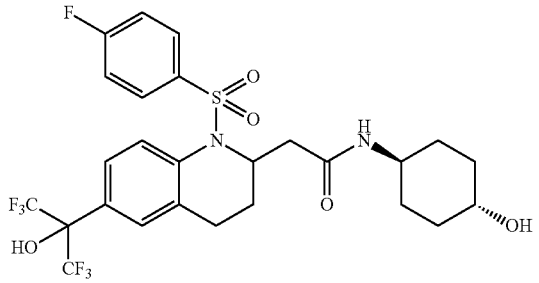 (racemic) | 612.6 | 2.22 | B | 613.2 |
| 75 | 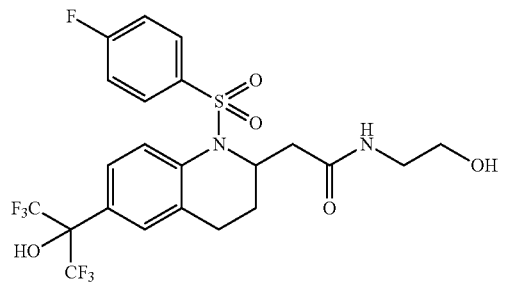 (racemic) | 558.5 | 2.13 | B | 559.0 |
| 76 | 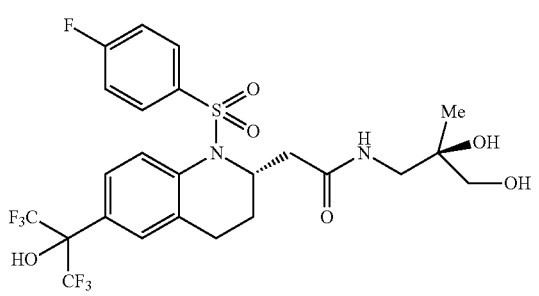 | 602.5 | 2.11 | B | 603.0 |
| 77 | 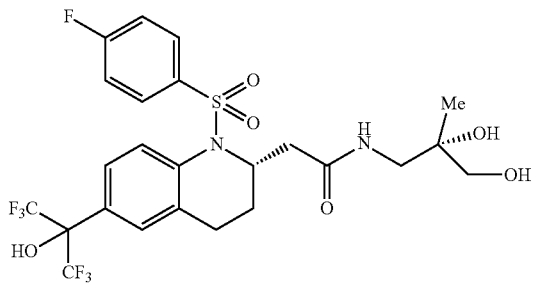 | 602.5 | 2.11 | B | 603.0 |

TABLE 1-continued
| Ex. No. | Structure | MW | HPLC ret. time (min.) | HPLC method | MS (M+1) |
|---|---|---|---|---|---|
| 78 | 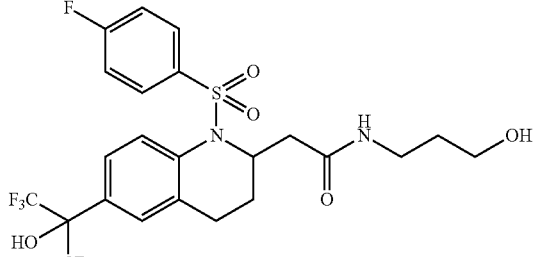 (racemic) | 572.1 | 2.16 | B | 573.1 |
| 79 | 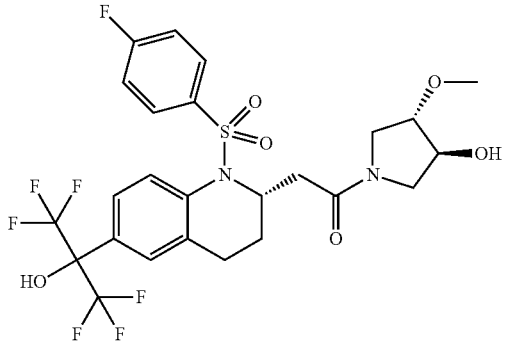 [SMILES: CO[C@H]1CN(C(=O)C[C@@H]2CCc3cc(C(O)(C(F)(F)F)C(F)(F)F)ccc3N2S(=O)(=O)c2ccc(F)cc2)C[C@@H]1O] | 614.5 | 1.67 | G | 615.3 |
| 80 | 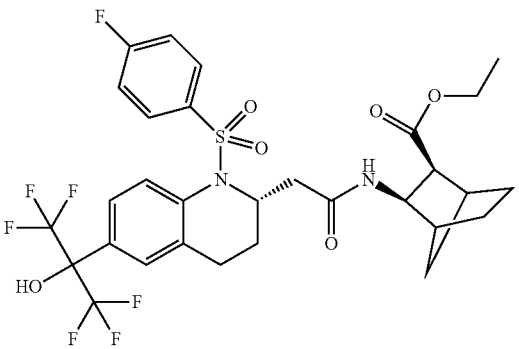 [SMILES: CCOC(=O)[C@H]1C2CCC(C2)[C@H]1NC(=O)C[C@@H]1CCc2cc(C(O)(C(F)(F)F)C(F)(F)F)ccc2N1S(=O)(=O)c1ccc(F)cc1] | 680.6 | 13.49 | H | 681.4 |
| 81 | 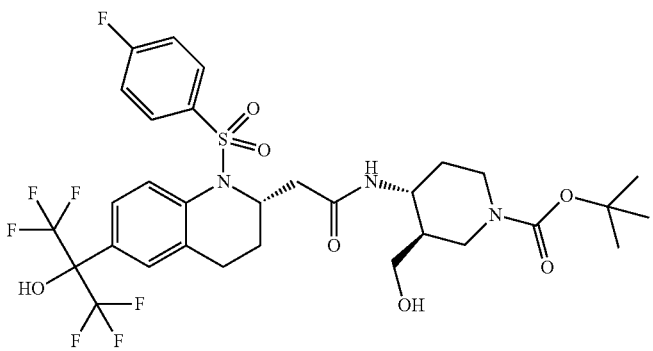 [SMILES: CC(C)(C)OC(=O)N1CC[C@@H](NC(=O)C[C@@H]2CCc3cc(C(O)(C(F)(F)F)C(F)(F)F)ccc3N2S(=O)(=O)c2ccc(F)cc2)[C@H](CO)C1] | 727.7 | 11.87 | H | 728.5 |

TABLE 1-continued

| Ex. No. | Structure | MW | HPLC ret. time (min.) | HPLC method | MS (M$^{+1}$) |
|---|---|---|---|---|---|
| 82 | 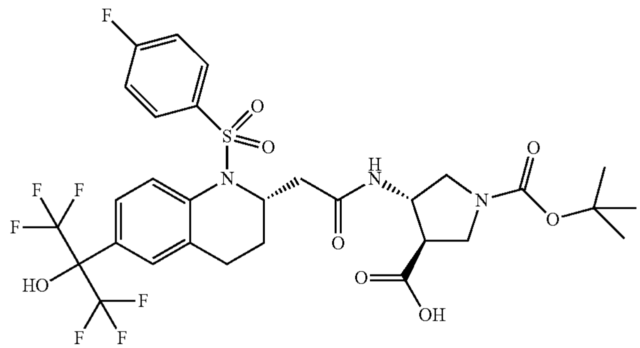 [SMILES: CC(C)(C)OC(=O)N1C[C@@H](NC(=O)C[C@@H]2CCc3cc(C(O)(C(F)(F)F)C(F)(F)F)ccc3N2S(=O)(=O)c2ccc(F)cc2)[C@H](C(=O)O)C1] | 727.7 | 11.47 | H | 729.3 |
| 83 | 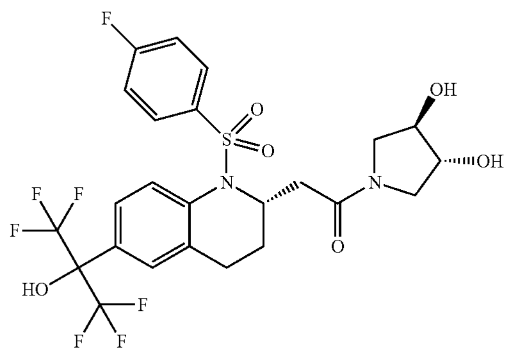 [SMILES: O=C(C[C@@H]1CCc2cc(C(O)(C(F)(F)F)C(F)(F)F)ccc2N1S(=O)(=O)c1ccc(F)cc1)N1C[C@@H](O)[C@H](O)C1] | 600.5 | 1.54 | G | 601.2 |
| 84 | 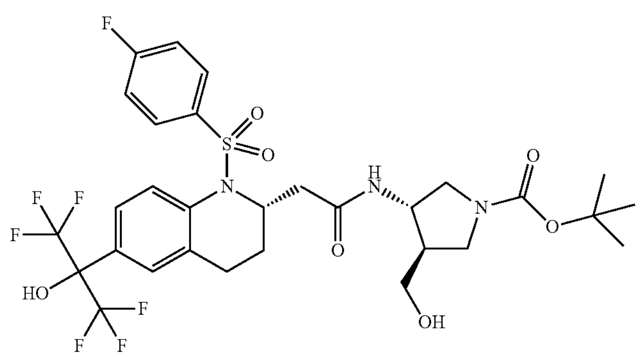 [SMILES: CC(C)(C)OC(=O)N1C[C@@H](CO)[C@H](NC(=O)C[C@@H]2CCc3cc(C(O)(C(F)(F)F)C(F)(F)F)ccc3N2S(=O)(=O)c2ccc(F)cc2)C1] | 713.6 | 11.42 | H | 714.4 |
| 85 | 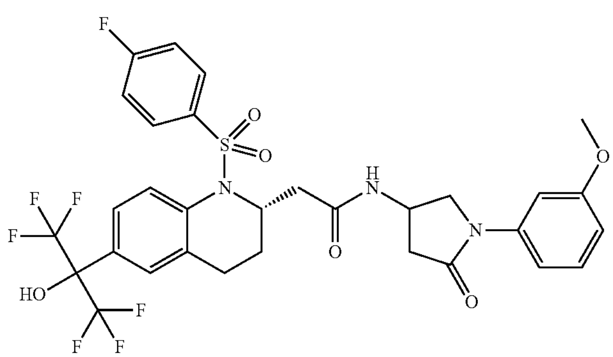 [SMILES: COc1cccc(N2CC(NC(=O)C[C@@H]3CCc4cc(C(O)(C(F)(F)F)C(F)(F)F)ccc4N3S(=O)(=O)c3ccc(F)cc3)CC2=O)c1] | 703.6 | 1.88 | G | 704.4 |

TABLE 1-continued

| Ex. No. | Structure | MW | HPLC ret. time (min.) | HPLC method | MS (M+1) |
|---|---|---|---|---|---|
| 86 | 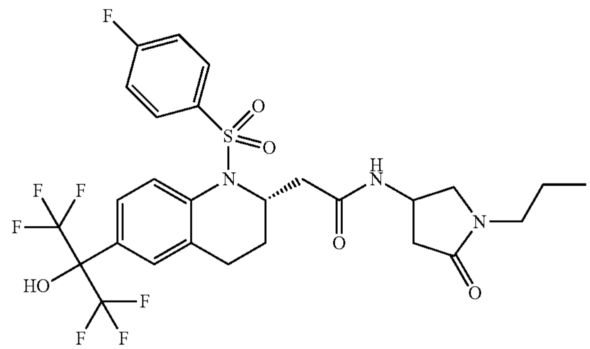 [SMILES: CCCN1CC(NC(=O)C[C@@H]2CCc3cc(C(O)(C(F)(F)F)C(F)(F)F)ccc3N2S(=O)(=O)c2ccc(F)cc2)CC1=O] | 639.6 | 1.75 | G | 640.3 |
| 87 | 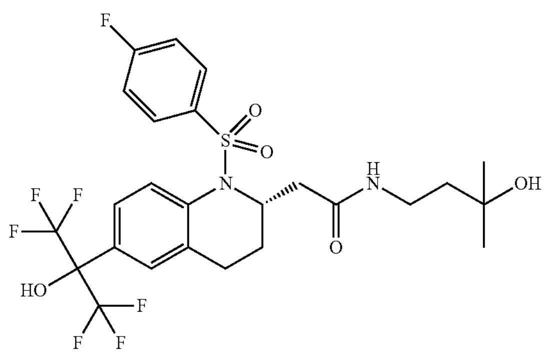 [SMILES: CC(C)(O)CCNC(=O)C[C@@H]1CCc2cc(C(O)(C(F)(F)F)C(F)(F)F)ccc2N1S(=O)(=O)c1ccc(F)cc1] | 600.6 | 1.73 | G | 601.3 |
| 88 | 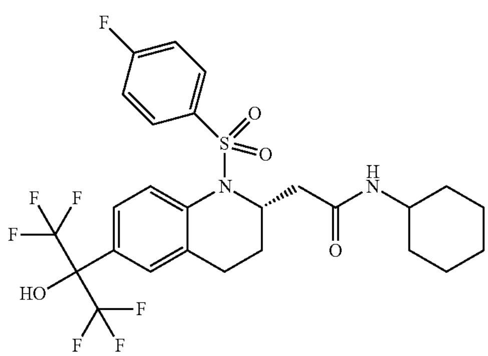 [SMILES: O=C(C[C@@H]1CCc2cc(C(O)(C(F)(F)F)C(F)(F)F)ccc2N1S(=O)(=O)c1ccc(F)cc1)NC1CCCCC1] | 596.6 | 2.08 | G | 697.3 |
| 89 | 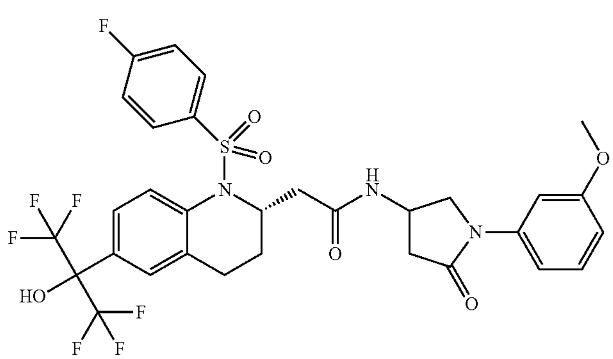 [SMILES: COc1cccc(N2CC(NC(=O)C[C@@H]3CCc4cc(C(O)(C(F)(F)F)C(F)(F)F)ccc4N3S(=O)(=O)c3ccc(F)cc3)CC2=O)c1] | 703.6 | 1.89 | G | 704.4 |

TABLE 1-continued
| Ex. No. | Structure | MW | HPLC ret. time (min.) | HPLC method | MS (M+1) |
|---|---|---|---|---|---|
| 90 | 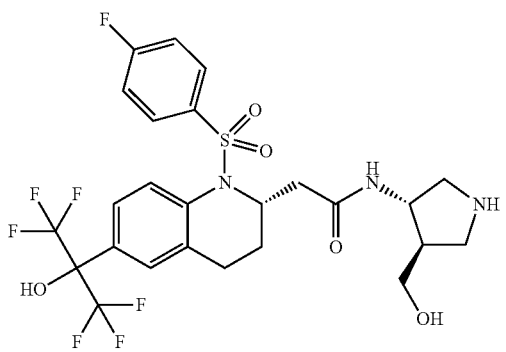 Diastereomer mixture | 613.6 | 7.61 | H | 614.2 |
| 91 | 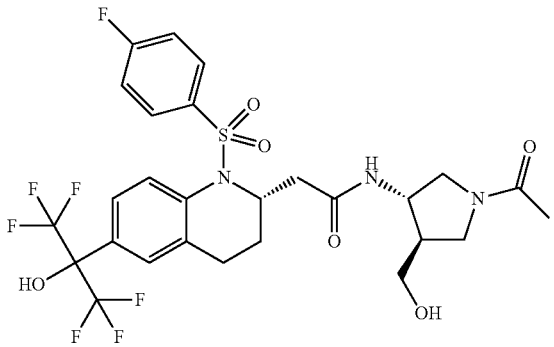 Diastereomer mixture | 655.6 | 9.39 | H | 656.3 |
| 92 | 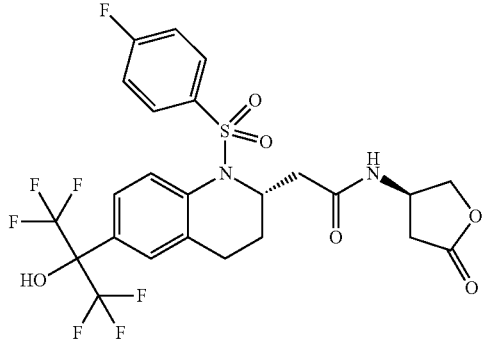 [SMILES: O=C(C[C@@H]1CCc2cc(C(O)(C(F)(F)F)C(F)(F)F)ccc2N1S(=O)(=O)c1ccc(F)cc1)N[C@H]1COC(=O)C1] | 598.5 | 1.66 | G | 599.2 |
| 93 | 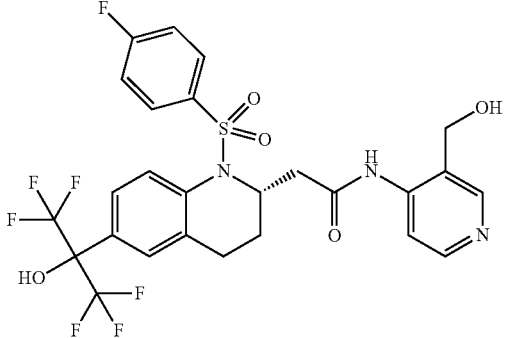 [SMILES: O=C(C[C@@H]1CCc2cc(C(O)(C(F)(F)F)C(F)(F)F)ccc2N1S(=O)(=O)c1ccc(F)cc1)Nc1ccncc1CO] | 621.5 | 1.63 | G | 622.2 |

TABLE 1-continued

| Ex. No. | Structure | MW | HPLC ret. time (min.) | HPLC method | MS (M+1) |
|---|---|---|---|---|---|
| 94 (BMT-095613) | Diastereomer mixture | 584.5 | 1.69 | G | 585.2 |
| 95 | 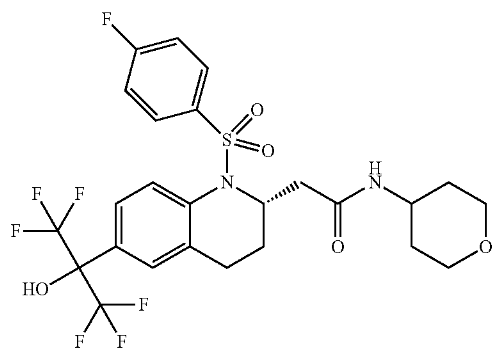 [SMILES: O=C(C[C@@H]1CCc2cc(C(O)(C(F)(F)F)C(F)(F)F)ccc2N1S(=O)(=O)c1ccc(F)cc1)NC1CCOCC1] | 598.5 | 1.71 | G | 599.2 |
| 96 | 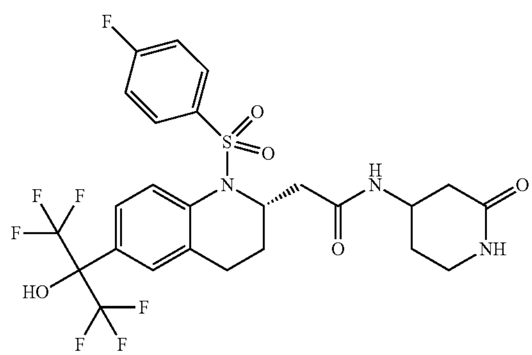 [SMILES: O=C1CC(NC(=O)C[C@@H]2CCc3cc(C(O)(C(F)(F)F)C(F)(F)F)ccc3N2S(=O)(=O)c2ccc(F)cc2)CCN1] | 611.5 | 1.53 | G | 612.2 |
| 97 | Diastereomer mixture | 638.6 | 1.86 | G | 639.3 |

TABLE 1-continued

| Ex. No. | Structure | MW | HPLC ret. time (min.) | HPLC method | MS (M+1) |
|---|---|---|---|---|---|
| 98 | 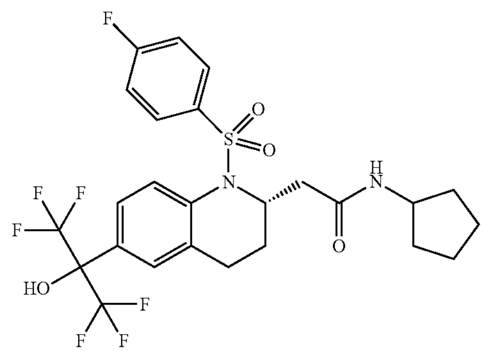 [SMILES: O=C(C[C@@H]1CCc2cc(C(O)(C(F)(F)F)C(F)(F)F)ccc2N1S(=O)(=O)c1ccc(F)cc1)NC1CCCC1] | 582.5 | 1.67 | G | 583.4 |
| 99 | 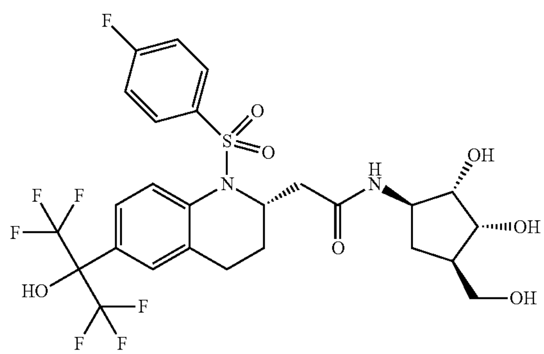 [SMILES: O=C(C[C@@H]1CCc2cc(C(O)(C(F)(F)F)C(F)(F)F)ccc2N1S(=O)(=O)c1ccc(F)cc1)N[C@@H]1C[C@H](CO)[C@@H](O)[C@H]1O] | 644.6 | 1.30 | G | 645.4 |
| 100 | Diastereomer mixture | 614.6 | 1.71 | G | 615.3 |
| 101 | Diastereomer mixture | 612.6 | 1.53 | G | 613.4 |

TABLE 1-continued
| Ex. No. | Structure | MW | HPLC ret. time (min.) | HPLC method | MS (M+1) |
|---|---|---|---|---|---|
| 102 | 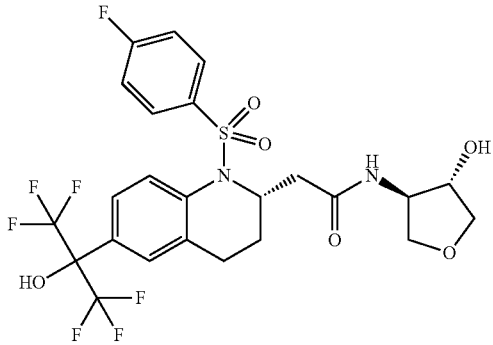 Diastereomer mixture | 600.5 | 1.38 | G | 601.3 |
| 103 | 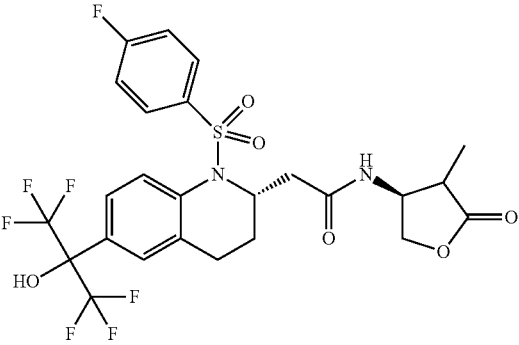 [SMILES: CC1(C)C(=O)OC[C@H]1NC(=O)C[C@@H]1CCc2cc(C(O)(C(F)(F)F)C(F)(F)F)ccc2N1S(=O)(=O)c1ccc(F)cc1] Diastereomer mixture | 612.5 | 1.53 | G | 613.4 |
| 104 | 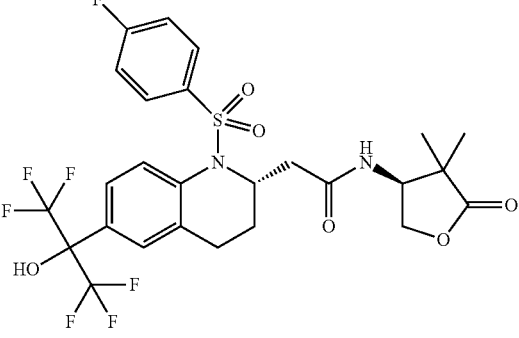 | 626.5 | 1.55 | G | 627.4 |
| 105 | 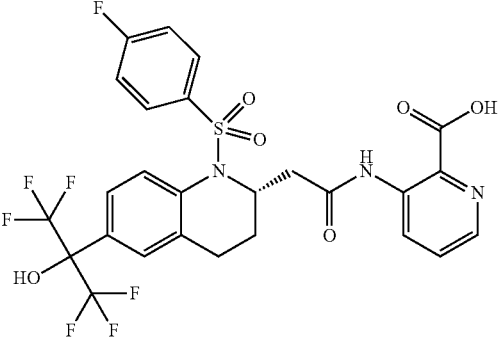 [SMILES: O=C(C[C@@H]1CCc2cc(C(O)(C(F)(F)F)C(F)(F)F)ccc2N1S(=O)(=O)c1ccc(F)cc1)Nc1cccnc1C(=O)O] | 635.5 | 10.19 | H | 636.3 |

TABLE 1-continued

| Ex. No. | Structure | MW | HPLC ret. time (min.) | HPLC method | MS (M+1) |
|---|---|---|---|---|---|
| 106 | Diastereomer mixture | 612.6 | 1.84 | G | 613.3 |
| 107 | Diastereomer mixture | 697.7 | 12.37 | H | 642.3 |
| 108 | Diastereomer mixture | 597.6 | 7.75 | H | 598.3 |
| 109 | 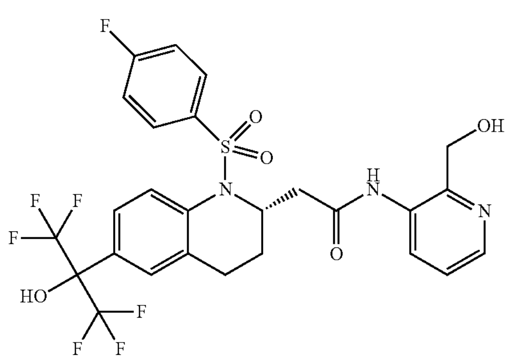 [SMILES: O=C(C[C@@H]1CCc2cc(C(O)(C(F)(F)F)C(F)(F)F)ccc2N1S(=O)(=O)c1ccc(F)cc1)Nc1cccnc1CO] | 621.5 | 1.47 | G | 622.2 |

TABLE 1-continued
| Ex. No. | Structure | MW | HPLC ret. time (min.) | HPLC method | MS (M+1) |
|---|---|---|---|---|---|
| 110 | 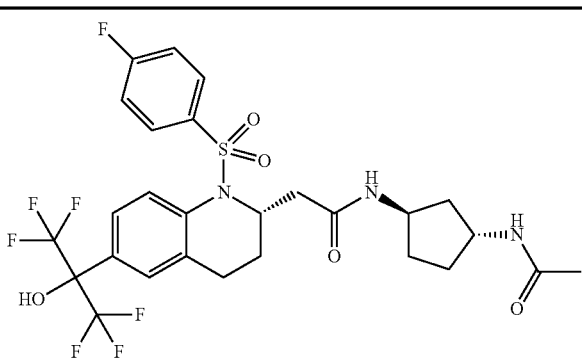<br>Diastereomer mixture | 639.6 | 1.63 | G | 640.4 |
| 111 | 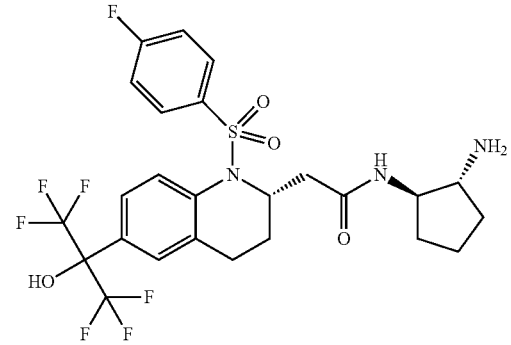<br>Diastereomer mixture | 597.6 | 7.99 | H | 598.3 |
| 112 | 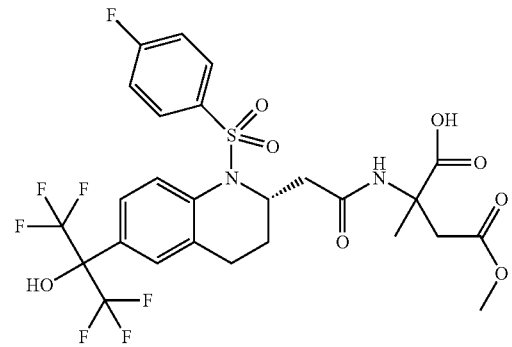<br>Diastereomer mixture | 658.5 | 11.16 | H | 659.4 |
| 113 | 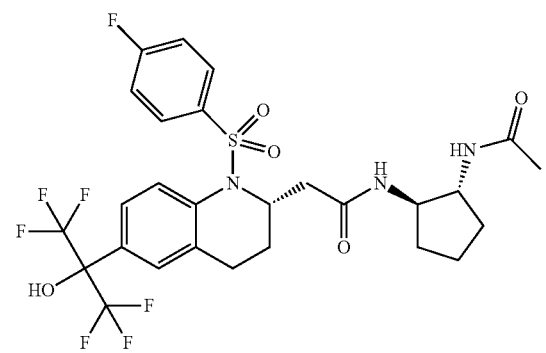<br>Diastereomer mixture | 639.6 | 1.48 | G | 640.4 |

TABLE 1-continued

| Ex. No. | Structure | MW | HPLC ret. time (min.) | HPLC method | MS (M+1) |
|---|---|---|---|---|---|
| 114 | 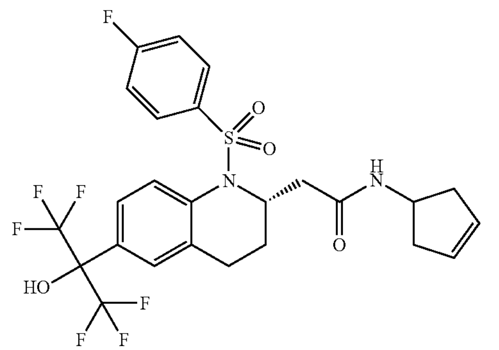 [SMILES: O=C(C[C@@H]1CCc2cc(C(O)(C(F)(F)F)C(F)(F)F)ccc2N1S(=O)(=O)c1ccc(F)cc1)NC1CC=CC1] | 580.5 | 2.33 | G | 581.3 |
| 115 | Diastereomer mixture | 612.5 | 11.32 | H | 613.3 |
| 116 | Diastereomer mixture | 614.5 | 10.62 | H | 615.3 |
| 117 | Diastereomer mixture | 614.5 | 1.93 | G | 615.3 |

TABLE 1-continued
| Ex. No. | Structure | MW | HPLC ret. time (min.) | HPLC method | MS (M+1) |
|---|---|---|---|---|---|
| 118 | 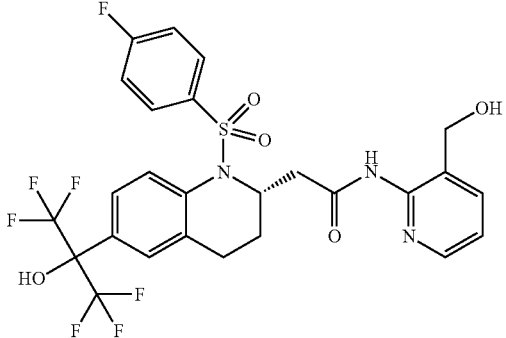 [SMILES: O=C(C[C@@H]1CCc2cc(C(O)(C(F)(F)F)C(F)(F)F)ccc2N1S(=O)(=O)c1ccc(F)cc1)Nc1ncccc1CO] | 621.5 | 2.64 | G | 622.3 |
| 119 | 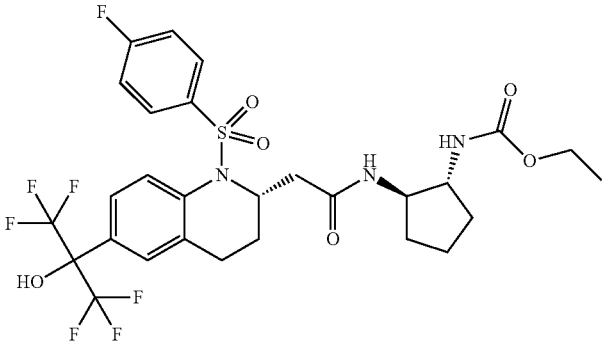  Diastereomer mixture | 669.6 | 1.94 | G | 670.3 |
| 120 | 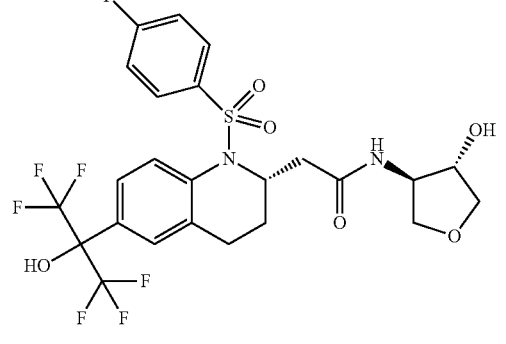 | 600.5 | 10.05 | H | 601.3 |
| 121 | 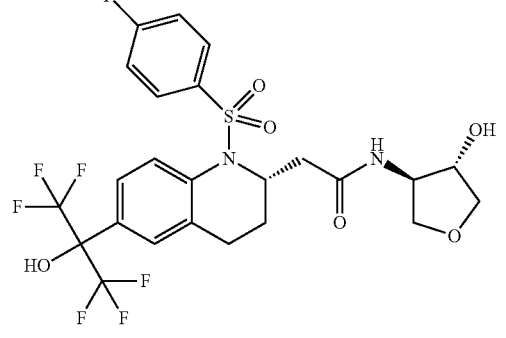 | 600.5 | 10.06 | H | 601.3 |

TABLE 1-continued
| Ex. No. | Structure | MW | HPLC ret. time (min.) | HPLC method | MS (M+1) |
|---|---|---|---|---|---|
| 122 | 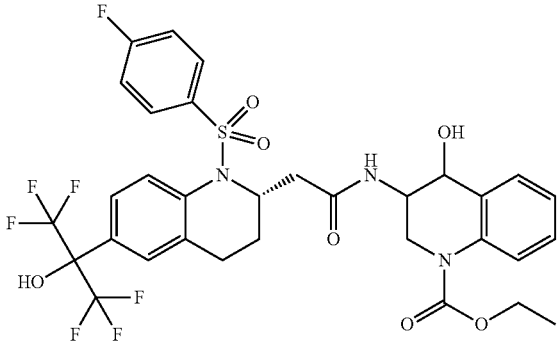 Diastereomer mixture | 733.7 | 1.94 | G | 734.5 |
| 123 | 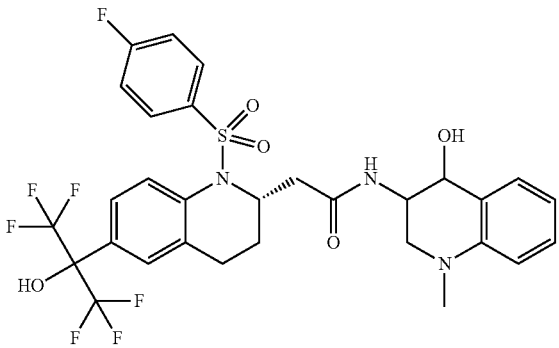 Diastereomer mixture | 675.6 | 1.90 | G | 676.5 |
| 124 | 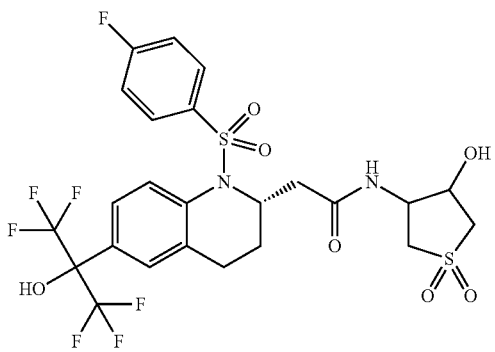 Diastereomer mixture | 648.6 | 1.63 | G | 649.4 |
| 125 | 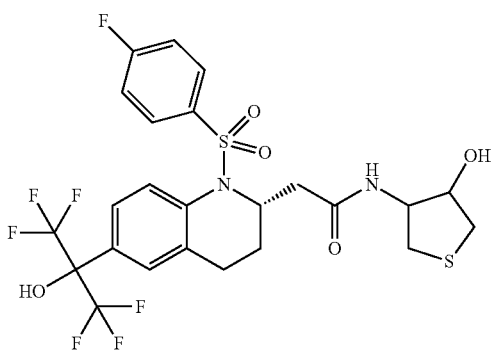 Diastereomer mixture | 616.6 | 1.73 | G | 617.4 |

TABLE 1-continued

| Ex. No. | Structure | MW | HPLC ret. time (min.) | HPLC method | MS (M$^{+1}$) |
|---|---|---|---|---|---|
| 126 | 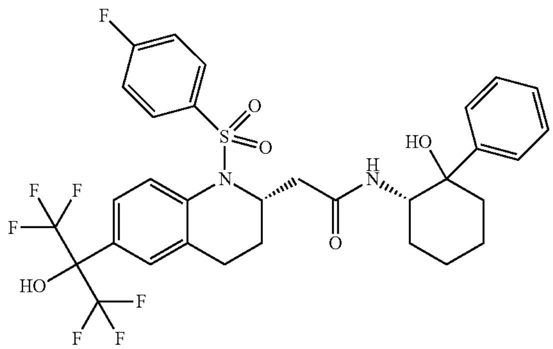 [SMILES: O=C(C[C@@H]1CCc2cc(C(O)(C(F)(F)F)C(F)(F)F)ccc2N1S(=O)(=O)c1ccc(F)cc1)N[C@H]1CCCCC1(O)c1ccccc1] | 688.7 | 2.06 | G | 689.5 |
| 127 | 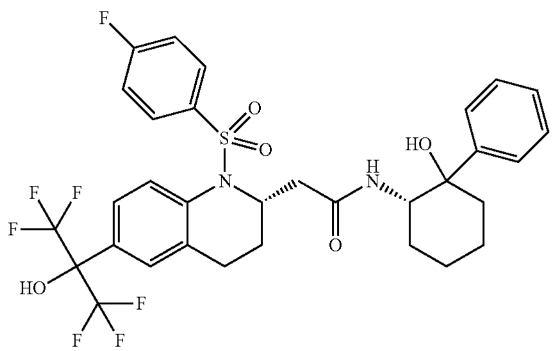 [SMILES: O=C(C[C@@H]1CCc2cc(C(O)(C(F)(F)F)C(F)(F)F)ccc2N1S(=O)(=O)c1ccc(F)cc1)N[C@H]1CCCCC1(O)c1ccccc1] | 688.7 | 2.09 | G | 689.5 |
| 129 | Diastereomer mixture | 636.5 | 1.86 | G | 637.4 |
| 130 | 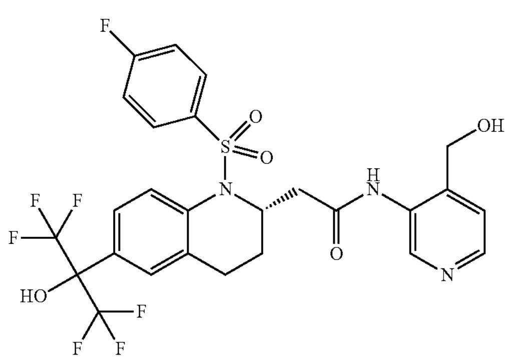 [SMILES: O=C(C[C@@H]1CCc2cc(C(O)(C(F)(F)F)C(F)(F)F)ccc2N1S(=O)(=O)c1ccc(F)cc1)Nc1cnccc1CO] | 621.5 | 1.88 | G | 622.3 |

TABLE 1-continued
| Ex. No. | Structure | MW | HPLC ret. time (min.) | HPLC method | MS (M$^{+1}$) |
|---|---|---|---|---|---|
| 131 | 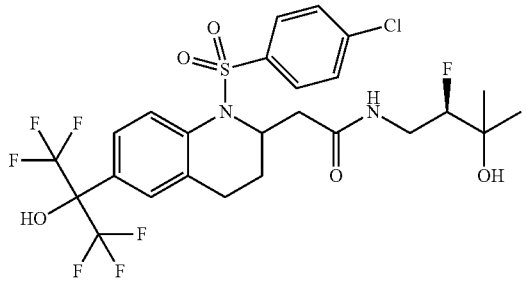 Diastereomer mixture | 635.0 | 1.91 | G | 635.3 |
| 132 | 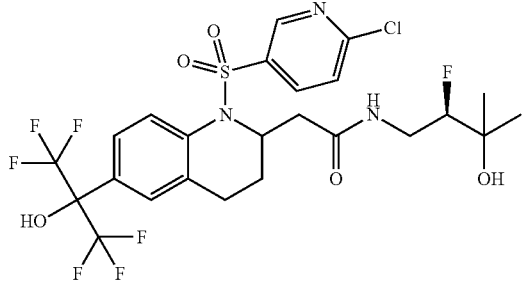 Diastereomer mixture | 636.0 | 1.77 | G | 636.3 |
| 133 | 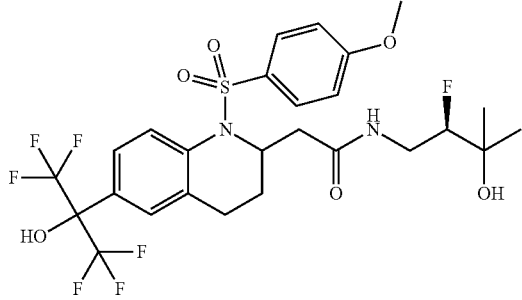 Diastereomer mixture | 630.6 | 1.78 | G | 631.4 |
| 134 | 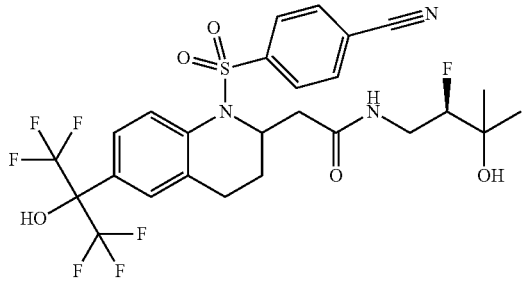 Diastereomer mixture | 625.6 | 1.73 | G | 626.4 |

TABLE 1-continued
| Ex. No. | Structure | MW | HPLC ret. time (min.) | HPLC method | MS (M+1) |
|---|---|---|---|---|---|
| 135 | 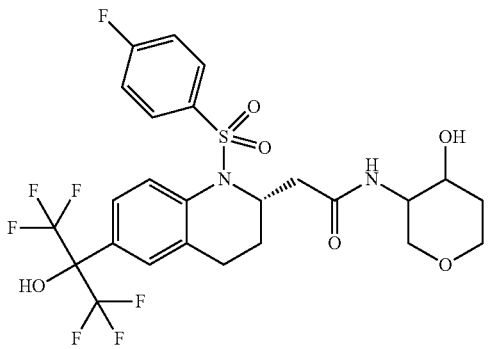 Diastereomer mixture | 614.5 | 10.36 | H | 615.3 |
| 136 | 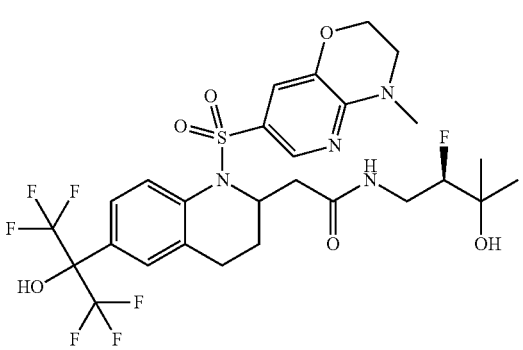 Diastereomer mixture | 672.6 | 1.62 | G | 673.5 |
| 137 | 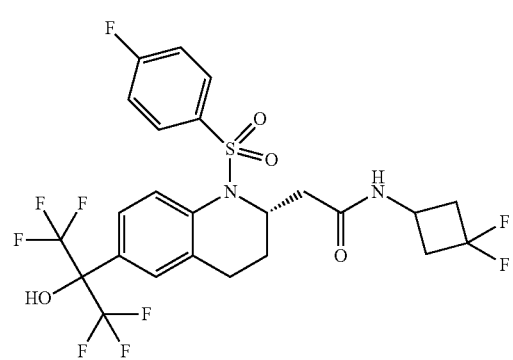 [SMILES: O=C(C[C@@H]1CCc2cc(C(O)(C(F)(F)F)C(F)(F)F)ccc2N1S(=O)(=O)c1ccc(F)cc1)NC1CC(F)(F)C1] | 604.5 | 1.67 | G | 605.2 |
| 138 | 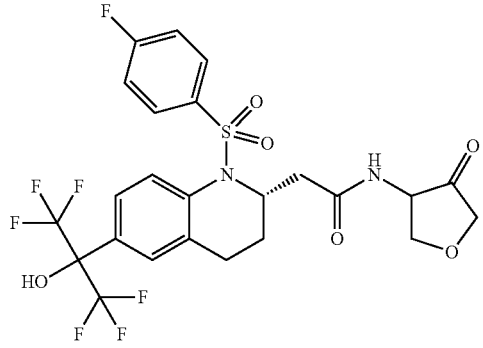 Diastereomer mixture | 598.5 | 11.09 | H | 599.2 |

TABLE 1-continued
| Ex. No. | Structure | MW | HPLC ret. time (min.) | HPLC method | MS (M+1) |
|---|---|---|---|---|---|
| 140 | 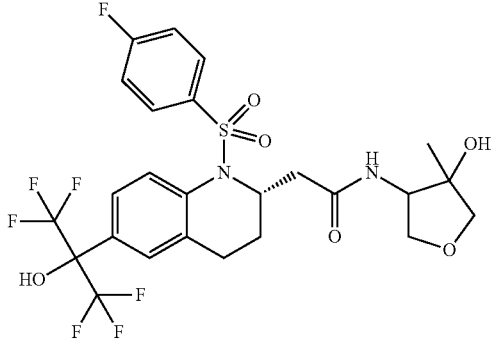 Diastereomer mixture | 614.5 | 1.66 | G | 615.2 |
| 141 | 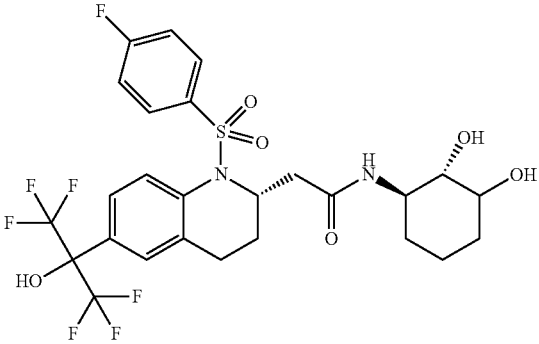 Diastereomer mixture | 628.6 | 1.66 | G | 629.2 |
| 142 | 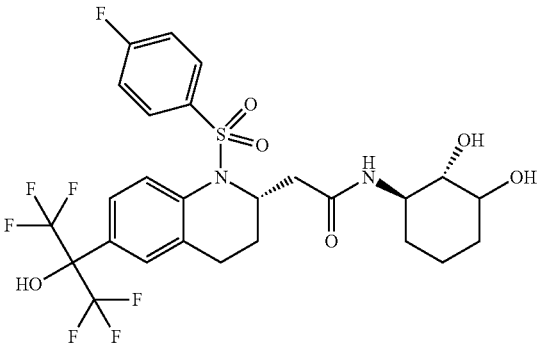 Diastereomer mixture | 628.6 | 1.67 | G | 629.2 |
| 143 | 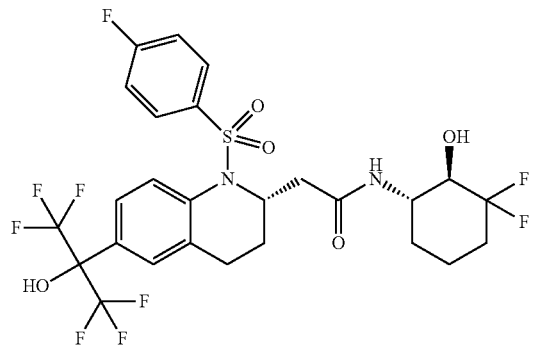 [SMILES: O=C(C[C@@H]1CCc2cc(C(O)(C(F)(F)F)C(F)(F)F)ccc2N1S(=O)(=O)c1ccc(F)cc1)N[C@H]1CCCC(F)(F)[C@@H]1O] | 648.5 | 1.84 | G | 649.3 |

TABLE 1-continued
| Ex. No. | Structure | MW | HPLC ret. time (min.) | HPLC method | MS (M+1) |
|---|---|---|---|---|---|
| 144 | 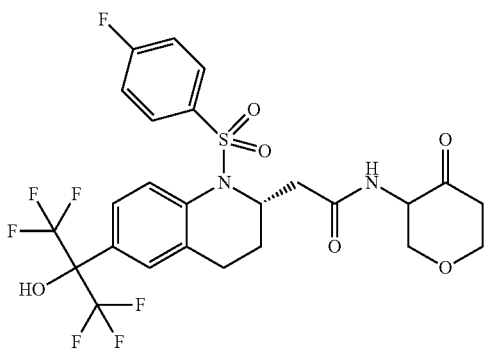 Diastereomer mixture | 612.5 | 1.77 | G | 613.2 |
| 145 | 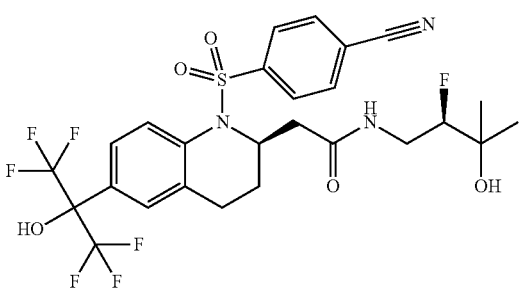 [SMILES: CC(C)(O)[C@H](F)CNC(=O)C[C@H]1CCc2cc(C(O)(C(F)(F)F)C(F)(F)F)ccc2N1S(=O)(=O)c1ccc(C#N)cc1] | 625.6 | 3.96 | F | 626.3 |
| 146 | 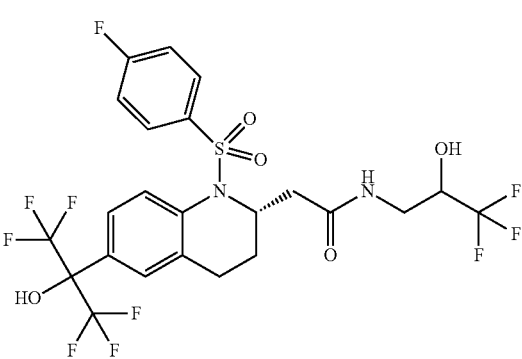 Diastereomer mixture | 626.5 | 1.58 | G | 627.2 |
| 147 | 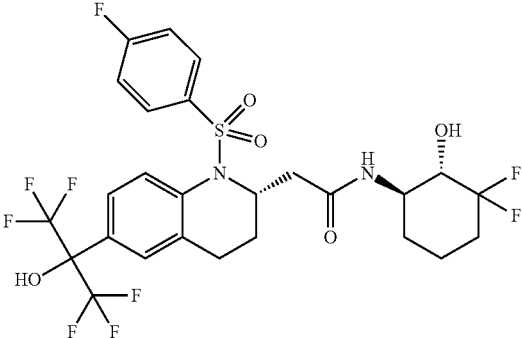 [SMILES: O=C(C[C@@H]1CCc2cc(C(O)(C(F)(F)F)C(F)(F)F)ccc2N1S(=O)(=O)c1ccc(F)cc1)N[C@@H]1CCCC(F)(F)[C@H]1O] | 648.5 | 1.56 | G | 649.3 |

TABLE 1-continued
| Ex. No. | Structure | MW | HPLC ret. time (min.) | HPLC method | MS (M+1) |
|---|---|---|---|---|---|
| 148 | 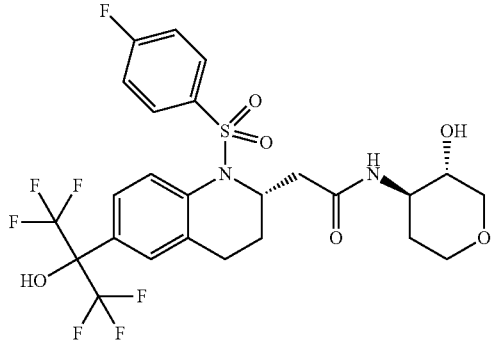<br>Diastereomer mixture | 614.5 | 1.83 | G | 615.3 |
| 149 | 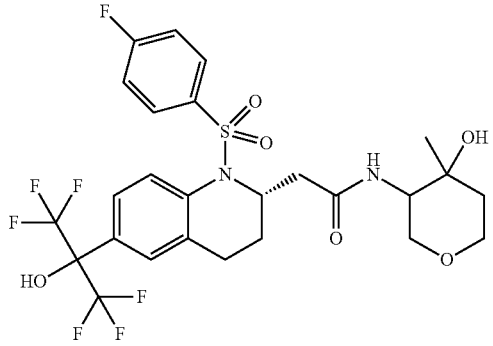<br>Diastereomer mixture | 628.6 | 1.68 | G | 629.3 |
| 150 | 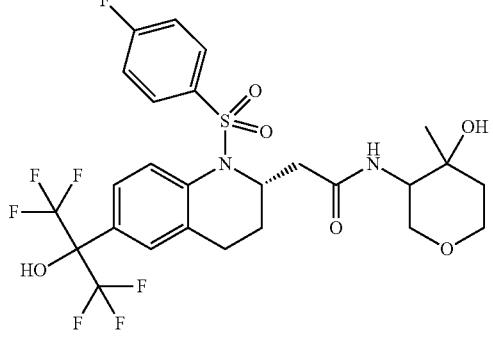<br>Diastereomer mixture | 628.6 | 1.69 | G | 592.2 |
| 151 | 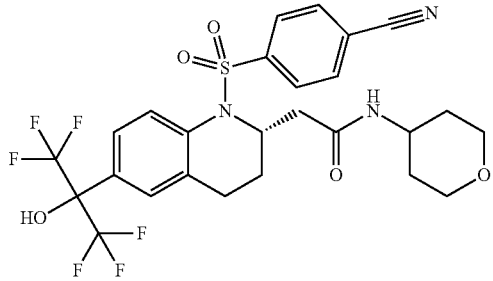 [SMILES: N#Cc1ccc(S(=O)(=O)N2c3ccc(C(O)(C(F)(F)F)C(F)(F)F)cc3CC[C@H]2CC(=O)NC2CCOCC2)cc1] | 605.6 | 1.65 | G | 606.3 |

TABLE 1-continued

| Ex. No. | Structure | MW | HPLC ret. time (min.) | HPLC method | MS (M$^{+1}$) |
|---|---|---|---|---|---|
| 152 | 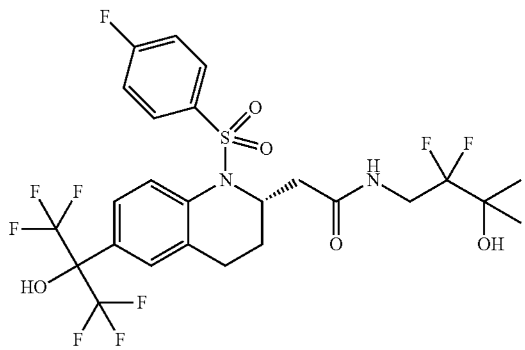 [SMILES: CC(C)(O)C(F)(F)CNC(=O)C[C@@H]1CCc2cc(C(O)(C(F)(F)F)C(F)(F)F)ccc2N1S(=O)(=O)c1ccc(F)cc1] | 636.5 | 1.74 | G | 637.3 |
| 153 | 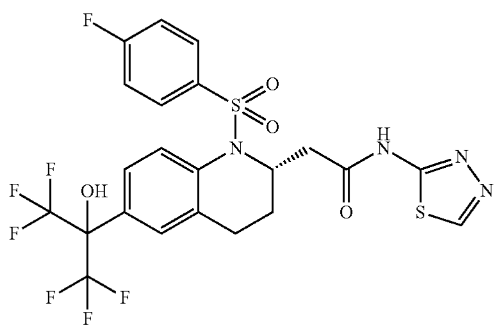 [SMILES: O=C(C[C@@H]1CCc2cc(C(O)(C(F)(F)F)C(F)(F)F)ccc2N1S(=O)(=O)c1ccc(F)cc1)Nc1nncs1] | 598.5 | 1.74 | B | 599.1 |
| 154 | 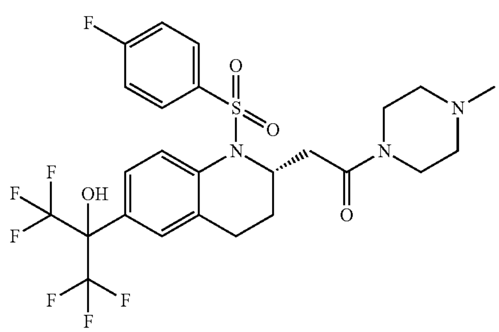 [SMILES: CN1CCN(C(=O)C[C@@H]2CCc3cc(C(O)(C(F)(F)F)C(F)(F)F)ccc3N2S(=O)(=O)c2ccc(F)cc2)CC1] | 597.6 | 1.71 | B | 598.1 |
| 155 | 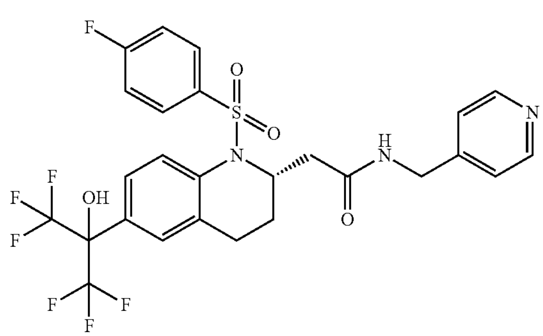 [SMILES: O=C(C[C@@H]1CCc2cc(C(O)(C(F)(F)F)C(F)(F)F)ccc2N1S(=O)(=O)c1ccc(F)cc1)NCc1ccncc1] | 605.5 | 1.69 | B | 606.1 |

TABLE 1-continued

| Ex. No. | Structure | MW | HPLC ret. time (min.) | HPLC method | MS (M+1) |
|---|---|---|---|---|---|
| 156 | Diastereomic Mixture | 612.6 | 1.88 | B | 613.1 |
| 157 | 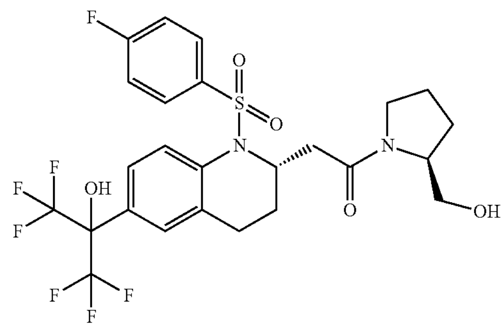 [SMILES: O=C(C[C@@H]1CCc2cc(C(O)(C(F)(F)F)C(F)(F)F)ccc2N1S(=O)(=O)c1ccc(F)cc1)N1CCC[C@H]1CO] | 598.5 | 1.74 | B | 599.1 |
| 158 | 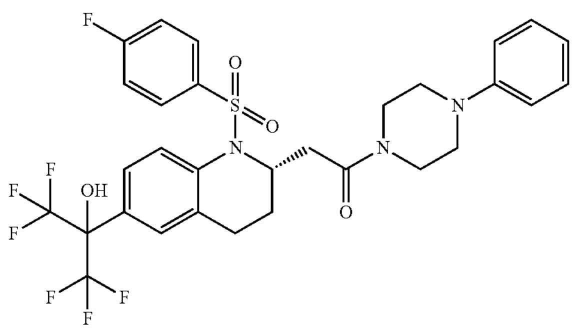 [SMILES: O=C(C[C@@H]1CCc2cc(C(O)(C(F)(F)F)C(F)(F)F)ccc2N1S(=O)(=O)c1ccc(F)cc1)N1CCN(c2ccccc2)CC1] | 659.6 | 2.05 | B | 660.2 |
| 159 | 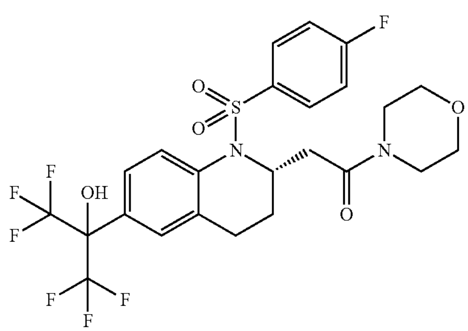 [SMILES: O=C(C[C@@H]1CCc2cc(C(O)(C(F)(F)F)C(F)(F)F)ccc2N1S(=O)(=O)c1ccc(F)cc1)N1CCOCC1] | 584.5 | 1.78 | B | 585.1 |

TABLE 1-continued
| Ex. No. | Structure | MW | HPLC ret. time (min.) | HPLC method | MS (M+1) |
|---|---|---|---|---|---|
| 160 | 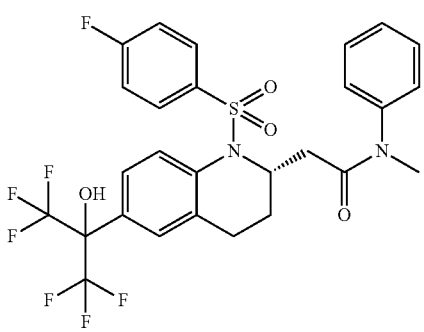 [SMILES: CN(C(=O)C[C@@H]1CCc2cc(C(O)(C(F)(F)F)C(F)(F)F)ccc2N1S(=O)(=O)c1ccc(F)cc1)c1ccccc1] | 604.5 | 2.05 | B | 605.1 |
| 161 | 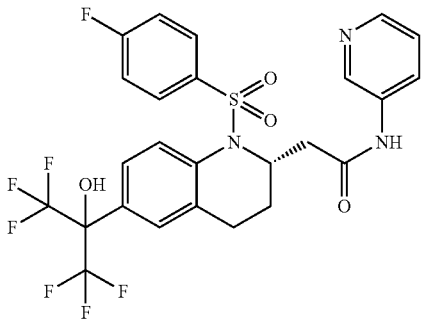 [SMILES: O=C(C[C@@H]1CCc2cc(C(O)(C(F)(F)F)C(F)(F)F)ccc2N1S(=O)(=O)c1ccc(F)cc1)Nc1cccnc1] | 591.5 | 1.77 | B | 592.1 |
| 162 | 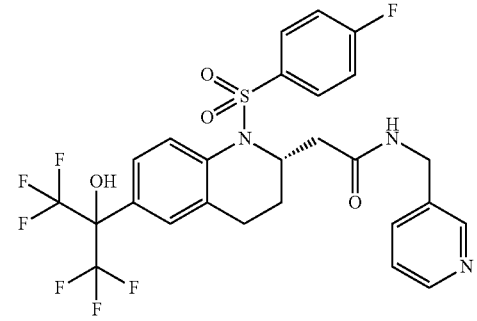 [SMILES: O=C(C[C@@H]1CCc2cc(C(O)(C(F)(F)F)C(F)(F)F)ccc2N1S(=O)(=O)c1ccc(F)cc1)NCc1cccnc1] | 605.5 | 1.71 | B | 606.1 |
| 163 | 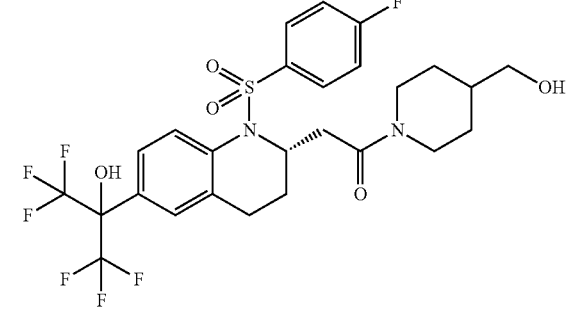 | 612.6 | 1.70 | B | 613.2 |

TABLE 1-continued

| Ex. No. | Structure | MW | HPLC ret. time (min.) | HPLC method | MS (M+1) |
|---|---|---|---|---|---|
| 164 | 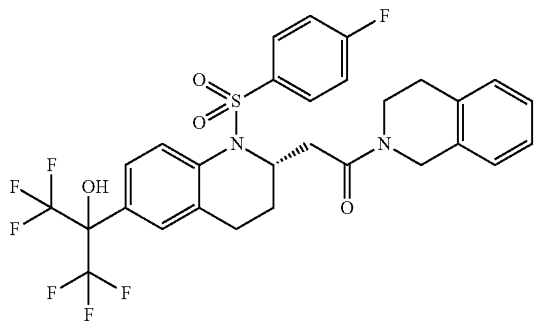 [SMILES: O=C(C[C@@H]1CCc2cc(C(O)(C(F)(F)F)C(F)(F)F)ccc2N1S(=O)(=O)c1ccc(F)cc1)N1CCc2ccccc2C1] | 630.6 | 2.15 | B | 631.2 |
| 165 | 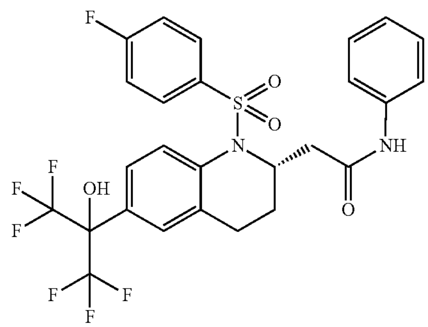 [SMILES: O=C(C[C@@H]1CCc2cc(C(O)(C(F)(F)F)C(F)(F)F)ccc2N1S(=O)(=O)c1ccc(F)cc1)Nc1ccccc1] | 590.5 | 2.05 | B | 591.1 |
| 168 | 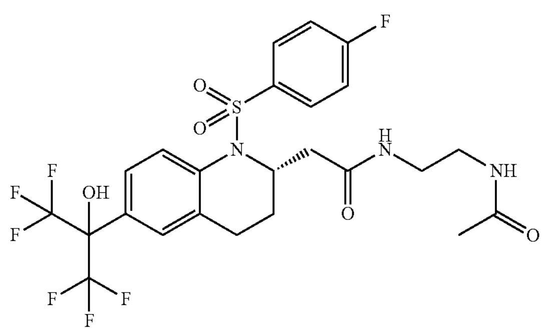 [SMILES: CC(=O)NCCNC(=O)C[C@@H]1CCc2cc(C(O)(C(F)(F)F)C(F)(F)F)ccc2N1S(=O)(=O)c1ccc(F)cc1] | 599.5 | 1.57 | B | 600.1 |
| 169 | Diastereomic Mixture | 673.7 | 1.66 | B | 674.2 |

TABLE 1-continued

| Ex. No. | Structure | MW | HPLC ret. time (min.) | HPLC method | MS (M+1) |
|---|---|---|---|---|---|
| 170 | 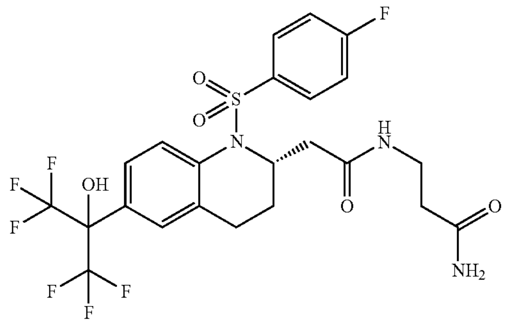 [SMILES: NC(=O)CCNC(=O)C[C@@H]1CCc2cc(C(O)(C(F)(F)F)C(F)(F)F)ccc2N1S(=O)(=O)c1ccc(F)cc1] | 585.5 | 1.53 | B | 586.1 |
| 171 | 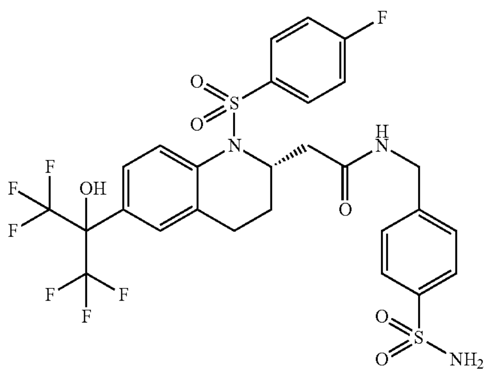 [SMILES: NS(=O)(=O)c1ccc(CNC(=O)C[C@@H]2CCc3cc(C(O)(C(F)(F)F)C(F)(F)F)ccc3N2S(=O)(=O)c2ccc(F)cc2)cc1] | 683.6 | 1.70 | B | 684.1 |
| 172 | 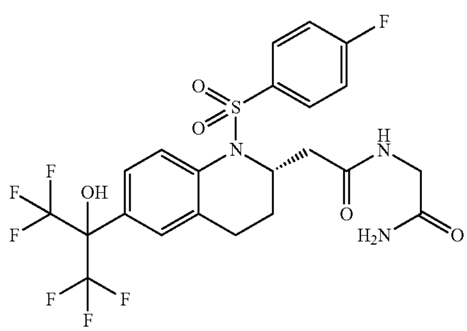 [SMILES: NC(=O)CNC(=O)C[C@@H]1CCc2cc(C(O)(C(F)(F)F)C(F)(F)F)ccc2N1S(=O)(=O)c1ccc(F)cc1] | 571.5 | 1.53 | B | 572.1 |
| 173 | 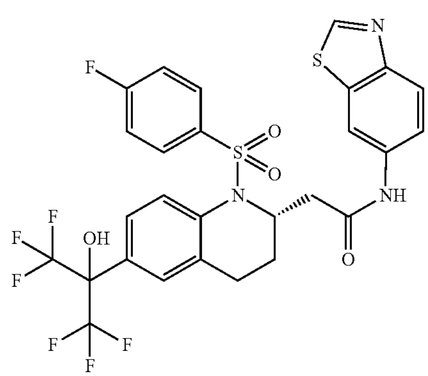 [SMILES: O=C(C[C@@H]1CCc2cc(C(O)(C(F)(F)F)C(F)(F)F)ccc2N1S(=O)(=O)c1ccc(F)cc1)Nc1ccc2ncsc2c1] | 647.6 | 1.93 | B | 648.1 |

TABLE 1-continued

| Ex. No. | Structure | MW | HPLC ret. time (min.) | HPLC method | MS (M$^{+1}$) |
|---|---|---|---|---|---|
| 174 | 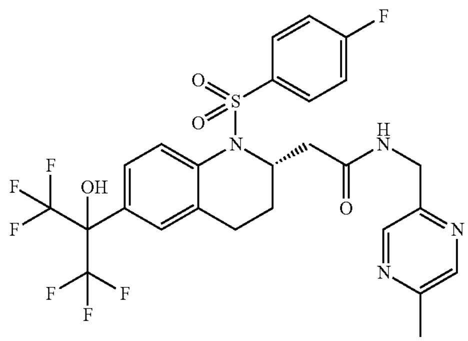 [SMILES: Cc1cnc(CNC(=O)C[C@@H]2CCc3cc(C(O)(C(F)(F)F)C(F)(F)F)ccc3N2S(=O)(=O)c2ccc(F)cc2)cn1] | 620.5 | 1.72 | B | 621.1 |
| 175 | 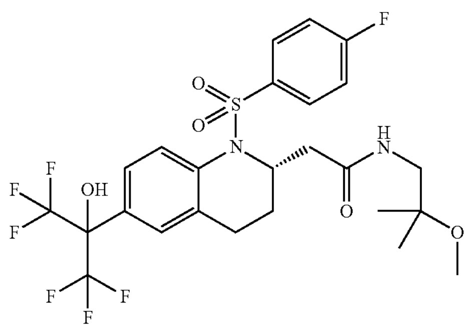 [SMILES: COC(C)(C)CNC(=O)C[C@@H]1CCc2cc(C(O)(C(F)(F)F)C(F)(F)F)ccc2N1S(=O)(=O)c1ccc(F)cc1] | 600.6 | 1.88 | B | 601.1 |
| 176 | 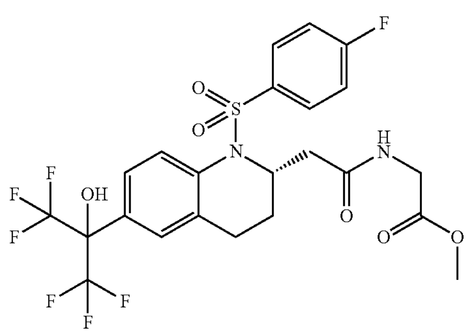 [SMILES: COC(=O)CNC(=O)C[C@@H]1CCc2cc(C(O)(C(F)(F)F)C(F)(F)F)ccc2N1S(=O)(=O)c1ccc(F)cc1] | 586.5 | 1.76 | B | 587.1 |
| 177 | 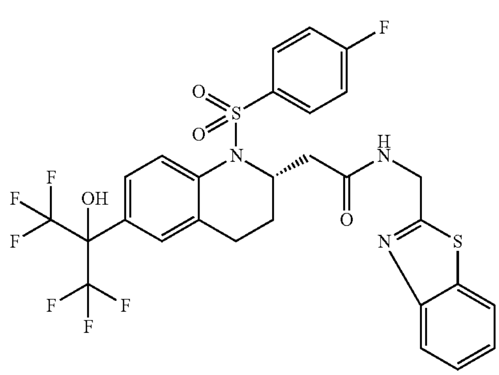 [SMILES: O=C(C[C@@H]1CCc2cc(C(O)(C(F)(F)F)C(F)(F)F)ccc2N1S(=O)(=O)c1ccc(F)cc1)NCc1nc2ccccc2s1] | 661.6 | 2.00 | B | 662.1 |

TABLE 1-continued

| Ex. No. | Structure | MW | HPLC ret. time (min.) | HPLC method | MS (M+1) |
|---|---|---|---|---|---|
| 178 | 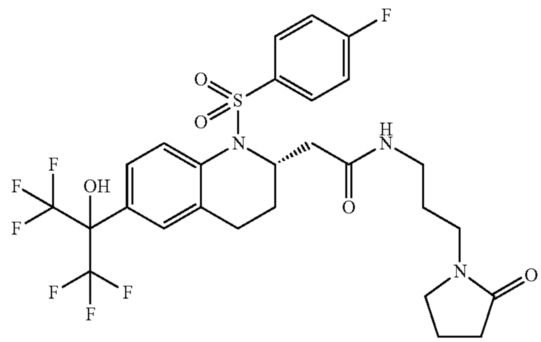 [SMILES: O=C(C[C@@H]1CCc2cc(C(O)(C(F)(F)F)C(F)(F)F)ccc2N1S(=O)(=O)c1ccc(F)cc1)NCCCN1CCCC1=O] | 639.6 | 1.68 | B | 640.2 |
| 179 | 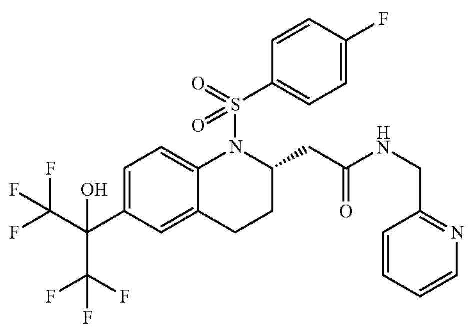 [SMILES: O=C(C[C@@H]1CCc2cc(C(O)(C(F)(F)F)C(F)(F)F)ccc2N1S(=O)(=O)c1ccc(F)cc1)NCc1ccccn1] | 605.5 | 1.48 | B | 606.1 |
| 180 | 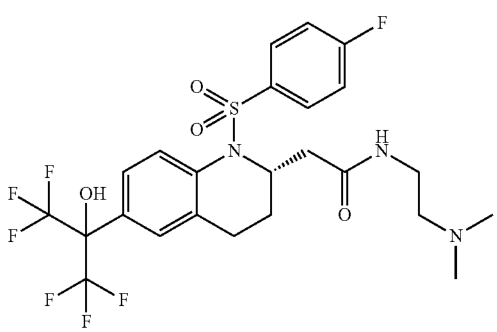 [SMILES: CN(C)CCNC(=O)C[C@@H]1CCc2cc(C(O)(C(F)(F)F)C(F)(F)F)ccc2N1S(=O)(=O)c1ccc(F)cc1] | 585.5 | 1.45 | B | 586.1 |
| 182 | 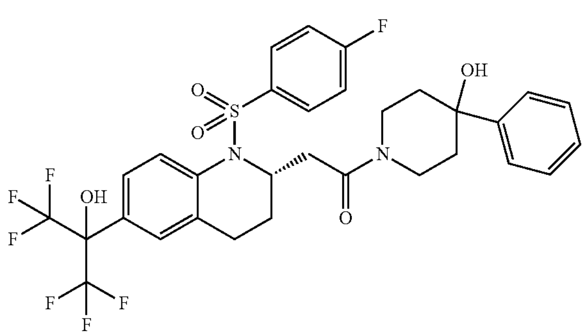 [SMILES: O=C(C[C@@H]1CCc2cc(C(O)(C(F)(F)F)C(F)(F)F)ccc2N1S(=O)(=O)c1ccc(F)cc1)N1CCC(O)(c2ccccc2)CC1] | 674.6 | 1.97 | B | 675.2 |

TABLE 1-continued
| Ex. No. | Structure | MW | HPLC ret. time (min.) | HPLC method | MS (M+1) |
|---|---|---|---|---|---|
| 183 | 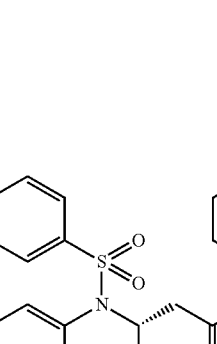 | 558.5 | 1.58 | B | 559.1 |
| 184 | 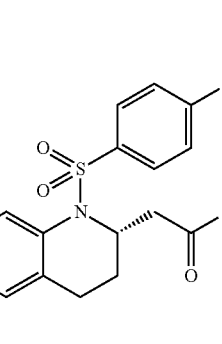 Diastereomic Mixture | 612.6 | 1.65 | B | 613.1 |
| 185 | 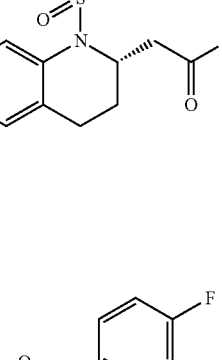 | 612.6 | 2.02 | B | 613.1 |
| 186 | 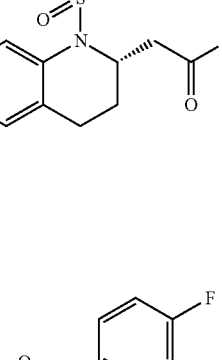 | 572.5 | 1.74 | B | 573.1 |

TABLE 1-continued
| Ex. No. | Structure | MW | HPLC ret. time (min.) | HPLC method | MS (M+1) |
|---|---|---|---|---|---|
| 187 | 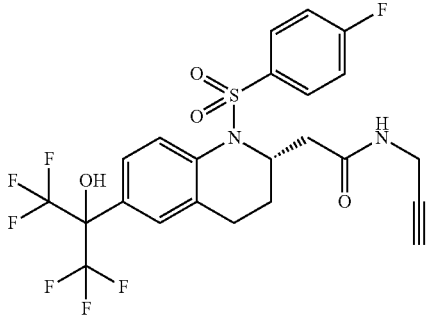 [SMILES: C#CCNC(=O)C[C@@H]1CCc2cc(C(O)(C(F)(F)F)C(F)(F)F)ccc2N1S(=O)(=O)c1ccc(F)cc1] | 552.5 | 1.79 | B | 553.1 |
| 188 | 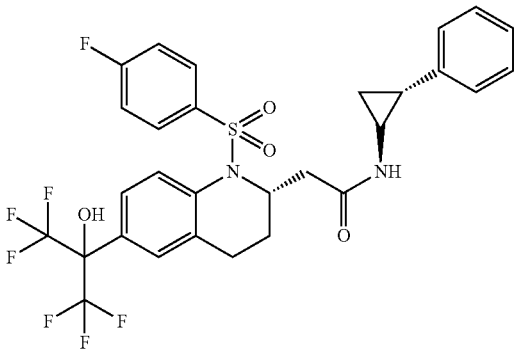 | 630.6 | 2.10 | B | 631.2 |
| 189 | 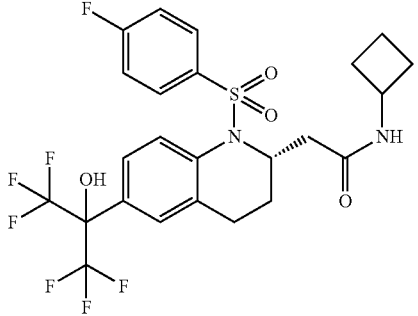 [SMILES: O=C(C[C@@H]1CCc2cc(C(O)(C(F)(F)F)C(F)(F)F)ccc2N1S(=O)(=O)c1ccc(F)cc1)NC1CCC1] | 568.5 | 1.92 | B | 569.1 |
| 190 | 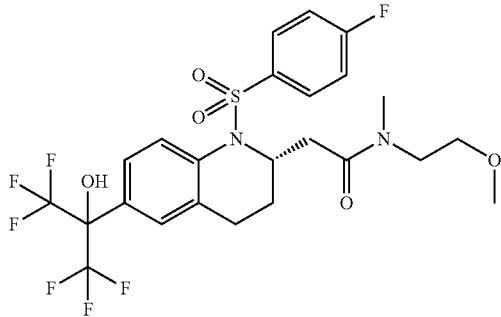 [SMILES: COCCN(C)C(=O)C[C@@H]1CCc2cc(C(O)(C(F)(F)F)C(F)(F)F)ccc2N1S(=O)(=O)c1ccc(F)cc1] | 586.5 | 1.86 | B | 587.1 |

TABLE 1-continued

| Ex. No. | Structure | MW | HPLC ret. time (min.) | HPLC method | MS (M$^{+1}$) |
|---|---|---|---|---|---|
| 191 | 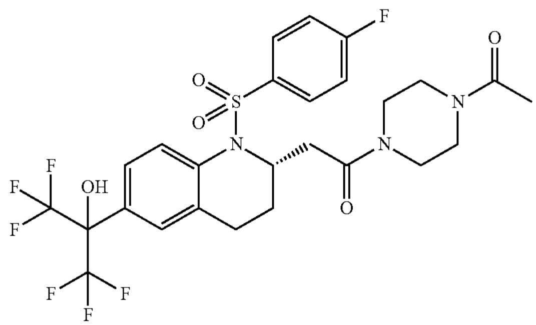 [SMILES: CC(=O)N1CCN(C(=O)C[C@@H]2CCc3cc(C(O)(C(F)(F)F)C(F)(F)F)ccc3N2S(=O)(=O)c2ccc(F)cc2)CC1] | 625.6 | 1.65 | B | 626.2 |
| 192 | 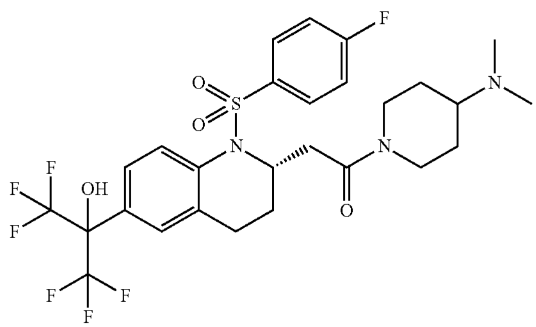 [SMILES: CN(C)C1CCN(C(=O)C[C@@H]2CCc3cc(C(O)(C(F)(F)F)C(F)(F)F)ccc3N2S(=O)(=O)c2ccc(F)cc2)CC1] | 625.6 | 1.56 | I | 626.2 |
| 193 | 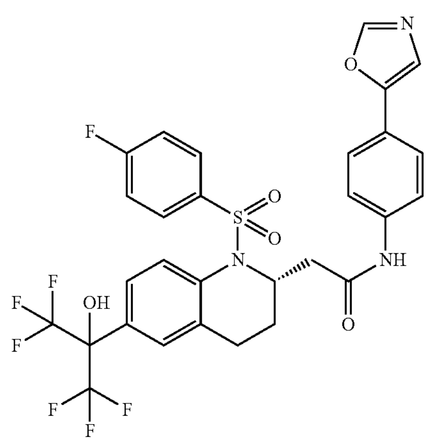 [SMILES: O=C(C[C@@H]1CCc2cc(C(O)(C(F)(F)F)C(F)(F)F)ccc2N1S(=O)(=O)c1ccc(F)cc1)Nc1ccc(-c2cnco2)cc1] | 657.6 | 1.94 | B | 658.2 |
| 194 | Diastereomic Mixture | 646.6 | 1.65 | I | 647.1 |

TABLE 1-continued

| Ex. No. | Structure | MW | HPLC ret. time (min.) | HPLC method | MS (M+1) |
|---|---|---|---|---|---|
| 195 | 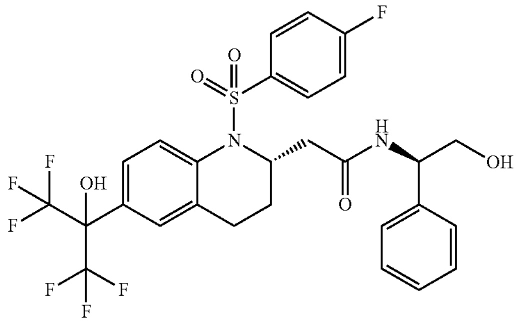 [SMILES: O=C(C[C@@H]1CCc2cc(C(O)(C(F)(F)F)C(F)(F)F)ccc2N1S(=O)(=O)c1ccc(F)cc1)N[C@@H](CO)c1ccccc1] | 634.6 | 1.82 | I | 635.1 |
| 197 | 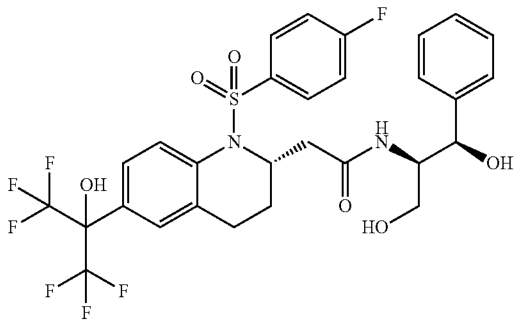 [SMILES: O=C(C[C@@H]1CCc2cc(C(O)(C(F)(F)F)C(F)(F)F)ccc2N1S(=O)(=O)c1ccc(F)cc1)N[C@H](CO)[C@H](O)c1ccccc1] | 664.6 | 1.76 | B | 665.1 |
| 198 | 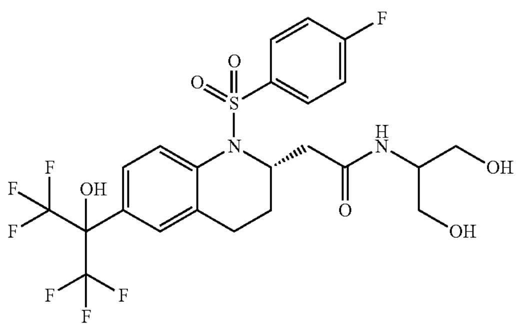 [SMILES: O=C(C[C@@H]1CCc2cc(C(O)(C(F)(F)F)C(F)(F)F)ccc2N1S(=O)(=O)c1ccc(F)cc1)NC(CO)CO] | 588.5 | 1.51 | B | 589.0 |
| 199 | 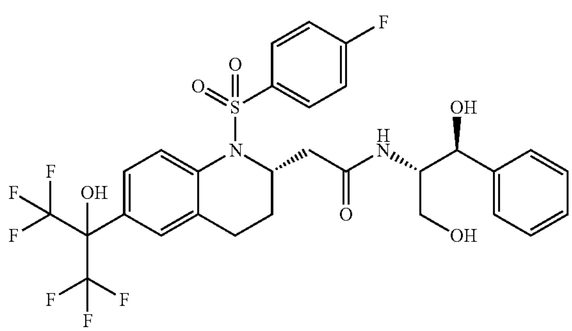 [SMILES: O=C(C[C@@H]1CCc2cc(C(O)(C(F)(F)F)C(F)(F)F)ccc2N1S(=O)(=O)c1ccc(F)cc1)N[C@@H](CO)[C@@H](O)c1ccccc1] | 664.6 | 1.76 | B | 665.1 |

TABLE 1-continued

| Ex. No. | Structure | MW | HPLC ret. time (min.) | HPLC method | MS (M+1) |
|---|---|---|---|---|---|
| 200 | 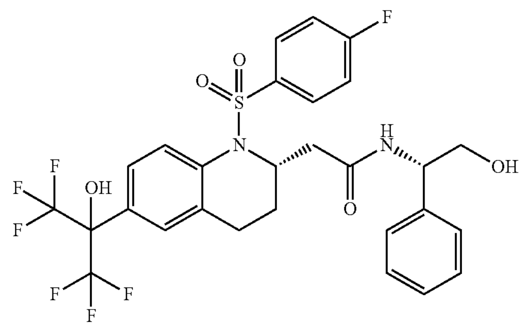 [SMILES: O=C(C[C@@H]1CCc2cc(C(O)(C(F)(F)F)C(F)(F)F)ccc2N1S(=O)(=O)c1ccc(F)cc1)N[C@H](CO)c1ccccc1] | 634.6 | 1.83 | B | 635.0 |
| 201 | 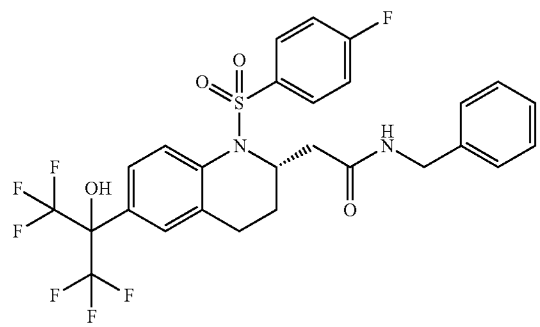 [SMILES: O=C(C[C@@H]1CCc2cc(C(O)(C(F)(F)F)C(F)(F)F)ccc2N1S(=O)(=O)c1ccc(F)cc1)NCc1ccccc1] | 604.5 | 1.98 | B | 605.0 |
| 202 | 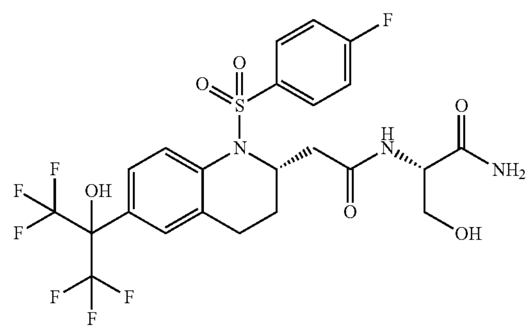 [SMILES: NC(=O)[C@H](CO)NC(=O)C[C@@H]1CCc2cc(C(O)(C(F)(F)F)C(F)(F)F)ccc2N1S(=O)(=O)c1ccc(F)cc1] | 601.5 | 1.49 | I | 602.0 |
| 203 | 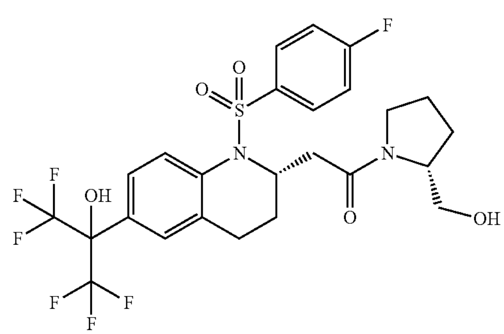 [SMILES: O=C(C[C@@H]1CCc2cc(C(O)(C(F)(F)F)C(F)(F)F)ccc2N1S(=O)(=O)c1ccc(F)cc1)N1CCC[C@@H]1CO] | 598.5 | 1.74 | B | 599.1 |

TABLE 1-continued

| Ex. No. | Structure | MW | HPLC ret. time (min.) | HPLC method | MS (M+1) |
|---|---|---|---|---|---|
| 204 | 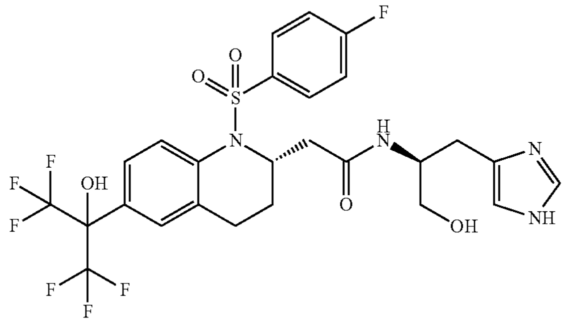 [SMILES: O=C(C[C@@H]1CCc2cc(C(O)(C(F)(F)F)C(F)(F)F)ccc2N1S(=O)(=O)c1ccc(F)cc1)N[C@H](CO)Cc1c[nH]cn1] | 638.6 | 1.40 | B | 639.1 |
| 205 | 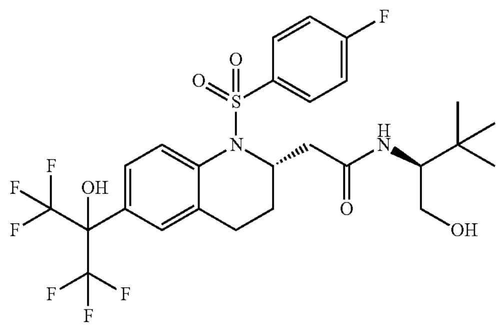 [SMILES: CC(C)(C)[C@@H](CO)NC(=O)C[C@@H]1CCc2cc(C(O)(C(F)(F)F)C(F)(F)F)ccc2N1S(=O)(=O)c1ccc(F)cc1] | 614.6 | 1.87 | B | 615.1 |
| 207 | 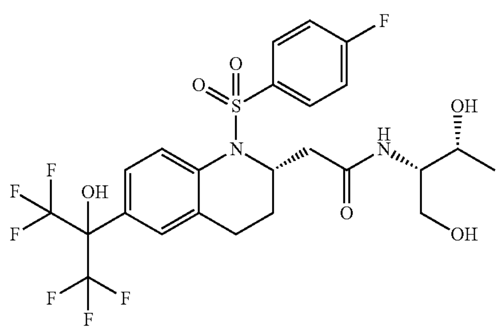 [SMILES: C[C@@H](O)[C@H](CO)NC(=O)C[C@@H]1CCc2cc(C(O)(C(F)(F)F)C(F)(F)F)ccc2N1S(=O)(=O)c1ccc(F)cc1] | 602.5 | 1.56 | B | 603.2 |
| 208 | 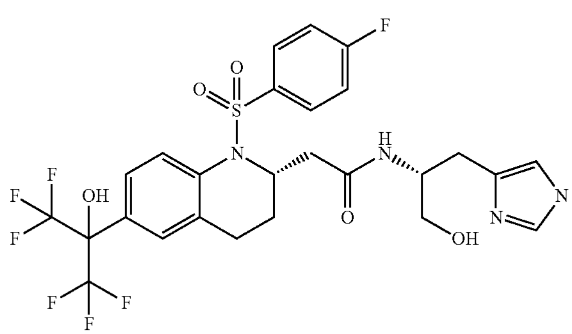 [SMILES: O=C(C[C@@H]1CCc2cc(C(O)(C(F)(F)F)C(F)(F)F)ccc2N1S(=O)(=O)c1ccc(F)cc1)N[C@@H](CO)Cc1c[nH]cn1] | 638.6 | 1.39 | B | 639.0 |

TABLE 1-continued

| Ex. No. | Structure | MW | HPLC ret. time (min.) | HPLC method | MS (M+1) |
|---|---|---|---|---|---|
| 209 | 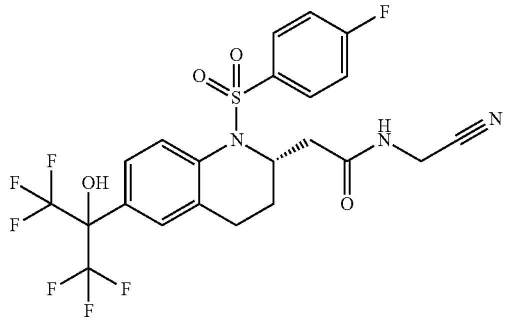 [SMILES: N#CCNC(=O)C[C@@H]1CCc2cc(C(O)(C(F)(F)F)C(F)(F)F)ccc2N1S(=O)(=O)c1ccc(F)cc1] | 553.5 | 1.73 | B | 554.1 |
| 210 | 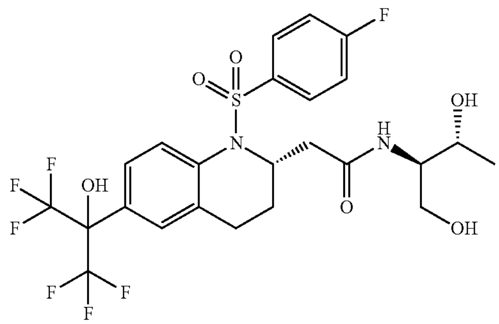 [SMILES: C[C@@H](O)[C@@H](CO)NC(=O)C[C@@H]1CCc2cc(C(O)(C(F)(F)F)C(F)(F)F)ccc2N1S(=O)(=O)c1ccc(F)cc1] | 602.5 | 1.57 | B | 603.2 |
| 211 | 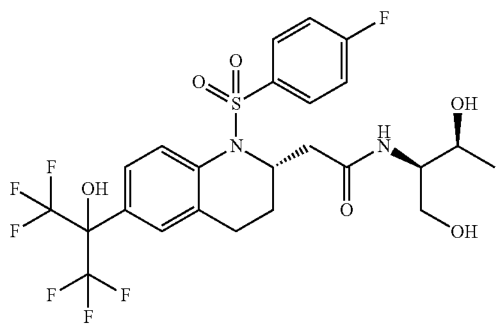 [SMILES: C[C@H](O)[C@@H](CO)NC(=O)C[C@@H]1CCc2cc(C(O)(C(F)(F)F)C(F)(F)F)ccc2N1S(=O)(=O)c1ccc(F)cc1] | 602.5 | 1.56 | B | 603.2 |
| 212 | 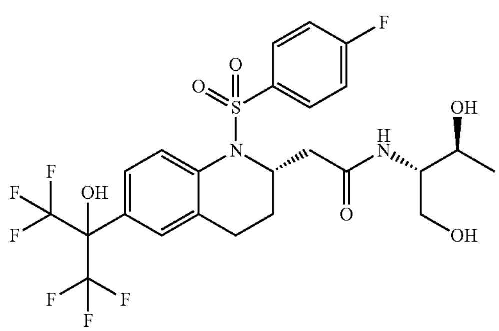 [SMILES: C[C@H](O)[C@H](CO)NC(=O)C[C@@H]1CCc2cc(C(O)(C(F)(F)F)C(F)(F)F)ccc2N1S(=O)(=O)c1ccc(F)cc1] | 602.5 | 1.60 | B | 603.1 |

TABLE 1-continued

| Ex. No. | Structure | MW | HPLC ret. time (min.) | HPLC method | MS (M+1) |
|---|---|---|---|---|---|
| 213 | 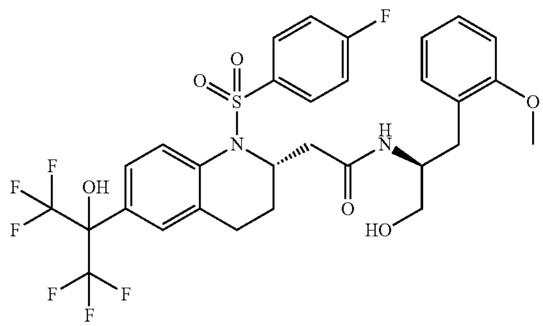 [SMILES: COc1ccccc1C[C@@H](CO)NC(=O)C[C@@H]1CCc2cc(C(O)(C(F)(F)F)C(F)(F)F)ccc2N1S(=O)(=O)c1ccc(F)cc1] | 678.6 | 1.89 | B | 679.0 |
| 214 | 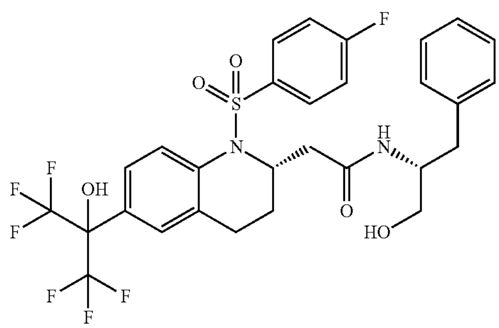 [SMILES: O=C(C[C@@H]1CCc2cc(C(O)(C(F)(F)F)C(F)(F)F)ccc2N1S(=O)(=O)c1ccc(F)cc1)N[C@@H](CO)Cc1ccccc1] | 648.6 | 1.90 | B | 649.1 |
| 215 | Diastereomer 1 | 635.6 | 1.43 | B | 636.0 |
| 216 | 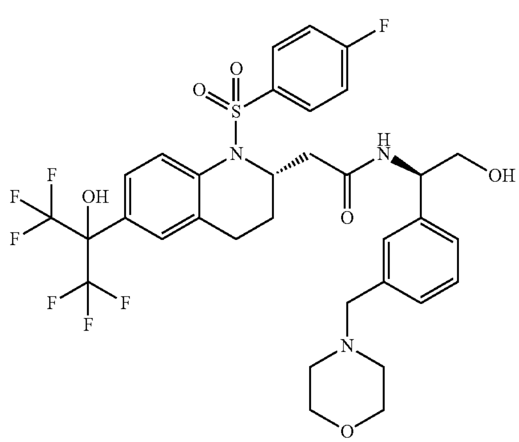 [SMILES: O=C(C[C@@H]1CCc2cc(C(O)(C(F)(F)F)C(F)(F)F)ccc2N1S(=O)(=O)c1ccc(F)cc1)N[C@@H](CO)c1cccc(CN2CCOCC2)c1] | 733.7 | 1.50 | B | 734.1 |

TABLE 1-continued

| Ex. No. | Structure | MW | HPLC ret. time (min.) | HPLC method | MS (M+1) |
|---|---|---|---|---|---|
| 217 | Diastereomer 2 | 635.6 | 1.62 | B | 636.1 |
| 218 | Diastereomeric Mixture | 683.6 | 0.87 | B | 684.0 |
| 219 | 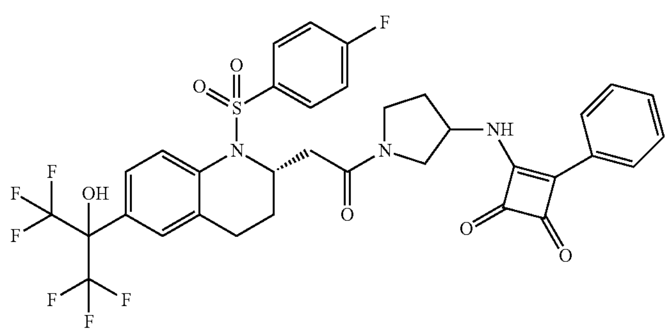 [SMILES: O=C(C[C@@H]1CCc2cc(C(O)(C(F)(F)F)C(F)(F)F)ccc2N1S(=O)(=O)c1ccc(F)cc1)N1CCC(Nc2c(-c3ccccc3)c(=O)c2=O)C1] | 739.7 | 1.97 | B | 740.2 |
| 220 | 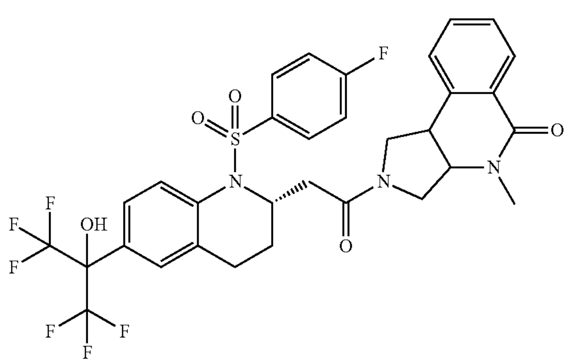 [SMILES: CN1C(=O)c2ccccc2C2CN(C(=O)C[C@@H]3CCc4cc(C(O)(C(F)(F)F)C(F)(F)F)ccc4N3S(=O)(=O)c3ccc(F)cc3)CC21] | 699.6 | 1.91 | B | 700.2 |

TABLE 1-continued

| Ex. No. | Structure | MW | HPLC ret. time (min.) | HPLC method | MS (M+1) |
|---|---|---|---|---|---|
| 221 | 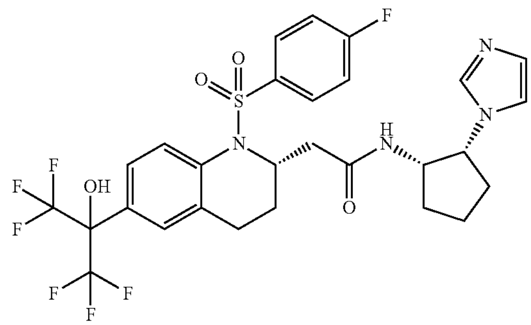 [SMILES: O=C(C[C@@H]1CCc2cc(C(O)(C(F)(F)F)C(F)(F)F)ccc2N1S(=O)(=O)c1ccc(F)cc1)N[C@H]1CCC[C@H]1n1ccnc1] | 648.6 | 1.58 | B | 649.2 |
| 222 | 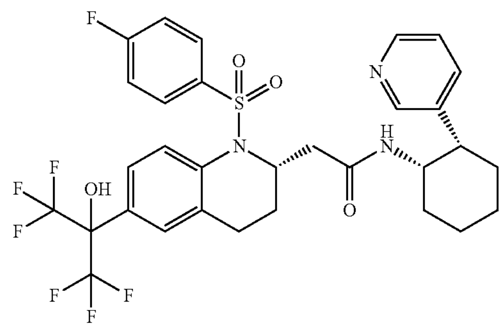 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@H]1c1cccnc1] | 673.7 | 1.70 | B | 674.2 |
| 223 | 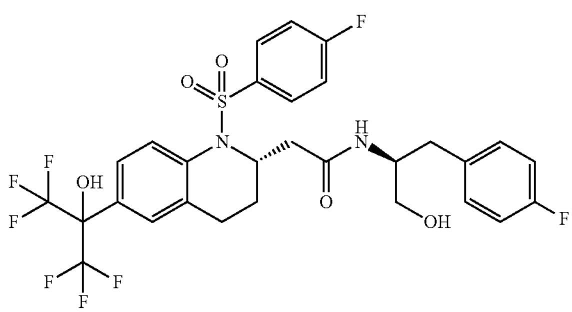 [SMILES: O=C(C[C@@H]1CCc2cc(C(O)(C(F)(F)F)C(F)(F)F)ccc2N1S(=O)(=O)c1ccc(F)cc1)N[C@H](CO)Cc1ccc(F)cc1] | 666.6 | 1.61 | B | 667.0 |
| 224 | 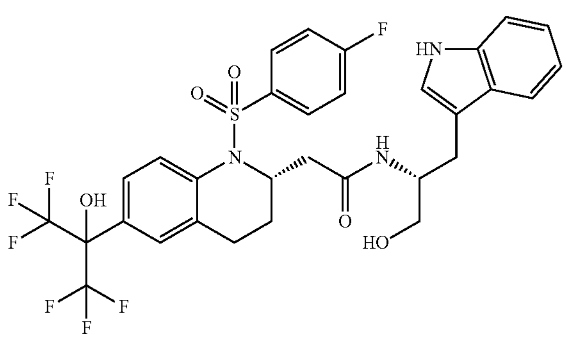 [SMILES: O=C(C[C@@H]1CCc2cc(C(O)(C(F)(F)F)C(F)(F)F)ccc2N1S(=O)(=O)c1ccc(F)cc1)N[C@@H](CO)Cc1c[nH]c2ccccc12] | 687.6 | 1.56 | B | 688.2 |

TABLE 1-continued
| Ex. No. | Structure | MW | HPLC ret. time (min.) | HPLC method | MS (M+1) |
|---|---|---|---|---|---|
| 225 | 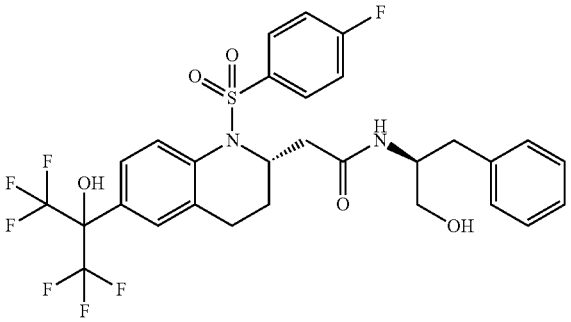 [SMILES: O=C(C[C@@H]1CCc2cc(C(O)(C(F)(F)F)C(F)(F)F)ccc2N1S(=O)(=O)c1ccc(F)cc1)N[C@H](CO)Cc1ccccc1] | 648.6 | 1.60 | B | 649.0 |
| 226 | 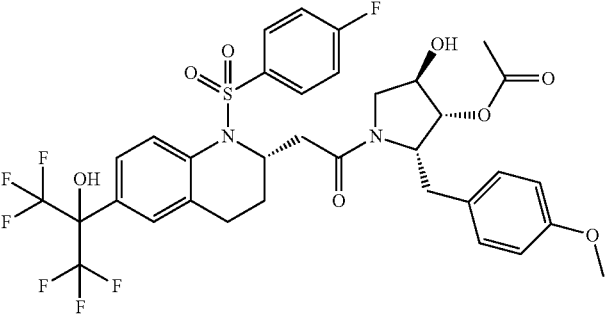 [SMILES: COc1ccc(C[C@H]2[C@@H](OC(C)=O)[C@H](O)CN2C(=O)C[C@@H]2CCc3cc(C(O)(C(F)(F)F)C(F)(F)F)ccc3N2S(=O)(=O)c2ccc(F)cc2)cc1] | 762.7 | 1.62 | B | 763.2 |
| 227 | 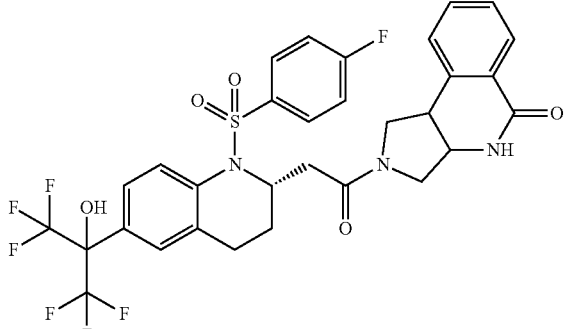<br>Diastereomeric Mixture | 685.6 | 1.52 | B | 686.2 |
| 228 | 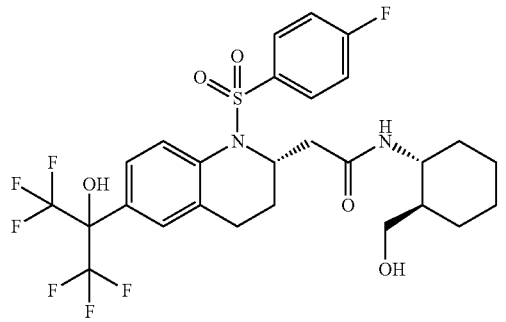<br>Diastereomeric Mixture | 626.6 | 1.59 | B | 627.1 |

TABLE 1-continued

| Ex. No. | Structure | MW | HPLC ret. time (min.) | HPLC method | MS (M+1) |
|---|---|---|---|---|---|
| 229 | 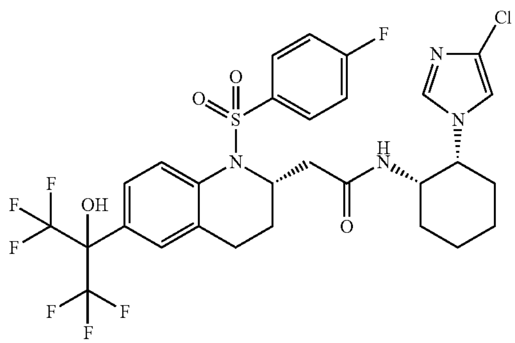 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@H]1n1cnc(Cl)c1] | 697.1 | 1.63 | B | 697.1 |
| 230 | 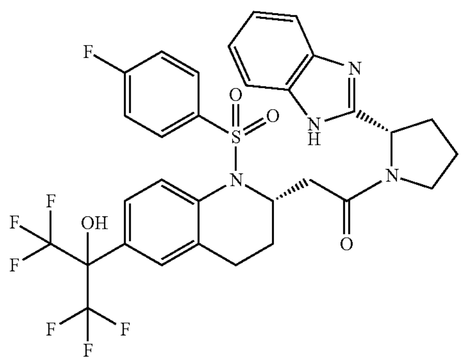 [SMILES: O=C(C[C@@H]1CCc2cc(C(O)(C(F)(F)F)C(F)(F)F)ccc2N1S(=O)(=O)c1ccc(F)cc1)N1CCC[C@H]1c1nc2ccccc2[nH]1] | 684.6 | 1.41 | B | 685.1 |
| 231 | Diastereomer 1 | 683.6 | 1.72 | B | 684.0 |
| 232 | Diastereomer 2 | 683.6 | 1.76 | B | 684.0 |

TABLE 1-continued

| Ex. No. | Structure | MW | HPLC ret. time (min.) | HPLC method | MS (M+1) |
|---|---|---|---|---|---|
| 233 | 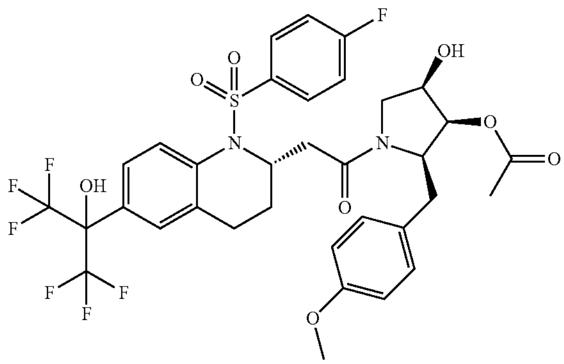 [SMILES: COc1ccc(C[C@@H]2[C@H](OC(C)=O)[C@H](O)CN2C(=O)C[C@@H]2CCc3cc(C(O)(C(F)(F)F)C(F)(F)F)ccc3N2S(=O)(=O)c2ccc(F)cc2)cc1] | 762.7 | 1.62 | B | 763.1 |
| 234 | Diastereomic Mixture | 626.6 | 1.60 | B | 627.1 |
| 235 | 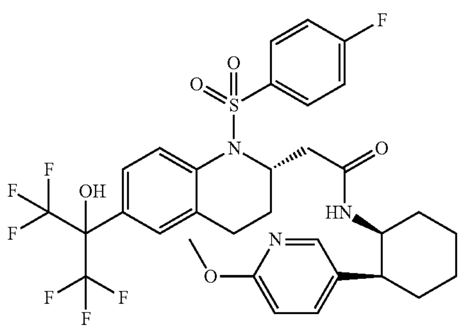 [SMILES: COc1ccc([C@@H]2CCCC[C@@H]2NC(=O)C[C@@H]2CCc3cc(C(O)(C(F)(F)F)C(F)(F)F)ccc3N2S(=O)(=O)c2ccc(F)cc2)cn1] | 703.7 | 2.03 | B | 704.3 |
| 236 | 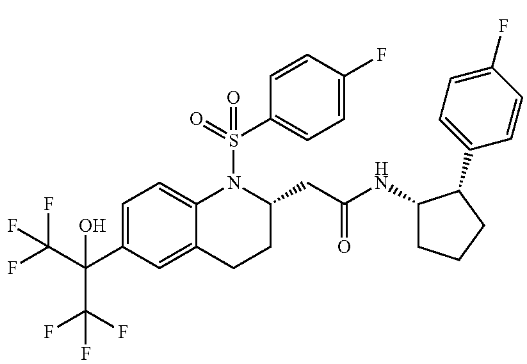 [SMILES: O=C(C[C@@H]1CCc2cc(C(O)(C(F)(F)F)C(F)(F)F)ccc2N1S(=O)(=O)c1ccc(F)cc1)N[C@H]1CCC[C@H]1c1ccc(F)cc1] | 676.6 | 1.87 | B | 677.1 |

TABLE 1-continued

| Ex. No. | Structure | MW | HPLC ret. time (min.) | HPLC method | MS (M+1) |
|---|---|---|---|---|---|
| 237 | 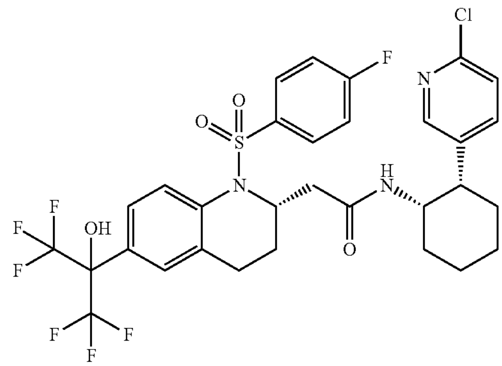 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@H]1c1ccc(Cl)nc1] | 708.1 | 1.81 | B | 708.1 |
| 238 | 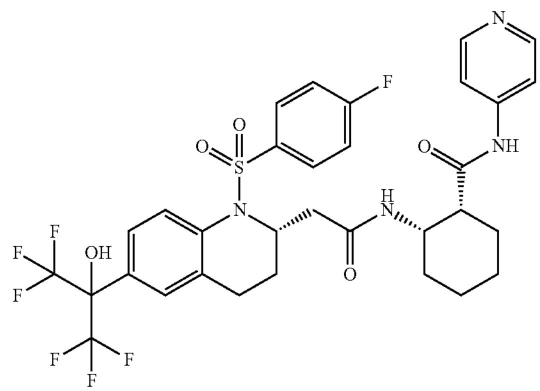 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@H]1C(=O)Nc1ccncc1] | 716.7 | 1.56 | B | 717.2 |
| 239 | 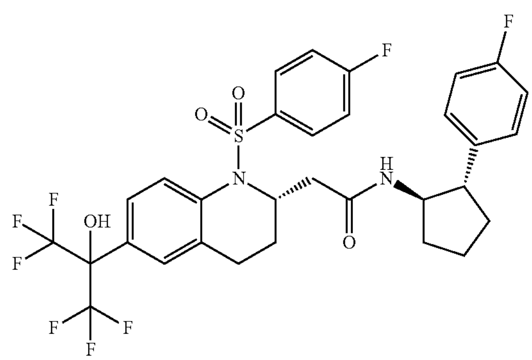 [SMILES: O=C(C[C@@H]1CCc2cc(C(O)(C(F)(F)F)C(F)(F)F)ccc2N1S(=O)(=O)c1ccc(F)cc1)N[C@@H]1CCC[C@H]1c1ccc(F)cc1] | 676.6 | 1.87 | B | 677.0 |
| 240 | Diastereomer 1 | 745.7 | 2.12 | B | 746.3 |

TABLE 1-continued

| Ex. No. | Structure | MW | HPLC ret. time (min.) | HPLC method | MS (M+1) |
|---|---|---|---|---|---|
| 241 | Diastereomer 2 | 745.7 | 2.27 | B | 746.2 |
| 242 | 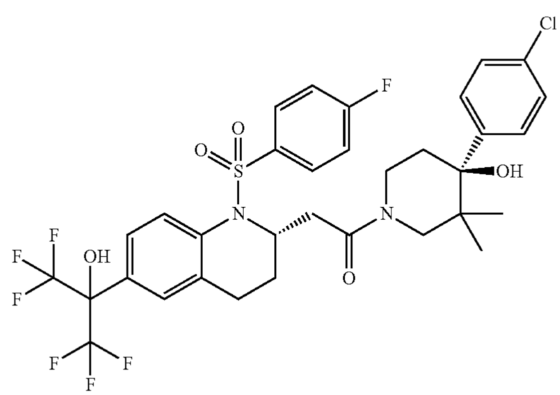 [SMILES: CC1(C)CN(C(=O)C[C@@H]2CCc3cc(C(O)(C(F)(F)F)C(F)(F)F)ccc3N2S(=O)(=O)c2ccc(F)cc2)CC[C@]1(O)c1ccc(Cl)cc1] | 737.1 | 1.94 | B | 737.1 |
| 243 | 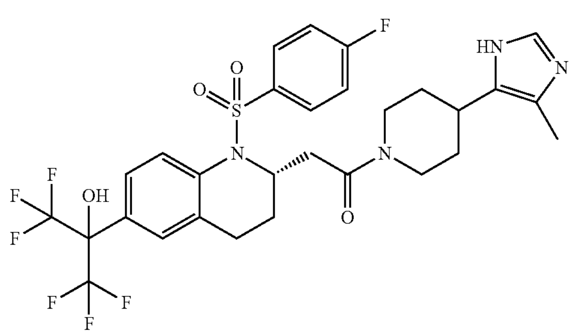 [SMILES: Cc1nc[nH]c1C1CCN(C(=O)C[C@@H]2CCc3cc(C(O)(C(F)(F)F)C(F)(F)F)ccc3N2S(=O)(=O)c2ccc(F)cc2)CC1] | 662.6 | 1.34 | B | 663.1 |
| 244 | 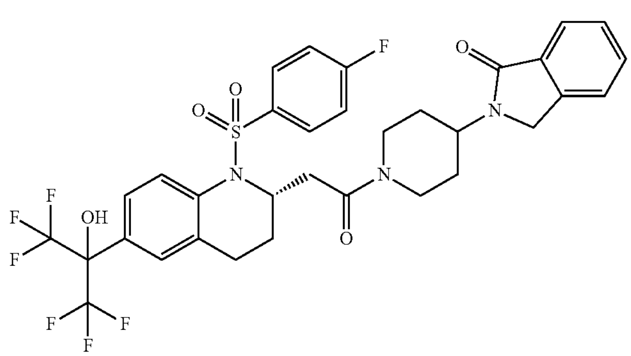 [SMILES: O=C(C[C@@H]1CCc2cc(C(O)(C(F)(F)F)C(F)(F)F)ccc2N1S(=O)(=O)c1ccc(F)cc1)N1CCC(N2Cc3ccccc3C2=O)CC1] | 713.7 | 1.61 | B | 714.1 |

TABLE 1-continued

| Ex. No. | Structure | MW | HPLC ret. time (min.) | HPLC method | MS (M+1) |
|---|---|---|---|---|---|
| 245 | 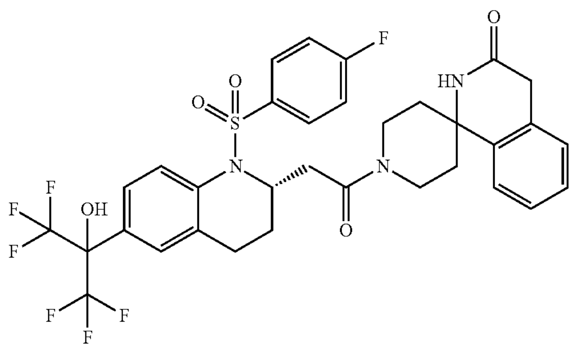 [SMILES: O=C1Cc2ccccc2C2(CCN(C(=O)C[C@@H]3CCc4cc(C(O)(C(F)(F)F)C(F)(F)F)ccc4N3S(=O)(=O)c3ccc(F)cc3)CC2)N1] | 713.7 | 1.57 | B | 714.2 |
| 246 | Diastereomer 1 | 703.5 | 1.73 | B | 703.0 |
| 247 | Diastereomer 2 | 703.5 | 1.75 | B | 703.0 |
| 248 | 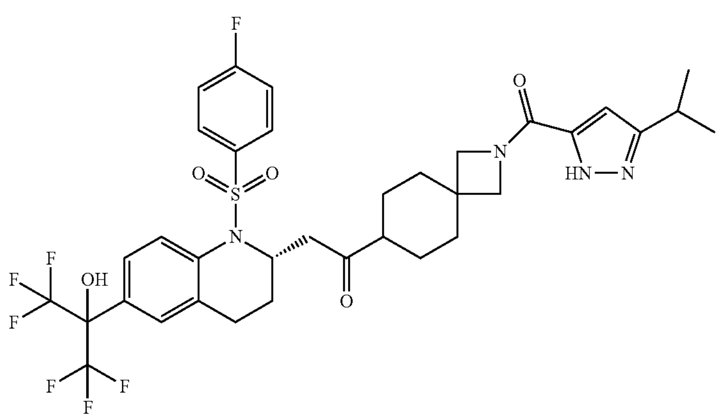 [SMILES: CC(C)c1cc(C(=O)N2CC3(CCC(C(=O)C[C@@H]4CCc5cc(C(O)(C(F)(F)F)C(F)(F)F)ccc5N4S(=O)(=O)c4ccc(F)cc4)CC3)C2)[nH]n1] | 759.7 | 1.56 | B | 760.2 |

TABLE 1-continued

| Ex. No. | Structure | MW | HPLC ret. time (min.) | HPLC method | MS (M+1) |
|---|---|---|---|---|---|
| 249 | 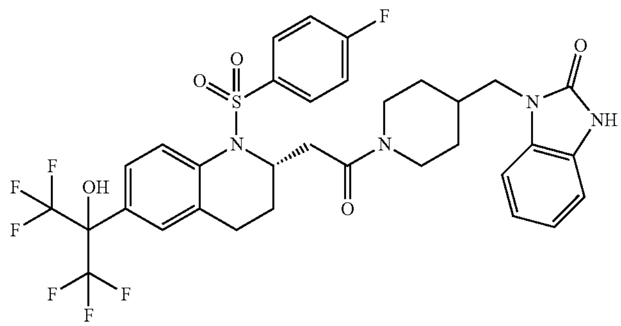 [SMILES: O=C(C[C@@H]1CCc2cc(C(O)(C(F)(F)F)C(F)(F)F)ccc2N1S(=O)(=O)c1ccc(F)cc1)N1CCC(Cn2c(=O)[nH]c3ccccc32)CC1] | 728.7 | 1.59 | B | 729.2 |
| 250 | 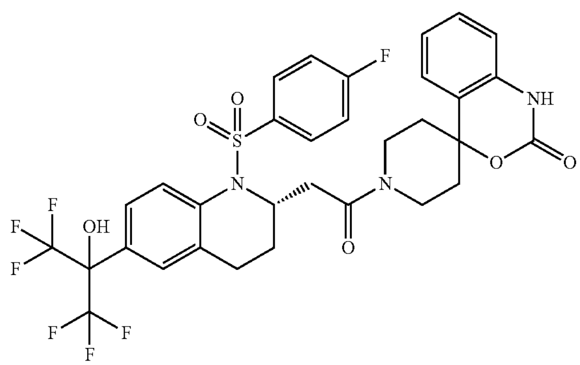 [SMILES: O=C1Nc2ccccc2C2(CCN(C(=O)C[C@@H]3CCc4cc(C(O)(C(F)(F)F)C(F)(F)F)ccc4N3S(=O)(=O)c3ccc(F)cc3)CC2)O1] | 715.6 | 1.57 | B | 716.2 |
| 251 | 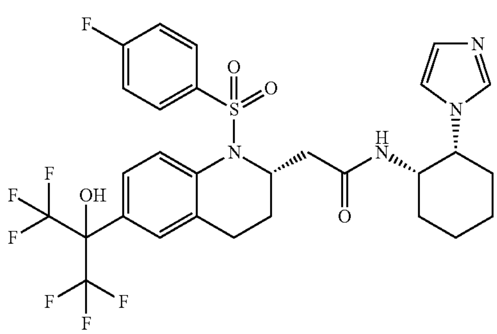 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@H]1n1ccnc1] | 662.6 | 0.98 | B | 663.1 |
| 252 | 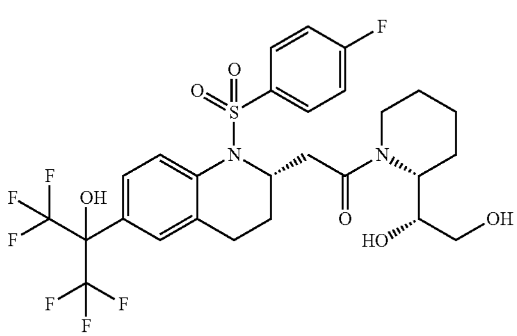 [SMILES: O=C(C[C@@H]1CCc2cc(C(O)(C(F)(F)F)C(F)(F)F)ccc2N1S(=O)(=O)c1ccc(F)cc1)N1CCCC[C@@H]1[C@@H](O)CO] | 642.6 | 1.41 | B | 643.2 |

TABLE 1-continued

| Ex. No. | Structure | MW | HPLC ret. time (min.) | HPLC method | MS (M+1) |
|---|---|---|---|---|---|
| 253 | 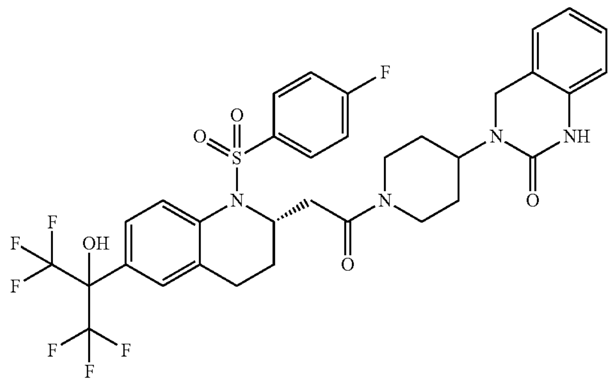 [SMILES: O=C(C[C@@H]1CCc2cc(C(O)(C(F)(F)F)C(F)(F)F)ccc2N1S(=O)(=O)c1ccc(F)cc1)N1CCC(N2Cc3ccccc3NC2=O)CC1] | 728.7 | 1.61 | B | 729.2 |
| 254 | 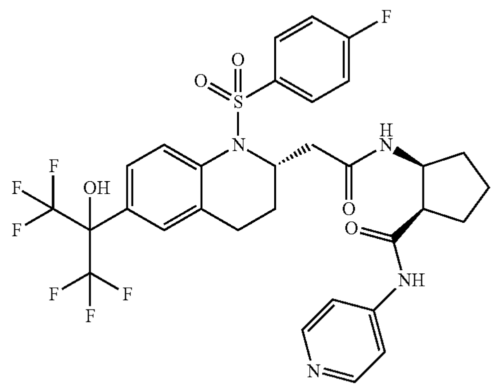 [SMILES: O=C(C[C@@H]1CCc2cc(C(O)(C(F)(F)F)C(F)(F)F)ccc2N1S(=O)(=O)c1ccc(F)cc1)N[C@H]1CCC[C@H]1C(=O)Nc1ccncc1] | 702.7 | 1.66 | B | 703.3 |
| 255 | Diastereomic Mixture | 792.8 | 1.67 | I | 793.2 |

TABLE 1-continued

| Ex. No. | Structure | MW | HPLC ret. time (min.) | HPLC method | MS (M+1) |
|---|---|---|---|---|---|
| 256 | 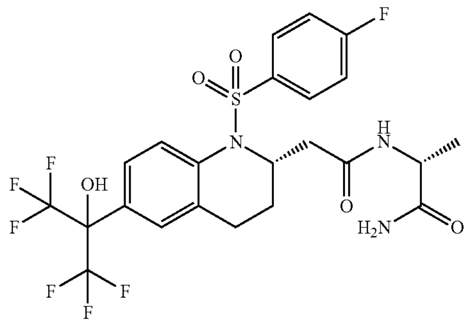 [SMILES: C[C@@H](NC(=O)C[C@@H]1CCc2cc(C(O)(C(F)(F)F)C(F)(F)F)ccc2N1S(=O)(=O)c1ccc(F)cc1)C(N)=O] | 585.5 | 1.37 | B | 586.0 |
| 257 | 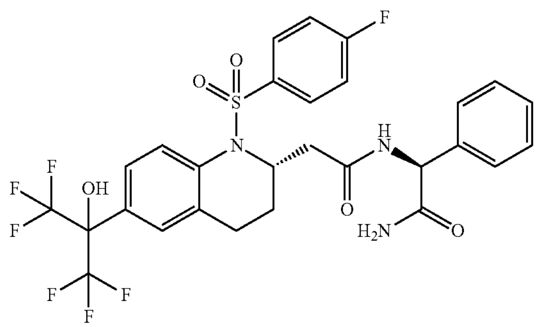 [SMILES: NC(=O)[C@@H](NC(=O)C[C@@H]1CCc2cc(C(O)(C(F)(F)F)C(F)(F)F)ccc2N1S(=O)(=O)c1ccc(F)cc1)c1ccccc1] | 647.6 | 1.50 | B | 648.0 |
| 258 | 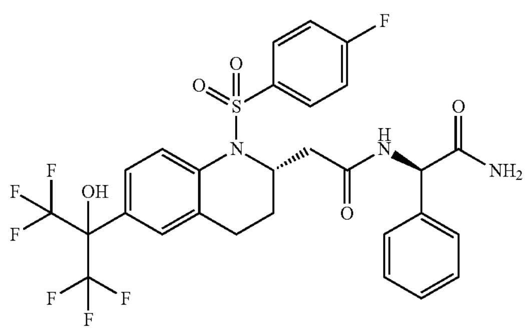 [SMILES: NC(=O)[C@H](NC(=O)C[C@@H]1CCc2cc(C(O)(C(F)(F)F)C(F)(F)F)ccc2N1S(=O)(=O)c1ccc(F)cc1)c1ccccc1] | 647.6 | 1.50 | B | 648.0 |
| 259 | 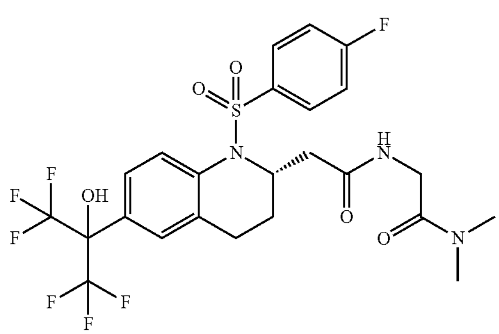 [SMILES: CN(C)C(=O)CNC(=O)C[C@@H]1CCc2cc(C(O)(C(F)(F)F)C(F)(F)F)ccc2N1S(=O)(=O)c1ccc(F)cc1] | 599.5 | 1.43 | B | 600.1 |

TABLE 1-continued

| Ex. No. | Structure | MW | HPLC ret. time (min.) | HPLC method | MS (M+1) |
|---|---|---|---|---|---|
| 260 | 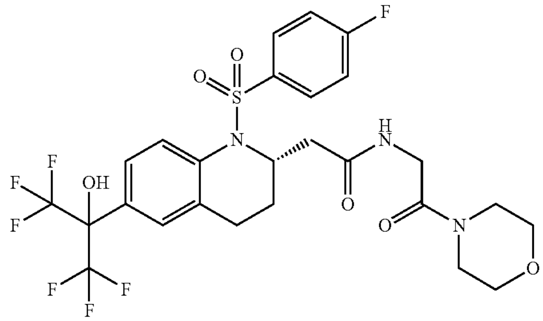 [SMILES: O=C(C[C@@H]1CCc2cc(C(O)(C(F)(F)F)C(F)(F)F)ccc2N1S(=O)(=O)c1ccc(F)cc1)NCC(=O)N1CCOCC1] | 641.6 | 1.42 | B | 642.1 |
| 261 | Diastereomic Mixture | 596.5 | 1.41 | B | 597.0 |
| 262 | 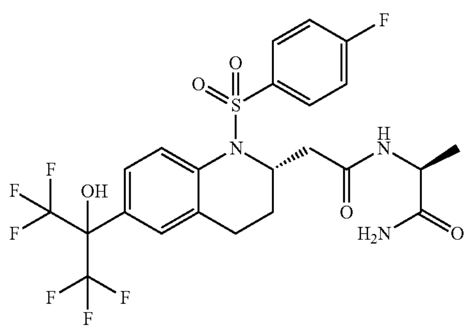 [SMILES: C[C@H](NC(=O)C[C@@H]1CCc2cc(C(O)(C(F)(F)F)C(F)(F)F)ccc2N1S(=O)(=O)c1ccc(F)cc1)C(N)=O] | 585.5 | 1.37 | B | 586.0 |
| 263 | 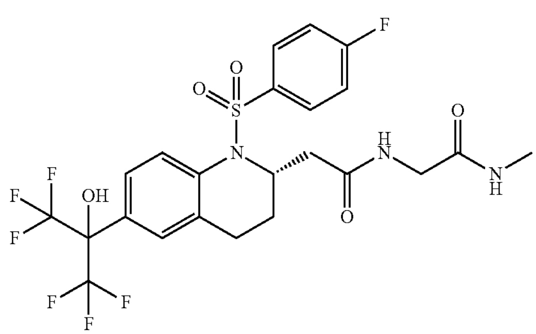 [SMILES: CNC(=O)CNC(=O)C[C@@H]1CCc2cc(C(O)(C(F)(F)F)C(F)(F)F)ccc2N1S(=O)(=O)c1ccc(F)cc1] | 585.5 | 0.94 | B | 586.0 |

TABLE 1-continued

| Ex. No. | Structure | MW | HPLC ret. time (min.) | HPLC method | MS (M+1) |
|---|---|---|---|---|---|
| 264 | 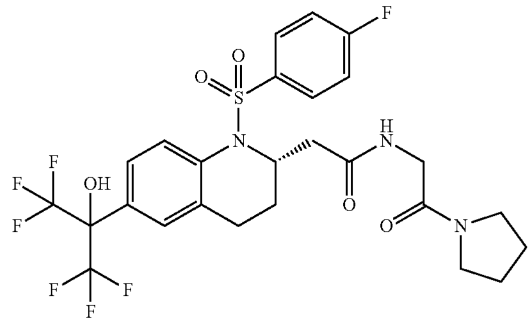 [SMILES: O=C(C[C@@H]1CCc2cc(C(O)(C(F)(F)F)C(F)(F)F)ccc2N1S(=O)(=O)c1ccc(F)cc1)NCC(=O)N1CCCC1] | 625.6 | 1.48 | B | 626.1 |
| 265 | Diastereomic Mixture | 645.6 | 1.36 | I | 646.2 |
| 266 | 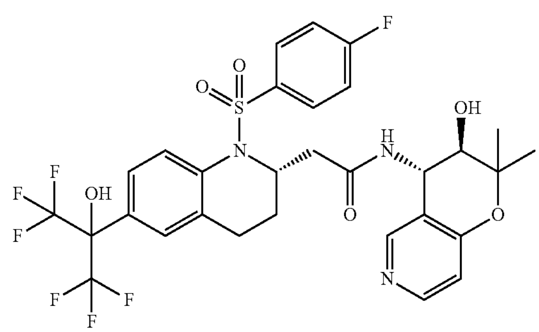 [SMILES: CC1(C)Oc2ccncc2[C@H](NC(=O)C[C@@H]2CCc3cc(C(O)(C(F)(F)F)C(F)(F)F)ccc3N2S(=O)(=O)c2ccc(F)cc2)[C@H]1O] | 691.6 | 1.34 | B | 692.1 |
| 267 | 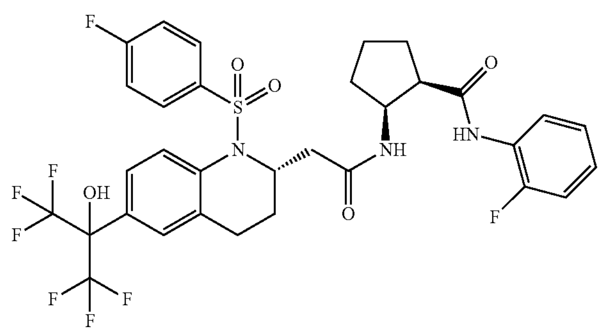 [SMILES: O=C(C[C@@H]1CCc2cc(C(O)(C(F)(F)F)C(F)(F)F)ccc2N1S(=O)(=O)c1ccc(F)cc1)N[C@H]1CCC[C@H]1C(=O)Nc1ccccc1F] | 720.6 | 1.59 | B | 722.1 |

TABLE 1-continued

| Ex. No. | Structure | MW | HPLC ret. time (min.) | HPLC method | MS (M+1) |
|---|---|---|---|---|---|
| 268 | 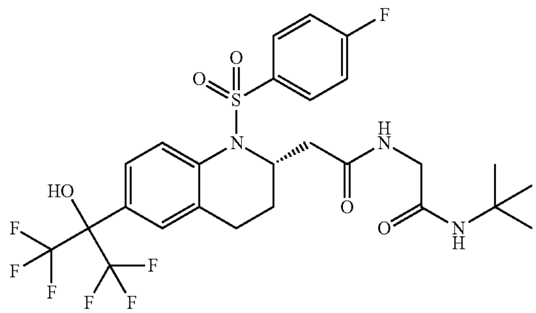 [SMILES: CC(C)(C)NC(=O)CNC(=O)C[C@@H]1CCc2cc(C(O)(C(F)(F)F)C(F)(F)F)ccc2N1S(=O)(=O)c1ccc(F)cc1] | 627.6 | 1.87 | B | 628.0 |
| 269 | 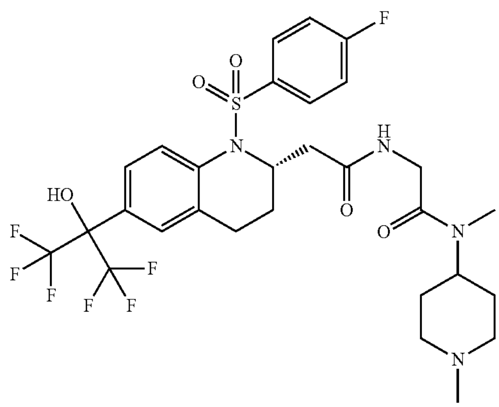 [SMILES: CN1CCC(N(C)C(=O)CNC(=O)C[C@@H]2CCc3cc(C(O)(C(F)(F)F)C(F)(F)F)ccc3N2S(=O)(=O)c2ccc(F)cc2)CC1] | 682.7 | 1.50 | B | 683.1 |
| 270 | 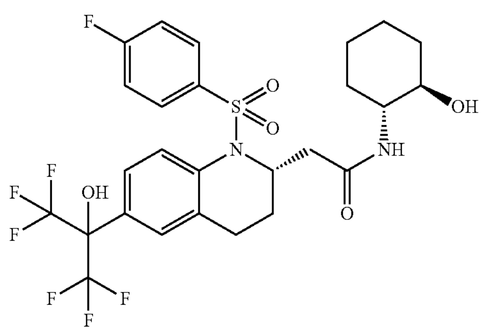 [SMILES: O=C(C[C@@H]1CCc2cc(C(O)(C(F)(F)F)C(F)(F)F)ccc2N1S(=O)(=O)c1ccc(F)cc1)N[C@@H]1CCCC[C@H]1O] | 612.6 | 1.80 | B | 613.0 |
| 271 | 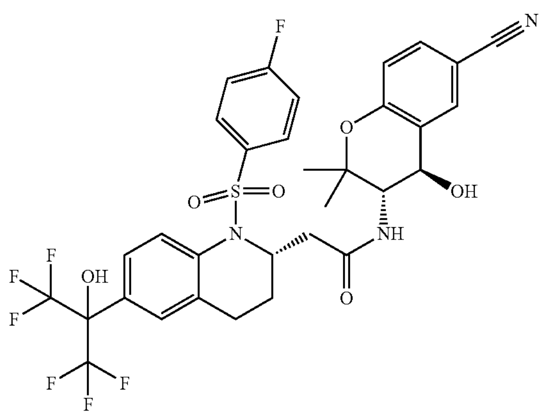 [SMILES: CC1(C)Oc2ccc(C#N)cc2[C@@H](O)[C@@H]1NC(=O)C[C@@H]1CCc2cc(C(O)(C(F)(F)F)C(F)(F)F)ccc2N1S(=O)(=O)c1ccc(F)cc1] | 715.6 | 1.99 | B | 716.1 |

TABLE 1-continued

| Ex. No. | Structure | MW | HPLC ret. time (min.) | HPLC method | MS (M+1) |
|---|---|---|---|---|---|
| 272 | 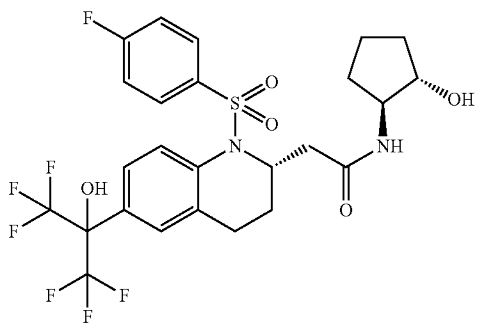 [SMILES: O=C(C[C@@H]1CCc2cc(C(O)(C(F)(F)F)C(F)(F)F)ccc2N1S(=O)(=O)c1ccc(F)cc1)N[C@H]1CCC[C@@H]1O] | 598.5 | 1.74 | B | 599.0 |
| 273 | 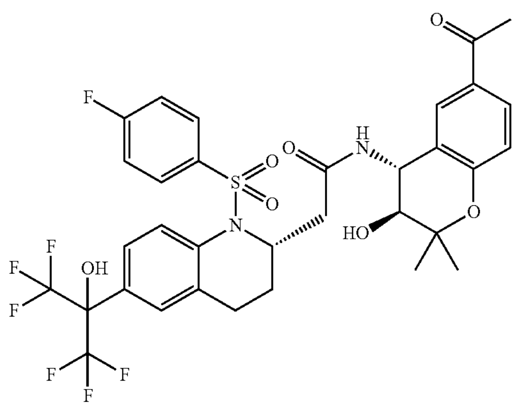 [SMILES: CC(=O)c1ccc2c(c1)[C@@H](NC(=O)C[C@@H]1CCc3cc(C(O)(C(F)(F)F)C(F)(F)F)ccc3N1S(=O)(=O)c1ccc(F)cc1)[C@H](O)C(C)(C)O2] | 732.7 | 1.97 | B | 733.0 |
| 274 | 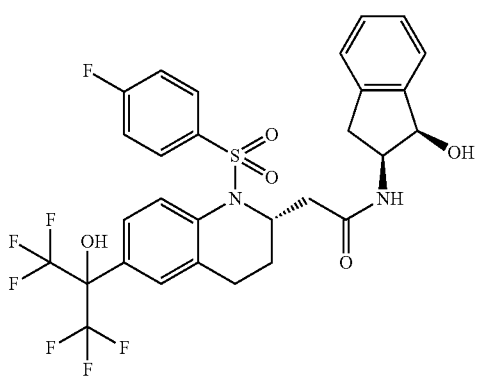 [SMILES: O=C(C[C@@H]1CCc2cc(C(O)(C(F)(F)F)C(F)(F)F)ccc2N1S(=O)(=O)c1ccc(F)cc1)N[C@H]1Cc2ccccc2[C@H]1O] | 646.6 | 1.92 | B | 647.0 |
| 275 | 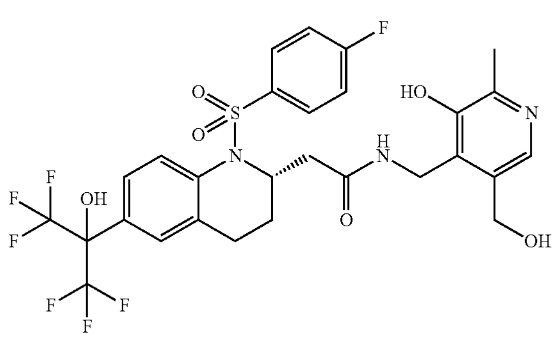 [SMILES: Cc1ncc(CO)c(CNC(=O)C[C@@H]2CCc3cc(C(O)(C(F)(F)F)C(F)(F)F)ccc3N2S(=O)(=O)c2ccc(F)cc2)c1O] | 665.6 | 1.55 | B | 666.0 |

TABLE 1-continued

| Ex. No. | Structure | MW | HPLC ret. time (min.) | HPLC method | MS (M+1) |
|---|---|---|---|---|---|
| 276 | 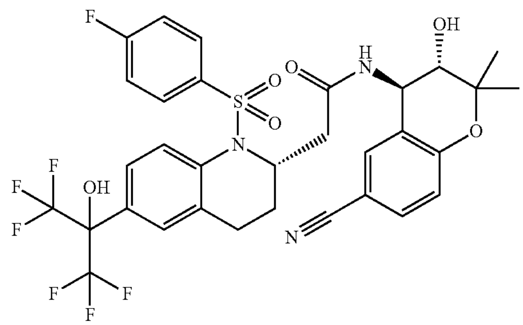 [SMILES: CC1(C)Oc2ccc(C#N)cc2[C@@H](NC(=O)C[C@@H]2CCc3cc(C(O)(C(F)(F)F)C(F)(F)F)ccc3N2S(=O)(=O)c2ccc(F)cc2)[C@@H]1O] | 715.6 | 2.00 | B | 716.0 |
| 277 | 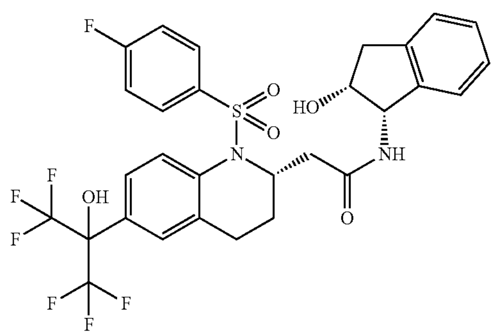 [SMILES: O=C(C[C@@H]1CCc2cc(C(O)(C(F)(F)F)C(F)(F)F)ccc2N1S(=O)(=O)c1ccc(F)cc1)N[C@H]1c2ccccc2C[C@H]1O] | 646.6 | 1.92 | B | 647.0 |
| 278 | 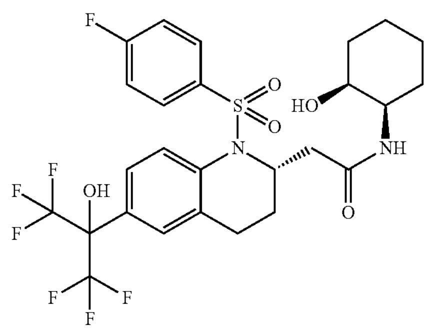 [SMILES: O=C(C[C@@H]1CCc2cc(C(O)(C(F)(F)F)C(F)(F)F)ccc2N1S(=O)(=O)c1ccc(F)cc1)N[C@@H]1CCCC[C@@H]1O] | 612.6 | 1.82 | B | 613.0 |
| 279 | 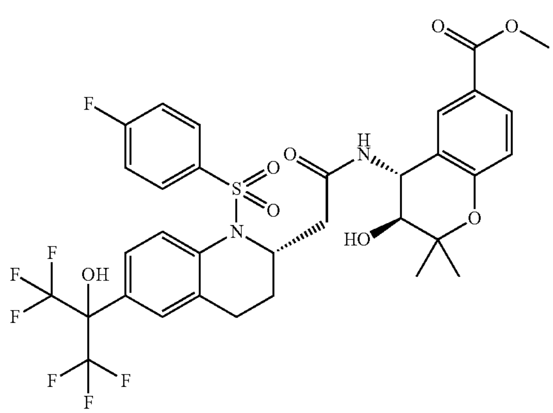 [SMILES: COC(=O)c1ccc2c(c1)[C@@H](NC(=O)C[C@@H]1CCc3cc(C(O)(C(F)(F)F)C(F)(F)F)ccc3N1S(=O)(=O)c1ccc(F)cc1)[C@H](O)C(C)(C)O2] | 748.7 | 2.03 | B | 749.0 |

TABLE 1-continued

| Ex. No. | Structure | MW | HPLC ret. time (min.) | HPLC method | MS (M+1) |
|---|---|---|---|---|---|
| 280 | 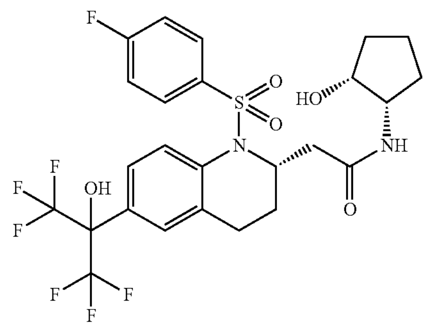 [SMILES: O=C(C[C@@H]1CCc2cc(C(O)(C(F)(F)F)C(F)(F)F)ccc2N1S(=O)(=O)c1ccc(F)cc1)N[C@H]1CCC[C@H]1O] | 598.5 | 1.75 | B | 599.0 |
| 281 | 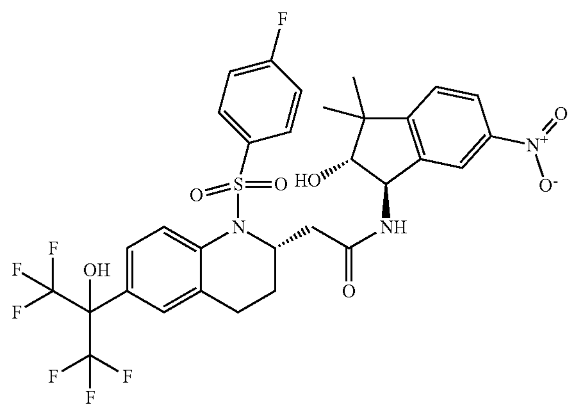 [SMILES: CC1(C)c2ccc([N+](=O)[O-])cc2[C@@H](NC(=O)C[C@@H]2CCc3cc(C(O)(C(F)(F)F)C(F)(F)F)ccc3N2S(=O)(=O)c2ccc(F)cc2)[C@@H]1O] | 719.6 | 2.03 | B | 720.1 |
| 282 | 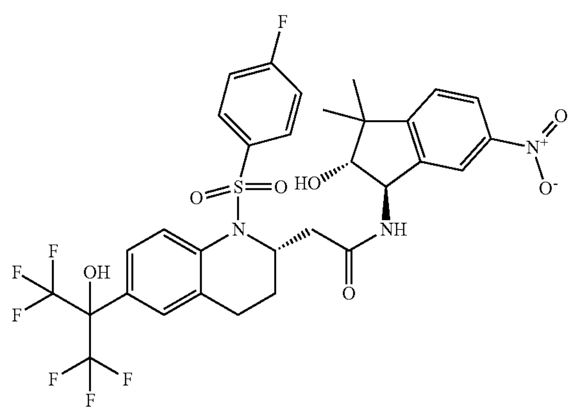 [SMILES: CC1(C)c2ccc([N+](=O)[O-])cc2[C@@H](NC(=O)C[C@@H]2CCc3cc(C(O)(C(F)(F)F)C(F)(F)F)ccc3N2S(=O)(=O)c2ccc(F)cc2)[C@@H]1O] | 719.6 | 2.01 | B | 720.1 |
| 283 | Diastereomic Mixture | 598.5 | 1.80 | B | 599.1 |

TABLE 1-continued
| Ex. No. | Structure | MW | HPLC ret. time (min.) | HPLC method | MS (M+1) |
|---|---|---|---|---|---|
| 284 | 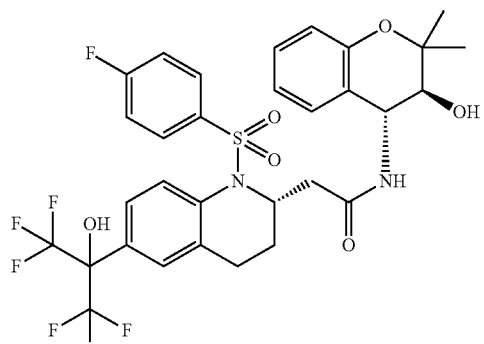 Diastereomer 1 | 690.6 | 2.06 | B | 691.0 |
| 285 | 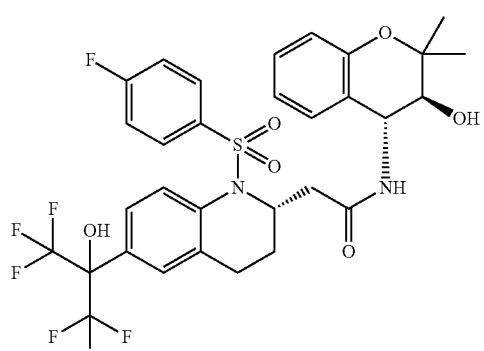 Diastereomer 2 | 690.6 | 2.03 | B | 691.0 |
| 286 | 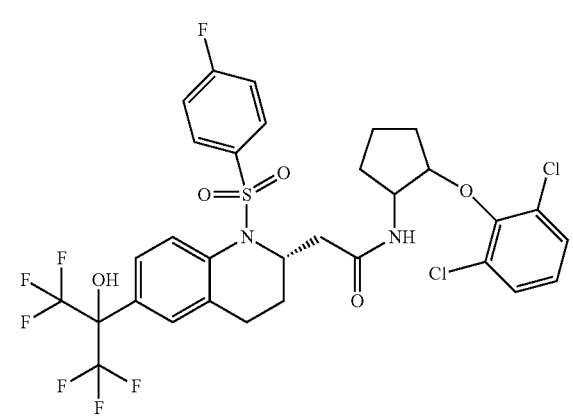 Diastereomic Mixture | 743.5 | 2.39 | B | 743.0 |

TABLE 1-continued

| Ex. No. | Structure | MW | HPLC ret. time (min.) | HPLC method | MS (M+1) |
|---|---|---|---|---|---|
| 287 | 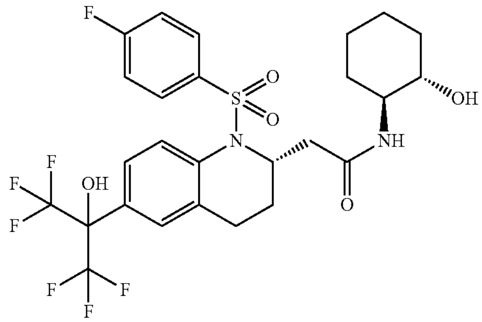 [SMILES: O=C(C[C@@H]1CCc2cc(C(O)(C(F)(F)F)C(F)(F)F)ccc2N1S(=O)(=O)c1ccc(F)cc1)N[C@H]1CCCC[C@@H]1O] | 612.6 | 1.81 | B | 613.0 |
| 288 | 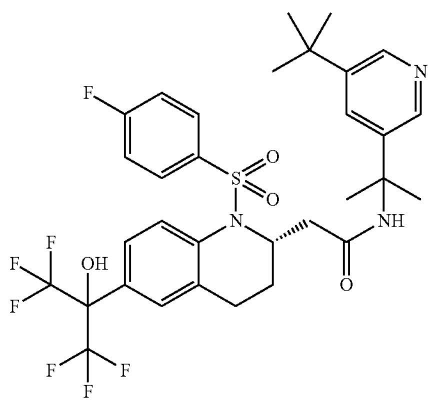 [SMILES: CC(C)(C)c1cncc(C(C)(C)NC(=O)C[C@@H]2CCc3cc(C(O)(C(F)(F)F)C(F)(F)F)ccc3N2S(=O)(=O)c2ccc(F)cc2)c1] | 689.7 | 1.73 | B | 690.3 |
| 289 | Diastereomic Mixture | 664.6 | 1.80 | B | 665.1 |

Example 290

(±) 1-((4-fluorophenyl)sulfonyl)-6-(1,1,1,3,3,3-hexafluoro-2-hydroxypropan-2-yl)-N-(2-hydroxy-2-methylpropyl)-1,2,3,4-tetrahydroquinoline-2-carboxamide

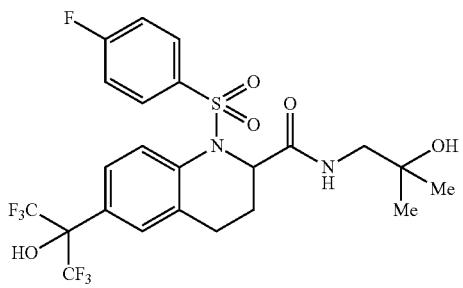 [SMILES: CC(C)(O)CNC(=O)C1CCc2cc(C(O)(C(F)(F)F)C(F)(F)F)ccc2N1S(=O)(=O)c1ccc(F)cc1]

To a solution of 1-((4-fluorophenyl)sulfonyl)-6-(1,1,1,3,3,3-hexafluoro-2-hydroxypropan-2-yl)-1,2,3,4-tetrahydroquinoline-2-carboxylic acid (intermediate 4, 20 mg, 0.040 mmol) in DMF (0.6 mL) was added DIEA (0.021 mL, 0.120 mmol), BOP (26.5 mg, 0.060 mmol) and 1-amino-2-methylpropan-2-ol (7.11 mg, 0.080 mmol). The resulting mixture was stirred at rt for 1 h. and purified via preparative HPLC (condition B) to yield the title compound (12.0 mg, 54.6% yield). The product had an HPLC ret. time=3.12 min.—Column: (condition A); LC/MS M+1=573.2. $^1$H NMR (400 MHz, METHANOL-$d_4$) δ 7.90 (d, J=8.6 Hz, 1H), 7.60 (d, J=8.6 Hz, 1H), 7.51-7.47 (m, 2H), 7.38-7.36 (m, 1H), 7.08 (t, J=8.6 Hz, 2H), 4.75 (t, J=6.8 Hz, 1H), 3.27-3.19 (m, 2H), 3.17-3.06 (m, 1H), 2.54 (s, 1H), 1.99-1.90 (m, 2H), 1.08 (s, 3H), 0.94 (s, 3H).

Example 291

(±) (1-((4-fluorophenyl)sulfonyl)-6-(1,1,1,3,3,3-hexafluoro-2-hydroxypropan-2-yl)-1,2,3,4-tetrahydroquinolin-2-yl)(4-hydroxypiperidin-1-yl)methanone

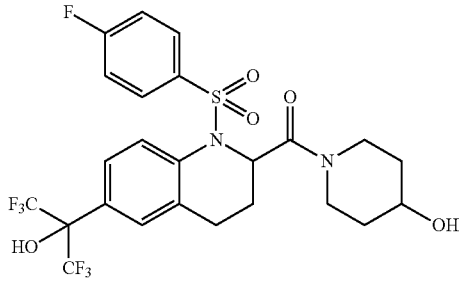 [SMILES: O=C(C1CCc2cc(C(O)(C(F)(F)F)C(F)(F)F)ccc2N1S(=O)(=O)c1ccc(F)cc1)N1CCC(O)CC1]

The compound was prepared in the same manner as outlined in Ex. 290 by substituting 1-amino-2-methylpropan-2-ol with piperidine-4-ol. The yield of the product was 11.4 mg (48.9% yield). The product had an HPLC ret. time=3.20 min.—Column: (condition A); LC/MS M+1=585.1. $^1$H NMR (500 MHz, DMSO-$d_6$) δ 7.84 (td, J=8.5, 5.2 Hz, 2H), 7.62 (d, J=8.9 Hz, 1H), 7.46 (d, J=8.4 Hz, 1H), 7.39 (td, J=8.8, 3.2 Hz, 2H), 7.35 (br. s., 1H), 5.50 (t, J=6.2 Hz, 1H), 4.83 (br. s., 1H), 4.02-3.87 (m, 2H), 3.84-3.64 (m, 2H), 2.25-2.12 (m, 2H), 1.95-1.78 (m, 1H), 1.75-1.62 (m, 2H), 1.54-1.45 (m, 1H), 1.44-1.34 (m, 1H), 1.31-1.19 (m, 1H).

Example 292

(±) 2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)-N-(2-hydroxy-2-methylpropyl)acetamide

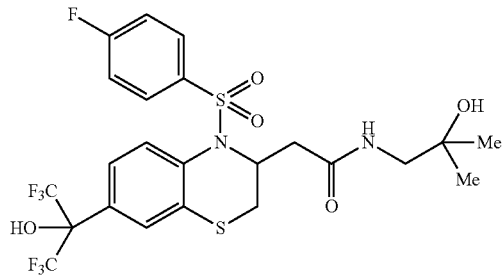

To a solution of (±) 2-(4-((4-fluorophenyl)sulfonyl)-7-(1,1,1,3,3,3-hexafluoro-2-hydroxypropan-2-yl)-3,4-dihydro-2H-benzo[b][1,4]thiazin-3-yl)acetic acid (intermediate 5,6 step F, 10 mg, 0.019 mmol) in DMF (0.6 mL) was added DIEA (9.82 µl, 0.056 mmol), BOP (12.44 mg, 0.028 mmol) and 1-amino-2-methylpropan-2-ol (3.34 mg, 0.037 mmol). The resulting mixture was stirred at rt for 1 h and purified using preparative HPLC (condition E) to yield the title compound (3.5 mg, 30.9% yield). The product had an HPLC ret. time=3.20 min.—Column: (condition A); LC/MS M+1=605.1. $^1$H NMR (500 MHz, METHANOL-$d_4$) δ 7.72-7.67 (m, 1H), 7.58-7.53 (m, 2H), 7.51-7.45 (m, 2H), 7.14 (t, J=8.7 Hz, 2H), 3.17 (s, 2H), 3.05-3.01 (m, 1H), 2.88 (s, 1H), 2.81 (dd, J=13.4, 4.0 Hz, 1H), 2.51 (dd, J=8.9, 7.4 Hz, 2H), 1.16 (s, 6H).

The Examples in TABLE 2 below were prepared in the same manner as above using racemic or homochiral acid (intermediates 5, 6) and the appropriate amine

TABLE 2

| Ex. No. | Structure | MW | HPLC ret. time (min.) | HPLC method | MS (M$^{+1}$) |
|---|---|---|---|---|---|
| 293 | (diastereomeric mixture) | 630.6 | 3.15 | E | 631.1 |

TABLE 2-continued

| Ex. No. | Structure | MW | HPLC ret. time (min.) | HPLC method | MS (M$^{+1}$) |
|---|---|---|---|---|---|
| 294 | 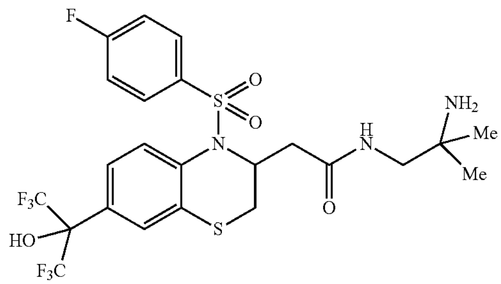 [SMILES: CC(C)(N)CNC(=O)CC1CSc2cc(C(O)(C(F)(F)F)C(F)(F)F)ccc2N1S(=O)(=O)c1ccc(F)cc1] | 603.6 | 2.75 | E | 604.2 |
| 295 | 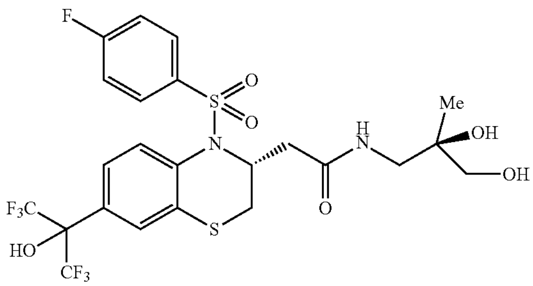 [SMILES: C[C@](O)(CO)CNC(=O)C[C@@H]1CSc2cc(C(O)(C(F)(F)F)C(F)(F)F)ccc2N1S(=O)(=O)c1ccc(F)cc1] | 620.6 | 3.07 | E | 621.2 |
| 296 | 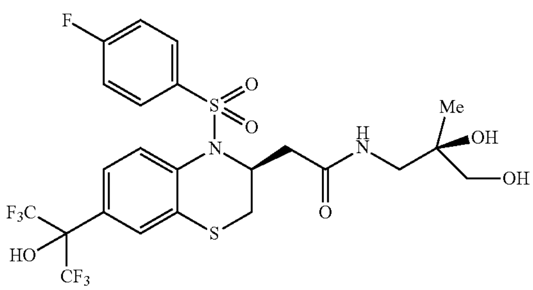 [SMILES: C[C@](O)(CO)CNC(=O)C[C@H]1CSc2cc(C(O)(C(F)(F)F)C(F)(F)F)ccc2N1S(=O)(=O)c1ccc(F)cc1] | 620.6 | 3.06 | E | 621.1 |
| 297 | 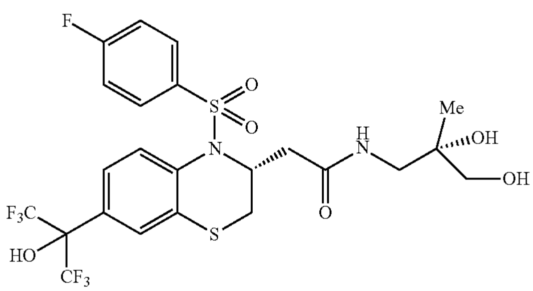 [SMILES: C[C@@](O)(CO)CNC(=O)C[C@@H]1CSc2cc(C(O)(C(F)(F)F)C(F)(F)F)ccc2N1S(=O)(=O)c1ccc(F)cc1] | 620.6 | 3.02 | E | 621.2 |
| 298 | 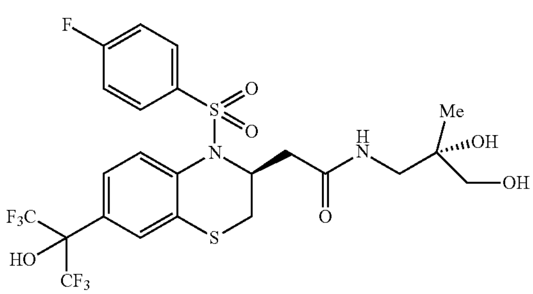 [SMILES: C[C@@](O)(CO)CNC(=O)C[C@H]1CSc2cc(C(O)(C(F)(F)F)C(F)(F)F)ccc2N1S(=O)(=O)c1ccc(F)cc1] | 620.6 | 3.02 | E | 621.2 |

Example 299

(S)-benzyl ((1-((4-fluorophenyl)sulfonyl)-6-(1,1,1,3,3,3-hexafluoro-2-hydroxypropan-2-yl)-1,2,3,4-tetrahydroquinolin-2-yl)methyl)carbamate To a solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (intermediate 1, 495 mg, 0.960 mmol) in Benzene (10 ml), diphenyl phosphorazidate (317 mg, 1.153 mmol) and TEA (0.201 ml, 1.441 mmol) were added and the contents heated to reflux for 1 hr. The reaction mixture was cooled to RT, benzyl alcohol (0.120 ml, 1.153 mmol) was added and the contents heated to reflux for 2 hrs. The reaction mixture was cooled to RT, saturated NaHCO$_3$ (10 ml) was added, the contents extracted with ethyl acetate (100 ml), washed with water, brine. dried (MgSO$_4$) and concentrated under vacuum. The residue was purified using silica gel chromatography, eluting with 20 to 60% ethyl acetate in hexane, to provide the title compound (490 mg, 0.790 mmol, 82%). LC/MS(M+1): 621.3; $^1$H NMR (400 MHz, CDCl$_3$) δ ppm 7.95-7.75 (m, 1H), 7.69-7.55 (m, 1H), 7.54-7.41 (m, 2H), 7.41-7.30 (m, 6H), 7.12-6.80 (m, 2H), 5.25 (br. s., 1H), 4.47-4.26 (m, 1H), 3.49 (m, 2H), 3.47-3.33 (m, 1H), 3.24-3.06 (m, 1H), 2.54-2.42 (m, 1H), 1.92-1.77 (m, 1H), 1.77-1.60 (m, 1H), 1.50 (m 1H).

Example 300

Step A: (S)-2-(2-(aminomethyl)-1-((4-fluorophenyl)sulfonyl)-1,2,3,4-tetrahydroquinolin-6-yl)-1,1,1,3,3,3-hexafluoropropan-2-ol, HCl

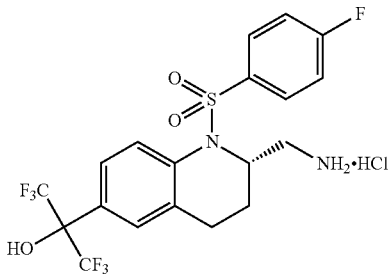

To a solution of (S)-benzyl ((1-((4-fluorophenyl)sulfonyl)-6-(1,1,1,3,3,3-hexafluoro-2-hydroxypropan-2-yl)-1,2,3,4-tetrahydroquinolin-2-yl)methyl)carbamate (example 299, 470 mg, 0.757 mmol) in MeOH (10 mL) was added 20% PALLADIUM ON CARBON (40.3 mg, 0.038 mmol) under a nitrogen atmosphere and the contents stirred under a H$_2$ atmosphere (balloon) for 4 hrs and filtered. To the filtrate was added 1N aqueous HCl (1 ml), the contents concentrated, azeotroped with toluene (2×10 mL) and dried under high vacuum to yield the title compound as HCl salt (390 mg, 0.746 mmol, 98%). LC/MS(M+1): 487.2; $^1$H NMR (400 MHz, CD$_3$OD) δ ppm 7.90 (d, J=8.8 Hz, 1H), 7.73-7.64 (m, 1H), 7.63-7.42 (m, 3H), 7.31-7.14 (m, 2H), 4.66-4.52 (m, 1H), 3.17-3.04 (m, 1H), 2.94 (m, 1H), 2.48 (m, 1H), 2.06-1.88 (m, 1H), 1.71-1.57 (m, 1H), 1.57-1.45 (m, 1H).

Step B: Cis-N—(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-4-hydroxycyclohexanecarboxamide

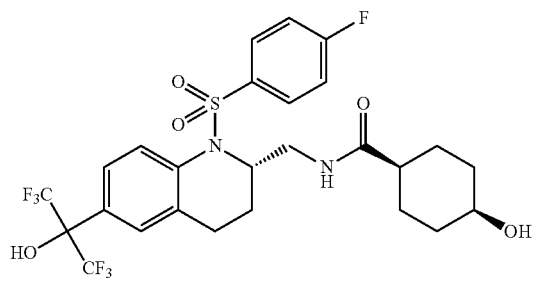 [SMILES: O=C(NC[C@@H]1CCc2cc(C(O)(C(F)(F)F)C(F)(F)F)ccc2N1S(=O)(=O)c1ccc(F)cc1)[C@H]1CC[C@@H](O)CC1]

BOP (16.5 mg, 0.037 mmol) was added to a solution of (S)-2-(2-(aminomethyl)-1-((4-fluorophenyl)sulfonyl)-1,2,3,4-tetrahydroquinolin-6-yl)-1,1,1,3,3,3-hexafluoropropan-2-ol. HCl (step A, 15 mg, 0.029 mmol), in DMF (1 ml) followed by DIPEA (0.020 ml, 0.115 mmol) and cis-4-hydroxycyclohexanecarboxylic acid (4.14 mg, 0.029 mmol) at RT and stirred for 1 hr. The mixture was purified by preparative HPLC (condition B) to provide the title compound (10.9 mg, 0.018 mmol, 62%). LC/MS(M+1): 613.3; $^1$H NMR (500 MHz, 1 to 1 mixture of CDCl$_3$ and CD$_3$OD) δ ppm 7.80 (d, J=8.4 Hz, 1H), 7.61 (s, 1H), 7.57-7.48 (m, 2H), 7.41 (s, 1H), 7.25-6.97 (m, 2H), 4.55-4.37 (m, 1H), 4.09-3.87 (m, 1H), 3.46-3.41 (m, 1H), 3.20 (m, 1H), 2.47 (m, 1H), 2.26-2.12 (m, 1H), 1.97-1.67 (m, 6H), 1.67-1.43 (m, 5H).

The Examples in TABLE 3 below were prepared in the same manner as above using homochiral amine (example 300, step A) and the appropriate acid.

TABLE 3

| Ex. No. | Structure | MW | HPLC ret. time (min.) | HPLC method | MS (M$^{+1}$) |
|---|---|---|---|---|---|
| 301 | 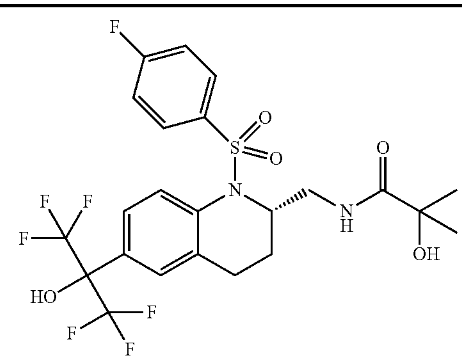 | 572.5 | 1.71 | G | 572.3 |

TABLE 3-continued

| Ex. No. | Structure | MW | HPLC ret. time (min.) | HPLC method | MS (M+1) |
|---|---|---|---|---|---|
| 302 | 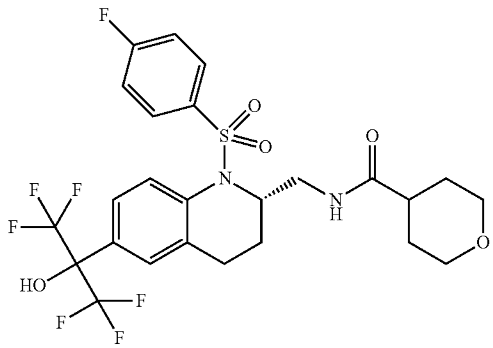 [SMILES: O=C(NC[C@@H]1CCc2cc(C(O)(C(F)(F)F)C(F)(F)F)ccc2N1S(=O)(=O)c1ccc(F)cc1)C1CCOCC1] | 598.5 | 1.73 | G | 599.3 |
| 303 | 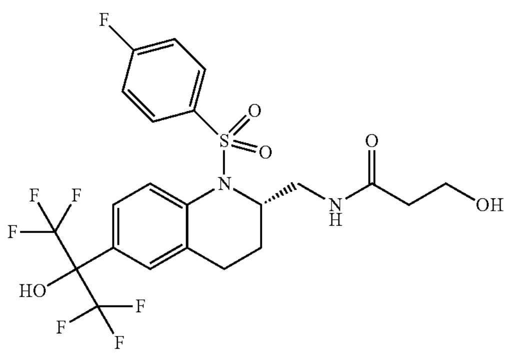 [SMILES: O=C(CCO)NC[C@@H]1CCc2cc(C(O)(C(F)(F)F)C(F)(F)F)ccc2N1S(=O)(=O)c1ccc(F)cc1] | 558.5 | 1.58 | G | 559.3 |
| 304 | Diastereomer mixture | 626.6 | 1.92 | G | 627.3 |
| 305 | 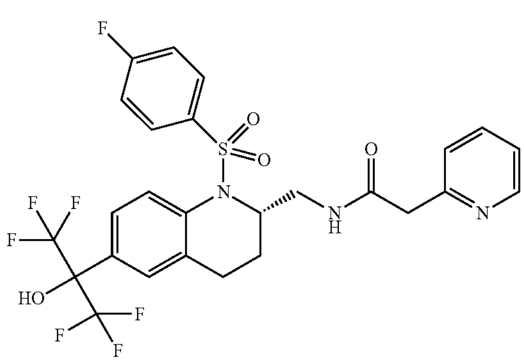 [SMILES: O=C(Cc1ccccn1)NC[C@@H]1CCc2cc(C(O)(C(F)(F)F)C(F)(F)F)ccc2N1S(=O)(=O)c1ccc(F)cc1] | 605.5 | 1.78 | G | 606.3 |

TABLE 3-continued

| Ex. No. | Structure | MW | HPLC ret. time (min.) | HPLC method | MS (M$^{+1}$) |
|---|---|---|---|---|---|
| 306 | 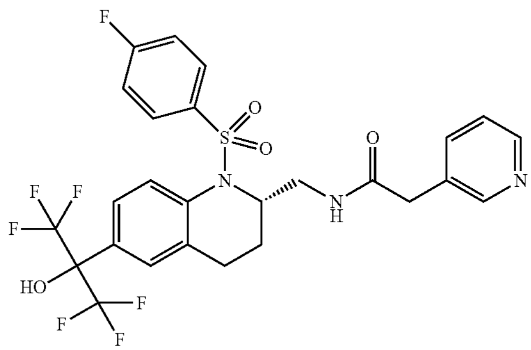 [SMILES: O=C(Cc1cccnc1)NC[C@@H]1CCc2cc(C(O)(C(F)(F)F)C(F)(F)F)ccc2N1S(=O)(=O)c1ccc(F)cc1] | 605.5 | 1.74 | G | 606.3 |
| 307 | 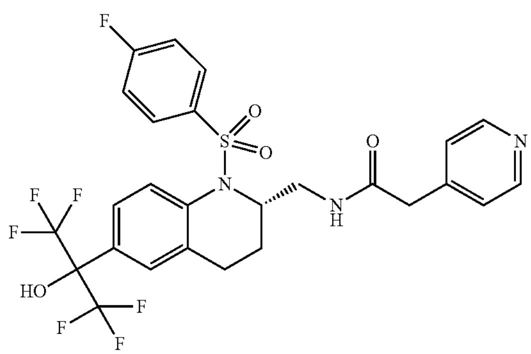 [SMILES: O=C(Cc1ccncc1)NC[C@@H]1CCc2cc(C(O)(C(F)(F)F)C(F)(F)F)ccc2N1S(=O)(=O)c1ccc(F)cc1] | 605.5 | 1.71 | G | 606.3 |
| 308 | 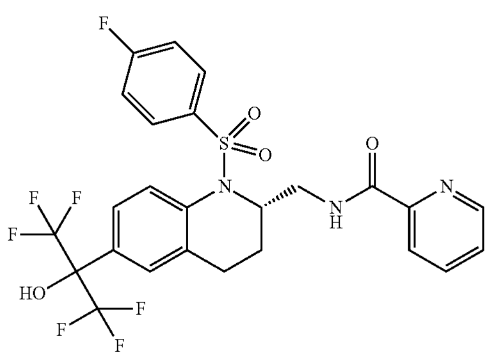 [SMILES: O=C(NC[C@@H]1CCc2cc(C(O)(C(F)(F)F)C(F)(F)F)ccc2N1S(=O)(=O)c1ccc(F)cc1)c1ccccn1] | 591.5 | 1.94 | G | 592.2 |
| 309 | 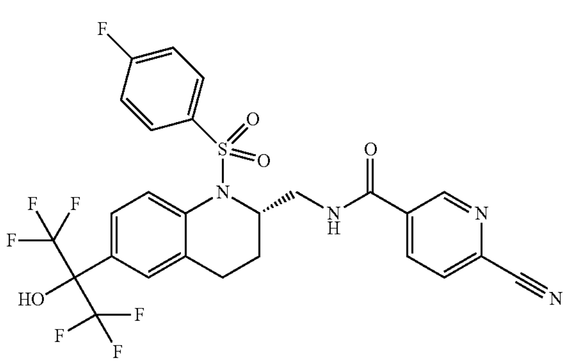 [SMILES: N#Cc1ccc(C(=O)NC[C@@H]2CCc3cc(C(O)(C(F)(F)F)C(F)(F)F)ccc3N2S(=O)(=O)c2ccc(F)cc2)cn1] | 616.5 | 1.88 | G | 617.2 |

TABLE 3-continued

| Ex. No. | Structure | MW | HPLC ret. time (min.) | HPLC method | MS (M+1) |
|---|---|---|---|---|---|
| 310 | 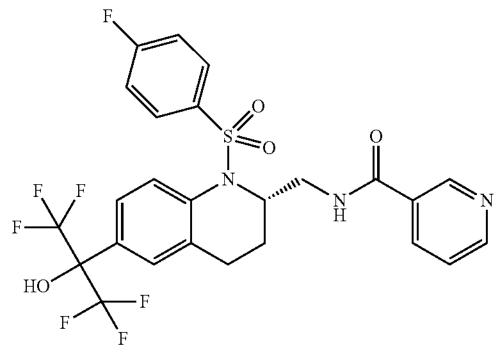 [SMILES: O=C(NC[C@@H]1CCc2cc(C(O)(C(F)(F)F)C(F)(F)F)ccc2N1S(=O)(=O)c1ccc(F)cc1)c1cccnc1] | 591.5 | 1.74 | G | 592.2 |
| 311 | 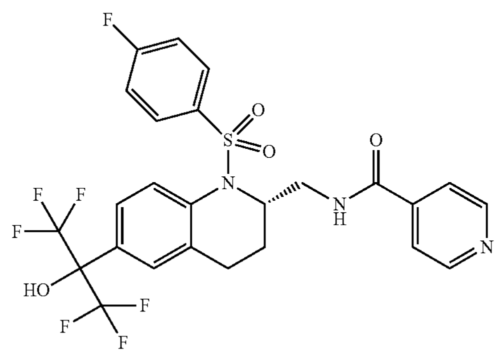 [SMILES: O=C(NC[C@@H]1CCc2cc(C(O)(C(F)(F)F)C(F)(F)F)ccc2N1S(=O)(=O)c1ccc(F)cc1)c1ccncc1] | 591.5 | 1.74 | G | 592.2 |
| 312 | Diastereomer mixture | 626.6 | 1.92 | G | 627.3 |
| 313 | 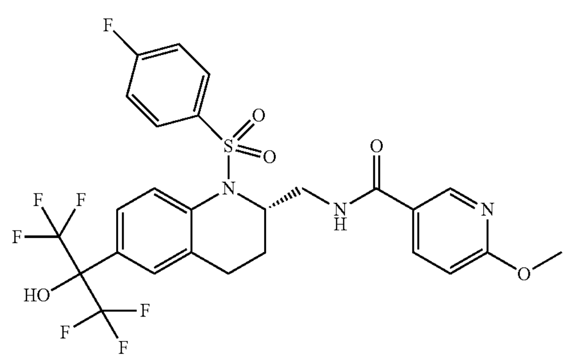 [SMILES: COc1ccc(C(=O)NC[C@@H]2CCc3cc(C(O)(C(F)(F)F)C(F)(F)F)ccc3N2S(=O)(=O)c2ccc(F)cc2)cn1] | 621.5 | 2.64 | G | 622.2 |

TABLE 3-continued

| Ex. No. | Structure | MW | HPLC ret. time (min.) | HPLC method | MS (M$^{+1}$) |
|---|---|---|---|---|---|
| 314 | 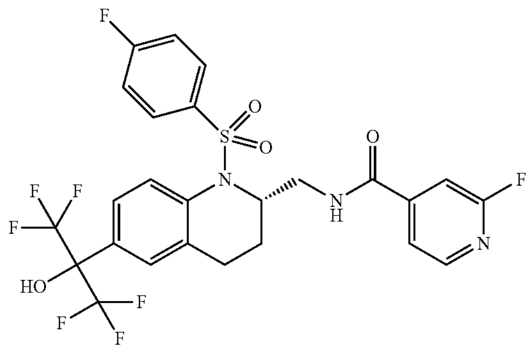 | 609.5 | 2.53 | G | 610.2 |
| 315 | 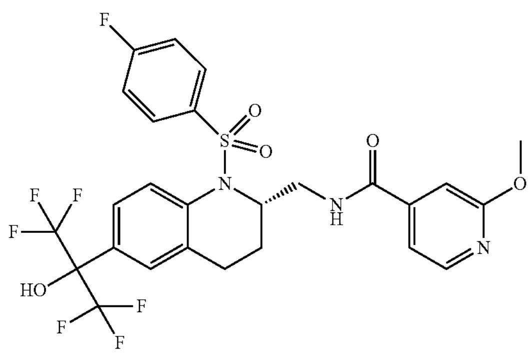 [SMILES: COc1cc(C(=O)NC[C@@H]2CCc3cc(C(O)(C(F)(F)F)C(F)(F)F)ccc3N2S(=O)(=O)c2ccc(F)cc2)ccn1] | 621.5 | 1.86 | G | 622.2 |
| 316 | Diastereomer mixture | 574.5 | 1.50 | G | 575.2 |
| 317 | 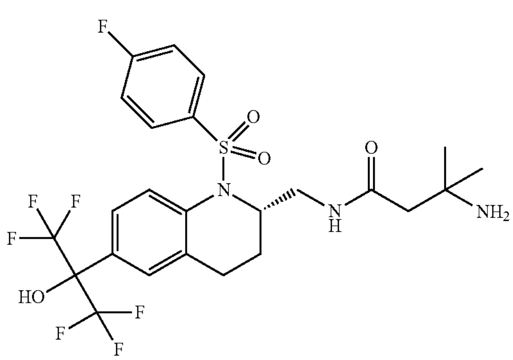 [SMILES: CC(C)(N)CC(=O)NC[C@@H]1CCc2cc(C(O)(C(F)(F)F)C(F)(F)F)ccc2N1S(=O)(=O)c1ccc(F)cc1] | 585.5 | 1.60 | G | 586.2 |

TABLE 3-continued

| Ex. No. | Structure | MW | HPLC ret. time (min.) | HPLC method | MS (M+1) |
|---|---|---|---|---|---|
| 318 | 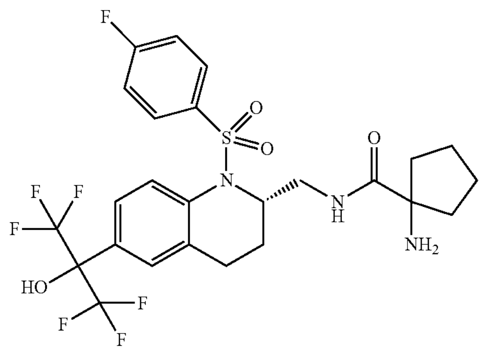 [SMILES: NC1(C(=O)NC[C@@H]2CCc3cc(C(O)(C(F)(F)F)C(F)(F)F)ccc3N2S(=O)(=O)c2ccc(F)cc2)CCCC1] | 597.6 | 1.72 | G | 598.2 |
| 319 | 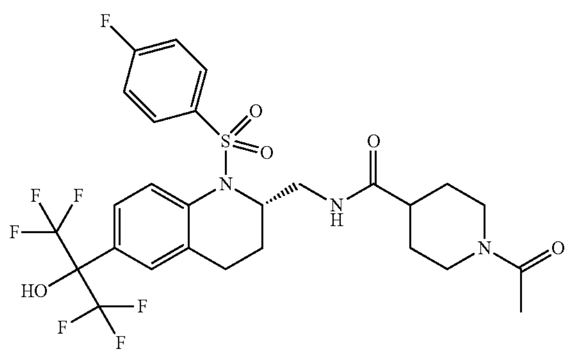 [SMILES: CC(=O)N1CCC(C(=O)NC[C@@H]2CCc3cc(C(O)(C(F)(F)F)C(F)(F)F)ccc3N2S(=O)(=O)c2ccc(F)cc2)CC1] | 639.6 | 1.62 | G | 640.2 |
| 320 | Diastereomer mixture | 611.5 | 1.73 | G | 612.3 |
| 321 | 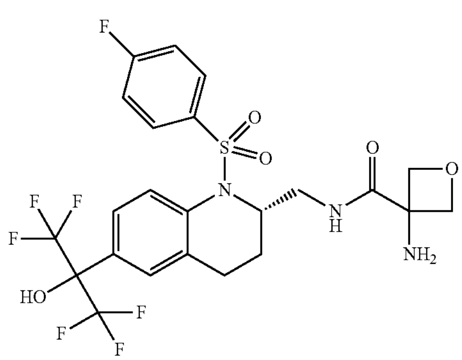 [SMILES: NC1(C(=O)NC[C@@H]2CCc3cc(C(O)(C(F)(F)F)C(F)(F)F)ccc3N2S(=O)(=O)c2ccc(F)cc2)COC1] | 585.5 | 1.57 | G | 586.2 |

TABLE 3-continued
| Ex. No. | Structure | MW | HPLC ret. time (min.) | HPLC method | MS (M+1) |
|---|---|---|---|---|---|
| 322 | 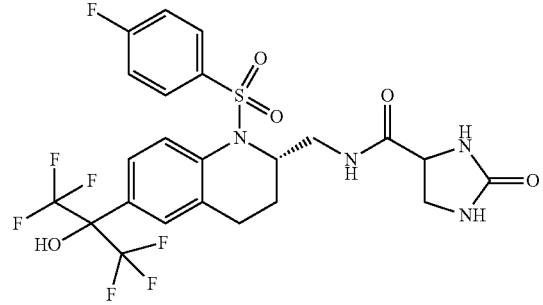 Diastereomeric Mixture | 598.5 | 1.46 | B | 598.9 |
| 323 | 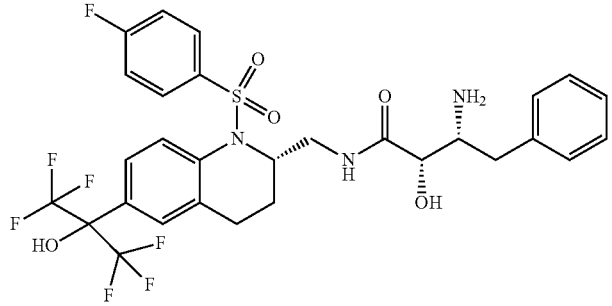 [SMILES: N[C@H](Cc1ccccc1)[C@H](O)C(=O)NC[C@@H]1CCc2cc(C(O)(C(F)(F)F)C(F)(F)F)ccc2N1S(=O)(=O)c1ccc(F)cc1] | 663.6 | 1.67 | B | 664.2 |
| 324 | 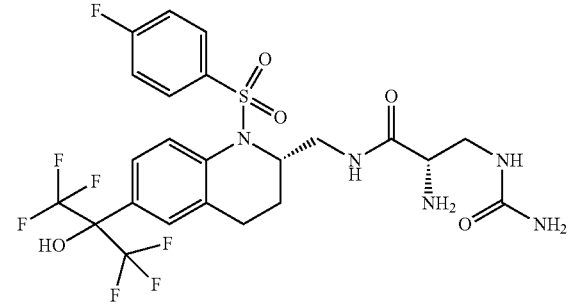 [SMILES: NC(=O)NC[C@H](N)C(=O)NC[C@@H]1CCc2cc(C(O)(C(F)(F)F)C(F)(F)F)ccc2N1S(=O)(=O)c1ccc(F)cc1] | 615.5 | 1.40 | B | 616.0 |
| 325 | 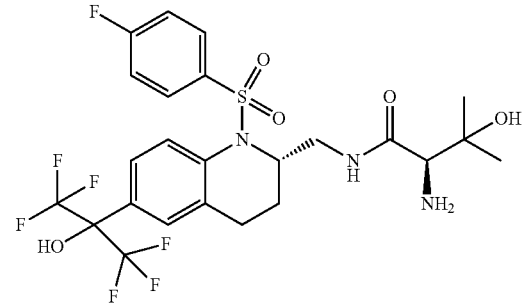 [SMILES: CC(C)(O)[C@@H](N)C(=O)NC[C@@H]1CCc2cc(C(O)(C(F)(F)F)C(F)(F)F)ccc2N1S(=O)(=O)c1ccc(F)cc1] | 601.5 | 1.54 | I | 602.0 |

TABLE 3-continued

| Ex. No. | Structure | MW | HPLC ret. time (min.) | HPLC method | MS (M+1) |
|---|---|---|---|---|---|
| 326 | 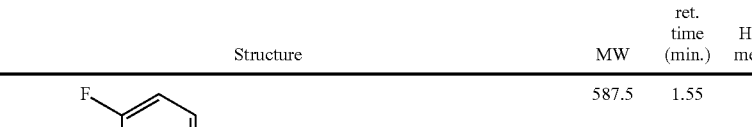 | 587.5 | 1.55 | I | 588.0 |

General RORγ Spa Binding Assay

The binding of potential ligands to RORγ is measured by competition with [$^3$H] 25-hydroxycholesterol using a scintillation proximity assay (SPA) binding assay. The ligand binding domain of human RORγ (A262-S507) with an N-terminal His tag is expressed in *E. coli* and purified using nickel affinity chromotography. 50 nM RORγ (A262-S507) is incubated with test compound at varying concentrations for 15 min at room temperature in PBS buffer containing 0.5% fatty acid free BSA. 10 nM of [$^3$H] 25-hydroxycholesterol is then added, and the reaction is incubated for 15 min. 4 mg/mL of Ysi Copper HIS-TAG SPA Beads (Perkin Elmer) are added, and the mixture is incubated for 30 min. The reaction is read on a MicroBeta Trilux scintillation plate reader (Perkin Elmer). IC$_{50}$ values are determined from the percentage inhibition of [$^3$H] 25-hydroxycholesterol binding.

IC$_{50}$ values of the compounds of the invention in the RORγ binding assay are provided below.

| Example # | RORgt Binding IC50, nM |
|---|---|
| 1 | 16.67 |
| 2 | 48.51 |
| 3 | 29.30 |
| 4 | 71.11 |
| 5 | 24.31 |
| 6 | 34.55 |
| 7 | 25.81 |
| 8 | 55.77 |
| 9 | 24.44 |
| 10 | 31.00 |
| 11 | 62.86 |
| 12 | 124.30 |
| 13 | 59.10 |
| 14 | 22.13 |
| 15 | 17.40 |
| 16 | 47.60 |
| 17 | 109.80 |
| 18 | 188.70 |
| 19 | 102.70 |
| 20 | 116.60 |
| 21 | 14.40 |
| 22 | 51.52 |
| 23 | 68.99 |
| 24 | 28.55 |
| 25 | 30.82 |
| 26 | 44.98 |
| 27 | 50.64 |

| Example # | RORgt Binding IC50, nM |
|---|---|
| 28 | 28.04 |
| 29 | 57.14 |
| 30 | 54.21 |
| 31 | 167.20 |
| 32 | 33.02 |
| 33 | 29.64 |
| 34 | 26.65 |
| 35 | 26.19 |
| 36 | 32.75 |
| 37A | 27.82 |
| 37B | 20.71 |
| 38 | 41.62 |
| 39A | 193.20 |
| 39B | 148.70 |
| 40 | 52.32 |
| 41 | 23.69 |
| 42 | 11.84 |
| 43 | 20.62 |
| 44 | 63.39 |
| 45 | 99.87 |
| 46 | 19.24 |
| 47 | 16.13 |
| 48 | 47.04 |
| 49 | 80.14 |
| 50 | 19.55 |
| 51 | 23.24 |
| 52 | 49.86 |
| 53 | 43.01 |
| 54 | 75.25 |
| 55 | 42.78 |
| 56 | 28.53 |
| 57 | 25.25 |
| 58 | 41.20 |
| 59 | 46.67 |
| 60 | 588.30 |
| 61 | 33.31 |
| 62 | 10.09 |
| 63 | 12.23 |
| 64 | 23.66 |
| 65 | 21.61 |
| 66 | 39.83 |
| 67 | 52.10 |
| 68 | 45.49 |
| 69 | 50.99 |
| 70 | 58.11 |
| 71 | 46.04 |
| 72 | 35.81 |
| 73 | 45.43 |
| 74 | 40.83 |
| 75 | 36.07 |
| 76 | 23.00 |
| 77 | 49.00 |

| Example # | RORgt Binding IC50, nM |
|---|---|
| 78 | 37.26 |
| 79 | 136.70 |
| 80 | 21.30 |
| 81 | 52.81 |
| 82 | 288.50 |
| 83 | 43.84 |
| 84 | 69.75 |
| 85 | 306.50 |
| 86 | 10.79 |
| 87 | 24.39 |
| 88 | 25.51 |
| 89 | 66.59 |
| 90 | 109.50 |
| 91 | 19.62 |
| 92 | 20.19 |
| 93 | 68.82 |
| 94 | 17.07 |
| 95 | 14.79 |
| 96 | 48.37 |
| 97 | 84.67 |
| 98 | 161.50 |
| 99 | 71.50 |
| 100 | 51.14 |
| 101 | 27.95 |
| 102 | 32.91 |
| 103 | 12.90 |
| 104 | 44.63 |
| 105 | 180.80 |
| 106 | 33.55 |
| 107 | 208.80 |
| 108 | 118.30 |
| 109 | 48.23 |
| 110 | 103.10 |
| 111 | 184.90 |
| 112 | 268.70 |
| 113 | 45.81 |
| 114 | 99.87 |
| 115 | |
| 116 | 26.48 |
| 117 | 64.22 |
| 118 | 149.40 |
| 119 | 70.00 |
| 120 | 14.79 |
| 121 | 16.90 |
| 122 | 69.17 |
| 123 | 42.66 |
| 124 | 41.68 |
| 125 | 22.96 |
| 126 | 40.38 |
| 127 | 42.88 |
| 129 | 12.98 |
| 130 | 41.71 |
| 131 | 35.79 |
| 132 | 39.22 |
| 133 | 34.58 |
| 134 | 73.61 |
| 135 | 80.00 |
| 136 | 1560.00 |
| 137 | 50.00 |
| 138 | 100.00 |
| 140 | 90.00 |
| 141 | 120.00 |
| 142 | 70.00 |
| 143 | 70.00 |
| 144 | 170.00 |
| 145 | 2590.00 |
| 146 | 40.00 |
| 147 | 150.00 |
| 148 | 70.00 |
| 149 | 110.00 |
| 150 | 220.00 |
| 151 | 250.00 |
| 152 | 50.00 |
| 153 | 24.52 |
| 154 | 33.73 |
| 155 | 10.04 |
| 156 | 25.66 |
| 157 | 30.26 |
| 158 | 110.20 |
| 159 | 28.82 |
| 160 | 144.90 |
| 161 | 26.95 |
| 162 | 41.60 |
| 163 | 12.37 |
| 164 | 366.30 |
| 165 | 18.81 |
| 168 | 24.76 |
| 169 | 44.71 |
| 170 | 24.77 |
| 171 | 49.67 |
| 172 | 17.03 |
| 173 | 30.01 |
| 174 | 143.80 |
| 175 | 10.32 |
| 176 | 22.22 |
| 177 | 192.20 |
| 178 | 29.33 |
| 179 | 124.70 |
| 180 | 37.81 |
| 182 | 32.00 |
| 183 | 19.89 |
| 184 | 18.92 |
| 185 | 52.37 |
| 186 | 73.30 |
| 187 | 18.92 |
| 188 | 20.97 |
| 189 | 43.93 |
| 190 | 161.70 |
| 191 | 30.89 |
| 192 | 110.30 |
| 193 | 26.34 |
| 194 | 16.12 |
| 195 | 35.04 |
| 197 | 55.98 |
| 198 | 35.03 |
| 199 | 30.60 |
| 200 | 34.36 |
| 201 | 118.20 |
| 202 | 65.47 |
| 203 | 27.28 |
| 204 | 40.24 |
| 205 | 55.74 |
| 207 | 45.87 |
| 208 | 95.29 |
| 209 | 19.88 |
| 210 | 46.90 |
| 211 | 35.27 |
| 212 | 68.07 |
| 213 | 30.72 |
| 214 | 46.93 |
| 215 | 51.15 |
| 216 | 76.48 |
| 217 | 31.08 |
| 218 | 29.53 |
| 219 | 67.10 |
| 220 | 29.86 |
| 221 | 17.81 |
| 222 | 44.71 |
| 223 | 20.12 |
| 224 | 16.94 |
| 225 | 17.68 |
| 226 | 28.68 |
| 227 | 16.39 |
| 228 | 33.74 |
| 229 | 64.39 |
| 230 | 111.10 |
| 231 | 53.52 |
| 232 | 47.54 |
| 233 | 22.16 |
| 234 | 23.18 |
| 235 | 41.24 |
| 236 | 18.91 |

-continued

| Example # | RORgt Binding IC50, nM |
|---|---|
| 237 | 63.60 |
| 238 | 26.04 |
| 239 | 33.68 |
| 240 | 42.19 |
| 241 | 61.52 |
| 242 | 26.07 |
| 243 | 23.56 |
| 244 | 65.06 |
| 245 | 59.35 |
| 246 | 66.06 |
| 247 | 25.28 |
| 248 | 57.29 |
| 249 | 89.10 |
| 250 | 31.19 |
| 251 | 40.11 |
| 252 | 16.46 |
| 253 | 172.20 |
| 254 | 14.45 |
| 255 | 56.62 |
| 256 | 34.67 |
| 257 | 32.97 |
| 258 | 41.85 |
| 259 | 25.44 |
| 260 | 17.35 |
| 261 | 22.52 |
| 262 | 23.85 |
| 263 | 49.28 |
| 264 | 28.49 |
| 265 | 47.41 |
| 266 | 83.74 |
| 267 | 30.37 |
| 268 | 37.38 |
| 269 | 198.70 |
| 270 | 21.87 |
| 271 | 50.51 |
| 272 | 31.86 |
| 273 | 104.00 |
| 274 | 29.36 |
| 275 | 71.01 |
| 276 | 100.20 |
| 277 | 54.76 |
| 278 | 24.26 |
| 279 | 137.10 |
| 280 | 23.14 |
| 281 | 49.15 |
| 282 | 17.36 |
| 283 | 36.30 |
| 284 | 116.40 |
| 285 | 107.50 |
| 286 | 170.10 |
| 287 | 68.38 |
| 288 | 112.40 |
| 289 | 71.92 |
| 290 | 579.40 |
| 291 | 182.00 |
| 292 | 16.87 |
| 293 | 46.67 |
| 294 | 178.70 |
| 295 | 24.35 |
| 296 | 69.69 |
| 297 | 35.59 |
| 298 | 133.90 |
| 299 | 260 |
| 300 | 70 |
| 301 | 40 |
| 302 | 40 |
| 303 | 70 |
| 304 | 30 |
| 305 | 140 |
| 306 | 190 |
| 307 | 30 |
| 308 | 80 |
| 309 | 50 |
| 310 | 60 |
| 311 | 30 |
| 312 | |
| 313 | 130 |
| 314 | 30 |
| 315 | 70 |
| 316 | 40 |
| 317 | 70 |
| 318 | 100 |
| 319 | 80 |
| 320 | 20 |
| 321 | 20 |
| 322 | 60 |
| 323 | 60 |
| 324 | 20 |
| 325 | 80 |
| 326 | 100 |

We claim:
1. A compound of the formula wherein:
X is $CH_2$ or S;
R is H;
$R_1$ is H;
$R_3$ is optionally substituted 6- to 10-membered monocyclic or bicyclic aryl or optionally substituted 5- to 10-membered monocyclic or bicyclic heteroaryl;
$R_4$ and $R_5$ are independently H, OH, optionally substituted $C_1$-$C_4$ alkyl, optionally substituted monocyclic or bicyclic $C_3$-$C_{10}$ cycloalkyl, optionally substituted monocyclic or bicyclic arylsulfonyl, optionally substituted dideutero-$C_1$-$C_4$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted 5- to 7-membered monocyclic heteroaryl, optionally substituted 8- to 10-membered bicyclo heteroaryl, optionally substituted $C_2$-$C_6$ alkenyl, or optionally substituted monocyclic or bicyclic $C_4$-$C_{10}$ cycloalkenyl; and
$R_6$ is selected from OH, optionally substituted $C_1$-$C_4$ alkyl, or optionally substituted halo-$C_1$-$C_4$-alkyl;
each $R_4$, $R_5$ and $R_6$ group being optionally substituted with 1 to 3 groups;
provided that only one of $R_4$, $R_5$ and $R_6$ can be hydroxy;
$R_{12}$ and $R_{13}$ are independently selected from H, optionally substituted $C_1$-$C_4$ alkyl, or optionally substituted monocyclic or bicyclic $C_3$-$C_{10}$ cycloalkyl;

is an optionally substituted 4- to 16-membered nitrogen containing monocyclic, bicyclic or tricyclic heterocyclo ring which contains 0, 1 or 2 additional heteroatoms selected from N, S and O; and
q is 1 or 2;
or a pharmaceutically acceptable salt, stereoisomer or tautomer thereof.

2. The compound according to claim 1 of the formula

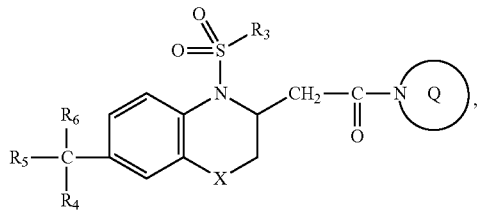

wherein:
X is $CH_2$ or S;
$R_6$ is OH;
$R_4$ and $R_5$ are each trihalo-$C_1$-$C_4$-alkyl;

is a 4- to 16-membered monocyclic, bicyclic or tricyclic heterocyclo ring which is optionally substituted with 0, 1 or 2 substituents; and
or a pharmaceutically acceptable salt, stereoisomer or tautomer thereof.

3. The compound according to claim 2, wherein

is an optionally substituted monocyclic, bicyclic or tricyclic 4- to 16-membered heterocyclo ring which is optionally substituted pyrazolidinyl

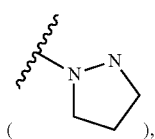

optionally substituted pyrrolidinyl

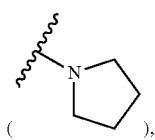

optionally substituted triazaspirodecanedione

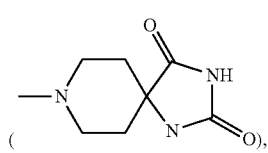

optionally substituted triazaspirononanedione

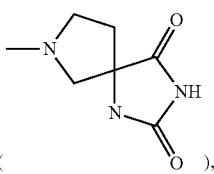

optionally substituted

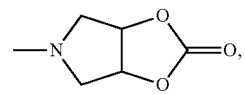

optionally substituted azetidinyl

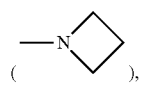

optionally substituted morpholinyl

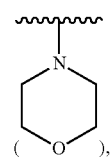

optionally substituted piperazinyl

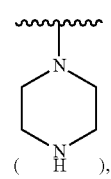

optionally substituted piperidinyl

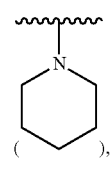

optionally substituted

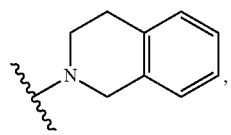 [SMILES: *N1CCc2ccccc2C1]

223 optionally substituted

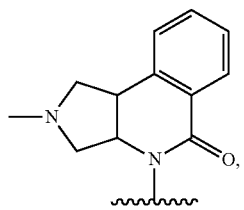 [SMILES: *N1C(=O)c2ccccc2C2CN(C)CC21]

optionally substituted

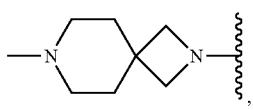 [SMILES: *N1CC2(CCN(C)CC2)C1]

optionally substituted

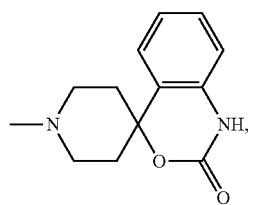 [SMILES: CN1CCC2(CC1)OC(=O)Nc1ccccc12]

optionally substituted

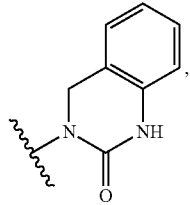 [SMILES: *N1Cc2ccccc2NC1=O]

optionally substituted

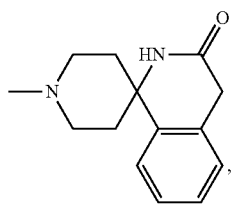 [SMILES: CN1CCC2(CC1)NC(=O)Cc1ccccc12]

optionally substituted

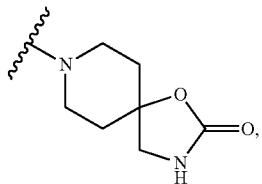 [SMILES: *N1CCC2(CC1)CNC(=O)O2]

224 optionally substituted pyrazolidinone

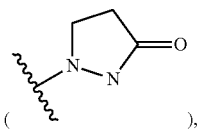

optionally substituted

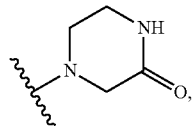 [SMILES: *N1CCNC(=O)C1]

optionally substituted or

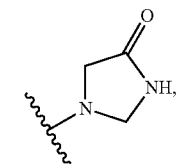 [SMILES: *N1CNC(=O)C1]

optionally substituted

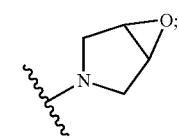 [SMILES: *N1CC2OC2C1]

or a pharmaceutically acceptable salt, stereoisomer or tautomer thereof.

4. The compound according to claim 3 wherein

where possible, is substituted with 1, 2, 3 or 4 groups independently selected from OH, $C_{1-6}$ alkoxycarbonylamino, oxo, amino, halo-$C_{1-4}$-alkyl, halo, $C_{1-6}$ alkyl, hydroxy-$C_{1-6}$-alkyl, amino-$C_{1-4}$-alkyl, phenylcarbonylamino, $C_{1-4}$-alkylaminocarbonylamino-$C_{1-4}$-alkyl, $C_{1-4}$-alkoxycarbonylamino-$C_{1-4}$-alkyl, aminocarbonyl, di-$C_{1-4}$-alkylamino, $C_{1-4}$ alkoxy, $C_{6-10}$aryl, $C_{1-4}$ alkylcarbonyl, $C_{1-4}$ alkylaminocarbonylamino, optionally substituted 4- to 10-membered monocyclic or bicyclic heteroaryl, $C_{1-4}$ alkylcarbonyloxy, $C_{1-4}$-alkoxyphenyl-$C_{1-4}$-alkyl, ($C_{6-10}$ aryl) 4- to 10-membered (dioxo) cycloalkenylamino aryl-$C_{1-4}$-alkyl, halophenyl, optionally substituted 4- to 10-membered monocyclic or bicyclic heterocyclo, optionally substituted 4- to 10-membered monocyclic heteroarylcarbonyl, optionally substituted 4- to 10-membered monocyclic or bicyclic heterocyclo-$C_{1-4}$-alkyl, or 4- to 10-membered monocyclic heteroarylphenyl-$C_{1-4}$-alkylaminocarbonyl, or a pharmaceutically acceptable salt, stereoisomer or tautomer thereof.

5. The compound as defined in claim 1, of the formula:

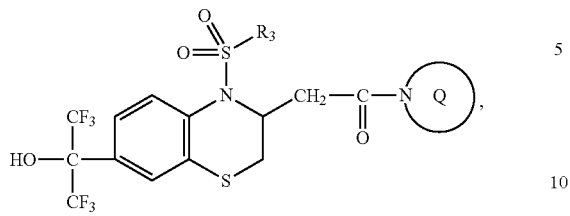

wherein:

is an optionally substituted 4- to 16-membered nitrogen containing monocyclic, bicyclic or tricyclic ring which contains 0, 1 or 2 additional heteroatoms selected from N, S and O;

or a pharmaceutically acceptable salt, stereoisomer or tautomer thereof.

6. A pharmaceutical composition comprising a compound, stereoisomeric form, N-oxide, pharmaceutically acceptable salt, solvate or hydrate according to claim 1 and a pharmaceutically acceptable carrier, excipient or diluent.

* * * * *